US009556448B2

(12) United States Patent
Olivier et al.

(10) Patent No.: US 9,556,448 B2
(45) Date of Patent: Jan. 31, 2017

(54) IDENTIFICATION AND THE USE OF KRP MUTANTS IN PLANTS

(75) Inventors: Jean Paul Olivier, Seattle, WA (US); Dayna L. Loeffler, Seattle, WA (US)

(73) Assignee: Targeted Growth, Inc., Seattle, WA (US)

(*) Notice: Subject to any disclaimer, the term of this patent is extended or adjusted under 35 U.S.C. 154(b) by 190 days.

(21) Appl. No.: 14/111,292

(22) PCT Filed: Apr. 11, 2012

(86) PCT No.: PCT/US2012/033047

§ 371 (c)(1), (2), (4) Date: Dec. 18, 2013

(87) PCT Pub. No.: WO2012/142106

PCT Pub. Date: Oct. 18, 2012

(65) Prior Publication Data

US 2014/0143900 A1 May 22, 2014

Related U.S. Application Data

(60) Provisional application No. 61/474,201, filed on Apr. 11, 2011.

(51) Int. Cl.

| | |
|---|---|
| ***C12N 15/00*** | (2006.01) |
| ***A01H 5/00*** | (2006.01) |
| ***C12N 15/82*** | (2006.01) |
| ***C07K 14/415*** | (2006.01) |
| ***A01H 1/04*** | (2006.01) |
| ***A01H 5/10*** | (2006.01) |

(52) U.S. Cl.

CPC ............. *C12N 15/8261* (2013.01); *A01H 1/04* (2013.01); *A01H 5/10* (2013.01); *C07K 14/415* (2013.01)

(58) Field of Classification Search

None

See application file for complete search history.

(56) References Cited

U.S. PATENT DOCUMENTS

| | | | | |
|---|---|---|---|---|
| 5,958,769 | A | 9/1999 | Roberts et al. | |
| 6,087,175 | A | 7/2000 | John | |
| 6,114,608 | A | 9/2000 | Mettler et al. | |
| 6,559,358 | B1 | 5/2003 | Murray | |
| 6,710,227 | B1 | 3/2004 | Inze et al. | |
| 7,122,658 | B1 | 10/2006 | Lappegard et al. | |
| 7,329,799 | B2 * | 2/2008 | Savidge | C07K 14/415 426/531 |
| 7,803,990 | B2 | 9/2010 | Abbitt | |
| 7,807,872 | B2 * | 10/2010 | Frankard | C07K 14/415 800/286 |
| 8,431,775 | B2 | 4/2013 | Hegstad et al. | |
| 8,742,205 | B2 | 6/2014 | Olivier et al. | |
| 9,062,323 | B2 | 6/2015 | Olivier et al. | |
| 2004/0019926 | A1 | 1/2004 | Frankard et al. | |
| 2007/0044171 | A1 | 2/2007 | Kovalic et al. | |
| 2007/0056058 | A1 * | 3/2007 | Olivier | C07K 14/415 800/290 |
| 2008/0134355 | A1 | 6/2008 | Van Camp | |
| 2008/0216193 | A1 | 9/2008 | Savidge et al. | |
| 2008/0307546 | A1 | 12/2008 | Veylder et al. | |
| 2009/0070894 | A1 * | 3/2009 | Frankard et al. | 800/278 |
| 2009/0087878 | A9 | 4/2009 | La Rosa et al. | |
| 2009/0144863 | A1 | 6/2009 | Song et al. | |
| 2011/0135647 | A1 | 6/2011 | Nakamura et al. | |
| 2012/0131698 | A1 | 5/2012 | Olivier et al. | |
| 2012/0284813 | A1 | 11/2012 | Olivier et al. | |
| 2014/0331362 | A1 | 11/2014 | Olivier et al. | |
| 2016/0002656 | A1 | 1/2016 | Olivier et al. | |

FOREIGN PATENT DOCUMENTS

| | | | |
|---|---|---|---|
| WO | WO-99/64599 | A | 12/1999 |
| WO | WO 00/60087 | A2 | 10/2000 |
| WO | WO-2005/007829 | A2 | 1/2005 |
| WO | WO-2005/024029 | A2 | 3/2005 |
| WO | WO 2006/081029 | A2 | 8/2006 |
| WO | WO 2007/016319 | A2 | 2/2007 |
| WO | WO 2009/092009 | A2 | 7/2009 |
| WO | WO-2010/099083 | A1 | 9/2010 |
| WO | WO 2012/142116 | A2 | 10/2012 |

OTHER PUBLICATIONS

Cheng et al, 2013, Plant J., 75:642-655.*

Extended European Search Report in corresponding European Patent Application No. 12771677.7, mailed Sep. 1, 2014.

Azzi et al., "Interaction Between the Cell-Cycle-Control Proteins $p34^{cdc2}$ and $p9^{CKShs2}$, Evidence for Two Cooperative Binding Domains in $p9^{CKShs2}$," *Eur. J. Biochem.* 203:353-360 (1992).

Coats et al., "Requirement of $p27^{Kip1}$ for Restriction Point Control of the Fibroblast Cell Cycle," *Science* 272:877-880 (1996).

Elmore et al., "Glyphosate-Resistant Soybean Cultivar Response to Glyphosate," *Agron. J.* 93:404-407 (2001).

(Continued)

*Primary Examiner* — Jason Deveau Rosen

(74) *Attorney, Agent, or Firm* — Cooley LLP

(57) ABSTRACT

The invention provides a plant cell, part, tissue culture or whole plant comprising at least one disrupted KRP gene of the present invention. The present invention also provides methods of increasing weight, size, and/or number of one or more organs, and/or yield of a plant by utilizing the disrupted KRP genes of the present invention. Furthermore, methods of breeding plants to produce new plants having increased weight, size, and/or number of one or more organs, and/or yield are provided. The present invention provides isolated Kinase Inhibitor Protein (KIP) Related Protein (KRP) polynucleotide sequences and isolated KRP polypeptide sequences and methods of their use. Exemplary plants include wheat, rice and soybean.

5 Claims, 14 Drawing Sheets

(56) References Cited

OTHER PUBLICATIONS

Elmore et at, "Glyphosate-Resistant Soybean Cultivar Yields Compared with Sister Lines," *Agron. J.* 93:408-412 (2001).
Feig and Cooper, "Inhibition of NIH 3T3 Cell Proliferation by a Mutant ras Protein with Preferential Affinity for GDP," *Mol. Cell. Biol.* 8:3235-3243 (1988).
Fernandez-Cornejo, *Agriculture Information Bulletin No. (AIB786)* 81 pp, Feb. 2004.
Fero et al., "A Syndrome of Multiorgan Hyperplasia with Features of Gigantism, Tumorigenesis, and Female Sterility in p27Kip1-Deficient Mice," *Cell* 85:733-744 (1996).
Firpo et al., "Inactivation of a Cdk2 Inhibitor during Interleukin 2-Induced Proliferation of Human T Lymphocytes," *Mol. Cell. Biol.* 14:4889-4901 (1994).
Jackson et al., "Expression Profiling Reveals Off-target Gene Regulation by RNAi," *Nature Biotech.* 21:635-637 (2003).
Jasinski et al., "The CDK Inhibitor NtKIS1a is Involved in Plant Development, Endoreduplication and Restores Normal Development of Cyclin D3; 1-Overexpressing Plants", *J. Cell Sci.* 115:973-982 (2002).
Jasinski et al., "Comparative Molecular and Functional Analyses of the Tobacco Cyclin-Dependent Kinase Inhibitor NtKIS1a and its Spliced Variant NtKIS1b," *Plant physiol.* 130:1871-1882 (2002).
Kiyokawa et al., "Enhanced Growth of Mice Lacking the Cyclin-Dependent Kinase Inhibitor Function of p27(Kip1)," Cell 85:721-732 (1996).
Koroleva, "CycD 1, it Putative G 1 Cyclin from *Antirrhimum majus*, Accelerates the Cell Cycle in Cultured Tobacco BY-2 Cells by Enhancing Both G1/S Entry and Progression Through S and G2 Phases," *The Plant Cell* 16:2364-2379 (2004).
Kwon T.K. et al. "Identification of cdk2 binding sites on the p27$^{Kipl}$ cyclin-dependent kinase inhibitor." *Oncogene.* Feb. 12, 1998; 16(6):755-62.
Lui et al., "The *Arabidopsis* Cdc2a-Interacting Protein ICK2 is Structurally Related to ICK1 and is a Potent Inhibitor of Cyclin-Dependent Kinase Activity in vitro," *Plant J.* 21:379-385 (2000).
Moloney et al., "High Efficiency Transformation of *Brassica napus* Using *Agrobacterium* Vectors," *Plant Cell Reports* 8:238 (1989).
Nakagami et al., "Phosphorylation of Retinoblastoma-Related Protein by the Cyclin D/Cyclin-Dependent Kinase Complex is Activated at the G1/S-Phase Transition in Tobacco," *Plant Cell* 14:1847-1857 (2002).
Nakayama et al., "Mice lacking p27$^{Kip1}$ Display Increased Body Size, Multiple Organ Hyperplasia, Retinal Dysplasia, and Pituitary Tumors," Cell85:707-720 (1996).
Polyak et al., "Cloning of p27$^{Kipl}$, a Cyclin-Dependent Kinase Inhibitor and a Potential Mediator of Extracellular Antimitogenic Signals," Cell78:59-66 (1994).
Russo et al., "Crystal Structure of the p27$^{Kipl}$ Cyclin-Dependent-Kinase Inhibitor Bound to the Cyclin A-Cdk2 Complex," *Nature* 382:325-331 (1996).
Schnittger et al., "Misexpression of the Cyclin-Dependent Kinase Inhibitor ICK1 IKRP 1 in Single-Celled Arabidopsis Trichomes Reduces Endoreduplication and Cell Size and Induces Cell Death," *Plant Cell* 15:303-315 (2003).
van den Heuvel and Marlow, "Distinct Roles for Cyclin-Dependent Kinases in Cell Cycle Control," *Science* 262:2050-2054 (1993).
Vlach et al., "Phosphorylation-Dependent Degradation of the Cyclin-Dependent Kinase Inhibitor p27$^{Kipl}$" *EMBO J.* 16:5334-44 (1997).
Wang et al., "A Plant Cyclin-Dependent Kinase Inhibitor Gene," *Nature* 386:451-452 (1997).
Wang et al., "ICK1, a Cyclin-Dependent Protein Kinase Inhibitor From *Arabidopsis thaliana* Interacts With Both Cdc2a and CycD3, and its Expression is Induced by Abscisic Acid," *Plant J.* 15:501-510 (1998).
Wang et al.,"Expression of the Plant Cyclin-Dependent Kinase Inhibitor ICK1 Affects Cell Division, Plant Growth and Morphology," *Plant J.* 24:613-623 (2000).
Wang et al., "Genome-Wide Analysis of the Cyclin Family in Arabidopsis and Comparative Phylogenetic Analysis of Plant Cyclin-Like Proteins," *Plant Physiol.* 135:1084-1099 (2004).
Zhou et al., "Plant CDK Inhibitors: Studies of Interactions With Cell Cycle Regulators in the Yeast Two-Hybrid System and Functional Comparisons in Transgenic *Arabidopsis* Plants," *Plant Cell Rep.* 20:967-975 (2002).
Zhou et al., "The Plant Cyclin-Dependent Kinase Inhibitor ICK1 has Distinct Functional Domains for in vivo Kinase Inhibition, Protein Instability and Nuclear Localization." *Plant J.* 35:476-489 (2003).
International Search Report based on International Patent Application No. PCT/US2012/033047, mailed on Jun. 28, 2012.
Written Opinion by International Search Authority based on International Patent Application No. PCT/US2012/033047, mailed on Jun. 28, 2012.
Nakai et al., "Arabidopsis KRPs have distinct inhibitory activity toward cyclin D2-associated kinases, including plant-specific B-type cyclin-dependent kinase", FEBS Letters, 580: 336-340 (2006).
U.S. Appl. No. 13/295,809, Office Action mailed Nov. 25, 2015, 16 pages.
U.S. Appl. No. 13/295,809, Office Action mailed Apr. 23, 2015, 14 pages.
U.S. Appl. No. 13/295,809, Office Action mailed Jun. 3, 2014, 16 pages.
U.S. Appl. No. 13/295,809, Office Action mailed Nov. 21, 2013, 32 pages.
U.S. Appl. No. 14/253,004, Office Action mailed Feb. 25, 2016, 19 pages.
Coelho et al., "Cyclin-Dependent Kinase Inhibitors in Maize Endosperm and Their Potential Role in Endoreduplication", Plant Physiology, 138: 2323-2336 (2005).
De Veylder et al., "Functional Analysis of Cyclin-Dependent Kinase Inhibitors of Arabidopsis," *Plant Cell*, 13: 1653-1667 (2001).
Devos et al., "Genome Relationships: The Grass Model in Current Research", The Plant Cell, 12: 637-646 (2000).
European Patent Application No. 06788753.9, Extended European Search Report mailed Apr. 15, 2009.
European Patent Application No. 15161572.1, Partial European Search Report dated Aug. 24, 2015.
European Patent Application No. 15161572.1, Extended European Search Report dated Nov. 9, 2015.
Inzé and De Veylder, "Cell Cycle Regulation in Plant Development", Annual Review in Genetics, 40: 77-105 (2005).
Leenhardt et al. "Wheat lipoxygenase activity induces greater loss of carotenoids than vitamin E during breadmaking", J Agric Food Chem., 54(5):1710-1715 (2006).
McKibbin et al., "Transcripts of Vp-1 homeologues are misspliced in modern wheat and ancestral species", PNAS, 99(15 ): 10203-10208 (2002).
NCBI BLAST alignment of SEQ ID No. 11 and SEQ ID No. 7 obtained from http://blast.ncbi.nlm.nih.gov/Biast.cgi on Nov. 11, 2013.
PCT/US2006/029349, International Search Report mailed Apr. 20, 2007.
PCT/US2006/029349, Written Opinion of the International Searching Authority, mailed Apr. 20, 2007.
PCT/US2006/029349, International Preliminary Report on Patentability, mailed Jan. 29, 2008.
PCT/US2011/060598, International Search Report and Written Opinion, mailed Mar. 22, 2013.
PCT/US2011/060598, International Preliminary Report on Patentability, dated May 14, 2013.
PCT/US2012/033047, International Preliminary Report on Patentability, dated Oct. 15, 2013.
PCT/US2012/033060, International Search Report, mailed Jul. 2, 2012.
PCT/US2012/033060, Written Opinion by International Search Authority, mailed Jul. 2, 2012.
PCT/US2012/033060, International Preliminary Report on Patentability, mailed Mar. 25, 2014.

(56) References Cited

OTHER PUBLICATIONS

Tranquilli and Dubcovsky, "Epistatic Interaction Between Vernalization Genes Vrn-Am1 and Vrn-Am2 in Diploid Wheat", The Journal of Heredity, 91(4): 304-306 (2000).
Yan et al., "Positional cloning of the wheat vernalization gene VRN1", PNAS, 100(10): 6263-6268 (2003).
U.S. Appl. No. 13/295,809, Office Action mailed Apr. 8, 2016, 17 pages.

* cited by examiner

FIG. 3

Cyclin binding box

CDK binding domain

KRP1A -TAQAQPAARSRVPPAAEIEEFFAAAEEAEARRFACKYNFDVARGVPLDSGRYEWTPAVSSS

K L S * S

SEQ ID NO: 153

KRP2D HYDLEAPARARHPPAAEIDEFFAAAEKAQAERFAAKYNFDVARGVPLNAGRFEWTPVATV-

S VT N C

SEQ ID NO: 154

KRP4A ---RVQAPARHIIPSSAEMNEFFSAAEQPQQAFIDKYNFDPVNDCPLPG-RYEWVKLD---

*

SEQ ID NO: 155

KRP5A ---RAQTPVCRYVPSSLEMDEFFAAAEQQHQTFRDKYNFCPARGCPLPG-RYEWTVLDC--

R D *

SEQ ID NO: 156

FIG. 11

```
TaKRP1A      192 P------AARSRVPPAAEIEEFFAAAEEAEARRFACKYNFDVARGVPLGSG---RYEWTP
TaKRP1D      193 P------AARSRVPPAAEIEEFFAAAEEAEARRFACKYNFDVARGVPLDSG---RYEWTP
TaKRP1B      190 P------AARSRIPPAAEIEEFFAAAEEAEARRFACKYNFDVARGVPLDSG---RYEWTP
Zeama_KRP_2  202 -------AAELIVPPAHEIQEFFAAAEAAQAKRFASKYNFDFVRGVPLDAGG--RFEWAP
ZmKRP7       184 -------AAELIVPPAHEIQEFFAAAEAAQAKRFASKYNFDFVRGVPLDAGG--RFEWAP
ZmKRP6       200 -------AAELIVPPAHEIQEFFAAAEAAQAKRFASKYNFDFVRGVPLDAGG--RFEWAP
ZmKRP8       214 S------AAELIVPPAQEIQEFFAA-----------------------------------
OsKrp1       206 Q------ATRPKIPPAAEIEAFFAAAEEAEAKRFAAKYNFDVVRGVPLDAG---RFEWTP
TaKRP2B      213 FHLDSEARAR--MPPAAEIDEFFAAAEKAQAEHFAAKYNFDVARGVPLNAG---RFEWTP
TaKRP2D      214 LHYDLEARARARMPPAAEIDEFFAAAEKAQAERFAAKYNFDVARGVPLNAG---RFEWTP
TaKRP2A      215 FRLDLEARAR--MPPAAEIDEFFAAAEKAQAERFAAKYNFDVARGVPLNAG---RFEWTP
TaKRP6-1      41 ------------SPPAEEMEAFFAAAEGDVARRFAAKYNYDVVTDAPMDG----RYEWVR
TaKRP6-2      41 ------------SPPAEEMEAFFAAAEGDVARRFAAKYNYNVVTDAPMDG----RYEWVR
TaKRP6-3      43 ------------SPPAEEMEGFFAAAEGDVARRFAAKYNYDVVADAPMDG----RYEWVR
ZmKRP3        65 ------------SPPAEEVEAFLAAAERGMARRFAVKYNYDVVKDAPMDGG---RYEWVR
OsKRP3       157 AAAAAGR-RPPLSPPEAEIEAFFAAAELAERRRFAEKYNYDIALDRPLQG----RYEWEP
ZmKRP5       152 SQTPSPSPSPPPPPTETEIEAFFADAELAERRRFAEAYNYDVALDRPLEG----RFEWVP
OsKRP2       186 GATTRSFRMMAPPAAAAEIEEFLAAAERSEAERFAAKYNFDVVRGVPLDAGGAGRFEWTA
TaKRP4B      144 -----------IIPCSAEMNEFFSAAEQPQQQAFIDKYNFDPVNDCPLPG----RYEWVK
TaKRP4D      144 -----------IIPCSAEMNEFFSAAEQPQQQAFIDKYNFDPVNDCPLPG----RYEWVK
TaKRP4A      144 -----------IIPSSAEMNEFFSAAEQPQQQAFIDKYNFDPVNDCPLPG----RYEWVK
OsKRP4       148 -----------IIPASAELEAFFAAEEQRQRQAFIDKYNFDPVNDCPLPG----RFEWVK
Zeama_KRP_1  144 -----------AVPSSREMNEYFAAEQRRQQQDFIDKYNFDPANDCPLPG----RFEWVK
ZmKRP9        14 -----------ALPSSTEMNEYFAAEQRRQQQAFIDKYNFDPVNDCPLPG----RFEWVK
ZmKRP1       166 -----------FIPSSLEMEEFFSAAEQQEQHSFREKYNFCPVNDCPLPG----RYEWAR
ZmKRP2       170 -----------FIPSSLEMEEFFSAAEQQEQHNFREKYNFCPVNDCPLPG----RYEWAR
OsKRP5       174 -----------YVPSSLEMEEFFAAAEQQQHQAFRERYNFCPVNDCPLPG----RYEWTR
TaKRP5A      162 -----------YVPSSLEMDEFFAAAEQQQHQTFRDKYNFCPARGCPLPG----RYEWTV
TaKRP5D      157 -----------YVPSSLEMDEFFAAAEQQQHQTFREKYNFCPASERPLPG----RYEWTV
TaKRP5B          ------------------------------------------------------------
consensus    241              .... ..........  ...... ..... . . .. .    ....
```

FIG. 11 (Continued)

```
TaKRP1A       243 AVSSS----  (amino acids 192-247 of SEQ ID NO: 87)
TaKRP1D       244 AVSSS----  (amino acids 193-248 of SEQ ID NO: 89)
TaKRP1B       241 AVSSN----  (amino acids 190-241 of SEQ ID NO: 88)
Zeama_KRP_2   253 VSI------  (SEQ ID NO: 157)
ZmKRP7        235 VSI------  (SEQ ID NO: 158)
ZmKRP6        251 VSI------  (SEQ ID NO: 159)
ZmKRP8            ---------  (SEQ ID NO: 160)
OsKrp1        257 VSSRS----  (amino acids 206-261 of SEQ ID NO: 99)
TaKRP2B       268 ATV------  (amino acids 213-271 of SEQ ID NO: 91)
TaKRP2D       271 ATV------  (amino acids 214-274 of SEQ ID NO: 92)
TaKRP2A       270 ATV------  (amino acids 215-273 of SEQ ID NO: 90)
TaKRP6-1       85 RP-------  (amino acids 41-87 of SEQ ID NO: 140)
TaKRP6-2       85 RP-------  (amino acids 41-87 of SEQ ID NO: 143)
TaKRP6-3       87 RP-------  (amino acids 43-89 of SEQ ID NO: 146)
ZmKRP3        110 RPG------  (SEQ ID NO: 161)
OsKRP3        212 ST-------  (SEQ ID NO: 162)
ZmKRP5        208 PLTGGRRW   (SEQ ID NO: 163)
OsKRP2        246 GSG------  (amino acids 186-249 of SEQ ID NO: 146)
TaKRP4B       189 D--------  (amino acids 144-190 of SEQ ID NO: 94)
TaKRP4D       189 D--------  (amino acids 144-190 of SEQ ID NO: 95)
TaKRP4A       189 D--------  (amino acids 144-190 of SEQ ID NO: 93)
OsKRP4        193 D--------  (amino acids 148-194 of SEQ ID NO: 109)
Zeama_KRP_1   189 D--------  (SEQ ID NO: 164)
ZmKRP9         59 D--------  (SEQ ID NO: 165)
ZmKRP1        211 DC-------  (SEQ ID NO: 166)
ZmKRP2        215 DC-------  (SEQ ID NO: 167)
OsKRP5        219 DC-------  (amino acids 174-221 of SEQ ID NO: 109)
TaKRP5A       207 DC-------  (amino acids 162-209 of SEQ ID NO: 96)
TaKRP5D       202 DC-------  (amino acids 157-204 of SEQ ID NO: 98)
TaKRP5B           ---------  (SEQ ID NO: 97)
consensus     301 .
```

FIG. 12

```
Gm0003x00821  125 EQITQT SLP----PQK PTELE  EFFAAAE DI---RKRFS K---------------
Gm0067x00001  110 EHITKT SR-------C PTESE E FFAAAE DI---QKRFT K---------------
Gm0013x00399  140 INSHRALSK-----AKA PTELE EEFFVAAE DI---QKRFQ KYN DIVKDVPLEG-R
Gm0053x00526  147 INSHRVLSK-----AKA PTELE EEFFAASE DI---QKRFQ YN DIVKDVPLEG-R
Gm0102x00087  135 AAVLKV -----------TPPKAE EEFFAMAE YE---QKRFTEKYNFDIVRDLPLEG-R
Gm0043        124 AAVRKL -----------TPPQAE EEFFAMAE YE---RKRFTEKYNFDIVRDLPLEG-R
BnKRP6_1      130 ADDRKSS-----PEVSKSPTPGE EFLSELESKD---QKRF KYNFDIVNDKPLQG-R
BnKRP6_2      132 ADDRKSS-----PEVSKSPTPAE EEFLSELENKD---QKRF KYNFDIVNDKPLQG-R
AtKRP6        139 ATKRKQ------PGVRKTPTAAE E LFSELESPDD-KKKQF EKYNFDIVNDEPLEG-R
AtKRP7        132 TEMRDQ KTEKKKMEKSPTQAE FFSAAE YE---QKRFTEKYN DIVNDTPLEG-R
BnKRP1_1      114 --EEKG S-----ATEQPPTAVE E FFVEAE QL---HDNFKKKYNFDFEK KPLEG-R
BnKRP1_2       50 --EDKG P-----TAEQPPTAVE EEFFVEAE QL---HDKFKKKYNFDFEK KPLEG-R
AtKRP1        135 EEEEKA L-----MTEMP-TESE E FFVEAE QL---KEKFKKKYNFDFEK KPLEG-R
Gm0119x00131  142 RTRQII ---EHVQR-N PTAYE EEFFAYAE QQ---QTIF KYNFDIVNDVPLPG-R
Gm0151x00019  146 RTRQII ---EHIQR-N PTAYE EEFFAYAE QQ---QTIF KYNFDIVN VPLPG-R
Gm0087x00306  161 TCSAEAYRRTEHAARRQ PTSRE EFFAEIEEAQ---QKKF EKYNFDPVN KPLSG-R
BnKRP4_1      185 SDNSNQ EDSFSGSHRH PTTPE EFFSAAEEEQ---QKQF EKYNFDPVN QPLPG-R
BnKRP4_2      184 SGNSNQ EDSFSGSHRH PTTPE EFFSAAEEEQ---QKQF EK---------------
AtKRP4        227 S-ESNQ EDSLSRSHRRRPTTPE EFFSGAEEEQ---QKQF EKYNFDPVN QPLPG-R
BnKRP5_1      149 ------------EATQS P H-E EEFFAFAEQQQ---Q FFTEKYNFDIVS NPLPG-R
BnKRP5_2      149 ------------EAIQS P H-E E FFAFAEQQQ---Q FFTEKYNFDIVS NPLPG-R
AtKRP5        143 ---------------KS Q---E E FFASAEQQQ---Q FF QKYNFDIVSDNPLPG-R
BnKRP3_1      139 ----------TPARDST PTIGE EEFFAYAEQQQ---Q LF EKYNFDIVNDVPLPG-G
BnKRP3_2      139 ----------TPTKDST PTIGE EEFFAYAEQQQ---Q LF EKYNFDIVNDVPLTG-R
AtKRP3        164 -----ATKEYTREQDNV PTTSE EEFFAYAEQQQ---Q LF EKYNFDIVNDIPLSG-R
AtKRP2        148 SRRRLR S------LHETVKEAE E FFQVAE DLRNKLLECSMKYNFDFEKDEPLGGGR
consensus     241       .          ...  *....... .*.     .. ........... . .. . .
```

FIG. 12 (Continued)

```
Gm0003x00821         ----------   (amino acids 125-162 of SEQ ID NO: 131)
Gm0067x00001         ----------   (amino acids 110-146 of SEQ ID NO: 132)
Gm0013x00399    191  YEWVQ KP--   (amino acids 140-198 of SEQ ID NO: 133)
Gm0053x00526    198  YEWVQ KP--   (amino acids 147-205 of SEQ ID NO: 134)
Gm0102x00087    181  YQWV  H---   (amino acids 135-187 of SEQ ID NO: 136)
Gm0043          170  YQWV  H---   (amino acids 124-176 of SEQ ID NO: 137)
BnKRP6_1        181  YKWD  K---   (SEQ ID NO: 168)
BnKRP6_2        183  YKWD  KPLK   (SEQ ID NO: 169)
AtKRP6          191  YKWD  ----   (SEQ ID NO: 170)
AtKRP7          188  YQWVS KP--   (SEQ ID NO: 171)
BnKRP1_1        163  YEWV  SE--   (SEQ ID NO: 172)
BnKRP1_2         99  YEWV  SE--   (SEQ ID NO: 173)
AtKRP1          185  YEWV  E---   (SEQ ID NO: 174)
Gm0119x00131    194  YEWVP LH--   (amino acids 142-201 of SEQ ID NO: 129)
Gm0151x00019    198  YEWVP LH--   (amino acids 146-206 of SEQ ID NO: 130)
Gm0087x00306    217  YEWE  KP--   (amino acids 161-204 of SEQ ID NO: 135)
BnKRP4_1        241   EWK  DD--   (SEQ ID NO: 175)
BnKRP4_2             ----------   (SEQ ID NO: 176)
AtKRP4          282   EWT  DD--   (SEQ ID NO: 177)
BnKRP5_1        192  YEW   VP--   (SEQ ID NO: 178)
BnKRP5_2        192  YEW   VP--   (SEQ ID NO: 179)
AtKRP5          182  YEWV  MP--   (SEQ ID NO: 180)
BnKRP3_1        185  YEWVQ SP--   (SEQ ID NO: 181)
BnKRP3_2        185  YEWVQ SP--   (SEQ ID NO: 182)
AtKRP3          215  YEWVQ KP--   (SEQ ID NO: 183)
AtKRP2          202  YEWV  NP--   (SEQ ID NO: 184)
consensus       301  ......
```

IDENTIFICATION AND THE USE OF KRP MUTANTS IN PLANTS

CROSS-REFERENCE TO RELATED APPLICATIONS

This application is a national stage of International Patent Application No. PCT/US2012/033047 filed on Apr. 11, 2012, which claims the benefit of U.S. Provisional Application Ser. No. 61/474,201, filed Apr. 11, 2011, each of the International Patent Application No. PCT/US2012/033047 and the U.S. Provisional Application Ser. No. 61/474,201 is hereby incorporated by reference in its entirety for all purposes.

TECHNICAL FIELD

The invention generally relates to compositions and methods for improving traits of agronomic and horticultural crops, including by increasing crop yield. More specifically, the present invention relates to compositions and methods for improving one or more agronomic or horticultural traits by disturbing one or more Kinase Inhibitor Protein (KIP) Related Proteins (KRP) in monocotyledonous and dicotyledonous plants.

BACKGROUND

The most important trait as a target for crop improvement is yield. Efforts to improve crop yields by developing new plant varieties can be divided into two approaches. One is to reduce crop yield losses by breeding or engineering crop varieties with increased resistance to abiotic stress conditions such as drought, cold, or salt or to biotic stress conditions resulting from pests or disease-causing pathogens. While this approach has value, it does not provide fundamentally improved crop yield in the absence of stress conditions and in fact, such resistance may direct plant resources that otherwise would be available for increased yield in the plant. The second approach is to breed or engineer new crop varieties in which the basic yield capacity is increased.

Classical breeding programs have initially produced substantial gains in improved yield in a variety of crops. A commonly experienced pattern though has been substantial gains in yield initially followed by incremental further improvements that become smaller and more difficult to obtain. More recently developed approaches based on molecular biology technologies have in principle offered the potential to achieve substantial improvement in crop yield by altering the timing, location, or level of expression of plant genes or heterologous genes that play a role in plant growth and/or development. Substantial progress has been made over the past twenty years in identifying plant genes and or heterologous genes that have a role in plant growth and/or development. Despite these gains in using molecular approaches, there continues to be a large unmet need for improved agronomic and horticultural plants produced through more conventional plant breeding. Because of the complexity of plant growth regulation and how it relates in the end to yield traits, it is still not obvious which, if any, of particular genes would be clear candidates to improve crop yield through either plant breeding and/or molecular techniques.

KRP proteins belong to a class of cell cycle inhibitors that bind to and inhibit cyclin/CDK kinase complexes. Mutation of conserved residues within KRP family members are expected to modify KRP's ability to function as an inhibitor of cyclin-CDK kinase complexes. Specifically, some mutations in KRP genes would lead to expression of a non-functional KRP cell cycle inhibitor or a cell cycle inhibitor with reduced activity. This loss of or reduced cyclin/CDK kinase inhibitory activity would lead to increased cyclin-CDK kinase activity in cells when normally these cells would have reduced cyclin-CDK activity. This loss of or reduced cyclin/CDK kinase inhibitory activity would lead to increased cell divisions in tissue where the normal wild-type KRP version is expressed. This increased cell division would result in positive agronomic traits such as increased yield, increased weight, size, and/or number of one or more organs, for example, increased seed size, larger plants, larger leaves, larger roots etc. For background on KRP-related technologies, see, for example, WO/2007/016319 and US20070056058, each of which is incorporated by reference in its entirety for all purposes. The present invention identifies new KRP genes and proteins and provides methods for their use in producing improved agronomic and horticultural plants through conventional plant breeding and/or molecular methodologies.

SUMMARY OF THE INVENTION

The inventors of the present invention have used Targeting Induced Local Lesions in Genomes (TILLING®) methods in plants to identify KRP mutants, for example, in monocot plants, such as plants in the Triticeae tribe (e.g., plants in the *Triticum* genus), and plants in the tribe of Oryzeae (e.g., plants in *Oryza* genus), or in dicot plants, for example, in *Glycine* spp. The identified KRP mutants can be used for increasing weight, size, and/or number of one or more organs in a plant. The organ can be any part of a plant, for example, organs that contribute to yield in a plant. In some embodiments, the organ is seed, leaf, branch, root, shoot, stigma, ovule, pollen, seed pods, seed heads, or tiller. For example, in some embodiments, the present invention provides methods for increasing plant seed weight, seed size, seed number and/or yield.

This invention describes the search for mutations in plant KRPs that are expressed in cells within the developing seed. The strategy was to identify KRP family member(s) with seed expression and TILL® for mutants in these KRPs. Certain mutants that affect KRP function can then be characterized for positive agronomical and horticultural traits such as increased yields, early emergence, accelerated growth etc. In addition, this same methodology can be used for KRPs expressed in other tissues such as leaves or stalks since increased cell divisions in these other tissues specific to the particular KRP expression pattern could also lead to positive agronomic traits.

To date, KRP family members in agriculturally, horticulturally and/or industrially important plant species and their expression patterns in developing seed have yet to be studied. The inventors' strategy was to identify KRPs that are expressed in the developing seed. KRPs with expression pattern during development in a tissue specific manner are identified. For example, the rice KRP4 gene (OsKRP4) showed almost exclusive expression in the developing seed. Equivalents to this sequence in rice and other plant species are also identified.

The present invention provides mutated KRP genes compared to a wild type KRP having nucleic acid sequence comprising a sequence selected from the group consisting of SEQ ID NOs: 60-86, 100-107, 111-128, fragments and variations derived from thereof, which encode a KRP gene.

In some embodiments, the KRP has an expression pattern in a tissue specific manner during development. In some embodiments, the expression is embryonic specific, pollen specific, or seed specific.

In some embodiments, the present invention provides mutated KRP genes compared to a wild type KRP comprising a sequence comprising a nucleic acid sequence that shares at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to SEQ ID NOs: 60-86, 100-107, 111-128, 138-139, 141-142, and 144-145.

In some embodiments, the present invention provides mutated KRP genes compared to a wild type KRP encoding an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to SEQ ID NO: 87-99, 108-110, 129-137, 140, 143, and 146.

For example, the present invention provides mutants in wheat (Ta) KRP1A, KRP1B, KRP1D, KRP2A, KRP2B, KRP2D, KRP4B, KRP4D, KRP5A, KRP5D, KRP6A, KRP6B, KRP6D. It appears that hexaploid wheat has been naturally selected to have what appear to be knock-out mutations in KRP4A and KRP5B. This was discovered during the course of TILLING®. For KRP4A, the gene appears to be completely missing from the hexaploid wheat genome, although it is still present in the tetraploid genome. For KRP5B, there appears to be one missing nucleotide in the gene, which would shift the translational frame and produce a predicted truncation a few amino acids further on.

The present invention in another aspect provides plant cells, plant parts, tissue culture, or whole plants comprising one or more disrupted KRP genes as described herein. In some embodiments, the present invention provides plant cells, plant parts, tissue culture or whole plants comprising at least one KRP gene, wherein the genome of the plant has one or more copies of the gene, and wherein the function of one or more copies of the KRP gene is disrupted.

In some embodiments, the plant is a monocot. In some embodiments, the monocot is a species in the Triticeae tribe or the Oryzeae tribe. In some embodiments, the plant in the Triticeae tribe is a plant in the *Triticum* genus, and wherein the plant in the Oryzeae tribe is a plant in the *Oryza* genus.

In some further embodiments, the plant in the *Triticum* genus is wheat, and wherein the plant in the *Oryza* genus is rice.

In some further embodiments, the wheat plant is tetraploid or hexaploid.

In some embodiments, the plant is a dicot. In some embodiments, the plant is a species in the Fabaceae family, for example, *Glycine* spp., such as soybean.

In some embodiments, the KRP in the wheat is TaKRP1, TaKRP2, TaKRP4, TaKRP5, TaKRP6, for example, SEQ ID NOs. 60-86, 138-139, 141-142, 144-145 or functional variants thereof, and the KRP in the rice is OsKRP1, OsKRP2, OsKRP4, or OsKRP5, for example, SEQ ID NOs. 100-107, or functional variants thereof; and the KRP in the *Glycine* spp. is Gm0003×00821, Gm0013×00399, Gm0043, Gm0053×00526, Gm0087×00306, Gm0102×00087, Gm0119×00131, Gm0151×00019, Gm0067×00001, for example, SEQ ID NOs. 111-128, or functional variants thereof. For example, in a tetraploid wheat plant, the KRP is TaKRP1A, TaKRP1B, TaKRP2A, TaKRP2B, TaKRP4A, TaKRP4B, TaKRP5A, TaKRP5B, TaKRP6A or TaKRP6B. In a hexaploid wheat, the KRP is TaKRP1A, TaKRP1B, TaKRP1D, TaKRP2A, TaKRP2B, TaKRP2D, TaKRP4A, TaKRP4B, TaKRP4D, TaKRP5A, TaKRP5B, TaKRP5D, TaKRP6A, TaKRP6B, or TaKRP6D.

In some embodiments, the KRP genes function is disrupted by nucleotide substitution, deletion, insertion, homologous recombination, T-DNA, transposon, double strand oligonucleotide, antisense oligonucleotide, inverted repeat, or combination thereof.

In some embodiments, the disrupted KRP in the plant cell, plant part, tissue culture or whole plant comprises one or more mutations selected from any one of mutations listed in Tables 2-12, 25, 28, 29-37 for a particular KRP gene.

In another aspect, the present invention provides methods for increasing weight, size, and/or number of one or more organs, for example, for increasing seed weight, seed size, seed number and/or yield in a plant comprising disrupting one or more KRPs in the plant. In one embodiment, the plant is a dicotyledon plant or a monocotyledon plant. In some embodiments, the plant can be a plant selected from the Triticeae tribe, the Oryzeae tribe, or the Fabaceae family, for example, wheat, rice, and soybean. In some embodiments, methods of disrupting a gene function include but are not limited to mutagenesis (e.g., chemical mutagenesis, radiation mutagenesis, transposon mutagenesis, insertional mutagenesis, signature tagged mutagenesis, site-directed mutagenesis, and natural mutagenesis), antisense, knock-outs, and/or RNA interference. In some embodiment, the plant with increased weight, size, and/or number of one or more organs, for example, a plant with increased seed weight, seed size, seed number and/or yield is not a genetically modified organism, or a transgenic plant. For example, the disruption of the KRP in the genome of the plant is simply due to natural mutation, or mutations induced by chemical mutagenesis or radiation mutagenesis.

In some embodiments, mutations described in the Tables 2-12, 25, 28, 29-37 can be integrated into species closely related to the plants in the Triticeae tribe, the Oryzeae tribe, the Fabaceae family, or plants closely related to wheat, rice, or soybean. In some embodiments, amino acids in conserved domains or sites compared to KRP orthologs in other species can be substituted or deleted to make mutants with reduced or abolished activity, and/or mutants that lead to loss-of-function (e.g., protein instability). In some embodiments, one or more KRPs in a plant are knocked down or knocked out by one or more methods available to one skilled in the art.

In some embodiments, one or more copies of one or more KRP genes are disrupted. For example, in a tetraploid wheat plant, one or two copies of a KRP gene are disrupted (e.g., KRP1A, KRP1B; KRP2A, KRP2B; KRP4A, KRP4B; KRP5A, KRP5B; and KRP6A, KRP6B); in a hexaploid wheat plant, one or more copies of one, two, or three copies of a KRP gene are disrupted (e.g., KRP1A, KRP1B, KRP1D; KRP2A, KRP2B, KRP2D; KRP4A, KRP4B, KRP4D; KRP5A, KRP5B, KRP5D; and KRP6A, KRP6B, KRP6D)

The present invention also provides a plant having increased weight, size, and/or number of one or more organs, for example, a plant with increased seed size, seed number, and/or seed yield compared to a wild type reference plant, wherein the plant has one or more mutations in one or more KRP genes. In some embodiments, said plant is a monocot plant. In some embodiments, said monocot plant is a plant from the Triticeae tribe or the Oryzeae tribe. In some embodiments, said plant is a wheat or a rice plant. In some embodiments, said plant is a dicot plant. In some embodiments, said dicot plant is from the Fabaceae family, such as a soybean plant.

The present invention further provides a seed, a fruit, a plant cell or a plant part of the transgenic plants as described herein. For example, the present invention provides a pollen of the plant, an ovule of the plant, a genetically related plant population comprising the plant, a tissue culture of regenerable cells of the plant. In some embodiments, the regenerable cells are derived from embryos, protoplasts, meristematic cells, callus, pollen, leaves, anthers, stems, petioles, roots, root tips, fruits, seeds, flowers, cotyledons, and/or hypocotyls.

The present invention also provides methods of decreasing the activity of one or more KRP proteins in a plant cell, plant part, tissue culture or whole plant comprising contacting the plant cell, plant part, tissue culture or whole plant with an inhibitory nucleic acid having complementarity to a gene encoding said KRP protein. In some embodiments, the plant is a plant from the Triticeae tribe or the Oryzeae tribe. In some embodiments, said plant is a wheat or a rice plant. In some embodiments, said plant is a dicot plant. In some embodiments, said dicot plant is from the Fabaceae family, such as a soybean plant.

The present invention also provides methods of breeding a crop species having increased weight, size, and/or number of one or more organs, for example, a crop species with increased seed size, seed number, seed weight and/or seed yield compared to a wild type reference plant, comprising incorporating the genetic materials of a plant with disrupted KRP(s) into a recipient plant.

In some embodiments, such methods comprise making a cross between a *Triticum* sp. mutant with one or more mutations listed in Tables 2-12 with a second *Triticum* sp. to produce an F1 plant, or with a species in the Triticeae tribe which can intercross with said first *Triticum* sp. The method may further comprise backcrossing the F1 plant to the second *Triticum* sp. or species in the Triticeae tribe; and repeating the backcrossing step to generate an near isogenic line, wherein the one or more mutations are integrated into the genome of said second *Triticum* sp. or the species in the Triticeae tribe; wherein the near isogenic line derived from the second *Triticum* sp. or the species in the Triticeae tribe with the integrated mutations has altered weight, size, and/or number of one or more organs, for example, altered seed weight, seed size, seed number, and/or seed yield. Optionally, such methods can be facilitated by molecular markers or TILLING®.

In some embodiments, such methods comprise making a cross between an *Oryza* sp. mutant with one or more mutations listed in Table 25 with a second *Oryza* sp. to produce an F1 plant, or with a species in the Oryzeae tribe which can intercross with said *Oryza* sp. The method may further comprise backcrossing the F1 plant to the second *Oryza* sp. or species in the Oryzeae tribe; and repeating the backcrossing step to generate an near isogenic line, wherein the one or more mutations are integrated into the genome of said second *Oryza* sp. or the species in the Oryzeae tribe; wherein the near isogenic line derived from the second *Oryza* sp. or the species in the Oryzeae tribe with the integrated mutations has altered weight, size, and/or number of one or more organs, for example, altered seed weight, seed size, seed number, and/or seed yield. Optionally, such methods can be facilitated by molecular markers or TILLING®.

In some embodiments, such methods comprise making a cross between a *Glycine* sp. mutant with one or more mutations listed in Tables 29-37 with a second *Glycine* sp. to produce an F1 plant, or with a species in the Fabaceae family which can intercross with said first *Glycine* sp. The method may further comprise backcrossing the F1 plant to the second *Glycine* sp. or species in the Fabaceae family; and repeating the backcrossing step to generate an near isogenic line, wherein the one or more mutations are integrated into the genome of said second *Glycine* sp. or species in the Fabaceae family; wherein the near isogenic line derived from the second *Glycine* sp. or species in the Fabaceae family with the integrated mutations has altered weight, size, and/or number of one or more organs, for example, altered seed weight, seed size, seed number, and/or seed yield. Optionally, such methods can be facilitated by molecular markers or TILLING®.

The present invention provides an isolated nucleic acid sequence comprising a sequence selected from the group consisting of SEQ ID NOs: 138, 139, 141, 142, 144, and 145, and fragments and variations derived from thereof, which encode a wheat KRP gene.

In one embodiment, the present invention provides an isolated polynucleotide encoding plant KRP protein, comprising a nucleic acid sequence that shares at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to SEQ ID NOs: 138, 139, 141, 142, 144, and 145.

The present invention further provides an isolated amino acid sequence (e.g., a peptide, polypeptide and the like) comprising a sequence selected from the group consisting of SEQ ID NOs: 140, 143, and 146 and fragments and variations derived from thereof, which form a KRP protein.

In some embodiments, the present invention provides an isolated amino acid sequence which forms a protein that shares an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to SEQ ID NOs: 140, 143, and 146.

In one embodiment, isolated polynucleotides of the present invention comprise a sequence selected from the group consisting of: (a) sequences recited in SEQ ID NOs: 138, 139, 141, 142, 144, and 145, or portions thereof; (b) complements of the sequences recited in SEQ ID NOs: 138, 139, 141, 142, 144, and 145, or portions thereof; (c) reverse complements of the sequences recited in SEQ ID NOs: 138, 139, 141, 142, 144, and 145 or portions thereof; (d) reverse sequences of the sequences recited in SEQ ID NOs: 138, 139, 141, 142, 144, and 145, or portions thereof; and (e) sequences having at least 50%, 75%, 90%, 95% or 98% identity, as defined herein, to a sequence of (a)-(d) or a specified region of a sequence of (a)-(d).

The present invention also provides a chimeric gene comprising the isolated nucleic acid sequence of any one of the polynucleotides described above operably linked to suitable regulatory sequences.

The present invention also provides recombinant constructs comprising the chimeric gene as described above.

The present invention further provides interfering RNA (RNAi) constructs based on nucleic acid sequences of the present invention. In some embodiments, the RNAi constructs are can be transformed into a wheat plant to down-regulate one or more KRPs. The RNAi construct can be, but is not limited to antisense oligonucleotide construct, double-strand oligonucleotide construct, siRNA construct, or inverted repeat construct. In some embodiment, the RNAi constructs comprise a plant promoter, such as a constitutive promoter, an inducible promoter, or a tissue-specific promoter. In some embodiments, the promoter is embryonic specific or seed specific.

BRIEF DESCRIPTION OF THE DRAWINGS

FIG. 3 depicts the C-terminal amino acid sequences that include the cyclin and cyclin-dependent kinase (CDK) binding domains for KRP1A, 2D, 4A and 5A. Nonsense and Type I severe missense TILLING® mutations tested in the in vitro kinase assay are indicated by asterisks or mutant amino acids, respectively, below the wild-type amino acids.

FIG. 11 depicts an alignment of rice (Os), corn (Zm) and wheat (Ta) KRP proteins.

FIG. 12 depicts an alignment of soy (Gm), *Arabidopsis* (At) and *Brassica napus* (Bn) KRP proteins.

SEQUENCES

Figure 1:
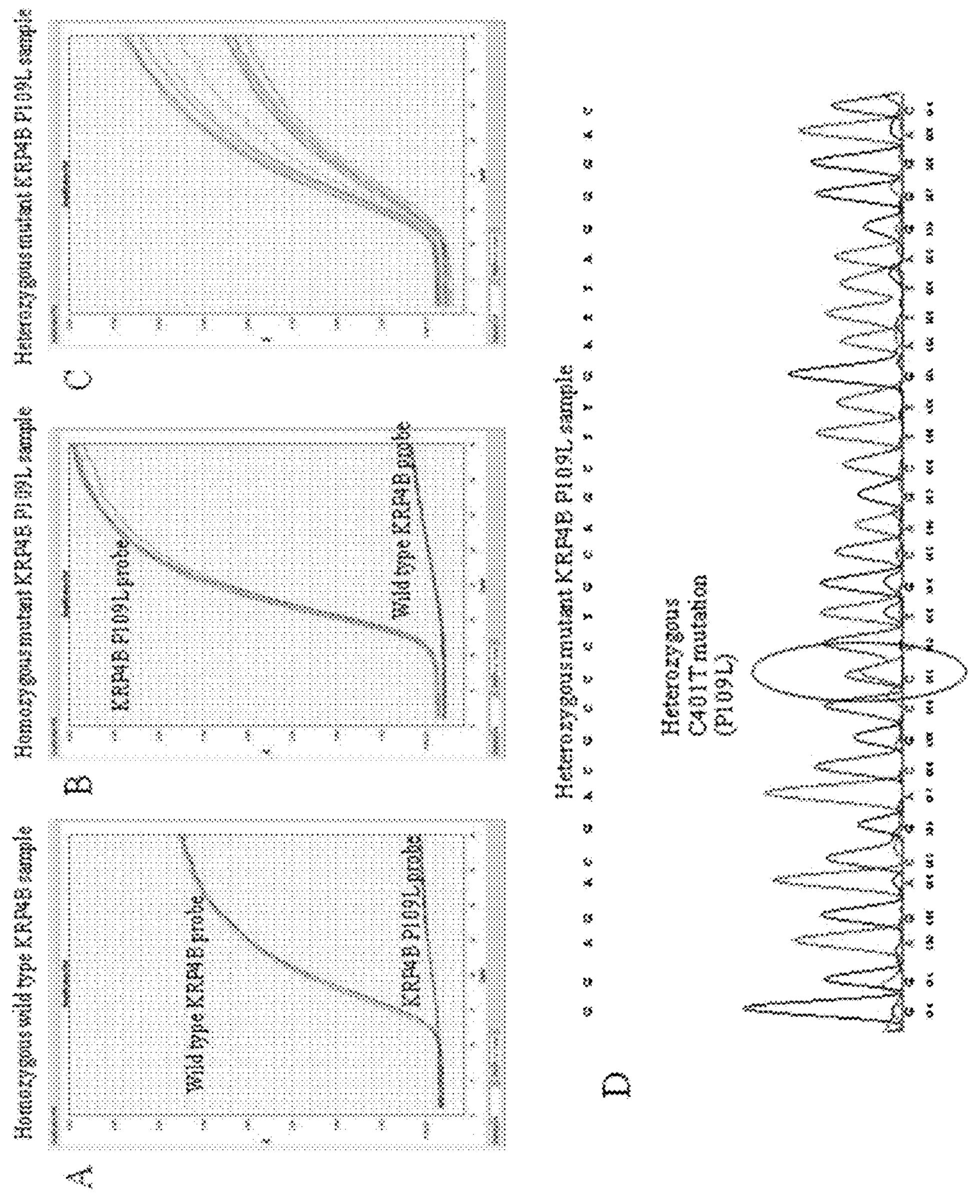
FIG. 1A depicts an amplification plot of fluorescence signal versus cycle number for a wheat genomic sample homozygous for the wild type allele of wheat KRP4B. The upper curve represents the amplification with the wild type probe, while the bottom curve represents the amplification with the mutant probe.
FIG. 1B depicts an amplification plot of fluorescence signal versus cycle number for a wheat genomic sample homozygous for the mutant allele of wheat KRP4B. The upper curve represents the amplification with the mutant probe, while the bottom curve represents the amplification with the wild type probe.
FIG. 1C depicts an amplification plot of fluorescence signal versus cycle number for a wheat genomic sample heterozygous for the mutant allele of wheat KRP4B.
FIG. 1D depicts a sequence chromatogram showing the two nucleotides detected in a wheat genomic sample heterozygous for the mutant allele of wheat KRP4B.

Sequence listings for SEQ ID No: 1-SEQ ID No: 152 are part of this application and are incorporated by reference herein. Sequence listings are provided at the end of this document.

DETAILED DESCRIPTION

All publications, patents and patent applications, including any drawings and appendices, and all nucleic acid sequences and polypeptide sequences identified by GenBank Accession numbers, herein are incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior art.

Definitions

As used herein, the verb "comprise" as is used in this description and in the claims and its conjugations are used in its non-limiting sense to mean that items following the word are included, but items not specifically mentioned are not excluded.

As used herein, the term "plant" refers to any living organism belonging to the kingdom Plantae (i.e., any genus/species in the Plant Kingdom). This includes familiar organisms such as but not limited to trees, herbs, bushes, grasses, vines, ferns, mosses and green algae. The term refers to both monocotyledonous plants, also called monocots, and dicotyledonous plants, also called dicots. Examples of particular plants include but are not limited to plants in the Triticeae tribe (e.g., plants in the *Triticum* genus), plants in the tribe of Oryzeae (e.g., plants in *Oryza* genus), plants in the Andropogoneae tribe (e.g., plants in the *Zea* genus, such has corn). Other non-limiting examples of plant include, potatoes, roses, apple trees, sunflowers, bananas, tomatoes, opo, pumpkins, squash, lettuce, cabbage, oak trees, guzmania, geraniums, hibiscus, clematis, poinsettias, sugarcane, taro, duck weed, pine trees, Kentucky blue grass, zoysia, coconut trees, *brassica* leafy vegetables (e.g. broccoli, broccoli raab, Brussels sprouts, cabbage, Chinese cabbage (Bok Choy and Napa), cauliflower, cavalo, collards, kale, kohlrabi, mustard greens, rape greens, and other *brassica* leafy vegetable crops), bulb vegetables (e.g. garlic, leek, onion (dry bulb, green, and Welch), shallot, and other bulb vegetable crops), citrus fruits (e.g. grapefruit, lemon, lime, orange, tangerine, citrus hybrids, pummelo, and other citrus fruit crops), cucurbit vegetables (e.g. cucumber, citron melon, edible gourds, gherkin, muskmelons (including hybrids and/or cultivars of cucumis melons), water-melon, cantaloupe, and other cucurbit vegetable crops), fruiting vegetables (including eggplant, ground cherry, pepino, pepper, tomato, tomatillo, and other fruiting vegetable crops), grape, leafy vegetables (e.g. romaine), root/tuber and corm vegetables (e.g. potato), and tree nuts (almond, pecan, pistachio, and walnut), berries (e.g., tomatoes, barberries, currants, elderberries, gooseberries, honeysuckles, mayapples, nannyberries, Oregon-grapes, see-buckthorns, hackberries, bearberries, lingonberries, strawberries, sea grapes, lackberries, cloudberries, loganberries, raspberries, salmonberries, thimbleberries, and wineberries), cereal crops (e.g., corn, rice, wheat, barley, sorghum, millets, oats, ryes, triticales, buckwheats, fonio, quinoa, oil palm), pome fruit (e.g., apples, pears), stone fruits (e.g., coffees, jujubes, mangos, olives, coconuts, oil palms, pistachios, almonds, apricots, cherries, damsons, nectarines, peaches and plums), vine (e.g., table grapes, wine grapes), fiber crops (e.g. hemp, cotton), ornamentals, and the like.

As used herein, the term "plant part" refers to any part of a plant including but not limited to the shoot, root, stem, seeds, stipules, leaves, petals, flowers, ovules, bracts, branches, petioles, internodes, bark, pubescence, tillers, rhizomes, fronds, blades, pollen, stamen, and the like. The two main parts of plants grown in some sort of media, such as soil, are often referred to as the "above-ground" part, also often referred to as the "shoots", and the "below-ground" part, also often referred to as the "roots".

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements are present, unless the context clearly requires that there is one and only one of the elements.

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the terms "polypeptide," "peptide," and "protein" are used interchangeably herein to refer to polymers of amino acids of any length. These terms also include proteins that are post-translationally modified through reactions that include glycosylation, acetylation and phosphorylation.

As used herein, the term "homologous" or "homologue" or "ortholog" is known in the art and refers to related sequences that share a common ancestor or family member and are determined based on the degree of sequence identity. The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

These terms describe the relationship between a gene found in one species, subspecies, variety, cultivar or strain and the corresponding or equivalent gene in another species, subspecies, variety, cultivar or strain. For purposes of this invention homologous sequences are compared. "Homologous sequences" or "homologues" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. The degree of sequence identity may vary, but in one embodiment, is at least 50% (when using standard sequence alignment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in *Current Protocols in Molecular Biology*

(F. M. Ausubel et al., eds., 1987) Supplement 30, section 7.718, Table 7.71. Some alignment programs are MacVector (Oxford Molecular Ltd, Oxford, U.K.), ALIGN Plus (Scientific and Educational Software, Pennsylvania) and AlignX (Vector NTI, Invitrogen, Carlsbad, Calif.). Another alignment program is Sequencher (Gene Codes, Ann Arbor, Mich.), using default parameters.

As used herein, the term "nucleotide change" refers to, e.g., nucleotide substitution, deletion, and/or insertion, as is well understood in the art. For example, mutations contain alterations that produce silent substitutions, additions, or deletions, but do not alter the properties or activities of the encoded protein or how the proteins are made.

As used herein, the term "protein modification" refers to, e.g., amino acid substitution, amino acid modification, deletion, and/or insertion, as is well understood in the art, As used herein, the term "derived from" refers to the origin or source, and may include naturally occurring, recombinant, unpurified, or purified molecules. A nucleic acid or an amino acid derived from an origin or source may have all kinds of nucleotide changes or protein modification as defined elsewhere herein.

As used herein, the term "at least a portion" or "fragment" of a nucleic acid or polypeptide means a portion having the minimal size characteristics of such sequences, or any larger fragment of the full length molecule, up to and including the full length molecule. For example, a portion of a nucleic acid may be 12 nucleotides, 13 nucleotides, 14 nucleotides, 15 nucleotides, 16 nucleotides, 17 nucleotides, 18 nucleotides, 19 nucleotides, 20 nucleotides, 22 nucleotides, 24 nucleotides, 26 nucleotides, 28 nucleotides, 30 nucleotides, 32 nucleotides, 34 nucleotides, 36 nucleotides, 38 nucleotides, 40 nucleotides, 45 nucleotides, 50 nucleotides, 55 nucleotides, and so on, going up to the full length nucleic acid. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as hybridization probe may be as short as 12 nucleotides; in one embodiment, it is 20 nucleotides. A portion of a polypeptide useful as an epitope may be as short as 4 amino acids. A portion of a polypeptide that performs the function of the full-length polypeptide would generally be longer than 4 amino acids.

As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988).

As used herein, the term "substantially complementary" means that two nucleic acid sequences have at least about 65%, preferably about 70% or 75%, more preferably about 80% or 85%, even more preferably 90% or 95%, and most preferably about 98% or 99%, sequence complementarities to each other. This means that primers and probes must exhibit sufficient complementarity to their template and target nucleic acid, respectively, to hybridize under stringent conditions. Therefore, the primer and probe sequences need not reflect the exact complementary sequence of the binding region on the template and degenerate primers can be used. For example, a non-complementary nucleotide fragment may be attached to the 5'-end of the primer, with the remainder of the primer sequence being complementary to the strand. Alternatively, non-complementary bases or longer sequences can be interspersed into the primer, provided that the primer has sufficient complementarity with the sequence of one of the strands to be amplified to hybridize therewith, and to thereby form a duplex structure which can be extended by polymerizing means. The non-complementary nucleotide sequences of the primers may include restriction enzyme sites. Appending a restriction enzyme site to the end(s) of the target sequence would be particularly helpful for cloning of the target sequence. A substantially complementary primer sequence is one that has sufficient sequence complementarity to the amplification template to result in primer binding and second-strand synthesis. The skilled person is familiar with the requirements of primers to have sufficient sequence complementarity to the amplification template.

As used herein, the terms "polynucleotide", "polynucleotide sequence", "nucleic acid sequence", "nucleic acid fragment", and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

As used herein, the phrase "a biologically active variant" or "functional variant" with respect to a protein refers to an amino acid sequence that is altered by one or more amino acids with respect to a reference sequence, while still maintains substantial biological activity of the reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variations can also include amino acid deletion or insertion, or both. Guidance in determining which amino acid residues can be substituted, inserted, or deleted without eliminating biological or immunological activity can be found using computer programs well known in the art, for example, DNASTAR software.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T vs. G/C content) of primer. A pair of bi-directional primers consists of one forward and one reverse primer as commonly used in the art of DNA amplification such as in PCR amplification.

The terms "stringency" or "stringent hybridization conditions" refer to hybridization conditions that affect the stability of hybrids, e.g., temperature, salt concentration, pH, formamide concentration and the like. These conditions are empirically optimized to maximize specific binding and minimize non-specific binding of primer or probe to its target nucleic acid sequence. The terms as used include reference to conditions under which a probe or primer will hybridize to its target sequence, to a detectably greater degree than other sequences (e.g. at least 2-fold over background). Stringent conditions are sequence dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of a complementary target sequence hybridizes to a perfectly matched probe or primer. Typically, stringent conditions will be those in which the salt concentration is less than about 1.0 M $Na^+$ ion, typically about 0.01 to 1.0 M Na+ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, 1M NaCl, 1% SDS at 37° C., and a wash in 0.1×SSC at 60° C. Hybridization procedures are well known in the art and are described by e.g. Ausubel et al., 1998 and Sambrook et al., 2001.

As used herein, "coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence.

As used herein, "regulatory sequences" may include, but are not limited to, promoters, translation leader sequences, introns, and polyadenylation recognition sequences.

As used herein, "promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity.

As used herein, a "plant promoter" is a promoter capable of initiating transcription in plant cells whether or not its origin is a plant cell, e.g. it is well known that *Agrobacterium* promoters are functional in plant cells. Thus, plant promoters include promoter DNA obtained from plants, plant viruses and bacteria such as *Agrobacterium* and *Bradyrhizobium* bacteria. A plant promoter can be a constitutive promoter or a non-constitutive promoter.

As used herein, a "constitutive promoter" is a promoter which is active under most conditions and/or during most development stages. There are several advantages to using constitutive promoters in expression vectors used in plant biotechnology, such as: high level of production of proteins used to select transgenic cells or plants; high level of expression of reporter proteins or scorable markers, allowing easy detection and quantification; high level of production of a transcription factor that is part of a regulatory transcription system; production of compounds that requires ubiquitous activity in the plant; and production of compounds that are required during all stages of plant development. Non-limiting exemplary constitutive promoters include, CaMV 35S promoter, opine promoters, ubiquitin promoter, actin promoter, alcohol dehydrogenase promoter, etc.

As used herein, a "non-constitutive promoter" is a promoter which is active under certain conditions, in certain types of cells, and/or during certain development stages. For example, tissue specific, tissue preferred, cell type specific, cell type preferred, inducible promoters, and promoters under development control are non-constitutive promoters. Examples of promoters under developmental control include promoters that preferentially initiate transcription in certain tissues, such as stems, leaves, roots, or seeds.

As used herein, "inducible" or "repressible" promoter is a promoter which is under chemical or environmental factors control. Examples of environmental conditions that may effect transcription by inducible promoters include anaerobic conditions, or certain chemicals, or the presence of light.

As used herein, a "tissue specific" promoter is a promoter that initiates transcription only in certain tissues. Unlike constitutive expression of genes, tissue-specific expression is the result of several interacting levels of gene regulation. As such, in the art sometimes it is preferable to use promoters from homologous or closely related plant species to achieve efficient and reliable expression of transgenes in particular tissues. This is one of the main reasons for the large amount of tissue-specific promoters isolated from particular plants and tissues found in both scientific and patent literature. Non-limiting tissue specific promoters include, beta-amylase gene or barley hordein gene promoters (for seed gene expression), tomato pz7 and pz130 gene promoters (for ovary gene expression), tobacco RD2 gene promoter (for root gene expression), banana TRX promoter and melon actin promoter (for fruit gene expression), and embryo specific promoters, e.g., a promoter associated with an amino acid permease gene (AAP1), an oleate 12-hydroxylase:desaturase gene from Lesquerella fendleri (LFAH12), an 2S2 albumin gene (2S2), a fatty acid elongase gene (FAE1), or a leafy cotyledon gene (LEC2).

As used herein, a "tissue preferred" promoter is a promoter that initiates transcription mostly, but not necessarily entirely or solely in certain tissues.

As used herein, a "cell type specific" promoter is a promoter that primarily drives expression in certain cell types in one or more organs, for example, vascular cells in roots, leaves, stalk cells, and stem cells.

As used herein, a "cell type preferred" promoter is a promoter that primarily drives expression mostly, but not necessarily entirely or solely in certain cell types in one or more organs, for example, vascular cells in roots, leaves, stalk cells, and stem cells.

As used herein, the "3' non-coding sequences" or "3' untranslated regions" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. (1989) Plant Cell 1:671-680.

As used herein, "RNA transcript" refers to the product resulting from RNA polymerase-catalyzed transcription of a DNA sequence. When the RNA transcript is a perfect complementary copy of the DNA sequence, it is referred to as the primary transcript. An RNA transcript is referred to as the mature RNA when it is an RNA sequence derived from post-transcriptional processing of the primary transcript. "Messenger RNA (mRNA)" refers to the RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

As used herein, the term "recombinant" refers to an artificial combination of two otherwise separated segments of sequence, e.g., by chemical synthesis or by the manipulation of isolated segments of nucleic acids by genetic engineering techniques.

As used herein, the phrases "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating.

The term "expression", as used herein, refers to the production of a functional end-product e.g., an mRNA or a protein (precursor or mature).

As used herein, the phrase "plant selectable or screenable marker" refers to a genetic marker functional in a plant cell. A selectable marker allows cells containing and expressing that marker to grow under conditions unfavorable to growth of cells not expressing that marker. A screenable marker facilitates identification of cells which express that marker.

As used herein, the term "inbred", "inbred plant" is used in the context of the present invention. This also includes any single gene conversions of that inbred. The term single allele converted plant as used herein refers to those plants which are developed by a plant breeding technique called backcrossing wherein essentially all of the desired morphological and physiological characteristics of an inbred are recovered in addition to the single allele transferred into the inbred via the backcrossing technique.

As used herein, the term "sample" includes a sample from a plant, a plant part, a plant cell, or from a transmission vector, or a soil, water or air sample.

As used herein, the term "offspring" refers to any plant resulting as progeny from a vegetative or sexual reproduction from one or more parent plants or descendants thereof. For instance an offspring plant may be obtained by cloning or selfing of a parent plant or by crossing two parent plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

As used herein, the term "cross", "crossing", "cross pollination" or "cross-breeding" refer to the process by which the pollen of one flower on one plant is applied (artificially or naturally) to the ovule (stigma) of a flower on another plant.

As used herein, the term "cultivar" refers to a variety, strain or race of plant that has been produced by horticultural or agronomic techniques and is not normally found in wild populations.

As used herein, the terms "dicotyledon" and "dicot" refer to a flowering plant having an embryo containing two seed halves or cotyledons. Dicotyledon plants at least include the Eudicot, Magnoliid, Amborella, Nymphaeales, Austrobaileyales, Chloranthales, and Ceratophyllum groups. Eudicots include these clades: Ranunculales, sabiales, Proteales, Trochodendrales, Buxales, and Core Eudicots (e.g., Berberidopsidales, Dilleniales, Gunnerales, Caryophyllales, Santalales, Saxifragales, Vitales, Rosids and Asterids). Non-limiting examples of dicotyledon plants include tobacco, tomato, pea, alfalfa, clover, bean, soybean, peanut, members of the Brassicaceae family (e.g., camelina, Canola, oilseed rape, etc.), amaranth, sunflower, sugarbeet, cotton, oaks, maples, roses, mints, squashes, daisies, nuts; cacti, violets and buttercups.

As used herein, the term "monocotyledon" or "monocot" refer to any of a subclass (Monocotyledoneae) of flowering plants having an embryo containing only one seed leaf and usually having parallel-veined leaves, flower parts in multiples of three, and no secondary growth in stems and roots. Non-limiting examples of monocotyledon plants include lilies, orchids, corn, rice, wheat, barley, sorghum, millets, oats, ryes, triticales, buckwheats, fonio, quinoa, grasses, such as tall fescue, goat grass, and Kentucky bluegrass; grains, such as wheat, oats and barley, irises, onions, palms. As used herein, the term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "genotype" refers to the genetic makeup of an individual cell, cell culture, tissue, organism (e.g., a plant), or group of organisms.

As used herein, the term "hemizygous" refers to a cell, tissue or organism in which a gene is present only once in a genotype, as a gene in a haploid cell or organism, a sex-linked gene in the heterogametic sex, or a gene in a segment of chromosome in a diploid cell or organism where its partner segment has been deleted.

As used herein, the terms "heterologous polynucleotide" or a "heterologous nucleic acid" or an "exogenous DNA segment" refer to a polynucleotide, nucleic acid or DNA segment that originates from a source foreign to the particular host cell, or, if from the same source, is modified from its original form. Thus, a heterologous gene in a host cell includes a gene that is endogenous to the particular host cell, but has been modified. Thus, the terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

As used herein, the term "heterologous trait" refers to a phenotype imparted to a transformed host cell or transgenic organism by an exogenous DNA segment, heterologous polynucleotide or heterologous nucleic acid.

As used herein, the term "heterozygote" refers to a diploid or polyploid individual cell or plant having different alleles (forms of a given gene) present at least at one locus.

As used herein, the term "heterozygous" refers to the presence of different alleles (forms of a given gene) at a particular gene locus.

As used herein, the terms "homolog" or "homologue" refer to a nucleic acid or peptide sequence which has a common origin and functions similarly to a nucleic acid or peptide sequence from another species.

As used herein, the term "homozygote" refers to an individual cell or plant having the same alleles at one or more or all loci. When the term is used with reference to a specific locus or gene, it means at least that locus or gene has the same alleles.

As used herein, the terms "homozygous" or "HOMO" refer to the presence of identical alleles at one or more or all loci in homologous chromosomal segments. When the terms are used with reference to a specific locus or gene, it means at least that locus or gene has the same alleles.

As used herein, the term "hybrid" refers to any individual cell, tissue or plant resulting from a cross between parents that differ in one or more genes.

As used herein, the term "inbred" or "inbred line" refers to a relatively true-breeding strain.

As used herein, the term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses affected such that a gene or a combination of genes, in heterozygous (hemizygous) or homozygous condition, imparts a desired trait to the plant.

As used herein, the terms "mutant" or "mutation" refer to a gene, cell, or organism with an abnormal genetic constitution that may result in a variant phenotype.

As used herein, the term "open pollination" refers to a plant population that is freely exposed to some gene flow, as opposed to a closed one in which there is an effective barrier to gene flow.

As used herein, the terms "open-pollinated population" or "open-pollinated variety" refer to plants normally capable of at least some cross-fertilization, selected to a standard, that may show variation but that also have one or more genotypic or phenotypic characteristics by which the population or the variety can be differentiated from others. A hybrid, which has no barriers to cross-pollination, is an open-pollinated population or an open-pollinated variety.

As used herein when discussing plants, the term "ovule" refers to the female gametophyte, whereas the term "pollen" means the male gametophyte.

As used herein, the term "phenotype" refers to the observable characters of an individual cell, cell culture, organism (e.g., a plant), or group of organisms which results from the interaction between that individual's genetic makeup (i.e., genotype) and the environment.

As used herein, the term "plant tissue" refers to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

As used herein, the term "self-crossing", "self pollinated" or "self-pollination" means the pollen of one flower on one plant is applied (artificially or naturally) to the ovule (stigma) of the same or a different flower on the same plant.

As used herein, the term "transformation" refers to the transfer of nucleic acid (i.e., a nucleotide polymer) into a cell. As used herein, the term "genetic transformation" refers to the transfer and incorporation of DNA, especially recombinant DNA, into a cell.

As used herein, the term "transformant" refers to a cell, tissue or organism that has undergone transformation. The original transformant is designated as "T0" or "$T_0$." Selfing the T0 produces a first transformed generation designated as "T1" or "$T_1$."

As used herein, the term "transgene" refers to a nucleic acid that is inserted into an organism, host cell or vector in a manner that ensures its function.

As used herein, the term "transgenic" refers to cells, cell cultures, organisms (e.g., plants), and progeny which have received a foreign or modified gene by one of the various methods of transformation, wherein the foreign or modified gene is from the same or different species than the species of the organism receiving the foreign or modified gene.

As used herein, the term "transposition event" refers to the movement of a transposon from a donor site to a target site.

As used herein, the term "variety" refers to a subdivision of a species, consisting of a group of individuals within the species that are distinct in form or function from other similar arrays of individuals.

As used herein, the term "vector", "plasmid", or "construct" refers broadly to any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744-12746).

As used herein, the phrase "seed size" refers to the volume of the seed material itself, which is the space occupied by the constituents of the seed.

As used herein, the phrase "seed number" refers to the average number of seeds produced from each fruit, each plant, or each predetermined area (e.g., 1 acre).

As used herein, the phrase "Test Weight" or "Grain Test Weight" is a determination of bulk density (mass/volume), measured for commerce under specific conditions defined in the U.S. by the USDA-FGIS. Test weight is a general indicator of grain quality and higher test weight normally means higher quality grain. Grain test weight in units of pounds per bushel specifies the weight of a "volume" bushel, which is 32 quarts (30,283 cubic centimeters) of grain. When grain is traded, samples are usually tested for quality, and test weight is one of the tests carried out. Test weights have been a part of U.S. grain grades since the United States Grain Standards Act was passed by Congress in 1916. U.S. grades for most grains specify test weight minimums for each grade level. For instance, the official minimum allowable test weight in the U.S. for No. 1 yellow corn is 56 lbs/bu and for No. 2 yellow corn is 54 lbs/bu (USDA-GIPSA, 1996). By law, a "weight" bushel of corn is exactly 56 pounds, a soybean bushel is 60 pounds, and a wheat bushel is 60 pounds, regardless of the test weight. The "weight" bushel is used for the basis of payment for grain, but price discounts are often tied to shipments of lower grade grain possessing low test weight.

As used herein, the phrase "Grain Apparent Density" refers to grain density determined in a fashion wherein the bulk density (mass/volume) of cereal seed is sometimes measured with the aid of a gas pycnometer, which typically uses helium and measures the volume of the sample. Grain kernels contain internal void spaces and intercellular spaces and are not completely porous to helium. Since the gas cannot reach all internal spaces, the volume of material comprising the kernel can be overestimated with gas pycnometry and a density lower than the "true density" of grain material is determined (Chang, C S (1988) Cereal Chem: 65:13-15).

As used herein, the phrase "Grain True Density" refers to the bulk density of grain, expressed as the quotient of mass divided by volume, whereby all void space not comprising solid materials of the seed has been eliminated before, or discounted in, determination of the volume used in the calculation (Chang, C S (1988) Cereal Chem: 65:13-15).

As used herein, the term "cyclin dependent kinase inhibitor" (also referred to herein as "CDK inhibitor" or "CKI") refers to a class of proteins that negatively regulate cyclin dependent kinases (CDKs). CKIs amenable to the present invention are those having separate polypeptide regions capable of independently binding a cyclin and a CDK. Such CKIs include, for example, identified families of plant CKIs (the seven identified *Arabidopsis* CKIs), having homology to Kinase Inhibitor Proteins (KIPs) in animals, referred to as KIP-related proteins (KRPs) (also known as Inhibitors of "CDKs," or "ICKs").

The term "naturally occurring," in the context of CKI polypeptides and nucleic acids, means a polypeptide or nucleic acid having an amino acid or nucleotide sequence that is found in nature, i.e., an amino acid or nucleotide sequence that can be isolated from a source in nature (an organism) and which has not been intentionally modified by human intervention. As used herein, laboratory strains of plants which may have been selectively bred according to classical genetics are considered naturally-occurring plants.

As used herein, "wild-type CKI gene" or "wild-type CKI nucleic acid" refers to a sequence of nucleic acid, corresponding to a CKI genetic locus in the genome of an organism, that encodes a gene product performing the normal function of the CKI protein encoded by a naturally-occurring nucleotide sequence corresponding to the genetic locus. A genetic locus can have more than one sequence or allele in a population of individuals, and the term "wild-type" encompasses all such naturally-occurring alleles that encode a gene product performing the normal function. "Wild-type" also encompasses gene sequences that are not necessarily naturally occurring, but that still encode a gene product with normal function (e.g., genes having silent mutations or encoding proteins with conservative substitutions).

As used herein, the term "wild-type CKI polypeptide" or "wild-type CKI protein" refers to a CKI polypeptide encoded by a wild-type gene. A genetic locus can have more than one sequence or allele in a population of individuals, and the term "wild-type" encompasses all such naturally-occurring alleles that encode a gene product performing the normal function.

Breeding Methods

Classic breeding methods can be included in the present invention to introduce one or more recombinant KRPs of the present invention into other plant varieties, or other close-related species that are compatible to be crossed with the transgenic plant of the present invention.

Open-Pollinated Populations.

The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes to flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988).

Mass Selection.

In mass selection, desirable individual plants are chosen, harvested, and the seed composited without progeny testing to produce the following generation. Since selection is based on the maternal parent only, and there is no control over pollination, mass selection amounts to a form of random mating with selection. As stated herein, the purpose of mass selection is to increase the proportion of superior genotypes in the population.

Synthetics.

A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (*Vicia*) or clones, as in herbage grasses, clovers and alfalfa, makes no difference in principle. Parents are selected on general combining ability, sometimes by test crosses or topcrosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enter a synthetic varies widely. In practice, numbers of parental lines range from 10 to several hundred, with 100-200 being the average. Broad based synthetics formed from 100 or more clones would be expected to be more stable during seed multiplication than narrow based synthetics.

Pedigreed Varieties.

A pedigreed variety is a superior genotype developed from selection of individual plants out of a segregating population followed by propagation and seed increase of self pollinated offspring and careful testing of the genotype over several generations. This is an open pollinated method that works well with naturally self pollinating species. This method can be used in combination with mass selection in variety development. Variations in pedigree and mass selection in combination are the most common methods for generating varieties in self pollinated crops.

Hybrids.

A hybrid is an individual plant resulting from a cross between parents of differing genotypes. Commercial hybrids are now used extensively in many crops, including corn (maize), sorghum, sugarbeet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, e.g., Wright, *Commercial Hybrid Seed Production* 8:161-176, In Hybridization of Crop Plants.

Targeting Induced Local Lesions in Genomes (TILLING)

TILLING (Targeting Induced Local Lesions in Genomes) is a method in molecular biology that allows directed identification of mutations in a specific gene. TILLING® was introduced in 2000, using the model plant *Arabidopsis thaliana*. TILLING® has since been used as a reverse genetics method in other organisms such as zebrafish, corn, wheat, rice, soybean, tomato and lettuce.

The method combines a standard and efficient technique of mutagenesis with a chemical mutagen (e.g., Ethyl methanesulfonate (EMS)) with a sensitive DNA screening-technique that identifies single base mutations (also called point mutations) in a target gene. EcoTILLING is a method that uses TILLING® techniques to look for natural mutations in individuals, usually for population genetics analysis. See Comai, et al., 2003. Efficient discovery of DNA polymorphisms in natural populations by Ecotilling. The Plant Journal 37, 778-786. Gilchrist et al. 2006. Use of Ecotilling as an efficient SNP discovery tool to survey genetic variation in wild populations of *Populus trichocarpa*. Mol. Ecol. 15, 1367-1378. Mejlhede et al. 2006. EcoTILLING for the identification of allelic variation within the powdery mildew resistance genes mlo and Mla of barley. Plant Breeding 125, 461-467. Nieto et al. 2007, EcoTILLING for the identification of allelic variants of melon eIF4E, a factor that controls virus susceptibility. BMC Plant Biology 7, 34-42, each of which is incorporated by reference hereby for all purposes. DEcoTILLING is a modification of TILLING® and EcoTILLING which uses an inexpensive method to identify fragments (Garvin et al., 2007, DEco-TILLING: An inexpensive method for SNP discovery that reduces ascertainment bias. Molecular Ecology Notes 7, 735-746).

The TILLING® method relies on the formation of heteroduplexes that are formed when multiple alleles (which could be from a heterozygote or a pool of multiple homozygotes and heterozygotes) are amplified in a PCR, heated, and then slowly cooled. A "bubble" forms at the mismatch of the two DNA strands (the induced mutation in TILLING® or the natural mutation or SNP in EcoTILLING), which is then cleaved by single stranded nucleases. The products are then separated by size on several different platforms.

Several TILLING® centers exists over the world that focus on agriculturally important species: UC Davis (USA), focusing on Rice; Purdue University (USA), focusing on Maize; University of British Columbia (CA), focusing on *Brassica napus*; John Innes Centre (UK), focusing on *Brassica rapa*; Fred Hutchinson Cancer Research, focusing on *Arabidopsis*; Southern Illinois University (USA), focusing on Soybean; John Innes Centre (UK), focusing on Lotus and Medicago; and INRA (France), focusing on Pea and Tomato.

More detailed description on methods and compositions on TILLING® can be found in references Nos. 1-35b, U.S. Pat. No. 5,994,075, US 2004/0053236 A1, WO 2005/055704, and WO 2005/048692, each of which is hereby incorporated by reference for all purposes.

Triticeae Tribe

Intense use of wild Triticeae can be seen in the Levant as early as 23,000 years ago. Triticeae is a tribe within the Pooideae subfamily of grasses that includes genera with many domesticated species. Major crop genera are found in this tribe including wheat (See Wheat taxonomy), barley, and rye; crops in other genera include some for human consumption and others used for animal feed or rangeland protection. Among the world's cultivated species, this tribe has some of the most complex genetic histories. An example is bread wheat, which contains the genomes of three species, only one of them originally a wheat *Triticum* species.

Genera in the Triticeae tribe include, but are not limited to, *Aegilops* (goat grasses—jointed goatgrass, Tausch goatgrass, etc.); *Agropyron* (crested wheatgrasses—Desert wheatgrass, quackgrass, etc.); *Amblyopyrum* (Slim wheat grass—*amblyopyrum*, etc.); *Australopyrum* (Australian wheatgrasses—velvet wheatgrass, pectinated wheatgrass, etc.); *Cockaynea* (See *Stenostachys; Cockaynea* is a younger, and hence invalid, name for *Stenostachys*, etc.); *Crithopsis* (delileana grass etc.); *Dasypyrum* (Mosquito grass; etc.); *Elymus* (*Elymus* (wild ryes—blue wildrye, Texas ryegrass, etc.); *Elytrigia; Eremium* (Argentine desert ryegrass, etc.); *Eremopyrum* (false wheatgrasses—tapertip false wheatgrass, annual wheatgrass, etc.); *Festucopsis; Haynaldia; Henrardia; Heteranthelium; Hordelymus; Hordeum* (barleys—common barley, foxtail barley, etc.); *Hystrix* (porcupine grass—bottlebrush grass, etc.); *Kengyilia; Leymus* (wild rye—American dune grass, lyme grass, etc.); *Lophopyrum* (tall wheatgrass); *Malacurus Pascopyrum* (western wheatgrass etc.); *Peridictyon; Psathyrostachys* (Russian wildrye, etc.); *Pseudoroegneria* (bluebunch wheatgrasses—beardless wheatgrass, etc.); *Secale* (Ryes—Cereal rye, Himalayan Rye, etc.); *Sitanion; Stenostachys* (New Zealand wheatgrasses, etc); *Taeniatherum* (medusahead etc.); *Thinopyrum* (intermediate wheatgrass, Russian wheatgrass, thick quackgrass, etc.); *Triticum* (Wheats—common wheat, durum wheat, etc.).

Triticeae and its sister tribe Bromeae (possible cultivars: Bromus mango S. America) when joined form a sister clade with Poeae and Aveneae (oats). Inter-generic gene flow characterized these taxa from the early stages. For example, Poeae and Aveneae share a genetic marker with barley and 10 other members of Triticeae, whereas all 19 genera of Triticeae bear a wheat marker along with Bromeae. Genera within Triticeae contain diploid, allotetraploid and/or allohexaploid genomes, the capacity to form allopolyploid genomes varies within the tribe. In this tribe, the majority of diploid species tested are closely related to *Aegilops*, the more distal members (earliest branch points) include *Hordeum* (Barley), *Eremian, Psathyrostachys.*

Many genera and species of Triticeae are exemplary of allopolyploids, having more chromosomes than seen in typical diploids. Typically allopolyploids are tetraploid or hexaploid, AABB or AABBDD. The creation of polyploid species results from natural random events tolerated by polyploid capable plants. Likewise natural allopolyploid plants may have selective benefits and may allow the recombination of distantly related genetic material facilitating at a later time a reversion back to diploid. Poulard wheat is an example of a stable allotetraploid wheat.

*Aegilops* appears to be basal to several taxa such as *Triticum, Ambylopyrum*, and *Crithopsis*. Certain species such as *Aegilops speltoides* could potentially represent core variants of the taxa. The generic placement may be more a matter of nomenclature. *Aegilops* and *Triticum* genera are very closely related as the *Aegilops* species occupy most of the basal branch points in bread wheat evolution indicating that *Triticum* genus evolved from *Aegilops* after an estimated 4 million years ago. The divergence of the genomes is followed by allotetraploidation of a speltoid goatgrass× basal wheat species *Triticum boeoticum* with strains in the Middle Eastern region giving rise to cultivated emmer wheat.

*Triticum* spp.

*Triticum* sp. is a grass cultivated worldwide. In 2007 world production of wheat was 607 million tons, making it the third most-produced cereal after maize (784 million tons) and rice (651 million tons). Globally, wheat is the leading source of vegetable protein in human food, having a higher protein content than either maize (corn) or rice, the other major cereals. In terms of total production tonnages used for food, it is currently second to rice as the main human food Wheat is planted to a limited extent as a forage crop for livestock, and its straw can be used as a construction material for roofing thatch. The husk of the grain, separated when milling white flour, is bran. Wheat germ is the embryo portion of the wheat kernel. It is a concentrated source of vitamins, minerals, and protein, and is sustained by the larger, starch storage region of the kernel—the endosperm.

Non-limiting examples of *Triticum* species include, *T. aestivum* (e.g., common wheat, or bread wheat, a.k.a. *Triticum aestivum* L. subsp. *Aestivum*; Club wheat, a.k.a. *Triticum aestivum* subspecies *compactum* (Host) MacKey; *Macha* wheat, a.k.a. *Triticum aestivum* subsp. *macha* (Dek. and Men.) MacKey; *Vavilovi* wheat, a.k.a. *Triticum aestivum* subsp. *vavilovi* (Tuman) Sears; Shot wheat, a.k.a. *Triticum aestivum* subsp. *sphacrococcum* (Pere.) MacKey), *T. aethiopicum, T. araraticum, T. boeoticum* (e.g., wild Einkorn, a.k.a. *Triticum boeotictim* Boiss), *T. carthlicum, T. compactum, T. dimitrium, T. dicoccoides* (e.g., wild emmer, a.k.a. *Triticum dicoccoides* (Koern. ex Ascb. & Graebn.) Aaronsohn.), *T. dicoccum* (e.g., Emmer), *T. durum* (e.g., durum wheat), *T. ispahanicum, T. karamyschevii, T. mocha, T. militinae, T. monococcum* (e.g., Einkorn, a.k.a. *Triticum monococcum* L.), *T. polonicum, T. spelta, T. sphaerococcum, T. timopheevii* (e.g. timopheevi wheat, a.k.a. *Triticum timopheevii* (Zbuk.) Zbuk.), *T. turanicum* (e.g., oriental wheat, a.k.a. *Triticum turanicum* jakubz), *T. turgidum* (e.g., poulard wheat, a.k.a. *Triticum turgidum* L.), *T. urartu, T. vavilovii*, and *T. zhukovskyi.*

Wheat genetics is more complicated than that of most other domesticated species. Some wheat species are diploid, with two sets of chromosomes, but many are stable polyploids, with four sets of chromosomes (tetraploid) or six (hexaploid). Most tetraploid wheats (e.g. emmer and durum wheat) are derived from wild emmer, *T. dicoccoides*. Wild emmer is itself the result of a hybridization between two diploid wild grasses, *T. urartu* and a wild goatgrass such as *Aegilops searsii* or *Ae. speltoides*. The unknown grass has never been identified among now surviving wild grasses, but the closest living relative is *Aegilops speltoides*. The hybridization that formed wild emmer (AABB) occurred in the wild, long before domestication, and was driven by natural selection. Hexaploid wheats evolved in farmers' fields. Common wheat (*Triticum aestivum,* 2n=42, AABBDD) is one of the most important cereal crops in the world. Either domesticated emmer or durum wheat hybridized with yet another wild diploid grass (*Aegilops cylindrica*) to make the hexaploid wheats, spelt wheat and bread wheat. These have three sets of paired chromosomes, three times as many as in diploid wheat. Synthetic hexaploids made by crossing the wild goatgrass wheat ancestor *Aegilops tauschii* and various durum wheats are now being deployed, and these increase the genetic diversity of cultivated wheats.

Plant breeding methods for *Triticum* spp. are well known. Non-limiting methods for *Triticum* spp. breeding and agriculturally important traits (e.g., improving wheat yield, biotic stress tolerance, and abiotic stress tolerance etc.) are described in references Nos. 36-51, U.S. Pat. No. 7,652,204, U.S. Pat. No. 6,197,518, U.S. Pat. No. 7,034,208, U.S. Pat. No. 7,528,297, U.S. Pat. No. 6,407,311, US20080040826, US20090300783, US20060223707, US20110027233, US20080028480, US20090320152, US20090320151, WO/2001/029237A2, WO/2008/025097A1, and WO/2003/057848A2, each of which is incorporated by reference in its entirety for all purposes.

Genetic materials may be transferred between *Triticum* spp. and other species, for example, some plant species in the Triticeae tribe. Xiang et al., describe somatic hybrids between wheat and *Setaria italica* (Genome 47: 680-688 (2004)); Ge et al. describe protoplast electrofusion between common wheat and Italian ryegrass (In Vitro Cellular and Developmental Biology—Plant 42(2):179-187. 2006); Yue e al. describe asymmetic somatic hybridization between *Aeleuropus littorulis sinensis* and wheat (Plant Science, Volume 161, Issue 2, July 2001, Pages 259-266); Cai et al. describe somatic hybrids between *Festuca arundinacea* Schreb. and wheat (*Triticum aestivum* L.); Xiang et al. describe asymmetric somatic hybridization between wheat and *Avena sativa* L. (Science in China, Vol 46(3), 243-252); Zhou et al. describe asymmetric somatic hybridization between wheat and asymmetric somatic hybridization between wheat and *Avena sativa Haynaldia villosa* (Science in China, 44(3): 294-304); Xia et al. describe asymmetric somatic hybridization between wheat and *Agropyron elongatum* (Host) Nevishi (Theor Appl Genet. 2003 July; 107(2):299-305. Epub 2003 Mar. 19); Li et al. describe symmetric somatic hybridization between wheat and *Psathyrostachys juncea* (Sheng Wu Gong Cheng Xue Bao. 2004 July; 20(4):610-4). More hybridization between *Triticum* spp. and other species are described in reference Nos. 77-86.

Oryzeae Tribe

The tribe Oryzeae (Poaceae), as conventionally delimited, includes approximately 12 genera and more than 70 species distributed throughout the tropical and temperate regions of the world (Clayton and Renvoize, 1986; Vaughan, 1994). As the largest tribe in the subfamily Ehrhartoideae, Oryzeae contains more than half of both genera and species of the subfamily (Guo et al., 2005, Watson and Dallwitz, 1999; GPWG, 2001).

Genera in the Oryzeae tribe include, but are not limited to, *Chikusichloa Koidz, Hygroryza Nees, Leersia* Sw., *Luziola Juss, Maltebrunia Kunth, Oryza* L., *Porteresia Tateoka, Potamophila* R.Br., *Prosphytochloa Schweick., Rhynchoryza Baill., Zizania* L., and *Zizaniopsis* Doll & Asch.

*Oryza* spp.

*Oryza* is a genus of seven to twenty species of grasses in the tribe Oryzeae, native to tropical and subtropical regions of Asia, Northern Australia and Africa. They are tall wetland grasses, growing to 1-2 m tall; the genus includes both annual and perennial species.

*Oryza* is situated within the tribe Oryzeae, which is characterized morphologically by its single flowered spikelets whose glumes are almost completely suppressed. In *Oryza*, two sterile lemma simulate glumes. The tribe Oryzeae is within the subfamily Bambusoideae, a group of Poaceae tribes with certain features of internal leaf anatomy in common. The Bambusoideae are in the family Poaceae, as they all have fibrous root systems, cylindrical stems, sheathing leaves with parallel veined blades, and inflorescences with spikelets.

Non-limiting *Oryza* spp. include, *O. sativa* (e.g., Asian rice), *O. barthii, O. glaberrima* (e.g., Africa rice), *O. longistaminata, O. meridionalis, O. nivara, O. rufipogon* (e.g., brownbeard rice and red rice), *O. punctata, O. latifolia, O. alta, O. grandiglumis, O. eichingeri, O. officinalis, O. rhisomatis, O. minuta, O. australiensis, O. granulata, O. meyeriana*, and *O. brachyantha.*

*Oryza sativa* contains two major subspecies: the sticky, short grained japonica or sinica variety, and the non-sticky, long-grained indica variety. Japonica are usually cultivated in dry fields, in temperate East Asia, upland areas of Southeast Asia and high elevations in South Asia, while indica are mainly lowland rices, grown mostly submerged, throughout tropical Asia. Rice is known to come in a variety of colors, including: white, brown, black, purple, and red. A third subspecies, which is broad-grained and thrives under tropical conditions, was identified based on morphology and initially called javanica, but is now known as tropical japonica. Examples of this variety include the medium grain 'Tinawon' and 'Unoy' cultivars, which are grown in the high-elevation rice terraces of the Cordillera Mountains of northern Luzon, Philippines. Glaszmann (1987) used isozymes to sort *Oryza sativa* into six groups: japonica, aromatic, indica, aus, rayada, and ashina; Garris et al. (2004) used SSRs to sort *Oryza sativa* into five groups; temperate japonica, tropical japonica and aromatic comprise the japonica varieties, while indica and aus comprise the indica varieties.

Plant breeding methods for *Oryza* spp. are well known. Non-limiting methods for *Oryza* spp. breeding and agriculturally important traits (e.g., improving wheat yield, biotic stress tolerance, and abiotic stress tolerance etc.) are described in references Nos. 56-76, US20050097639, US20040168232. US20100287664, US20080109919, U.S. Pat. No. 5,981,842, and US20050183173, WO/2003/000904A2.

Genetic materials may be transferred between *Oryza* spp. and other species, for example, some plant species in the Oryzeae tribe. Yan et al. (Plant Cell Rep. 2004 March; 22(8):569-75. Epub 2003 Nov. 1.) and Yu et al. (Phytochemistry. 2008 July; 69(10):1989-96) describe asymmetric somatic hybridization between *O. meyeriana* L. and *O. sativa* L; and Shan et al. describe asymmetric somatic hybridization between rice (*O. sativa*) and wild rice (*Zizania latfolia* Griseb.). Somatic hybrid plants of rice and barnyard grass (Terada et al., 1987), interspecies somatic hybrids between cultivated and wild species (Hayashi et al., 1988), and diploid hybrid plants form the cell fusion of haploid cells (Toriyama and Hinata 1988) have been reported. More hybridization between *Oryza* spp. and other species are described in reference Nos. 86-92.

Fabaceae Family and Soybean

Fabaceae or Leguminosae is a large and economically important family of flowering plants, which is commonly known as the legume family, pea family, bean family or pulse family. The name 'Fabaceae' comes from the defunct genus *Faba*, now included into *Vicia*. Leguminosae is an older name still considered valid, and refers to the typical fruit of these plants, which are called legumes.

Fabaceae is the third largest family of flowering plants, behind Orchidaceae and Asteraceae, with 730 genera and over 19,400 species, according to the Royal Botanical Gardens. The largest genera are *Astragalus* with more than 2,000 species, *Acacia* with more than 900 species, and *Indigofera* with around 700 species. Other large genera include *Crotalaria* with 600 species and *Mimosa* with 500 species.

The species of this family are found throughout the world, growing in many different environments and climates. A number are important agricultural plants, including: *Glycine max* (soybean), *Phaseolus* (beans), *Pisum sativum* (pea), *Cicer arietinum* (chickpeas), *Medicago sativa* (alfalfa), *Arachis hypogaea* (peanut), *Ceratonia siliqua* (carob), and *Glycyrrhiza glabra* (licorice), which are among the best known members of Fabaceae. A number of species are also weedy pests in different parts of the world, including: *Cytisus scoparius* (broom) and *Pueraria lobata* (kudzu), and a number of *Lupinus* species.

The soybean (U.S.) or soya bean (UK) (*Glycine max*) is a species of legume native to East Asia, widely grown for its edible bean which has numerous uses. The plant is classed as an oilseed rather than a pulse. Fat-free (defatted) soybean meal is a primary, low-cost, source of protein for animal feeds and most prepackaged meals; soy vegetable oil is another valuable product of processing the soybean crop. For example, soybean products such as textured vegetable protein (TVP) are important ingredients in many meat and dairy analogues.

Kinase Inhibitor Protein (KIP) Related Protein (KRP)

Plants have cyclin dependent kinases (CDK) that regulate the transitions between different phases of the cell cycle (Verkest et al., 2005, Switching the Cell Cycle. Kip-Related Proteins in Plant Cell Cycle Control, Plant Physiology, November 2005, Vol. 139, pp. 1099-1106, incorporated by reference in its entirety herein).

In *Arabidopsis* (*Arabidopsis thaliana*), at least two classes of CDKs are involved in cell cycle regulation: the A-type CDKs that are represented by only one gene in the model species *Arabidopsis* (designated Arath;CDKA;1) and the B-type CDK family that has four members, grouped into the B1 (Arath;CDKB1;1 and Arath;CDKB1;2) and B2 (Arath;CDKB2;1 and Arath;CDKB2;2) subclasses (Vandepoele et al., 2002, Genome-wide analysis of core cell cycle genes in *Arabidopsis*. Plant Cell 14: 903-916). A-type CDKs display kinase activity from late G1 phase until the end of mitosis, suggesting a role for this particular CDK at both the G1-to-S and G2-to-M transition points (Magyar et al., 1997; Porceddu et al., 2001; Sorrell et al., 2001). A central role for CDKA;1 in controlling cell number has been demonstrated using transgenic tobacco (*Nicotiana tabacum*) plants with reduced A-type CDK activity (Hemerly et al., 1995). The requirement for Arath;CKDA;1 at least for entry into mitosis has been demonstrated as well by cdka; 1 null mutants that fail to progress through the second mitosis during male gametophytic development (Nowack et al., 2005). The group of B-type CDKs displays a peak of activity at the G2-to-M phase transition only (Magyar et al., 1997; Porceddu et al., 2001; Sorrell et al., 2001), suggesting that they play a role at the onset of, or progression through, mitosis. Correspondingly, cells of plants with reduced B-type CDK activity arrest in the G2 phase of the cell cycle (Porceddu et al., 2001; Boudolf et al., 2004).

CDK is regulated by cyclins. Plant cyclins are very complicated. There are at least 49 different cyclins in *Arabidopsis*, which were classified into seven subclasses (A, B, C, D, H, P, and T) (Vandepoele et al., 2002; Wang et al., 2004). CDK are also regulated by docking of small proteins, generally known as CDK inhibitors (CKIs). CKIs have been identified in many organisms, e.g., budding yeast (*Saccharomyces cerevisiae*), fission yeast (*Schizosaccharomyces pombe*), mammals, and plants, see, Mendenhall, 1998; Kwon T. K. et al. 1998; Vlach J. et al. 1997; Russo et al., 1996; Wang et al., 1997, 1998 and 2000; Lui et al., 2000; De Veylder et al., 2001; Jasinski et al., 2002a, 2002b; Coelho et al., 2005; Jasinski S. et al., 2002, each of which is incorporated by reference in its entirety).

Plant CKIs are also known as KIP Related Proteins (KRPs). They have cyclin binding and CDK binding domains at their C-terminal, however the mechanism regulating this protein stability and function remains unknown (Zhou et al., 2003a; Weinl et al. 2005). KRP activity can be both regulated at the transcriptional level or at the posttranslational level (Wang et al., 1998; De Veylder et al., 2001; Jasinski et al., 2002b; Ormenese et al., 2004; Coqueret, 2003; Hengst, 2004; Verkest et al., 2005; Coelho et al., 2005, each of which is incorporated by reference in its entirety). KRPs in plant normally localize in nucleus (Jasinski et al., 2002b; Zhou et al., 2003a; Weinl et al., 2005).

KRP can function as an integrator of developmental signals, and control endocycle onset, in different cell cycle programs (e.g., proliferation, endoreduplication, and cell cycle exit). See Wang et al., 1998; Richard et al., 2001; Himanen et al., 2002; Grafi and Larkins, 1995; Joube's et al., 1999; Verkest et al., 2005; Weinl et al., 2005; Boudolf et al., 2004b.

KRP Mutations

The present invention further provides disrupted KRP polynucleotides and KRP amino acid sequences compared to a wild type KRP gene or a wild type KRP protein. In some embodiments, the present invention provides mutations in one or more KRP genes that can be used to increase weight, size, and/or number of one or more organs, for example, to increase seed size, seed number, seed weight, and/or seed yield in a plant.

The mutations in a mutated KRP gene of the present invention can be in the coding region or the non-coding region of the KRP genes. The mutations can either lead to, or not lead to amino acid changes in the encoded KRP polypeptides. In some embodiments, the mutations can be missense, severe missense, silent, nonsense mutations. For example, the mutation can be nucleotide substitution, insertion, deletion, or genome re-arrangement, which in turn may lead to reading frame shift, splicing change, amino acid substitution, insertion, deletion, and/or polypeptides truncation. As a result, the mutant KRP gene encodes a KRP polypeptide having less inhibition activity on a cyclin/CDK complex compared to a polypeptide encoded by its corresponding wild-type KRP gene.

As used herein, a nonsense mutation is a point mutation, e.g., a single-nucleotide polymorphism (SNP), in a sequence of DNA that results in a premature stop codon, or a nonsense codon in the transcribed mRNA, and in a truncated, incomplete, and usually nonfunctional protein product. A missense mutation (a type of nonsynonymous mutation) is a point mutation in which a single nucleotide is changed, resulting in a codon that codes for a different amino acid (mutations that change an amino acid to a stop codon are considered nonsense mutations, rather than missense mutations). This can render the resulting protein nonfunctional. Silent mutations are DNA mutations that do not result in a change to the amino acid sequence of a protein. They may occur in a non-coding region (outside of a gene or within an intron), or they may occur within an exon in a manner that does not alter the final amino acid sequence. A severe missense mutation changes the amino acid, which lead to dramatic changes in conformation, charge status etc.

The mutations can be located at any portion of a KRP gene, for example, at the 5', the middle, or the 3' of a KRP gene, resulting mutations in any portions of the encoded KRP protein, for example, in the CDK binding domain or the cyclin binding domain, so long as the mutated gene encodes a mutant KRP polypeptide partially or completely lose the ability to inhibit one or more cyclin/CDK complexes, compared to the protein encoded by the corresponding wild type KRP gene. The KRP and the cyclin/CDK complexes can belong to the same plant species, different plant species in the same genus, or different plant species in different species.

The present invention provides effective systems to test if a candidate mutant KRP protein loses the inhibition ability on a cyclin/CDK complex compared to a wild type KRP protein. The effective systems comprise a kinase assay (the "in vitro KRP-Cylin-CDK kinase assay"), a non-limiting example of which is described herein.

Basically in this kinase assay is an in vitro kinase assay. In the assay, a candidate mutant KRP derived from a wild type KRP of a plant species A, the wild type KRP protein of the plant species A, a wild type cyclin protein of a plant species B, and a wild type CDK protein of the plant species B, are recombinantly expressed and purified. Then, the recombinant wild type cyclin protein and the wild type CDK protein are mixed to form a complex (alternatively, the cyclin protein and the CDK protein can be co-expressed and co-purified as a complex). In some embodiments, the recombinant proteins are expressed in insect cells. Plant species A can be the same as or different from plant species B. This kinase activity of said complex is then monitored with a standard kinase assay described below. A substrate protein that can be activated (i.e., phosphorylated) by the Cyclin-CDK complex is selected. Such substrate protein can be Histone HI (HHI) or recombinant tobacco retinoblastoma protein (Nt Rb). At least three mixtures can be made by adding recombinant proteins into a kinase buffer cocktail according to the table below:

| Compositions | Mixture I | Mixture II | Mixture III |
|---|---|---|---|
| I. Kinase complex comprising the wild-type cyclin protein and the wild-type CDK protein of the plant species B | at concentration of C1 | at concentration of C1 | at concentration of C1 |
| II. Wild-type KRP protein of the plant species A | 0 | at concentration of C2* | 0 |

-continued

| Compositions | Mixture I | Mixture II | Mixture III |
|---|---|---|---|
| III. Candidate mutant KRP derived from the wild-type KRP of the plant species A | 0 | 0 | at concentration of C3** |
| IV. Substrate | at concentration of C4 | at concentration of C4 | at concentration of C4 |
| Kinase Activity | 100% (no inhibition) | X % (wt inhibition) | Y % (mutant inhibition) |

*C2 is an amount of WT KRP that is sufficient to give between 0% and 20% kinase activity compared to mixture I.

**C3 should be no more than 50X C2

A non-limiting example of the kinase buffer cocktail comprises KAB: 50 mM Tris pH 8.0, 10 mM $MgCl_2$, 100 μM ATP plus 0.5 μCi/ml 32 PγATP and the substrate protein. Concentrations C1, C2, and C3 can be determined and optimized by one skilled in the art depending on experiment conditions.

To determine if a candidate mutant KRP loses inhibition ability on the kinase complex, C2 should be about equimolar with C1; and, C3 should be no more than 50× of C2, or no more than 40× of C2, or no more than 30× of C2, or no more than 20× of C2, or no more than 10× of C2, or no more than 5× of C2. For example, in some instances the amount of C3 is about 1×, or about 2×, or about 3×, or about 4×, or about 5×, or about 6×, or about 7×, or about 8×, or about 9×, or about 10×, or about 11×, or about 12×, or about 13×, or about 14×, or about 15×, or about 16×, or about 17×, or about 18×, or about 19×, or about 20× of the amount of C2. In some situations, however, the amount of C3 may be about 25×, or about 30×, or about 35×, or about 40×, or about 45×, or about 50× of the amount of C2. As discussed elsewhere herein, the amount of C3 which is utilized in any particular situation must be physiologically achievable in a plant cell, tissue or whole plant in order to have a dominant negative effect on the wild-type KRP.

Composition I and/or Composition III are incubated on ice for a certain amount of time (e.g., 30 minutes). Subsequently, Composition II is then added to the mixture and incubated at 4° C. for certain amount of time (e.g., 30 mins) to allow binding to the kinase complex. The kinase reaction is then initiated by adding the buffer cocktail (KAB) and to the kinase complex mixture (I, II, or III) and incubated at 27° C. for a certain amount of time (e.g., 30 minutes) to allow reaction to complete. The kinase reaction in each mixture is stopped with an equal volume of 2× Laemmli buffer and boiled for 5 minutes. Next, monitor [$^{32}$P] phosphate incorporation to the substrate protein by autoradiography and/or Molecular Dynamics PhosphorImager following SDS-PAGE in each mixture. The signal strength of [$^{32}$P] phosphate incorporation in Mixture I is set as 100% percent recovery of kinase function. The strength of [$^{32}$P] phosphate incorporation in Mixture II is compared to that of Mixture I, calculated as X %; the strength of [$^{32}$P] phosphate incorporation in Mixture III is compared to that of Mixture I, calculated as Y %. For example, if the signal strength is half of what is observed for Mixture I, the calculated percent recovery of kinase activity is 50%.

The X % is compared with Y %, and the effect of the tested mutant KRP is calculated as follows: let Z % (Y %−X %), and Zmax % is the maximum Z % within the allowable range of C2 and C3; if Zmax % is not statistically higher than 0% (i.e., Y %≤X %), the tested mutant KRP does not lose inhibition activity on the complex compared to the corresponding wild type KRP; if Zmax % is statistically higher that 0% (i.e., Y %>X %), but less than 30%, the tested mutant KRP has weak inhibition activity compared to the tested wild-type KRP; if Zmax % is higher that 30%, but less than 50%, the tested mutant KRP substantially loses inhibition activity compared to the tested wild-type KRP; if Zmax % is higher that 50%, the tested mutant KRP strongly loses inhibition activity compared to the tested wild-type KRP. In some embodiments, the mutant KRPs of the present invention do not substantially inhibit the kinase activity of the cyclin/CDK complex, even when present in large molar excess over the cyclin/CDK complex. Mutant KRPs with a Zmax % value higher than 0% are particularly useful for increasing weight, size, and/or number of one or more organs, for example, for increasing seed yield, seed size, seed number, and/or seed yield in a plant.

The CDK protein and the cyclin protein in the cyclin/CDK complex can be derived from any plant, for example, any dicot plants or monocot plants, especially agriculturally or industrially important plants. The CDK protein and the cyclin protein can be derived from the same plant species, or from different species. The KRP protein can be derived from the same species from which the CDK protein and the cyclin protein are derived, or from different plant species. In some embodiments, the Cyclin/CDK complexes comprise a CDK protein selected from the group consisting of *Zea mays* CDK A;1 (ZmCDKA;1), *Zea mays* CDK A;2 (ZmCDKA;2), wheat CDKs (e.g., GenBank Accession No. AAD10483, and rice CDKs (e.g., GenBank Accession No. NP_001048772 and NP_001045731), and CDKs from a plant in the Triticeae tribe or Oryzeae tribe, or the Fabaceae family; the cyclin protein selected from the group consisting of *Zea mays* Cyclin D1, D2, D3, D4, D5, D6, D7, wheat cyclin proteins (e.g., GenBank Accession No. AAQ08041 (cyclin D2)), rice cyclin proteins (e.g., GenBank Accession Nos. Q67V81 (cyclin-D1;1), Q8H339 (cyclin-D1;2), Q0J233 (cyclin-D2;1), Q10K98 (cyclin-D2;3), Q69QB8 (cyclin-D3;1), Q0DQA9 (cyclin-D5;1), Q53 MB7 (cyclin-D7;1)), cyclin proteins from a plant in the Triticeae tribe or Oryzeae tribe, or the Fabaceae family, and combinations thereof, and the wild-type KRPs are selected from the group consisting of wheat KRP1 (TaKRP1), wheat KRP2 (TaKRP2), wheat KRP3 (TaKRP3), wheat KRP4 (TaKRP4), wheat KRP5 (TaKRP5), wheat KRP6 (TaKRP6), for example, SEQ ID NOs. 87-98, 140, 143, and 146, or functional variants thereof, rice KRP1, rice KRP2, rice KRP3, rice KRP4, rice KRP5, rice KRP6, rice KRP7, for example, SEQ ID NOs. 99, 108-110, or functional variants thereof, soy KRPs, for example, SEQ ID NOs. 129-137, or functional variants thereof, KRPs from a plant in the Triticeae tribe or Oryzeae tribe, the Fabaceae family, and combinations thereof. For example, the wild-type KRP is wheat KRP1, wheat KRP2, wheat KRP4, wheat KRP5, or wheat KRP6. The numbering of the KRPs in wheat or rice does not necessarily correspond to the numbering of the KRPs in other species (e.g., *Ara-*

*bidopsis* or maize). For example, wheat KRP1 is not necessarily equivalent or orthologous to *Arabidopsis* KRP1.

In some embodiments, the *Zea mays* cyclin is selected from the 59 cyclins described in Hu et al., 2010, which is incorporated herein by reference in its entirety. In some embodiments, *Zea mays* cyclin is selected from the 21 cyclin D proteins described in Hu et al., 2010. For example, the cyclin is selected from the group consisting of *Zea mays* cyclin D1;1, D2;1, D2;2, D3;1, D3;2, D4;1, D4;2, D4;3, D4;4, D4;5, D4;6, D4;7, D4;8, D4;9, D4;10, D5;1, D5;2, D5;3, D5;4, D6;1, D7;1, and combination thereof.

In some embodiments, said mutant KRP is derived from a wheat KRP. In some embodiments, the mutant KRP is derived from wheat KRP1 (A, B, or D), wheat KRP2 (A, B, or D), wheat KRP4 (A, B, or D), wheat KRP5 (A, B, or D), or wheat KRP6 (A, B, or D). In some embodiments, said mutant KRP is derived from a rice KRP. In some embodiments, the mutant KRP is derived from rice KRP1, rice KRP2, rice KRP3, rice KRP4, or rice KRP5. In some embodiments, said mutant KRP is derived from a soybean KRP. In some other embodiments, said mutant KRP is derived from a biologically active variant, or fragment thereof of wild-type wheat, rice or soybean KRPs. The mutant KRP can be natural mutation, or a mutation induced artificially by methods well known to one skilled in the art.

Mutant KRP protein of the present invention can have one or more modifications to the wild-type KRP, or biologically active variant, or fragment thereof. Particularly suitable modifications include amino acid substitutions, insertions, deletions, or truncation. For example, amino acid substitutions can be generated as modifications in the CDK or the cyclin-binding region that reduce or eliminate binding. Similarly, amino acid substitutions can be generated as modifications in the CDK or the cyclin-binding region of the KRP that reduce or eliminate the inhibitory activity of the KRP towards the Cyclin/CDK complex. In typical embodiments, at least one non-conservative amino acid substitution, insertion, or deletion in the CDK binding region or the cyclin binding region is made to disrupt or modify binding of the CKI polypeptide to a CDK or cyclin protein. The substitutions may be single, where only one amino acid in the molecule has been substituted, or they may be multiple, where two or more amino acids have been substituted in the same molecule. Insertional KRP mutants are those with one or more amino acids inserted immediately adjacent to an amino acid at a particular position in the wild-type KRP protein molecule, biologically active variant, or fragment thereof. The insertion can be one or more amino acids. The insertion can consist, e.g., of one or two conservative amino acids. Amino acids similar in charge and/or structure to the amino acids adjacent to the site of insertion are defined as conservative. Alternatively, mutant KRP protein includes the insertion of an amino acid with a charge and/or structure that is substantially different from the amino acids adjacent to the site of insertion. In some other embodiments, the mutant KRP is a truncated protein losing one or more domains compared to the corresponding wild type KRP protein.

Methods of Increasing Organ Weight, Organ Size, Organ Number and/or Yield

The present invention further provides methods of increasing weight, size, and/or number of one or more organs, for example, methods of increasing seed weight, seed size, seed number, and/or yield in a plant. The plant can be a dicot plant or a monocot plant. In some embodiments, the plant is a monocot plant. In some embodiments, the plant is a plant species in the Triticeae tribe or Oryzeae tribe, or the Fabaceae family, for example, a wheat plant or a rice plant. In some embodiments, the methods comprise disrupting one or more KRPs in the plant. The disruption can be at genomic level, transcriptional level, post-transcriptional level, translational level, and/or post translational level. In some embodiments, the methods comprise introducing one or more mutations into one or more KRP genes in the plant. In some embodiments, the methods comprise knocking-down expression of one or more KRP genes in the plant. In some embodiments, the methods comprise knocking-down KRP mRNAs stability in the plant. In some embodiments, the methods comprise down-regulating one or more KRP proteins activity in the plant.

For example, in some embodiments, the methods comprise introducing one or more KRP mutants of the present invention into the genome of the plant. In some embodiments, the methods comprise hybridizing a first plant having one or more mutated KRPs of the present invention with a second plant. In some embodiments, the hybridizing step comprises crossing the first plant with the second plant. In some embodiments, the hybridizing step comprises transferring the genetic materials in the first plant to the second plant through in vitro breeding, e.g., somatic hybridization.

Alternatively, the methods comprise mutating one or more KRPs in a plant. Methods of mutating a target gene have been known to one skilled in the art. These methods include, but are not limited to, mutagenesis (e.g., chemical mutagenesis, radiation mutagenesis, transposon mutagenesis, insertional mutagenesis, signature tagged mutagenesis, site-directed mutagenesis, and natural mutagenesis), TILLING®, homologous recombination, knock-outs/knock-ins, antisense and RNA interference. Various types of mutagenesis can be used to produce and/or isolate variant nucleic acids that encode for protein molecules and/or to further modify/mutate the proteins of the present invention. They include but are not limited to site-directed, random point mutagenesis, homologous recombination, DNA shuffling, mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like. For more information of mutagenesis in plants, such as agents, protocols, see reference Nos. 94 to 98, each of which is herein incorporated by reference in its entity).

In some embodiments, random mutations in KRP genes are created in vitro. For example, a library of KRP genes with one or more random mutations can be generated, and the produced mutant KRP genes are subjected to the in vitro KRP-Cylin-CDK kinase assay described herein to determine if the mutant KRP genes can be used for increasing weight, size, and/or number of one or more organs, for example, for increasing seed size, seed number, seed weight and/or yield. Methods for in vitro mutagenesis include, but are not limited to error-prone PCR, Rolling circle error-prone PCR, mutator strains, temporary mutator strains, insertion mutagenesis, chemical mutagenesis (e.g., EMS, nitrous acid etc.), DNA shuffling, and site directed random mutagenesis. More methods are described in Chusacultanachai et al, Fujii et al., Braman, and Trower. Commercial random mutagenesis kits are available, such as Random Mutagenesis Kits from Jena Bioscience. cat. No. PP-101, Diversify® PCR random mutagenesis kit from Clontech.

In some embodiments, mutated KRPs of the present invention are generated in vivo by methods such as TILLING®, site-directed mutagenesis, homologous recombination, etc. The produced mutant KRP genes are screened and subjected to the in vitro KRP-Cylin-CDK kinase assay described herein to determine if the mutant KRP genes can be used for increasing weight, size, and/or number of one or more organs, for example, for increasing seed size, seed number, seed weight and/or yield.

In some embodiments, the methods comprise knocking down expression of one or more KRPs in the plant. Techniques which can be employed in accordance with the present invention to knock down gene expression, include, but are not limited to: (1) disrupting a gene's transcript, such as disrupting a gene's mRNA transcript; (2) disrupting the function of a polypeptide encoded by a gene, or (3) disrupting the gene itself.

For example, antisense RNA, ribozyme, dsRNAi, RNA interference (RNAi) technologies can be used in the present invention to target RNA transcripts of one or more KRP genes. Antisense RNA technology involves expressing in, or introducing into, a cell an RNA molecule (or RNA derivative) that is complementary to, or antisense to, sequences found in a particular mRNA in a cell. By associating with the mRNA, the antisense RNA can inhibit translation of the encoded gene product. The use of antisense technology to reduce or inhibit the expression of specific plant genes has been described, for example in European Patent Publication No. 271988, Smith et al., Nature, 334:724-726 (1988); Smith et. al., Plant Mol. Biol., 14:369-379 (1990)).

A ribozyme is an RNA that has both a catalytic domain and a sequence that is complementary to a particular mRNA. The ribozyme functions by associating with the mRNA (through the complementary domain of the ribozyme) and then cleaving (degrading) the message using the catalytic domain.

RNA interference (RNAi) is the process of sequence-specific, post-transcriptional gene silencing or transcriptional gene silencing in animals and plants, initiated by double-stranded RNA (dsRNA) that is homologous in sequence to the silenced gene. The RNAi technique is discussed, for example, in Elibashir, et al., Methods Enzymol. 26:199 (2002); McManus & Sharp, Nature Rev. Genetics 3:737 (2002); PCT application WO 01/75164; Martinez et al., Cell 110:563 (2002); Elbashir et al., supra; Lagos-Quintana et al., Curr. Biol. 12:735 (2002); Tuschl et al., Nature Biotechnol. 20:446 (2002); Tuschl, Chembiochem. 2:239 (2001); Harborth et al., J. Cell Sci. 114:4557 (2001); et al., EMBO J. 20:6877 (2001); Lagos-Quintana et al., Science 294:8538 (2001); Hutvagner et al., loc cit, 834; Elbashir et al., Nature 411:494 (2001).

The term "dsRNA" or "dsRNA molecule" or "double-strand RNA effector molecule" refers to an at least partially double-strand ribonucleic acid molecule containing a region of at least about 19 or more nucleotides that are in a double-strand conformation. The double-stranded RNA effector molecule may be a duplex double-stranded RNA formed from two separate RNA strands or it may be a single RNA strand with regions of self-complementarity capable of assuming an at least partially double-stranded hairpin conformation (i.e., a hairpin dsRNA or stem-loop dsRNA). In various embodiments, the dsRNA consists entirely of ribonucleotides or consists of a mixture of ribonucleotides and deoxynucleotides, such as RNA/DNA hybrids. The dsRNA may be a single molecule with regions of self-complementarity such that nucleotides in one segment of the molecule base pair with nucleotides in another segment of the molecule. In one aspect, the regions of self-complementarity are linked by a region of at least about 3-4 nucleotides, or about 5, 6, 7, 9 to 15 nucleotides or more, which lacks complementarity to another part of the molecule and thus remains single-stranded (i.e., the "loop region"). Such a molecule will assume a partially double-stranded stem-loop structure, optionally, with short single stranded 5' and/or 3' ends. In one aspect the regions of self-complementarity of the hairpin dsRNA or the double-stranded region of a duplex dsRNA will comprise an Effector Sequence and an Effector Complement (e.g., linked by a single-stranded loop region in a hairpin dsRNA). The Effector Sequence or Effector Strand is that strand of the double-stranded region or duplex which is incorporated in or associates with RISC. In one aspect the double-stranded RNA effector molecule will comprise an at least 19 contiguous nucleotide effector sequence, preferably 19 to 29, 19 to 27, or 19 to 21 nucleotides, which is a reverse complement to the RNA of KRPs, or an opposite strand replication intermediate, or the anti-genomic plus strand or non-mRNA plus strand sequences of KRPs. In one embodiment, said double-stranded RNA effector molecules are provided by providing to a plant, plant tissue, or plant cell an expression construct comprising one or more double-stranded RNA effector molecules. In one embodiment, the expression construct comprise a double-strand RNA derived from any one of SEQ ID NOs 60-86, 100-107, 111-128, 138-139, 141-142, and 144-145. One skilled in the art will be able to design suitable double-strand RNA effector molecule based on the nucleotide sequences of KRPs in the present invention.

In some embodiments, the dsRNA effector molecule of the invention is a "hairpin dsRNA", a "dsRNA hairpin", "short-hairpin RNA" or "shRNA", i.e., an RNA molecule of less than approximately 400 to 500 nucleotides (nt), or less than 100 to 200 nt, in which at least one stretch of at least 15 to 100 nucleotides (e.g., 17 to 50 nt, 19 to 29 nt) is based paired with a complementary sequence located on the same RNA molecule (single RNA strand), and where said sequence and complementary sequence are separated by an unpaired region of at least about 4 to 7 nucleotides (or about 9 to about 15 nt, about 15 to about 100 nt, about 100 to about 1000 nt) which forms a single-stranded loop above the stem structure created by the two regions of base complementarity. The shRNA molecules comprise at least one stem-loop structure comprising a double-stranded stem region of about 17 to about 100 bp; about 17 to about 50 bp; about 40 to about 100 bp; about 18 to about 40 bp; or from about 19 to about 29 bp; homologous and complementary to a target sequence to be inhibited; and an unpaired loop region of at least about 4 to 7 nucleotides, or about 9 to about 15 nucleotides, about 15 to about 100 nt, about 100 to about 1000 nt, which forms a single-stranded loop above the stem structure created by the two regions of base complementarity. It will be recognized, however, that it is not strictly necessary to include a "loop region" or "loop sequence" because an RNA molecule comprising a sequence followed immediately by its reverse complement will tend to assume a stem-loop conformation even when not separated by an irrelevant "stuffer" sequence.

The plants with disrupted one or more KRPs of the present invention can be used for many purposes. In one embodiment, a plant of the present invention is used as a donor plant of genetic material which can be transferred to a recipient plant to produce a plant with desired agronomic traits which has the transferred genetic material and having increased weight, size, and/or number of one or more organs, for example, having increased seed weight, seed size, seed number and/or yield. Any suitable method known in the art can be applied to transfer genetic material from a donor plant to a recipient plant. In most cases, such genetic material is genomic material.

Descriptions of other breeding methods that are commonly used for different traits and crops can be found in one of several reference books (e.g., R. W. Allard, 1960, Principles of Plant Breeding, John Wiley and Son, pp. 115-161; N. W. Simmonds, 1979, Principles of Crop Improvement, Longman Group Limited; W. R. Fehr, 1987, Principles of Crop Development, Macmillan Publishing Co.; N. F. Jensen, 1988, Plant Breeding Methodology, John Wiley & Sons).

In some embodiments, a backcross breeding process is used. The backcross breeding process comprises the following steps: (a) crossing a first wheat plants having one or more disrupted KRP genes with a second plant that comprise the desired trait(s); (b) selecting the $F_1$ progeny plants that have the desired trait(s); (c) crossing the selected $F_1$ progeny plants with the first wheat plant or the second wheat plant to produce backcross progeny plants; (d) selecting for backcross progeny plants that have the desired trait(s) and one or more disrupted KRP genes to produce selected backcross progeny plants; and (e) repeating steps (c) and (d) one, two, three, four, five six, seven, eight, nine, or more times in succession to produce selected, second, third, fourth, fifth, sixth, seventh, eighth, ninth, or higher backcross progeny plants that comprise said disrupted KRP genes, and/or the desired trait(s).

The invention further provides methods for developing wheat varieties in a wheat breeding program using plant breeding techniques including recurrent selection, backcrossing, pedigree breeding, molecular markers (Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs). Amplified Fragment Length Polymorphisms (AFLPs), and Simple Sequence Repeats (SSRs) which are also referred to as Microsatellites, etc.) enhanced selection, genetic marker enhanced selection, and transformation. Seeds, plants, and part(s) thereof produced by such breeding methods are also part of the invention.

In one embodiment, the whole genome of the plants of the present invention with disrupted KRP(s) is transferred into a recipient plant. This can be done by conventional breeding such as crossing, or somatic hybridization. In another embodiment, at least the parts having the disrupted KRP(s) of the donor plant's genome are transferred. This can be done by crossing donor plants to a recipient plant to create a F1 plant, followed with one or more backcrosses to one of the parent plants to give plants with the desired genetic background. Molecular marker assisted breeding can be utilized to monitor the transfer of the genetic material. The produced offsprings can be selected for having increased weight, size, and/or number of one or more organs, for example, having increased seed weight, seed size, seed number and/or yield.

In one embodiment, the recipient plant is an elite line having one or more certain agronomically important traits. As used herein, "agronomically important traits" include any phenotype in a plant or plant part that is useful or advantageous for human use. Examples of agronomically important traits include but are not limited to those that result in increased biomass production, increased food production, improved food quality, decrease in cracking, quicker color change when the fruit matures etc. Additional examples of agronomically important traits includes pest resistance, vigor, development time (time to harvest), enhanced nutrient content, increase in seed oil content, novel growth patterns, flavors or colors, salt, heat, drought and cold tolerance, and the like.

Other agronomically important traits include resistance to biotic and/or abiotic stresses. As used herein, the phrase "biotic stress" or "biotic pressure" refers to a situation where damage is done to plants by other living organisms, such as bacteria, viruses, fungi, parasites, insects, weeds, animals and human. As used herein, the phrase "abiotic stress" or "abiotic pressure" refers to the negative impact of non-living factors on plants in a specific environment. The non-living variable must influence the environment beyond its normal range of variation to adversely affect the population performance or individual physiology of plants in a significant way. Non-limiting examples of stressors are high winds, extreme temperatures, drought, flood, and other natural disasters, such as tornados and wildfires.

In some embodiments, the method comprises i) making a cross between a plant with one or more disrupted KRP genes to a second plant to produce a F1 plant, for example, a wheat, a rice, or a soybean plant with one or more disrupted KRP genes. Optionally, the method further comprises ii) backcrossing the F1 plant to the first or the second plant; and iii) repeating the backcrossing step to generate a near isogenic line, wherein the one or more disrupted KRPs are integrated into the genome of the second plant.

In some embodiments, the disrupted KRP gene is a wheat KRP selected from the group consisting of TaKRP1A, TaKRP1B, TaKRP1D, TaKRP2A, TaKRP2B, TaKRP2D, TaKRP4A, TaKRP4B, TaKRP4D, TaKRP5A, TaKRP5B, TaKRP5D, TaKRP6A, TaKRP6B, or TaKRP6D, for example, SEQ ID NOs. 60-86, 138-139, 141-142, and 144-145, or functional variants thereof. In some embodiments, the first plant comprises one or more mutations selected from any one of mutations listed in Tables 2-12 for a particular KRP gene.

In some embodiments, the disrupted KRP gene is a rice KRP selected from the group consisting of OsKRP1, OSKRP2, OsKRP4, and OsKRP5, for example, SEQ ID NOs. 100-107, or functional variants thereof. In some embodiments, the first plant comprises one or more mutations selected from any one of mutations listed in Table 25 for a particular KRP gene.

In some embodiments, the disrupted KRP gene is a soybean KRP. In some embodiments, the KRP is selected from the group consisting of Gm0003×00821, Gm0013×00399, Gm0043, Gm0053×00526, Gm0087×00306, Gm0102×00087, Gm0119×00131, Gm0151×00019, Gm0067×00001, for example, SEQ ID NOs. 111-128, or functional variants thereof. In some embodiments, the first plant comprises one or more mutations selected from any one of mutations listed in Tables 29-37 for a particular KRP gene.

In some embodiments, the methods of the present invention can increase the average weight, size, and/or number of one or more organs, for example, the average seed weight, seed size, seed number and/or yield of a plant by at least 5%, at least 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, or greater when compared to a control plant not having disrupted KRP(s).

The mutated KRPs in a plant genome can be viewed as quantitative trait loci (QTLs) related to weight, size, and/or number of one or more organs, for example, QTLs related to seed weight, seed size, seed number and/or yield of for yield. A QTL is a region of DNA that is associated with a particular phenotypic trait—these QTLs are often found on different chromosomes. Knowing the number of QTLs that explains variation in a particular phenotypic trait informs about the genetic architecture of the trait. It may tell that plant with preferred phenotype is controlled by many genes of small effect, or by a few genes of large effect. Therefore, QTL mapping can be applied to determine the parts of the donor plant's genome comprising the mutated KRPs, and facilitate the breeding methods.

One or more of such QTLs of mutated KRPs in a donor can be transferred to a recipient plant, confirming the phenotype of having increased weight, size, and/or number of one or more organs, for example, having increased seed weight, seed size, seed number, and/or yield. In some further embodiments, the QTLs related to mutated KRPs can be combined with one or more other QTLs that contribute to agriculturally important phenotypes, such as yield enhancement, resistance to biotic and abiotic stresses, etc. The primers in the present invention used for genotyping the mutated KRPs can be used as molecular markers indicating the presence or absence of the mutated KRPs. Instead, molecular marks closely linked to the mutated KRPs can be also used. Methods of developing molecular markers and their applications are described by Avise (Molecular markers, natural history, and evolution, Publisher: Sinauer Associates, 2004, ISBN 0878930418, 9780878930418), Srivastava et al. (Plant biotechnology and molecular markers, Publisher: Springer, 2004, ISBN1402019114, 9781402019111), and Vienne (Molecular markers in plant genetics and biotechnology, Publisher: Science Publishers, 2003), each of which is incorporated by reference in its entirety.

Without wishing to be bond by any theory, besides increased seed size, seed number, seed weight and/or yield, a plant having one or more disrupted KRPs may have one or more other phenotypes that are agriculturally or industrially important, which include, but are not limited to, increased plant vigor, organ size, increased adaptability to the environment, increased oil production, increased biomass production, and traits that allow a plant to grow better under certain environments with specific temperatures, soil conditions and levels of sunlight and precipitation compared to a wild type control plant.

Tissue Culture and Grafting

Modern plant tissue culture is performed under aseptic conditions under filtered air. Living plant materials from the environment are naturally contaminated on their surfaces (and sometimes interiors) with microorganisms, so surface sterilization of starting materials (explants) in chemical solutions (usually alcohol or bleach) is required. Explants are then usually placed on the surface of a solid culture medium, but are sometimes placed directly into a liquid medium, particularly when cell suspension cultures are desired. Solid and liquid media are generally composed of inorganic salts plus a few organic nutrients, vitamins and plant hormones. Solid media are prepared from liquid media with the addition of a gelling agent, usually purified agar.

The composition of the medium, particularly the plant hormones and the nitrogen source (nitrate versus ammonium salts or amino acids) have profound effects on the morphology of the tissues that grow from the initial explant. For example, an excess of auxin will often result in a proliferation of roots, while an excess of cytokinin may yield shoots. A balance of both auxin and cytokinin will often produce an unorganized growth of cells, or callus, but the morphology of the outgrowth will depend on the plant species as well as the medium composition. As cultures grow, pieces are typically sliced off and transferred to new media (subcultured) to allow for growth or to alter the morphology of the culture. The skill and experience of the tissue culturist are important in judging which pieces to culture and which to discard. As shoots emerge from a culture, they may be sliced off and rooted with auxin to produce plantlets which, when mature, can be transferred to potting soil for further growth in the greenhouse as normal plants.

The tissue obtained from the plant to culture is called an explant. Based on work with certain model systems, particularly tobacco, it has often been claimed that a totipotent explant can be grown from any part of the plant. However, this concept has been vitiated in practice. In many species explants of various organs vary in their rates of growth and regeneration, while some do not grow at all. The choice of explant material also determines if the plantlets developed via tissue culture are haploid or diploid. Also the risk of microbial contamination is increased with inappropriate explants. Thus it is very important that an appropriate choice of explant be made prior to tissue culture.

The specific differences in the regeneration potential of different organs and explants have various explanations. The significant factors include differences in the stage of the cells in the cell cycle, the availability of or ability to transport endogenous growth regulators, and the metabolic capabilities of the cells. The most commonly used tissue explants are the meristematic ends of the plants like the stem tip, auxiliary bud tip and root tip. These tissues have high rates of cell division and either concentrate or produce required growth regulating substances including auxins and cytokinins. Some explants, like the root tip, are hard to isolate and are contaminated with soil microflora that become problematic during the tissue culture process. Certain soil microflora can form tight associations with the root systems, or even grow within the root. Soil particles bound to roots are difficult to remove without injury to the roots that then allows microbial attack. These associated microflora will generally overgrow the tissue culture medium before there is significant growth of plant tissue. Aerial (above soil) explants are also rich in undesirable microflora. However, they are more easily removed from the explant by gentle rinsing, and the remainder usually can be killed by surface sterilization. Most of the surface microflora do not form tight associations with the plant tissue. Such associations can usually be found by visual inspection as a mosaic, de-colorization or localized necrosis on the surface of the explant.

An alternative for obtaining uncontaminated explants is to take explants from seedlings which are aseptically grown from surface-sterilized seeds. The hard surface of the seed is less permeable to penetration of harsh surface sterilizing agents, such as hypochlorite, so the acceptable conditions of sterilization used for seeds can be much more stringent than for vegetative tissues.

Tissue cultured plants are clones, if the original mother plant used to produce the first explants is susceptible to a pathogen or environmental condition, the entire crop would be susceptible to the same problem, and conversely any positive traits would remain within the line also. Plant tissue culture is used widely in plant science; it also has a number of commercial applications. Applications include:

1. Micropropagation is widely used in forestry and in floriculture. Micropropagation can also be used to conserve rare or endangered plant species.

2. A plant breeder may use tissue culture to screen cells rather than plants for advantageous characters, e.g. pathogen resistance/tolerance.

3. Large-scale growth of plant cells in liquid culture inside bioreactors as a source of secondary products, like recombinant proteins used as biopharmaceuticals.

4. To cross distantly related species by protoplast fusion and regeneration of the novel hybrid.

5. To cross-pollinate distantly related species and then tissue culture the resulting embryo which would otherwise normally die (Embryo Rescue).

6. For production of doubled monoploid (dihaploid) plants from haploid cultures to achieve homozygous lines more rapidly in breeding programs, usually by treatment with colchicine which causes doubling of the chromosome number.

7. As a tissue for transformation, followed by either short-term testing of genetic constructs or regeneration of transgenic plants.

8. Certain techniques such as meristem tip culture can be used to produce clean plant material from infected stock, such as potatoes and many species of soft fruit.

9. Micropropagation using meristem and shoot culture to produce large numbers of identical individuals.

Non-limiting exemplary tissue culture methods for wheat, rice, maize have been described by Trione et al., Dodig, et al., O'Hara et al., Zaidi et al., Wang et al., Ting et al., Hawes et al., and Sheridan, each of which is incorporated by reference in its entirety.

The present invention also provides a cutting, a rootstock, a scion, or an explant from the plants of the present invention.

Grafting is a method of asexual plant propagation widely used in agriculture and horticulture where the tissues of one plant are encouraged to fuse with those of another. It is most commonly used for the propagation of trees and shrubs grown commercially. In most cases, one plant is selected for its roots, and this is called the stock or rootstock. The other plant is selected for its stems, leaves, flowers, or fruits and is called the scion. The scion contains the desired genes to be duplicated in future production by the stock/scion plant. In stem grafting, a common grafting method, a shoot of a selected, desired plant cultivar is grafted onto the stock of another type. In another common form called budding, a dormant side bud is grafted on the stem of another stock plant, and when it has fused successfully, it is encouraged to grow by cutting out the stem above the new bud.

For successful grafting to take place, the vascular cambium tissues of the stock and scion plants must be placed in contact with each other. Both tissues must be kept alive until the graft has taken, usually a period of a few Weeks. Successful grafting only requires that a vascular connection takes place between the two tissues. A physical weak point often still occurs at the graft, because the structural tissue of the two distinct plants, such as wood, may not fuse.

Exemplary grafting techniques include, approach grafting, budding grafting (patch budding, chip budding, T-budding), cleft grafting, side grafting, whip grafting, stub grafting, awl grafting, veneer grafting, bark grafting, tongue grafting, et al. Detailed non-limiting grafting methods for wheat and maize are described by Lacadena, 1968, and Katsumi et al., each of which is incorporated by reference in its entirety.

Plant Transformation

The polynucleotides of the present invention can be transformed into a plant. The most common method for the introduction of new genetic material into a plant genome involves the use of living cells of the bacterial pathogen *Agrobacterium tumefaciens* to literally inject a piece of DNA, called transfer or T-DNA, into individual plant cells (usually following wounding of the tissue) where it is targeted to the plant nucleus for chromosomal integration. There are numerous patents governing *Agrobacterium* mediated transformation and particular DNA delivery plasmids designed specifically for use with *Agrobacterium*—for example, U.S. Pat. No. 4,536,475, EP0265556, EP0270822, WO8504899, WO8603516, U.S. Pat. No. 5,591,616, EP0604662, EP0672752, WO8603776, WO9209696, WO9419930, WO9967357, U.S. Pat. No. 4,399,216, WO8303259, U.S. Pat. No. 5,731,179, EP068730, WO9516031, U.S. Pat. No. 5,693,512, U.S. Pat. No. 6,051,757 and EP904362A1. *Agrobacterium*-mediated plant transformation involves as a first step the placement of DNA fragments cloned on plasmids into living *Agrobacterium* cells, which are then subsequently used for transformation into individual plant cells. *Agrobacterium*-mediated plant transformation is thus an indirect plant transformation method. Methods of *Agrobacterium*-mediated plant transformation that involve using vectors with no T-DNA are also well known to those skilled in the art and can have applicability in the present invention. See, for example, U.S. Pat. No. 7,250,554, which utilizes P-DNA instead of T-DNA in the transformation vector.

Direct plant transformation methods using DNA have also been reported. The first of these to be reported historically is electroporation, which utilizes an electrical current applied to a solution containing plant cells (M. E. Fromm et al., Nature, 319, 791 (1986); H. Jones et al., Plant Mol. Biol., 13, 501 (1989) and H. Yang et al., Plant Cell Reports, 7, 421 (1988). Another direct method, called "biolistic bombardment", uses ultrafine particles, usually tungsten or gold, that are coated with DNA and then sprayed onto the surface of a plant tissue with sufficient force to cause the particles to penetrate plant cells, including the thick cell wall, membrane and nuclear envelope, but without killing at least some of them (U.S. Pat. No. 5,204,253, U.S. Pat. No. 5,015,580). A third direct method uses fibrous forms of metal or ceramic consisting of sharp, porous or hollow needle-like projections that literally impale the cells, and also the nuclear envelope of cells. Both silicon carbide and aluminum borate whiskers have been used for plant transformation (Mizuno et al., 2004; Petolino et al., 2000; U.S. Pat. No. 5,302,523 US Application 20040197909) and also for bacterial and animal transformation (Kaepler et al., 1992; Raloff, 1990; Wang, 1995). There are other methods reported, and undoubtedly, additional methods will be developed. However, the efficiencies of each of these indirect or direct methods in introducing foreign DNA into plant cells are invariably extremely low, making it necessary to use some method for selection of only those cells that have been transformed, and further, allowing growth and regeneration into plants of only those cells that have been transformed.

For efficient plant transformation, a selection method must be employed such that whole plants are regenerated from a single transformed cell and every cell of the transformed plant carries the DNA of interest. These methods can employ positive selection, whereby a foreign gene is supplied to a plant cell that allows it to utilize a substrate present in the medium that it otherwise could not use, such as mannose or xylose (for example, refer U.S. Pat. No. 5,767,378; U.S. Pat. No. 5,994,629). More typically, however, negative selection is used because it is more efficient, utilizing selective agents such as herbicides or antibiotics that either kill or inhibit the growth of nontransformed plant cells and reducing the possibility of chimeras. Resistance genes that are effective against negative selective agents are provided on the introduced foreign DNA used for the plant transformation. For example, one of the most popular selective agents used is the antibiotic kanamycin, together with the resistance gene neomycin phosphotransferase (nptII), which confers resistance to kanamycin and related antibiotics (see, for example, Messing & Vierra, *Gene* 19: 259-268 (1982); Bevan et al., *Nature* 304:184-187 (1983)). However, many different antibiotics and antibiotic resistance genes can be used for transformation purposes (refer U.S. Pat. No. 5,034,322, U.S. Pat. No. 6,174,724 and U.S. Pat. No. 6,255,560). In addition, several herbicides and herbicide resistance genes have been used for transformation purposes, including the bar gene, which confers resistance to the herbicide phosphinothricin (White et al., *Nucl Acids Res* 18: 1062 (1990), Spencer et al., *Theor Appl Genet* 79: 625-631 (1990), U.S. Pat. No. 4,795,855, U.S. Pat. No. 5,378,824 and U.S. Pat. No. 6,107,549). In addition, the dhfr gene, which confers resistance to the anticancer agent methotrexate, has been used for selection (Bourouis et al., *EMBO J.* 2(7): 1099-1104 (1983).

The expression control elements used to regulate the expression of a given protein can either be the expression control element that is normally found associated with the coding sequence (homologous expression element) or can be a heterologous expression control element. A variety of homologous and heterologous expression control elements are known in the art and can readily be used to make expression units for use in the present invention. Transcription initiation regions, for example, can include any of the various opine initiation regions, such as octopine, mannopine, nopaline and the like that are found in the Ti plasmids of *Agrobacterium tumefaciens*. Alternatively, plant viral promoters can also be used, such as the cauliflower mosaic virus 19S and 35S promoters (CaMV 19S and CaMV 35S promoters, respectively) to control gene expression in a plant (U.S. Pat. Nos. 5,352,605; 5,530,196 and 5,858,742 for example). Enhancer sequences derived from the CaMV can also be utilized (U.S. Pat. Nos. 5,164,316; 5,196,525; 5,322,938; 5,530,196; 5,352,605; 5,359,142; and 5,858,742 for example). Lastly, plant promoters such as prolifera promoter, fruit specific promoters, Ap3 promoter, heat shock promoters, seed specific promoters, etc. can also be used.

Either a gamete specific promoter, a constitutive promoter (such as the CaMV or Nos promoter), an organ specific promoter (e.g., stem specific promoter), or an inducible promoter is typically ligated to the protein or antisense encoding region using standard techniques known in the art. The expression unit may be further optimized by employing supplemental elements such as transcription terminators and/or enhancer elements. The expression cassette can comprise, for example, a seed specific promoter (e.g. the phaseolin promoter (U.S. Pat. No. 5,504,200). The term "seed specific promoter", means that a gene expressed under the control of the promoter is predominantly expressed in plant seeds with no or no substantial expression, typically less than 10% of the overall expression level, in other plant tissues. Seed specific promoters have been well known in the art, for example, U.S. Pat. Nos. 5,623,067, 5,717,129, 6,403,371, 6,566,584, 6,642,437, 6,777,591, 7,081,565, 7,157,629, 7,192,774, 7,405,345, 7,554,006, 7,589,252, 7,595,384, 7,619,135, 7,642,346, and US Application Publication Nos. 20030005485, 20030172403, 20040088754, 20040255350, 20050125861, 20050229273, 20060191044, 20070022502, 20070118933, 20070199098, 20080313771, and 20090100551.

Thus, for expression in plants, the expression units will typically contain, in addition to the protein sequence, a plant promoter region, a transcription initiation site and a transcription termination sequence. Unique restriction enzyme sites at the 5' and 3' ends of the expression unit are typically included to allow for easy insertion into a preexisting vector.

In the construction of heterologous promoter/structural gene or antisense combinations, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette can also contain a transcription termination region downstream of the structural gene to provide for efficient termination. The termination region may be obtained from the same gene as the promoter sequence or may be obtained from different genes. If the mRNA encoded by the structural gene is to be efficiently processed, DNA sequences which direct polyadenylation of the RNA are also commonly added to the vector construct. Polyadenylation sequences include, but are not limited to the *Agrobacterium* octopine synthase signal (Gielen et al., EMBO J 3:835-846 (1984)) or the nopaline synthase signal (Depicker et al., Mol. and Appl. Genet. 1:561-573 (1982)). The resulting expression unit is ligated into or otherwise constructed to be included in a vector that is appropriate for higher plant transformation. One or more expression units may be included in the same vector. The vector will typically contain a selectable marker gene expression unit by which transformed plant cells can be identified in culture. Usually, the marker gene will encode resistance to an antibiotic, such as G418, hygromycin, bleomycin, kanamycin, or gentamicin or to an herbicide, such as glyphosate (Round-Up) or glufosinate (BASTA) or atrazine. Replication sequences, of bacterial or viral origin, are generally also included to allow the vector to be cloned in a bacterial or phage host, preferably a broad host range prokaryotic origin of replication is included. A selectable marker for bacteria may also be included to allow selection of bacterial cells bearing the desired construct. Suitable prokaryotic selectable markers include resistance to antibiotics such as ampicillin, kanamycin or tetracycline. Other DNA sequences encoding additional functions may also be present in the vector, as is known in the art. For instance, in the case of *Agrobacterium* transformations, T-DNA sequences will also be included for subsequent transfer to plant chromosomes.

To introduce a desired gene or set of genes by conventional methods requires a sexual cross between two lines, and then repeated back-crossing between hybrid offspring and one of the parents until a plant with the desired characteristics is obtained. This process, however, is restricted to plants that can sexually hybridize, and genes in addition to the desired gene will be transferred.

Recombinant DNA techniques allow plant researchers to circumvent these limitations by enabling plant geneticists to identify and clone specific genes for desirable traits, such as resistance to an insect pest, and to introduce these genes into already useful varieties of plants. Once the foreign genes have been introduced into a plant, that plant can then be used in conventional plant breeding schemes (e.g., pedigree breeding, single-seed-descent breeding schemes, reciprocal recurrent selection) to produce progeny which also contain the gene of interest.

Genes can be introduced in a site directed fashion using homologous recombination. Homologous recombination permits site specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451,513; 5,501,967 and 5,527,695.

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and *Agrobacterium*-mediated transformation. See, for example, U.S. Pat. Nos. 5,405,765; 5,472,869; 5,538,877; 5,538,880; 5,550,318; 5,641,664; 5,736,369 and 5,736,369; International Patent Application Publication Nos. WO2002/038779 and WO/2009/117555; Lu et al., (Plant Cell Reports, 2008, 27:273-278); Watson et al., Recombinant DNA, Scientific American Books (1992); Hinchee et al., Bio/Tech. 6:915-922 (1988); McCabe et al., Bio/Tech. 6:923-926 (1988); Toriyama et al., Bio/Tech. 6:1072-1074 (1988); Fromm et al., Bio/Tech. 8:833-839 (1990); Mullins et al., Bio/Tech. 8:833-839 (1990); Hiei et al., Plant Molecular Biology 35:205-218 (1997); Ishida et al., Nature Biotechnology 14:745-750 (1996); Zhang et al., Molecular Biotechnology 8:223-231 (1997); Ku et al., Nature Biotechnology 17:76-80 (1999); and, Raineri et al., Bio/Tech. 8:33-38 (1990)), each of which is expressly incorporated herein by reference in their entirety.

*Agrobacterium tumefaciens* is a naturally occurring bacterium that is capable of inserting its DNA (genetic information) into plants, resulting in a type of injury to the plant known as crown gall. Most species of plants can now be transformed using this method, including cucurbitaceous species.

Microprojectile bombardment is also known as particle acceleration, biolistic bombardment, and the gene gun (Biolistic® Gene Gun). The gene gun is used to shoot pellets that are coated with genes (e.g., for desired traits) into plant seeds or plant tissues in order to get the plant cells to then express the new genes. The gene gun uses an actual explosive (.22 caliber blank) to propel the material. Compressed air or steam may also be used as the propellant. The Biolistic® Gene Gun was invented in 1983-1984 at Cornell University by John Sanford, Edward Wolf, and Nelson Allen. It and its registered trademark are now owned by E. I. du Pont de Nemours and Company. Most species of plants have been transformed using this method.

A transgenic plant formed using *Agrobacterium* transformation methods typically contains a single gene on one chromosome, although multiple copies are possible. Such transgenic plants can be referred to as being hemizygous for the added gene. A more accurate name for such a plant is an independent segregant, because each transformed plant represents a unique T-DNA integration event (U.S. Pat. No. 6,156,953). A transgene locus is generally characterized by the presence and/or absence of the transgene. A heterozygous genotype in which one allele corresponds to the absence of the transgene is also designated hemizygous (U.S. Pat. No. 6,008,437).

General transformation methods, and specific methods for transforming certain plant species (e.g., maize, rice, wheat, barley, soybean) are described in U.S. Pat. Nos. 4,940,838, 5,464,763, 5,149,645, 5,501,967, 6,265,638, 4,693,976, 5,635,381, 5,731,179, 5,693,512, 6,162,965, 5,693,512, 5,981,840, 6,420,630, 6,919,494, 6,329,571, 6,215,051, 6,369,298, 5,169,770, 5,376,543, 5,416,011, 5,569,834, 5,824,877, 5,959,179, 5,563,055, and 5,968,830, each of which is incorporated by reference in its entirety.

This invention is further illustrated by the following examples which should not be construed as limiting. The contents of all references, patents and published patent applications cited throughout this application, as well as the Figures and the Sequence Listing, are incorporated herein by reference.

EXAMPLES

Materials and Methods

Mutagenesis

In one embodiment of the present invention, wheat seeds of tetraploid wheat (*Triticum turgidum*) cultivar 'Kronos' and the hexaploid wheat (*Triticum aestivum*) cultivar 'Express' (PVP #9000012) were vacuum infiltrated in $H_2O$ (approximately 1,000 seeds/100 ml $H_2O$ for approximately 4 minutes). The seeds were then placed on a shaker (45 rpm) in a fume hood at ambient temperature. The mutagen ethyl methanesulfonate (EMS) was added to the imbibing seeds to final concentrations ranging from about 0.75% to about 1.2% (v/v). Following an 18 hour incubation period, the EMS solution was replaced 4 times with fresh $H_2O$. The seeds were then rinsed under running water for about 1 hour. Finally, the mutagenized seeds were planted (96/tray) in potting soil and allowed to germinate indoors. Plants that were four to six weeks old were transferred to the field to grow to fully mature M1 plants. The mature M1 plants were allowed to self-pollinate and then seeds from the M1 plant were collected and planted to produce M2 plants.

DNA Preparation

DNA from these M2 plants was extracted and prepared in order to identify which M2 plants carried a mutation at their KRP loci. The M2 plant DNA was prepared using the methods and reagents contained in the Qiagen® (Valencia, Calif.) DNeasy® 96 Plant Kit. Approximately 50 mg of frozen plant sample was placed in a sample tube with a tungsten bead, frozen in liquid nitrogen and ground 2 times for 1 minute each at 20 Hz using the Retsch® Mixer Mill MM 300. Next 400 μl of solution AP1 [Buffer AP1, solution DX and RNAse (100 mg/ml)] at 80° C. was added to the sample. The tube was sealed and shaken for 15 seconds. Following the addition of 130 μl Buffer AP2, the tube was shaken for 15 seconds. The samples were placed in a freezer at minus 20° C. for at least 1 hour. The samples were then centrifuged for 20 minutes at 5,600×g. A 400 μl aliquot of supernatant was transferred to another sample tube. Following the addition of 600 μl of Buffer AP3/E, this sample tube was capped and shaken for 15 seconds. A filter plate was placed on a square well block and 1 ml of the sample solution was applied to each well and the plate was sealed.

The plate and block were centrifuged for 4 minutes at 5,600×g. Next, 800 µl of Buffer AW was added to each well of the filter plate, sealed and spun for 15 minutes at 5,600×g in the square well block. The filter plate was then placed on a new set of sample tubes and 80 µl of Buffer AE was applied to the filter. It was capped and incubated at room temperature for 1 minute and then spun for 2 minutes at 5,600×g. This step was repeated with an additional 80 µl Buffer AE. The filter plate was removed and the tubes containing the pooled filtrates were capped. The individual samples were then normalized to a DNA concentration of 5 to 10 ng/µl.

TILLING®

The M2 DNA was pooled into groups of two individual plants. The DNA concentration for each individual within the pool was approximately 1 to 2 ng/µl with a final concentration of 2 to 4 ng./µl for the entire pool. Then, 5 or 10 µl of the pooled DNA samples (or 10 to 40 ng) was arrayed on microtiter plates and subjected to gene-specific PCR.

PCR amplification was performed in 15 or 20 µl reaction volumes containing 10 to 40 ng pooled DNA. A reaction included 1.24 µl of 10× ExTaq buffer (Takara®), 0.73 µl of 25 mM $MgCl_2$, 1.98 µl of 10 mM dNTPs, 0.066 µl of 100 µM primer mix, and 0.11 µl of 5 U/µl Ex-Taq (Takara®) DNA polymerase, with 6.87 µl $H_2O$. PCR additives such as dimethyl sulfoxide (DMSO), betaine or Polymer-Aide PCR Enhancer (Sigma Aldrich®, St. Louis, Mo.) can be used to increase PCR efficiency. PCR amplification was performed using an MJ Research® thermal cycler as follows: 95° C. for 2 minutes; 8 cycles of "touchdown PCR" (94° C. for 20 second, followed by annealing step starting at 70-68° C. for 30 seconds and decreasing 1° C. per cycle, then a temperature ramp of 0.5° C. per second to 72° C. followed by 72° C. for 1 minute); 25-45 cycles of 94° C. for 20 seconds, 63-67.5° C. for 30 seconds, ramp 0.5° C./sec to 72° C., 72° C. for 1 minute; 72° C. for 8 minutes; 98° C. for 8 minutes; 80° C. for 20 seconds; 60 cycles of 80° C. for 7 seconds −0.3 degrees/cycle.

The PCR primers (Eurofins MWG/Operon, Huntsville, Ala.) were mixed as follows:

12.5% 100 µM IRD-700 labeled left primer
37.5% 100 µM left primer
25% 100 µM IRD-800 labeled right primer
25% 100 µM right primer A label can be attached to each primer as described or to only one of the primers. Alternatively, Cy5.5 modified primers could be used. The label was coupled to the oligonucleotide using conventional phosphoramidite chemistry.

PCR products (15 or 20 µl) were digested in 96-well plates. Next, 30 µl of a solution containing 10 mM HEPES [4-(2-hydroxyethyl)-1-piperazineethanesulfonic acid] (pH 7.5), 10 mM $MgSO_4$, 0.002% (w/v) Triton® X-100, 20 ng/ml of bovine serum albumin, 5 ul of SURVEYOR® Nuclease (Transgenomic, Inc.) and 5 ul of SURVEYOR® Enhancer (Transgenomic, Inc.) were added with mixing on ice, and the plate was incubated at 45° C. for 30 minutes. Reactions were stopped by addition of 10 µl of a 2.5 M NaCl solution with 0.5 mg/ml blue dextran and 75 mM EDTA, followed by the addition of 80 µl isopropanol. The reactions were precipitated at room temperature, spun at 4,000 rpm for 30 minutes in an Eppendorf Centrifuge 5810. Pellets were resuspended in 6 µl of 33% formamide with 0.017% bromophenol blue dye, heated at 80° C. for 7 minutes and then at 95° C. for 5 minutes. Samples were transferred to a membrane comb using a comb-loading robot (MWG Biotech). The comb was inserted into a slab acrylamide gel (6.5%) and electrophoresed for 4 h 15 min at 1,500-V, 40-W, and 40-mA limits at 50° C.

During electrophoresis, the gel was imaged using a LI-COR® (Lincoln, Nebr.) scanner which was set at a channel capable of detecting the IR Dye 700 and 800 labels. The gel image showed sequence-specific pattern of background bands common to all 96 lanes. Rare events, such as mutations, create new bands that stand out above the background pattern. Plants with bands indicative of mutations of interest were evaluated by TILLING® individual members of a pool mixed with wild type DNA and then sequencing individual PCR products.

Example 1

TILLING for *Triticum* KRP Mutants

Genome-specific primers were designed and used to TILL for wheat KRPs (Table 1).

TABLE 1

Genome-specific primers used for TILLING ® of wheat KRP genes

| Gene/ Genome† | Primer name | Primer Sequence (5' → 3') | SEQ ID NO |
|---|---|---|---|
| KRP1A_2-4 | | | |
| | TaKRP1A_L | GGATACGATTCGAGATCTCCTTTTTGAC | 6 |
| | TaKRP1A_R | TGATAATGGTGGGAATATGTGAGCGAGTG | 7 |
| KRP1B_2-4 | | | |
| | TaKRP1B_L | AAACAGCAAGGTGAGGGAATTGGGGTC | 8 |
| | TaKRP1B_R | TAATGTTCTTTCCGGAGCATCTTTTTCC | 9 |
| KRP1D_2-4 | | | |
| | TaKRP1D_L | GGATACAATTCGAGATCTCCTTTTTGCTG | 10 |
| | TaKRP1D_R | TAATGCTTCTTTCCGGAGCATCTTTTTCC | 11 |
| KRP2A2 | | | |
| | TaKRP2A2L1 | GCCACTCACTGCCCTAGAATTCTCCGTA | 12 |
| | TaKRP2A2R1 | CAATTTGGATGGGGAGAGAGAGAGAGCTAGTGT | 13 |

TABLE 1-continued

Genome-specific primers used for TILLING ® of wheat KRP genes

| Gene/ Genome† | Primer name | Primer Sequence (5' → 3') | SEQ ID NO |
|---|---|---|---|
| KRP2B2 | | | |
| | TaKRP2B2L2 | GTCCACTGCCCTAAATTCTCCGCTACTT | 14 |
| | TaKRP2B2_altR | GCCGTGGCCTAGTGAAAGGTAAAAAGAAA | 15 |
| KRP2D2 | | | |
| | KRP2D2_ENDEX1_L | TCCACTGCCCTAGAATTCTCCGCTAAT | 16 |
| | KRP2D2_ENDEX4_R | GTCATTTGCATCATGCTCTGCTCACAC | 17 |
| KRP4B2 | | | |
| | KRP4B_L_2_3_NEW | TTCCTTATTTTTTATGACTATTGATATGTGTT CTTC | 18 |
| | WKP4_BR2 | GTGGTCATTACAGAATGAGCTGCTAACCGTT | 19 |
| KRP4D2 | | | |
| | KRP4D_L_2_3_NEW | TTACGACCACCGATGATATCGATATGTG | 20 |
| | KRP4D_R_2_3_NEW | CATTGGAGTTTTGAGGGATTAGGGTGT | 21 |
| KRP5A1 | | | |
| | TaKRP5A1_L | GGCAAGTACATGCGCAAGAGCAAGG | 22 |
| | TaKRP5A1_R | GATTTTCTTCTCCATCAGGATTGAAGCGC | 23 |
| KRP5A2 | | | |
| | TaKRP5A2_L | CACATTGTGTGATGTGGGGCACTTGTTA | 24 |
| | TaKRP5_ALL_EST_R | GAGCTACTGCTGACTGCGGGCTAACTCTA | 25 |
| KRP5D2 | | | |
| | TaKRP5D_L_Z_2 | TGTCTAGCGTGGGGCACTTGCAAATA | 26 |
| | TaKRP5_ALL_EST_R | GAGCTACTGCTGACTGCGGGCTAACTCTA | 27 |

†number after genome letter refers to the exons or the region of the KRP gene TILL'ed. i.e. 2-4 mean exons 2-4, and the number 2 means the latter half of the gene (includes the cyclin/CDK binding domains). The number 1 means the first part of the KRP gene, excluding the cyclin/CDK binding domains.

Example 2

Mutations of *Triticum* KRP Genes Identified in TILLING®

Screening of the TILLING® population for KRP mutants resulted in plants with silent, splice, nonsense (premature stop codons) and/or missense (severe or non-severe) mutations in KRP1, KRP2, KRP4 and KRP5 (A, B, and D genomes) genes.

Positions and effects of mutations in KRP1, KRP2, KRP4 and KRP5 (A, B, and D genomes) genes are displayed in Tables 2 to 12 below (* indicates the mutation results in a stop codon, =indicates silent mutation).

TABLE 2

Summary of *Triticum turgidum* ssp. *durum* (tetraploid) KRP4B mutants

| Nucleotide Change^ | Effect | Gene | Mutation Score | Mutation Identifier |
|---|---|---|---|---|
| G389A | R4K[£] | KRP4B2[§] | Severe Missense | 4xKRP4B2-m1 |
| G390A | R4= | KRP4B2 | Silent | 4xKRP4B2-m2 |

TABLE 2-continued

Summary of *Triticum turgidum* ssp. *durum* (tetraploid) KRP4B mutants

| Nucleotide Change^ | Effect | Gene | Mutation Score | Mutation Identifier |
|---|---|---|---|---|
| C400T | P8S | KRP4B2 | Severe Missense | 4xKRP4B2-m3 |
| C408T | S10= | KRP4B2 | Silent | 4xKRP4B2-m4 |
| C457T | P27S | KRP4B2 | Missense | 4xKRP4B2-m5 |
| G461A | S28N | KRP4B2 | Missense | 4xKRP4B2-m6 |
| C465T | H29= | KRP4B2 | Silent | 4xKRP4B2-m7 |
| G486A | V36= | KRP4B2 | Silent | 4xKRP4B2-m8 |
| G496A | A40T | KRP4B2 | Missense | 4xKRP4B2-m9 |
| G520A | A48T | KRP4B2 | Missense | 4xKRP4B2-m10 |
| G525A | E49= | KRP4B2 | Silent | 4xKRP4B2-m11 |
| C540T | F54= | KRP4B2 | Silent | 4xKRP4B2-m12 |
| G550A | E58K | KRP4B2 | Severe Missense | 4xKRP4B2-m13 |
| G564A | Q62= | KRP4B2 | Silent | 4xKRP4B2-m14 |
| G587A | Intron | KRP4B2 | | 4xKRP4B2-m15 |
| G635A | Intron | KRP4B2 | | 4xKRP4B2-m16 |
| C652A | Intron | KRP4B2 | | 4xKRP4B2-m17 |
| C802T | N75= | KRP4B2 | Silent | 4xKRP4B2-m18 |
| G803A | D76N | KRP4B2 | Severe Missense | 4xKRP4B2-m19 |
| C810T | P78L | KRP4B2 | Severe Missense | 4xKRP4B2-m20 |

TABLE 2-continued

Summary of *Triticum turgidum* ssp. *durum* (tetraploid) KRP4B mutants

| Nucleotide Change^ | Effect | Gene | Mutation Score | Mutation Identifier |
|---|---|---|---|---|
| C812T | L79F | KRP4B2 | Severe Missense | 4xKRP4B2-m21 |
| C815T | P80S | KRP4B2 | Missense | 4xKRP4B2-m22 |
| T870C | Non-coding | KRP4B2 | | 4xKRP4B2-m23 |
| C894T | Non-coding | KRP4B2 | | 4xKRP4B2-m24 |

§The designation "2" indicates that exons 2-3 of wheat KRP4B were TILLed.

£Amino acid numbering does not start from the beginning Methionine.

^Nucleotide numbering is dependent upon the location of TILLING ® primers.

TABLE 3

Summary of *Triticum aestivum* (hexaploid) KRP1A mutants

| Nucleotide Change^ | Effect | Gene | Mutation Score | Mutation Identifier |
|---|---|---|---|---|
| G512A | A140= | Krp1A§ | Silent | KRP1A-m1 |
| G522A | A144T | Krp1A | Missense | KRP1A-m2 |
| C676T | P162S | Krp1A | Missense | KRP1A-m3 |
| C539T | N149= | Krp1A | Silent | KRP1A-m4 |
| G547A | R152K | Krp1A | Missense | KRP1A-m5 |
| G652A | E154K | Krp1A | Missense | KRP1A-m6 |
| G550A | Intron | Krp1A | | KRP1A-m7 |
| A554G | Intron | Krp1A | | KRP1A-m8 |
| C564T | Intron | Krp1A | | KRP1A-m9 |
| C618T | Intron | Krp1A | | KRP1A-m10 |
| G652A | E154K | Krp1A | Missense | KRP1A-m11 |
| G654A | E154= | Krp1A | Silent | KRP1A-m12 |
| G657A | T155= | Krp1A | Silent | KRP1A-m13 |
| C659T | T156M | Krp1A | Severe Missense | KRP1A-m14 |
| C661T | P157S | Krp1A | Severe Missense | KRP1A-m15 |
| C676T | P162S | Krp1A | Missense | KRP1A-m16 |
| C694T | L168= | Krp1A | Silent | KRP1A-m17 |
| G725A | G178D | Krp1A | Missense | KRP1A-m18 |
| C739T | P183S | Krp1A | Missense | KRP1A-m19 |
| C746T | T185M | Krp1A | Missense | KRP1A-m20 |
| C748T | P186S | Krp1A | Missense | KRP1A-m21 |
| C749T | P186L | Krp1A | Missense | KRP1A-m22 |
| C756T | A188= | Krp1A | Silent | KRP1A-m23 |
| C762T | A190= | Krp1A | Silent | KRP1A-m24 |
| C766T | P192S | Krp1A | Missense | KRP1A-m25 |
| C767T | P192L | Krp1A | Missense | KRP1A-m26 |
| C787T | P199S | Krp1A | Missense | KRP1A-m27 |
| C788T | P199L | Krp1A | Severe Missense | KRP1A-m28 |
| G808A | E206K | Krp1A | Missense | KRP1A-m29 |
| C818T | A209V | Krp1A | Severe Missense | KRP1A-m30 |
| G826A | E212K | Krp1A | Severe Missense | KRP1A-m31 |
| G828A | E212= | Krp1A | Silent | KRP1A-m32 |
| G832A | A214T | Krp1A | Missense | KRP1A-m33 |
| C834T | A214= | Krp1A | Silent | KRP1A-m34 |
| G879A | Intron | Krp1A | | KRP1A-m35 |
| G880A | Intron | Krp1A | | KRP1A-m36 |
| C925T | Intron | Krp1A | | KRP1A-m37 |
| G939A | Intron | Krp1A | | KRP1A-m38 |
| G940A | Intron | Krp1A | | KRP1A-m39 |
| G961A | A228T | Krp1A | Missense | KRP1A-m40 |
| G965A | R229H | Krp1A | Missense | KRP1A-m41 |
| C974T | P232L | Krp1A | Severe Missense | KRP1A-m42 |
| C978T | L233= | Krp1A | Silent | KRP1A-m43 |
| C983T | S235F | Krp1A | Severe Missense | KRP1A-m44 |
| G985A | G236S | Krp1A | Severe Missense | KRP1A-m45 |
| G999A | W240* | Krp1A | Nonsense | KRP1A-m46 |
| C1002T | T241= | Krp1A | Silent | KRP1A-m47 |
| C1003T | P242S | Krp1A | Missense | KRP1A-m48 |
| G1016A | S246N | Krp1A | Severe Missense | KRP1A-m49 |
| G1019A | S247N | Krp1A | Severe Missense | KRP1A-m50 |

TABLE 3-continued

Summary of *Triticum aestivum* (hexaploid) KRP1A mutants

| Nucleotide Change^ | Effect | Gene | Mutation Score | Mutation Identifier |
|---|---|---|---|---|
| C1020T | S247= | Krp1A | Silent | KRP1A-m51 |
| G1027A | Non-coding | Krp1A | | KRP1A-m52 |
| G1037A | Non-coding | Krp1A | | KRP1A-m53 |
| G1043A | Non-coding | Krp1A | | KRP1A-m54 |
| G1051A | Non-coding | Krp1A | | KRP1A-m55 |

§Exons 2-4 of wheat KRP1A were TILLed.

^Nucleotide numbering is dependent upon the location of TILLING ® primers.

TABLE 4

Summary of *Triticum aestivum* (hexaploid) KRP1B mutants

| Nucleotide Change^ | Effect | Gene | Mutation Score | Mutation Identifier |
|---|---|---|---|---|
| C562T | G136= | Krp1B§ | Silent | KRP1B-m1 |
| C567T | A138V | Krp1B | Missense | KRP1B-m2 |
| C589T | G145= | Krp1B | Silent | KRP1B-m3 |
| C595T | N147= | Krp1B | Silent | KRP1B-m4 |
| G597A | R148H | Krp1B | Missense | KRP1B-m5 |
| G603A | R150K | Krp1B | Missense | KRP1B-m6 |
| G606A | Splice Junction | Krp1B | Splice | KRP1B-m7 |
| G614A | Intron | Krp1B | | KRP1B-m8 |
| G662A | Intron | Krp1B | | KRP1B-m9 |
| C667T | Intron | Krp1B | | KRP1B-m10 |
| C674T | Intron | Krp1B | | KRP1B-m11 |
| C679T | Intron | Krp1B | | KRP1B-m12 |
| G708A | E152K | Krp1B | Severe Missense | KRP1B-m13 |
| G710A | E152= | Krp1B | Silent | KRP1B-m14 |
| C715T | T154M | Krp1B | Severe Missense | KRP1B-m15 |
| C718T | P155L | Krp1B | Severe Missense | KRP1B-m16 |
| C721T | S156F | Krp1B | Severe Missense | KRP1B-m17 |
| G724A | S157N | Krp1B | Missense | KRP1B-m18 |
| C741T | L163= | Krp1B | Silent | KRP1B-m19 |
| G752A | L166= | Krp1B | Silent | KRP1B-m20 |
| G769A | G172D | Krp1B | Missense | KRP1B-m21 |
| C776T | N174= | Krp1B | Silent | KRP1B-m22 |
| C787T | S178L | Krp1B | Missense | KRP1B-m23 |
| G788A | S178= | Krp1B | Silent | KRP1B-m24 |
| G797A | P181= | Krp1B | Silent | KRP1B-m25 |
| C798T | Q182* | Krp1B | Nonsense | KRP1B-m26 |
| C802T | T183M | Krp1B | Missense | KRP1B-m27 |
| G803A | T183= | Krp1B | Silent | KRP1B-m28 |
| C805T | P184L | Krp1B | Missense | KRP1B-m29 |
| C808T | T185I | Krp1B | Severe Missense | KRP1B-m30 |
| C811T | A186V | Krp1B | Missense | KRP1B-m31 |
| C812T | A186= | Krp1B | Silent | KRP1B-m32 |
| C827T | A191= | Krp1B | Silent | KRP1B-m33 |
| G828A | A192T | KRP1B | Missense | KRP1B-m34 |
| G830A | A192= | Krp1B | Silent | KRP1B-m35 |
| G832A | R193K | Krp1B | Missense | KRP1B-m36 |
| G839A | R195= | Krp1B | Silent | KRP1B-m37 |
| C843T | P197S | Krp1B | Severe Missense | KRP1B-m38 |
| G857A | E201= | Krp1B | Silent | KRP1B-m39 |
| C874T | A207V | Krp1B | Severe Missense | KRP1B-m40 |
| G876A | A208T | Krp1B | Missense | KRP1B-m41 |
| G879A | A209T | KRP1B | Severe Missense | KRP1B-m42 |
| G882A | E210K | Krp1B | Severe Missense | KRP1B-m43 |
| G884A | E210= | Krp1B | Silent | KRP1B-m44 |
| G885A | E211K | Krp1B | Missense | KRP1B-m45 |
| G891A | E213K | Krp1B | Missense | KRP1B-m46 |
| A897C | R215= | Krp1B | Silent | KRP1B-m47 |
| G918A | Intron | Krp1B | | KRP1B-m48 |
| C927T | Intron | Krp1B | | KRP1B-m49 |
| G929A | Intron | Krp1B | | KRP1B-m50 |
| C930A | Intron | Krp1B | | KRP1B-m51 |
| G934A | Intron | Krp1B | | KRP1B-m52 |
| C942T | Intron | Krp1B | | KRP1B-m53 |
| G960A | Intron | Krp1B | | KRP1B-m54 |
| C965T | Intron | KRP1B | | KRP1B-m55 |
| G966A | Intron | KRP1B | | KRP1B-m56 |
| G972A | Intron | Krp1B | | KRP1B-m57 |

TABLE 4-continued

Summary of *Triticum aestivum* (hexaploid) KRP1B mutants

| Nucleotide Change^ | Effect | Gene | Mutation Score | Mutation Identifier |
|---|---|---|---|---|
| G983A | Intron | Krp1B | | KRP1B-m58 |
| C1006T | Y221= | Krp1B | Silent | KRP1B-m59 |
| C1015T | D224= | Krp1B | Silent | KRP1B-m60 |
| C1034T | L231F | Krp1B | Severe Missense | KRP1B-m61 |
| G1044A | G234D | Krp1B | Severe Missense | KRP1B-m62 |
| C1045T | G234= | Krp1B | Silent | KRP1B-m63 |
| C1046T | R235W | Krp1B | Severe Missense | KRP1B-m64 |
| G1064A | A241T | Krp1B | Missense | KRP1B-m65 |
| C1065T | A241V | Krp1B | Missense | KRP1B-m66 |
| A1084C | Intron | Krp1B | | KRP1B-m67 |
| C1086T | Intron | KRP1B | | KRP1B-m68 |
| G1088A | Intron | Krp1B | | KRP1B-m69 |
| G1094A | Intron | Krp1B | | KRP1B-m70 |
| C1095T | Intron | Krp1B | | KRP1B-m71 |

§Exons 2-4 of wheat KRP1B were TILLed.

^Nucleotide numbering is dependent upon the location of TILLING ® primers.

TABLE 5

Summary of *Triticum aestivum* (hexaploid) KRP1D mutants

| Nucleotide Change^ | Effect | Gene | Mutation Score | Mutation Identifier |
|---|---|---|---|---|
| G638A | Splice Junction | Krp1D_2-4§ | Splice | Krp1D_2-4-m1 |
| C652T | P158S | Krp1D_2-4 | Severe Missense | Krp1D_2-4-m2 |
| C666T | F162= | Krp1D_2-4 | Silent | Krp1D_2-4-m3 |
| C668T | P163L | Krp1p_2-4 | Missense | Krp1D_2-4-m4 |
| C675T | D165= | Krp1D_2-4 | Silent | Krp1D_2-4-m5 |
| C685T | L169= | Krp1D_2-4 | Silent | Krp1D_2-4-m6 |
| C692T | S171L | Krp1D_2-4 | Missense | Krp1D_2-4-m7 |
| C697T | L173= | Krp1D_2-4 | Silent | Krp1D_2-4-m8 |
| G700A | A174T | Krp1D_2-4 | Missense | Krp1D_2-4-m9 |
| C701T | A174V | Krp1D_2-4 | Missense | Krp1D_2-4-m10 |
| G723A | S181= | Krp1D_2-4 | Silent | Krp1D_2-4-m11 |
| G738A | T186= | Krp1D_2-4 | Silent | Krp1D_2-4-m12 |
| C758T | P193L | Krp1D_2-4 | Missense | Krp1D_2-4-m13 |
| C761T | A194V | Krp1D_2-4 | Severe Missense | Krp1D_2-4-m14 |
| G765A | A195= | Krp1D_2-4 | Silent | Krp1D_2-4-m15 |
| G767A | R196K | Krp1D_2-4 | Missense | Krp1D_2-4-m16 |
| C778T | P200S | Krp1D_2-4 | Severe Missense | Krp1D_2-4-m17 |
| G780A | P200= | Krp1D_2-4 | Silent | Krp1D_2-4-m18 |
| G798A | E206= | Krp1D_2-4 | Silent | Krp1D_2-4-m19 |
| C809T | A210V | Krp1D_2-4 | Severe Missense | Krp1D_2-4-m20 |
| G817A | E213K | Krp1D_2-4 | Severe Missense | Krp1D_2-4-m21 |
| C831T | A217= | Krp1D_2-4 | Silent | Krp1D_2-4-m22 |
| G833A | R218K | Krp1D_2-4 | Missense | Krp1D_2-4-m23 |
| G845A | C222Y | Krp1D_2-4 | Missense | Krp1D_2-4-m24 |
| G870A | Intron | Krp1D_2-4 | | Krp1D_2-4-m25 |
| C911T | Intron | Krp1D_2-4 | | Krp1D_2-4-m26 |
| C933T | Intron | Krp1D_2-4 | | Krp1D_2-4-m27 |
| C938T | Intron | Krp1D_2-4 | | Krp1D_2-4-m28 |
| C956T | D227= | Krp1D_2-4 | Silent | Krp1D_2-4-m29 |
| C963T | R230C | Krp1D_2-4 | Severe Missense | Krp1D_2-4-m30 |
| G967A | G231D | Krp1D_2-4 | Missense | Krp1D_2-4-m31 |
| C974T | P233= | Krp1D_2-4 | Silent | Krp1D_2-4-m32 |
| C975T | L234F | Krp1D_2-4 | Severe Missense | Krp1D_2-4-m33 |
| C983T | S236= | Krp1D_2-4 | Silent | Krp1D_2-4-m34 |
| C986T | G237= | Krp1D_2-4 | Silent | Krp1D_2-4-m35 |
| C1001T | T242= | Krp1D_2-4 | Silent | Krp1D_2-4-m36 |

TABLE 5-continued

Summary of *Triticum aestivum* (hexaploid) KRP1D mutants

| Nucleotide Change^ | Effect | Gene | Mutation Score | Mutation Identifier |
|---|---|---|---|---|
| C1006T | A244V | Krp1D_2-4 | Missense | Krp1D_2-4-m37 |
| G1026A | Non-coding | Krp1D_2-4 | | Krp1D_2-4-m38 |
| G1060A | Non-coding | Krp1D_2-4 | | Krp1D_2-4-m39 |
| C1028T | Non-coding | Krp1D_2-4 | | Krp1D_2-4-m40 |
| G1041A | Non-coding | Krp1D_2-4 | | Krp1D_2-4-m41 |

§The designation "2-4" indicates that Exons 2-4 of wheat KRP1D were TILLed.

^Nucleotide numbering is dependent upon the location of TILLING ® primers.

TABLE 6

Summary of *Triticum aestivum* (hexaploid) KRP2A mutants

| Nucleotide Change^ | Effect | Gene | Mutation Score | Mutation Identifier |
|---|---|---|---|---|
| G568A | Intron | KRP2A2§ | | KRP2A2-m1 |
| G584A | C153Y | KRP2A2 | Severe Missense | KRP2A2-m2 |
| C597T | D157= | KRP2A2 | Silent | KRP2A2-m3 |
| G601A | E159K | KRP2A2 | Missense | KRP2A2-m4 |
| C606T | S160= | KRP2A2 | Silent | KRP2A2-m5 |
| C608T | S161F | KRP2A2 | Severe Missense | KRP2A2-m6 |
| G614A | S163N | KRP2A2 | Missense | KRP2A2-m7 |
| G631A (part of WH16) | G169S | KRP2A2 | Missense | KRP2A2-m8 |
| G632A | G169D | KRP2A2 | Missense | KRP2A2-m9 |
| C651T | Intron | KRP2A2 | | KRP2A2-m10 |
| C663T | Intron | KRP2A2 | | KRP2A2-m11 |
| G669A | Intron | KRP2A2 | | KRP2A2-m12 |
| G742A | Intron | KRP2A2 | | KRP2A2-m13 |
| G764A | Intron | KRP2A2 | | KRP2A2-m14 |
| G765A | Intron | KRP2A2 | | KRP2A2-m15 |
| G773A | Splice Junction | KRP2A2 | Splice | KRP2A2-m16 |
| G774A | R172= (splice) | KRP2A2 | Splice | KRP2A2-m17 |
| C783T | T175= | KRP2A2 | Silent | KRP2A2-m18 |
| C787T | P177S | KRP2A2 | Severe Missense | KRP2A2-m19 |
| G813A | L185= | KRP2A2 | Silent | KRP2A2-m20 |
| C819T | D187= | KRP2A2 | Silent | KRP2A2-m21 |
| G825A | E189= | KRP2A2 | Silent | KRP2A2-m22 |
| G835A | A193T | KRP2A2 | Missense | KRP2A2-m23 |
| G838A | A194T | KRP2A2 | Missense | KRP2A2-m24 |
| C839T | A194V | KRP2A2 | Missense | KRP2A2-m25 |
| C843T | D195= | KRP2A2 | Silent | KRP2A2-m26 |
| G852A | K198= | KRP2A2 | Silent | KRP2A2-m27 |
| G860A | R201H | KRP2A2 | Missense | KRP2A2-m28 |
| G864A | R202= | KRP2A2 | Silent | KRP2A2-m29 |
| G873A | P205= | KRP2A2 | Silent | KRP2A2-m30 |
| G874A | A206T | KRP2A2 | Missense | KRP2A2-m31 |
| C875T | A206V | KRP2A2 | Missense | KRP2A2-m32 |
| C893T | A212V | KRP2A2 | Missense | KRP2A2-m33 |
| G895A | A213T | KRP2A2 | Severe Missense | KRP2A2-m34 |
| C903T | F215= | KRP2A2 | Silent | KRP2A2-m35 |
| G919A | A221T | KRP2A2 | Missense | KRP2A2-m36 |
| G929A | R224K | KRP2A2 | Missense | KRP2A2-m37 |
| C934T | P226S | KRP2A2 | Severe Missense | KRP2A2-m38 |
| G940A | A228T | KRP2A2 | Severe Missense | KRP2A2-m39 |
| C951T | I231= | KRP2A2 | Silent | KRP2A2-m40 |
| G952A | D232N | KRP2A2 | Missense | KRP2A2-m41 |
| G955A | E233K | KRP2A2 | Missense | KRP2A2-m42 |
| C963T | F235= | KRP2A2 | Silent | KRP2A2-m43 |
| C966T | A236= | KRP2A2 | Silent | KRP2A2-m44 |
| G978A | K240= | KRP2A2 | Silent | KRP2A2-m45 |
| C981T | A241= | KRP2A2 | Silent | KRP2A2-m46 |
| G984A | Q242= | KRP2A2 | Silent | KRP2A2-m47 |
| C996T | F246= | KRP2A2 | Silent | KRP2A2-m48 |
| C998T | A247V | KRP2A2 | Severe Missense | KRP2A2-m49 |

TABLE 6-continued

| Summary of *Triticum aestivum* (hexaploid) KRP2A mutants | | | | |
|---|---|---|---|---|
| Nucleotide Change^ | Effect | Gene | Mutation Score | Mutation Identifier |
| G1005A | Splice Junction | KRP2A2 | Splice | KRP2A2-m50 |
| G1011A | Intron | KRP2A2 | | KRP2A2-m51 |
| G1026A | Intron | KRP2A2 | | KRP2A2-m52 |
| C1046T | Intron | KRP2A2 | | KRP2A2-m53 |
| C1070T | Intron | KRP2A2 | | KRP2A2-m54 |
| C1076T | Intron | KRP2A2 | | KRP2A2-m55 |
| C1084T | Intron | KRP2A2 | | KRP2A2-m56 |
| G1086A | Intron | KRP2A2 | | KRP2A2-m57 |
| A1089G | Intron | KRP2A2 | | KRP2A2-m58 |
| C1092T | Intron | KRP2A2 | | KRP2A2-m59 |
| C1104T | Intron | KRP2A2 | | KRP2A2-m60 |
| G1109A | Intron | KRP2A2 | | KRP2A2-m61 |
| C1110T | Intron | KRP2A2 | | KRP2A2-m62 |
| T1111A | Intron | KRP2A2 | | KRP2A2-m63 |
| C1118T | Intron | KRP2A2 | | KRP2A2-m64 |
| C1121T | Intron | KRP2A2 | | KRP2A2-m65 |
| G1124A | K249= | KRP2A2 | Silent | KRP2A2-m66 |
| G1134A | D253N | KRP2A2 | Severe Missense | KRP2A2-m67 |
| G1137A | V254I | KRP2A2 | Missense | KRP2A2-m68 |
| C1143T | R256C | KRP2A2 | Severe Missense | KRP2A2-m69 |
| C1145T | R256= | KRP2A2 | Silent | KRP2A2-m70 |
| G1146A | G257S | KRP2A2 | Severe Missense | KRP2A2-m71 |
| G1147A | G257D | KRP2A2 | Severe Missense | KRP2A2-m72 |
| G1149A(part of WH16) | V258M | KRP2A2 | Severe Missense | KRP2A2-m73 |
| C1152T | P259S | KRP2A2 | Severe Missense | KRP2A2-m74 |
| C1162T | A262V | KRP2A2 | Severe Missense | KRP2A2-m75 |
| G1165A | G263D | KRP2A2 | Severe Missense | KRP2A2-m76 |
| C1167T | R264W | KRP2A2 | Severe Missense | KRP2A2-m77 |
| G1169A | R264= | KRP2A2 | Silent | KRP2A2-m78 |
| G1194A | V273I | KRP2A2 | Missense | KRP2A2-m79 |
| G1201A | Non-coding | KRP2A2 | | KRP2A2-m80 |
| C1216T | Non-coding | KRP2A2 | | KRP2A2-m81 |
| G1225A | Non-coding | KRP2A2 | | KRP2A2-m82 |
| G1227A | Non-coding | KRP2A2 | | KRP2A2-m83 |
| G1230A | Non-coding | KRP2A2 | | KRP2A2-m84 |
| G1254A | Non-coding | KRP2A2 | | KRP2A2-m85 |

[§]The designation "2" indicates that exons 2-4 of wheat KRP2A were TILLed.
^Nucleotide numbering is dependent upon the location of TILLING ® primers.

TABLE 7

| Summary of *Triticum aestivum* (hexaploid) KRP2B mutants | | | | |
|---|---|---|---|---|
| Nucleotide Change^ | Effect | Gene | Mutation Score | Mutation Identifier |
| C27A | Non-coding | KRP2B2[§] | | KRP2B2-m1 |
| G57A | V7M[£] | KRP2B2 | Missense | KRP2B2-m2 |
| C67T | S10F | KRP2B2 | Severe Missense | KRP2B2-m3 |
| C111T | Intron | KRP2B2 | | KRP2B2-m4 |
| C115T | Intron | KRP2B2 | | KRP2B2-m5 |
| C233T | Intron | KRP2B2 | | KRP2B2-m6 |
| G241A | E23K | KRP2B2 | Missense | KRP2B2-m7 |
| G243A | E23= | KRP2B2 | Silent | KRP2B2-m8 |
| C248T | T25M | KRP2B2 | Severe Missense | KRP2B2-m9 |
| C250T | P26S | KRP2B2 | Severe Missense | KRP2B2-m10 |
| C263T | S30L | KRP2B2 | Missense | KRP2B2-m11 |
| C283T | L37= | KRP2B2 | Silent | KRP2B2-m12 |
| G286A | E38K | KRP2B2 | Missense | KRP2B2-m13 |
| C295T | Q41* | KRP2B2 | Nonsense | KRP2B2-m14 |
| G304A | D44N | KRP2B2 | Missense | KRP2B2-m15 |
| G307A | E45K | KRP2B2 | Missense | KRP2B2-m16 |
| G315A | K47= | KRP2B2 | Silent | KRP2B2-m17 |
| C322T | R50C | KRP2B2 | Missense | KRP2B2-m18 |
| G326A | R51K | KRP2B2 | Missense | KRP2B2-m19 |
| G329A | R52K | KRP2B2 | Missense | KRP2B2-m20 |
| C338T | A55V | KRP2B2 | Missense | KRP2B2-m21 |
| G340A | A56T | KRP2B2 | Missense | KRP2B2-m22 |
| G358A | A62T | KRP2B2 | Severe Missense | KRP2B2-m23 |
| C366T | F64= | KRP2B2 | Silent | KRP2B2-m24 |
| C375T | D67= | KRP2B2 | Silent | KRP2B2-m25 |
| G379A | E69K | KRP2B2 | Missense | KRP2B2-m26 |
| G403A | A77T | KRP2B2 | Missense | KRP2B2-m27 |
| G405A | A77= | KRP2B2 | Silent | KRP2B2-m28 |
| C497T | Intron | KRP2B2 | | KRP2B2-m29 |
| C503T | Intron | KRP2B2 | | KRP2B2-m30 |
| G523A | Intron | KRP2B2 | | KRP2B2-m31 |
| G527A | Intron | KRP2B2 | | KRP2B2-m32 |
| C553T | Intron | KRP2B2 | | KRP2B2-m33 |
| G591A | Splice Junction | KRP2B2 | Splice | KRP2B2-m34 |
| C623T | L109F | KRP2B2 | Severe Missense | KRP2B2-m35 |
| G643A | E115= | KRP2B2 | Silent | KRP2B2-m36 |
| G646A | W116* | KRP2B2 | Nonsense | KRP2B2-m37 |
| G653A | V119M | KRP2B2 | Missense | KRP2B2-m38 |
| C671T | Non-coding | KRP2B2 | | KRP2B2-m39 |
| C675T | Non-coding | KRP2B2 | | KRP2B2-m40 |
| C689T | Non-coding | KRP2B2 | | KRP2B2-m41 |
| G692A | Non-coding | KRP2B2 | | KRP2B2-m42 |
| T699A | Non-coding | KRP2B2 | | KRP2B2-m43 |
| G705A | Non-coding | KRP2B2 | | KRP2B2-m44 |
| G714A | Non-coding | KRP2B2 | | KRP2B2-m45 |
| G812A | Non-coding | KRP2B2 | | KRP2B2-m46 |
| G860A | Non-coding | KRP2B2 | | KRP2B2-m47 |
| C862T | Non-coding | KRP2B2 | | KRP2B2-m48 |

[§]The designation "2" indicates that exons 2-4 of wheat KRP2B were TILLed.
[£]Amino acid numbering does not start from the beginning Methionine.
^Nucleotide numbering is dependent upon the location of TILLING ® primers.

TABLE 8

| Summary of *Triticum aestivum* (hexaploid) KRP2D mutants | | | | |
|---|---|---|---|---|
| Nucleotide Change^ | Effect | Gene | Mutation Score | Mutation Identifier |
| G551A | Intron | KRP2D2[§] | | KRP2D2-m1 |
| G584A | A151T | KRP2D2 | Severe Missense | KRP2D2-m2 |
| G586A | A151= | KRP2D2 | Silent | KRP2D2-m3 |
| G588A | C152Y | KRP2D2 | Missense | KRP2D2-m4 |
| C596T | R155C | KRP2D2 | Severe Missense | KRP2D2-m5 |
| G597A | R155H | KRP2D2 | Missense | KRP2D2-m6 |
| G604A | V157= | KRP2D2 | Silent | KRP2D2-m7 |
| G609A | S159N | KRP2D2 | Missense | KRP2D2-m8 |
| C610T | S159= | KRP2D2 | Silent | KRP2D2-m9 |
| C613T | S160= | KRP2D2 | Silent | KRP2D2-m10 |
| G614A | V161I | KRP2D2 | Missense | KRP2D2-m11 |
| C616T | V161= | KRP2D2 | Silent | KRP2D2-m12 |
| G618A | S162N | KRP2D2 | Missense | KRP2D2-m13 |
| G633A | G167D | KRP2D2 | Missense | KRP2D2-m14 |
| C638T | R169W | KRP2D2 | Severe Missense | KRP2D2-m15 |
| G639A | R169Q | KRP2D2 | Severe Missense | KRP2D2-m16 |
| G640A | R169= | KRP2D2 | Silent | KRP2D2-m17 |
| G646A | Splice Junction | KRP2D2 | Splice | KRP2D2-m18 |
| C652T | Intron | KRP2D2 | | KRP2D2-m19 |
| C653T | Intron | KRP2D2 | | KRP2D2-m20 |
| C655T | Intron | KRP2D2 | | KRP2D2-m21 |
| G663A | Intron | KRP2D2 | | KRP2D2-m22 |
| C668T | Intron | KRP2D2 | | KRP2D2-m23 |
| C682T | Intron | KRP2D2 | | KRP2D2-m24 |
| G761A | Intron | KRP2D2 | | KRP2D2-m25 |
| G762A | Intron | KRP2D2 | | KRP2D2-m26 |
| G769A | Intron | KRP2D2 | | KRP2D2-m27 |
| G778A | R171= | KRP2D2 | Silent | KRP2D2-m28 |

TABLE 8-continued

Summary of *Triticum aestivum* (hexaploid) KRP2D mutants

| Nucleotide Change^ | Effect | Gene | Mutation Score | Mutation Identifier |
|---|---|---|---|---|
| G780A | R172K | KRP2D2 | Missense | KRP2D2-m29 |
| G784A | E173= | KRP2D2 | Silent | KRP2D2-m30 |
| C786T | T174M | KRP2D2 | Severe Missense | KRP2D2-m31 |
| G787A | T174= | KRP2D2 | Silent | KRP2D2-m32 |
| G790A | T175= | KRP2D2 | Silent | KRP2D2-m33 |
| C799T | S178= | KRP2D2 | Silent | KRP2D2-m34 |
| G805A | S180= | KRP2D2 | Silent | KRP2D2-m35 |
| C806T | P181S | KRP2D2 | Severe Missense | KRP2D2-m36 |
| G817A | L184= | KRP2D2 | Silent | KRP2D2-m37 |
| G819A | S185N | KRP2D2 | Missense | KRP2D2-m38 |
| C823T | D186= | KRP2D2 | Silent | KRP2D2-m39 |
| C836T | Q191* | KRP2D2 | Nonsense | KRP2D2-m40 |
| C840T | A192V | KRP2D2 | Severe Missense | KRP2D2-m41 |
| G844A | A193= | KRP2D2 | Silent | KRP2D2-m42 |
| C847T | D194= | KRP2D2 | Silent | KRP2D2-m43 |
| C863T | R200C | KRP2D2 | Severe Missense | KRP2D2-m44 |
| C865T | R200= | KRP2D2 | Silent | KRP2D2-m45 |
| G868A | R201= | KRP2D2 | Silent | KRP2D2-m46 |
| G870A | R202K | KRP2D2 | Missense | KRP2D2-m47 |
| G871A | R202= | KRP2D2 | Silent | KRP2D2-m48 |
| C876T | P204L | KRP2D2 | Missense | KRP2D2-m49 |
| G877T | P204= | KRP2D2 | Silent | KRP2D2-m50 |
| G878A | A205T | KRP2D2 | Missense | KRP2D2-m51 |
| C885T | T207M | KRP2D2 | Missense | KRP2D2-m52 |
| G886A | T207= | KRP2D2 | Silent | KRP2D2-m53 |
| G896A | A211T | KRP2D2 | Missense | KRP2D2-m54 |
| C897T | A211V | KRP2D2 | Missense | KRP2D2-m55 |
| G899A | A212T | KRP2D2 | Missense | KRP2D2-m56 |
| C902T | P213S | KRP2D2 | Missense | KRP2D2-m57 |
| G907A | L214= | KRP2D2 | Silent | KRP2D2-m58 |
| C908T | H215Y | KRP2D2 | Missense | KRP2D2-m59 |
| G914A | D217N | KRP2D2 | Missense | KRP2D2-m60 |
| C916T | D217= | KRP2D2 | Silent | KRP2D2-m61 |
| G920A | E219K | KRP2D2 | Missense | KRP2D2-m62 |
| G923A | A220T | KRP2D2 | Missense | KRP2D2-m63 |
| G925A | A220= | KRP2D2 | Silent | KRP2D2-m64 |
| G933A | R223K | KRP2D2 | Missense | KRP2D2-m65 |
| G935A | A224T | KRP2D2 | Missense | KRP2D2-m66 |
| G940A | R225= | KRP2D2 | Silent | KRP2D2-m67 |
| C947T | P228S | KRP2D2 | Missense | KRP2D2-m68 |
| G953A | A230T | KRP2D2 | Missense | KRP2D2-m69 |
| C964T | D233= | KRP2D2 | Silent | KRP2D2-m70 |
| T968A | F235I | KRP2D2 | Severe Missense | KRP2D2-m71 |
| C970T | F235= | KRP2D2 | Silent | KRP2D2-m72 |
| C976T | A237= | KRP2D2 | Silent | KRP2D2-m73 |
| C978T | A238V | KRP2D2 | Severe Missense | KRP2D2-m74 |
| G980A | A239T | KRP2D2 | Severe Missense | KRP2D2-m75 |
| G982A | A239= | KRP2D2 | Silent | KRP2D2-m76 |
| G988A | K241= | KRP2D2 | Silent | KRP2D2-m77 |
| C991T | A242= | KRP2D2 | Silent | KRP2D2-m78 |
| G995A | A244T | KRP2D2 | Severe Missense | KRP2D2-m79 |
| G1000A | E245= | KRP2D2 | Silent | KRP2D2-m80 |
| C1001T | R246C | KRP2D2 | Severe Missense | KRP2D2-m81 |
| C1006T | F247= | KRP2D2 | Silent | KRP2D2-m82 |
| C1008T | A248V | KRP2D2 | Severe Missense | KRP2D2-m83 |
| G1010A | A249T | KRP2D2 | Missense | KRP2D2-m84 |
| C1011T | A249V | KRP2D2 | Missense | KRP2D2-m85 |
| G1022A | Intron | KRP2D2 | | KRP2D2-m86 |
| C917insA, G1035A | Insertion, intron | KRP2D2 | Add new aa, cyclin- and CDK-binding gone | KRP2D2-m87 |
| G1037A | Intron | KRP2D2 | | KRP2D2-m88 |
| G1045A | Intron | KRP2D2 | | KRP2D2-m89 |
| C1048T | Intron | KRP2D2 | | KRP2D2-m90 |
| G1069A | Intron | KRP2D2 | | KRP2D2-m91 |
| C1094T | Intron | KRP2D2 | | KRP2D2-m92 |
| C1100T | Intron | KRP2D2 | | KRP2D2-m93 |
| G1106A | Intron | KRP2D2 | | KRP2D2-m94 |
| C1116T | Intron | KRP2D2 | | KRP2D2-m95 |
| C1119T | Intron | KRP2D2 | | KRP2D2-m96 |
| G1126A | Splice Junction | KRP2D2 | Splice | KRP2D2-m97 |
| G1137A | D254N | KRP2D2 | Severe Missense | KRP2D2-m98 |
| C1139T | D254= | KRP2D2 | Silent | KRP2D2-m99 |
| C1142T | V255= | KRP2D2 | Silent | KRP2D2-m100 |
| C1144T | A256V | KRP2D2 | Missense | KRP2D2-m101 |
| G1145A | A256= | KRP2D2 | Silent | KRP2D2-m102 |
| C1146T | R257C | KRP2D2 | Severe Missense | KRP2D2-m103 |
| G1154A | V259= | KRP2D2 | Silent | KRP2D2-m104 |
| C1156T | P260L | KRP2D2 | Severe Missense | KRP2D2-m105 |

[§]The designation "2" indicates that exons 2-4 of wheat KRP2D were TILLed.

^Nucleotide numbering is dependent upon the location of TILLING ® primers.

TABLE 9

Summary of *Triticum aestivum* (hexaploid) KRP4B mutants

| Nucleotide Change^ | Effect | Gene | Mutation Score | Mutation Identifier |
|---|---|---|---|---|
| G370A | Non-coding | KRP4B2[§] | | 6xKRP4B2-m1 |
| C378T | Non-coding | KRP4B2 | | 6xKRP4B2-m2 |
| C401T | P8L[£] | KRP4B2 | Severe Missense | 6xKRP4B2-m3 |
| C408T | S10= | KRP4B2 | Silent | 6xKRP4B2-m4 |
| C422T | S15L | KRP4B2 | Missense | 6xKRP4B2-m5 |
| G424A | G16R | KRP4B2 | Missense | 6xKRP4B2-m6 |
| G429A | T17= | KRP4B2 | Silent | 6xKRP4B2-m7 |
| C440T | P21L | KRP4B2 | Severe Missense | 6xKRP4B2-m8 |
| C474T | S32= | KRP4B2 | Silent | 6xKRP4B2-m9 |
| A489G | Q37= | KRP4B2 | Silent | 6xKRP4B2-m10 |
| G525A | E49= | KRP4B2 | Silent | 6xKRP4B2-m11 |
| C537T | F53= | KRP4B2 | Silent | 6xKRP4B2-m12 |
| C540T | F54= | KRP4B2 | Silent | 6xKRP4B2-m13 |
| C545T | A56V | KRP4B2 | Missense | 6xKRP4B2-m14 |
| G550A | E58K | KRP4B2 | Severe Missense | 6xKRP4B2-m15 |
| G780A | Splice Junction | KRP4B2 | Splice | 6xKRP4B2-m16 |
| G780A | Splice Junction | KRP4B2 | Splice | 6xKRP4B2-m17 |
| C810T | P78L | KRP4B2 | Severe Missense | 6xKRP4B2-m18 |
| C812T | L79F | KRP4B2 | Severe Missense | 6xKRP4B2-m19 |
| G832A | W85* | KRP4B2 | Nonsense | 6xKRP4B2-m20 |
| G846A | *90= | KRP4B2 | Silent | 6xKRP4B2-m21 |
| G846A | *90= | KRP4B2 | Silent | 6xKRP4B2-m22 |
| G858A | Non-coding | KRP4B2 | | 6xKRP4B2-m23 |
| G867A | Non-coding | KRP4B2 | | 6xKRP4B2-m24 |
| G922A | Non-coding | KRP4B2 | | 6xKRP4B2-m25 |

[§]The designation "2" indicates that exons 2-3 of wheat KRP4B were TILLed.

[£]Amino acid numbering does not start from the beginning Methionine.

^Nucleotide numbering is dependent upon the location of TILLING ® primers.

TABLE 10

Summary of *Triticum aestivum* (hexaploid) KRP4D mutants

| Nucleotide Change^ | Effect | Gene | Mutation Score | Mutation Identifier |
|---|---|---|---|---|
| C332T | Non-coding | KRP4D2[§] | | KRP4D2-m1 |
| G388A | R1=[£] | KRP4D2 | Silent | KRP4D2-m2 |
| C393T | T3I | KRP4D2 | Severe Missense | KRP4D2-m3 |
| G397A | R4= | KRP4D2 | Silent | KRP4D2-m4 |
| G400A | E5= | KRP4D2 | Silent | KRP4D2-m5 |
| C407T | P8S | KRP4D2 | Severe Missense | KRP4D2-m6 |
| C409T | P8= | KRP4D2 | Silent | KRP4D2-m7 |
| G418A | L11= | KRP4D2 | Silent | KRP4D2-m8 |
| T421C | I12= | KRP4D2 | Silent | KRP4D2-m9 |
| G425A | D14N | KRP4D2 | Missense | KRP4D2-m10 |

TABLE 10-continued

Summary of *Triticum aestivum* (hexaploid) KRP4D mutants

| Nucleotide Change^ | Effect | Gene | Mutation Score | Mutation Identifier |
|---|---|---|---|---|
| C435T | T17M | KRP4D2 | Missense | KRP4D2-m11 |
| C447T | P21L | KRP4D2 | Severe Missense | KRP4D2-m12 |
| G462A | R26K | KRP4D2 | Missense | KRP4D2-m13 |
| C469T | S28= | KRP4D2 | Silent | KRP4D2-m14 |
| C481T | S32= | KRP4D2 | Silent | KRP4D2-m15 |
| C500T | P39S | KRP4D2 | Missense | KRP4D2-m16 |
| G503A | A40T | KRP4D2 | Missense | KRP4D2-m17 |
| C518T | P45S | KRP4D2 | Severe Missense | KRP4D2-m18 |
| C519T | P45L | KRP4D2 | Severe Missense | KRP4D2-m19 |
| C525T | S47L | KRP4D2 | Missense | KRP4D2-m20 |
| G527A | A48T | KRP4D2 | Missense | KRP4D2-m21 |
| G532A | E49= | KRP4D2 | Silent | KRP4D2-m22 |
| C547T | F54= | KRP4D2 | Silent | KRP4D2-m23 |
| G556A | A57= | KRP4D2 | Silent | KRP4D2-m24 |
| G559A | E58= | KRP4D2 | Silent | KRP4D2-m25 |
| C566T | Q61* | KRP4D2 | Nonsense | KRP4D2-m26 |
| G571A | Q62= | KRP4D2 | Silent | KRP4D2-m27 |
| C572T | Q63* | KRP4D2 | Nonsense | KRP4D2-m28 |
| C577T | A64= | KRP4D2 | Silent | KRP4D2-m29 |
| G593A | Intron | KRP4D2 | | KRP4D2-m30 |
| G732A | Intron | KRP4D2 | | KRP4D2-m31 |
| C761T | Intron | KRP4D2 | | KRP4D2-m32 |
| C775T | Intron | KRP4D2 | | KRP4D2-m33 |
| G780A | Splice Junction | KRP4D2 | Splice | KRP4D2-m34 |
| G791A | D72N | KRP4D2 | Severe Missense | KRP4D2-m35 |
| C810T | P78L | KRP4D2 | Severe Missense | KRP4D2-m36 |
| C815T | P80S | KRP4D2 | Missense | KRP4D2-m37 |
| G819A | G81D | KRP4D2 | Severe Missense | KRP4D2-m38 |
| C820T | G81= | KRP4D2 | Silent | KRP4D2-m39 |
| C853T | Non-coding | KRP4D2 | | KRP4D2-m40 |
| G858A | Non-coding | KRP4D2 | | KRP4D2-m41 |
| G863A | Non-coding | KRP4D2 | | KRP4D2-m42 |
| C882T | Non-coding | KRP4D2 | | KRP4D2-m43 |
| C889A | Non-coding | KRP4D2 | | KRP4D2-m44 |

[§]The designation "2" indicates that exons 2-3 of wheat KRP4D were TILLed.

[£]Amino acid numbering does not start from the beginning Methionine.

^Nucleotide numbering is dependent upon the location of TILLING ® primers.

TABLE 11

Summary of *Triticum aestivum* (hexaploid) KRP5A mutants

| Nucleotide Change^ | Effect | Gene | Mutation Score | Mutation Identifier |
|---|---|---|---|---|
| G84A | G25S | Krp5A1[§] | Severe Missense | Krp5A1-m1 |
| C90T | R27C | Krp5A1 | Severe Missense | Krp5A1-m2 |
| C95T | T28= | Krp5A1 | Silent | Krp5A1-m3 |
| C100T | S30F | Krp5A1 | Severe Missense | Krp5A1-m4 |
| C101T | S30= | Krp5A1 | Silent | Krp5A1-m5 |
| C110T | L33= | Krp5A1 | Silent | Krp5A1-m6 |
| C112T | A34V | Krp5A1 | Severe Missense | Krp5A1-m7 |
| G114A | A35T | Krp5A1 | Silent | Krp5A1-m8 |
| G116A | A35= | Krp5A1 | Silent | Krp5A1-m9 |
| C130T | A40V | Krp5A1 | Missense | Krp5A1-m10 |
| G134A | P41= | Krp5A1 | Silent | Krp5A1-m11 |
| C137T | S42= | Krp5A1 | Silent | Krp5A1-m12 |
| C259T | A83V | Krp5A1 | Missense | Krp5A1-m13 |
| C405T | Intron | Krp5A1 | | Krp5A1-m14 |
| C139T | P43L | Krp5A1 | Missense | Krp5A1-m15 |
| C150G | R47G | Krp5A1 | Missense | Krp5A1-m16 |
| C150T | R47C | Krp5A1 | Missense | Krp5A1-m17 |
| G156A | G49S | Krp5A1 | Missense | Krp5A1-m18 |
| G162A | E51K | Krp5A1 | Missense | Krp5A1-m19 |
| G171A | D54N | Krp5A1 | Missense | Krp5A1-m20 |
| C173T | D54= | Krp5A1 | Silent | Krp5A1-m21 |
| G194A | R61= | Krp5A1 | Silent | Krp5A1-m22 |
| G196A | R62K | Krp5A1 | Severe Missense | Krp5A1-m23 |
| G197A | R62= | Krp5A1 | Silent | Krp5A1-m24 |
| G206A | K65= | Krp5A1 | Silent | Krp5A1-m25 |
| G212A | P67= | Krp5A1 | Silent | Krp5A1-m26 |

TABLE 11-continued

Summary of *Triticum aestivum* (hexaploid) KRP5A mutants

| Nucleotide Change^ | Effect | Gene | Mutation Score | Mutation Identifier |
|---|---|---|---|---|
| C216T | P69S | Krp5A1 | Severe Missense | Krp5A1-m27 |
| G219A | G70R | Krp5A1 | Missense | Krp5A1-m28 |
| C224T | P71= | Krp5A1 | Silent | Krp5A1-m29 |
| G234A | E75K | Krp5A1 | Missense | Krp5A1-m30 |
| G236A | E75= | Krp5A1 | Silent | Krp5A1-m31 |
| G240A | A77T | Krp5A1 | Missense | Krp5A1-m32 |
| G245A | P78= | Krp5A1 | Silent | Krp5A1-m33 |
| C249T | P80S | Krp5A1 | Severe Missense | Krp5A1-m34 |
| G251A | P80= | Krp5A1 | Silent | Krp5A1-m35 |
| C252T | P81S | Krp5A1 | Missense | Krp5A1-m36 |
| C257T | A82= | Krp5A1 | Silent | Krp5A1-m37 |
| G272A | R87= | Krp5A1 | Silent | Krp5A1-m38 |
| G278A | E89= | Krp5A1 | Silent | Krp5A1-m39 |
| C279T | Q90* | Krp5A1 | Nonsense | Krp5A1-m40 |
| G284A | A91= | Krp5A1 | Silent | Krp5A1-m41 |
| G290A | S93= | Krp5A1 | Silent | Krp5A1-m42 |
| C292T | S94L | Krp5A1 | Missense | Krp5A1-m43 |
| C296T | F95= | Krp5A1 | Silent | Krp5A1-m44 |
| C298T | A96V | Krp5A1 | Missense | Krp5A1-m45 |
| C302T | A97= | Krp5A1 | Silent | Krp5A1-m46 |
| G307A | G99D | Krp5A1 | Severe Missense | Krp5A1-m47 |
| C321T | L104F | Krp5A1 | Missense | Krp5A1-m48 |
| G357A | D116N | Krp5A1 | Severe Missense | Krp5A1-m49 |
| C368T | D119= | Krp5A1 | Silent | Krp5A1-m50 |
| C375T | Intron | Krp5A1 | | Krp5A1-m51 |
| G382A | Intron | Krp5A1 | | Krp5A1-m52 |
| C395T | Intron | Krp5A1 | | Krp5A1-m53 |
| C403T | Intron | Krp5A1 | | Krp5A1-m54 |
| C404T | Intron | Krp5A1 | | Krp5A1-m55 |
| C405T | Intron | Krp5A1 | | Krp5A1-m56 |
| C169T | Non-coding | Krp5A2[¥] | | Krp5A1-m57 |
| C199T | Non-coding | Krp5A2 | | Krp5A1-m58 |
| T201G | Non-coding | Krp5A2 | | Krp5A1-m59 |
| C213T | Non-coding | Krp5A2 | | Krp5A1-m60 |
| G227A | Non-coding | Krp5A2 | | Krp5A1-m61 |
| G232A | G1S[£] | Krp5A2 | Severe Missense | Krp5A1-m62 |
| G246A | T5= | Krp5A2 | Silent | Krp5A1-m63 |
| G257A | S9N | Krp5A2 | Missense | Krp5A1-m64 |
| G273A | S14= | Krp5A2 | Silent | Krp5A1-m65 |
| G274A | E15K | Krp5A2 | Severe Missense | Krp5A1-m66 |
| G276A | E15= | Krp5A2 | Silent | Krp5A1-m67 |
| C290T | P20L | Krp5A2 | Severe Missense | Krp5A1-m68 |
| C296T | S22L | Krp5A2 | Severe Missense | Krp5A1-m69 |
| C302T | T24I | Krp5A2 | Missense | Krp5A1-m70 |
| G305A | G25E | Krp5A2 | Missense | Krp5A1-m71 |
| G333A | R34= | Krp5A2 | Silent | Krp5A1-m72 |
| G345A | P38= | Krp5A2 | Silent | Krp5A1-m73 |
| G346A | V39I | Krp5A2 | Missense | Krp5A1-m74 |
| C351T | C40= | Krp5A2 | Silent | Krp5A1-m75 |
| G353A | R41H | Krp5A2 | Severe Missense | Krp5A1-m76 |
| C354T | R41= | Krp5A2 | Silent | Krp5A1-m77 |
| C366T | S45= | Krp5A2 | Silent | Krp5A1-m78 |
| G369A | S46= | Krp5A2 | Silent | Krp5A1-m79 |
| G372A | L47= | Krp5A2 | Silent | Krp5A1-m80 |
| C395T | A55V | Krp5A2 | Missense | Krp5A1-m81 |
| G402A | E57= | Krp5A2 | Silent | Krp5A1-m82 |
| G408A | Q59= | Krp5A2 | Silent | Krp5A1-m83 |
| C414T | H61= | Krp5A2 | Silent | Krp5A1-m84 |
| G426A | R65= | Krp5A2 | Silent | Krp5A1-m85 |
| G427A | D66N | Krp5A2 | Severe Missense | Krp5A1-m86 |
| G436A | Intron | Krp5A2 | | Krp5A1-m87 |
| N474A | Intron | Krp5A2 | | Krp5A1-m88 |
| C495T | Intron | Krp5A2 | | Krp5A1-m89 |
| G499A | Intron | Krp5A2 | | Krp5A1-m90 |
| G513A | K67= | Krp5A2 | | Krp5A1-m91 |
| C526T | P72S | Krp5A2 | Missense | Krp5A1-m92 |
| C537T | G75= | Krp5A2 | Silent | Krp5A1-m93 |
| C541T | P77S | Krp5A2 | Severe Missense | Krp5A1-m94 |
| C548T | P79L | Krp5A2 | Severe Missense | Krp5A1-m95 |
| G555A | R81= | Krp5A2 | Silent | Krp5A1-m96 |
| G568A | V86M | Krp5A2 | Severe Missense | Krp5A1-m97 |
| C593T | Non-coding | Krp5A2 | | Krp5A1-m98 |
| C599T | Non-coding | Krp5A2 | | Krp5A1-m99 |
| G608A | Non-coding | Krp5A2 | | Krp5A1-m100 |
| C614T | Non-coding | Krp5A2 | | Krp5A1-m101 |

TABLE 11-continued

Summary of *Triticum aestivum* (hexaploid) KRP5A mutants

| Nucleotide Change^ | Effect | Gene | Mutation Score | Mutation Identifier |
|---|---|---|---|---|
| C617T | Non-coding | Krp5A2 | | Krp5A1-m102 |
| C626T | Non-coding | Krp5A2 | | Krp5A1-m103 |
| C627T | Non-coding | Krp5A2 | | Krp5A1-m104 |
| C635T | Non-coding | Krp5A2 | | Krp5A1-m105 |
| C650T | Non-coding | Krp5A2 | | Krp5A1-m106 |
| G653A | Non-coding | Krp5A2 | | Krp5A1-m107 |
| G659A | Non-coding | Krp5A2 | | Krp5A1-m108 |
| G668A | Non-coding | Krp5A2 | | Krp5A1-m109 |

§The designation "1" indicates that exon 1 of wheat KRP5A was TILLed.

¥The designation "2" indicates that exons 2-3 of wheat KRP5A were TILLed.

£Amino acid numbering does not start from the beginning Methionine.

^Nucleotide numbering is dependent upon the location of TILLING ® primers.

TABLE 12

Summary of *Triticum aestivum* (hexaploid) KRP5D mutants

| Nucleotide Change^ | Effect | Gene | Mutation Score | Mutation Identifier |
|---|---|---|---|---|
| C205T | S9=£ | Krp5D2§ | Silent | Krp5D2-m1 |
| C206T | L10= | Krp5D2 | Silent | Krp5D2-m2 |
| G226A | T16= | Krp5D2 | Silent | Krp5D2-m3 |
| G229A | M17I | Krp5D2 | Missense | Krp5D2-m4 |
| G240A | G21E | Krp5D2 | Severe Missense | Krp5D2-m5 |
| G247A | A23= | Krp5D2 | Silent | Krp5D2-m6 |
| C249T | T24I | Krp5D2 | Severe Missense | Krp5D2-m7 |
| G258A | R27H | Krp5D2 | Missense | Krp5D2-m8 |
| C271T | R31= | Krp5D2 | Silent | Krp5D2-m9 |
| C272T | R32C | Krp5D2 | Severe Missense | Krp5D2-m10 |
| G280A | A34= | Krp5D2 | Silent | Krp5D2-m11 |
| G286A | T36= | Krp5D2 | Silent | Krp5D2-m12 |
| G290A | V38I | Krp5D2 | Missense | Krp5D2-m13 |
| C295T | C39= | Krp5D2 | Silent | Krp5D2-m14 |
| C296T | R40C | Krp5D2 | Severe Missense | Krp5D2-m15 |
| G302A | V42I | Krp5D2 | Missense | Krp5D2-m16 |
| G309A | S44N | Krp5D2 | Severe Missense | Krp5D2-m17 |
| C310T | S44= | Krp5D2 | Silent | Krp5D2-m18 |
| C312T | S45L | Krp5D2 | Missense | Krp5D2-m19 |
| G322A | M48I | Krp5D2 | Missense | Krp5D2-m20 |
| G323A | D49N | Krp5D2 | Missense | Krp5D2-m21 |
| G328A | E50= | Krp5D2 | Silent | Krp5D2-m22 |
| C339T | A54V | Krp5D2 | Missense | Krp5D2-m23 |
| C340T | A54= | Krp5D2 | Silent | Krp5D2-m24 |
| G344A | E56K | Krp5D2 | Severe Missense | Krp5D2-m25 |
| G369A | R64K | Krp5D2 | Missense | Krp5D2-m26 |
| G371A | E65K | Krp5D2 | Severe Missense | Krp5D2-m27 |
| G376A | Splice Junction | Krp5D2 | Splice | Krp5D2-m28 |
| C392T | Intron | Krp5D2 | | Krp5D2-m29 |
| G481A | Splice Junction | Krp5D2 | Splice | Krp5D2-m30 |
| C485T | Y67= | Krp5D2 | Silent | Krp5D2-m31 |
| C496T | P71L | Krp5D2 | Missense | Krp5D2-m32 |
| G506A | E74= | Krp5D2 | Silent | Krp5D2-m33 |
| C510T | P76S | Krp5D2 | Severe Missense | Krp5D2-m34 |
| C513T | L77F | Krp5D2 | Severe Missense | Krp5D2-m35 |
| C517T | P78L | Krp5D2 | Severe Missense | Krp5D2-m36 |
| G519A | G79R | Krp5D2 | Severe Missense | Krp5D2-m37 |
| G520A | G79E | Krp5D2 | Severe Missense | Krp5D2-m38 |
| G530A | E82= | Krp5D2 | Silent | Krp5D2-m39 |
| G532A | W83* | Krp5D2 | Nonsense | Krp5D2-m40 |
| C548T | C88= | Krp5D2 | Silent | Krp5D2-m41 |

§The designation "2" indicates that exons 2-3 of wheat KRP5D were TILLed.

£Amino acid numbering does not start from the beginning Methionine.

^Nucleotide numbering is dependent upon the location of TILLING ® primers.

Example 3

Wheat Breeding Program

The wheat KRP TILLING® mutants are prioritized for the breeding program in the following manner: 1) Nonsense and splice mutants; 2) Type I severe missense; and 3) Type II severe missense. Type I severe missense mutations are non-conservative amino acid substitutions in regions of the KRP protein known to be essential for binding to cyclin or cyclin-dependent kinase (CDK) and are predicted by SIFT analysis to be deleterious to protein function. Type II severe missense mutations are non-conservative amino acid substitutions outside of the cyclin and CDK binding domains but which satisfy two additional criteria. First, they are in regions of the protein determined by BLOCKS analysis (Henikoff, S. and Henikoff J. G. (1991) *Nucleic Acids Res.,* 19, 6565-6572) to be evolutionarily conserved and therefore possibly of functional significance. Secondly, they have a SIFT (Ng, P. C. and Henikoff, S. (2003) *Nucleic Acids Res*. July 1; 31(13): 3812-3814) score of less than 0.05, and are therefore predicted to be deleterious to protein function.

Tables 13 to 22 list wheat KRP TILLING® mutants that are in the breeding program and is a subset of the mutants listed in Tables 2 to 12. A given wheat (WH) group is a number that identifies a particular mutation in a particular gene.

M3 seed homozygous or heterozygous for a given KRP TILLING® mutation is grown. Backcrosses with the hexaploid spring background parent Express are performed, ideally through several rounds (to the BC3 or BC4 level), to eliminate deleterious background mutations. Background mutations could contribute to undesirable traits such as delayed maturity, premature senescence, increased susceptibility to wheat pathogens, slow germination, and/or sterility. The progeny of each backcross (F1, BC1, BC2, etc.) are also selfed to produce F2 lines. F2 lines are genotyped to identify ones that are homozygous for the wild type or for the krp mutant allele. Homozygote wild type and mutant siblings are seed expanded to F3 for field trials.

Wheat krp mutant alleles are introgressed into other spring and winter wheat to transfer the yield enhancement to commercial varieties.

Crosses between mutants are done to generate multiple stack mutants within a given KRP gene (e.g. krp1A/1B, krp1B/krp1D, krp1A/1B/1D, etc., all possible combinations) or across different KRP genes (e.g. krp1A/2A, krp2B/krp4B, krp4D/krp5A, krp1B/krp2A/krp5D, etc., all possible combinations).

The overall grain yield per unit area is determined (e.g. lbs/acre) and yield components such as seed count, seed size/weight (thousand kernel weight), seed per spike, head (spike) number, spike length, awn length, and/or tiller number, are measured. Agronomic characteristics such as stand rate, maturity rate and peduncle rate are also measured.

TABLE 13

*Triticum aestivum* (hexaploid) KRP2A TILLING ® Mutants in breeding program

| WH group | Gene | Nuc_Change from start codon | Effect-from beginning Met |
|---|---|---|---|
| 1 | KRP2A2 | G569A | C153Y |
| 2 | KRP2A2 | C593T | S161F |
| 3 | KRP2A2 | G758A | Splice junction-intron2/exon3 |

TABLE 13-continued

| *Triticum aestivum* (hexaploid) KRP2A TILLING ® Mutants in breeding program | | | |
|---|---|---|---|
| WH group | Gene | Nuc_Change from start codon | Effect-from beginning Met |
| 4 | KRP2A2 | G759A | Splice junction-intron2/exon3 |
| 5 | KRP2A2 | C772T | P177S (and P77S on 5A2, hom) |
| 6 | KRP2A2 | G880A | A213T |
| 7 | KRP2A2 | G880A | A213T |
| 8 | KRP2A2 | C919T | P226S |
| 9 | KRP2A2 | G925A | A228T |
| 10 | KRP2A2 | C983T | A247V |
| 11 | KRP2A2 | G990A | Splice junction - exon3/intron3 |
| 12 | KRP2A2 | G1119A | D253N |
| 13 | KRP2A2 | C1128T | R256C |
| 14 | KRP2A2 | G1131A | G257S |
| 15 | KRP2A2 | G1132A | G257D |
| 16 | KRP2A2 | G1134A | V258M and G169S |
| 17 | KRP2A2 | C1137T | P259S |
| 18 | KRP2A2 | C1147T | A262V |
| 19 | KRP2A2 | G1150A | G263D |
| 20 | KRP2A2 | C1152T | R264W |

TABLE 14

| *Triticum aestivum* (hexaploid) KRP2B TILLING ® Mutants in breeding program | | | |
|---|---|---|---|
| WH group | Gene | Nuc_Change from start codon | Effect-from beginning Met |
| 21 | KRP2B2 | G569A | V156M |
| 22 | KRP2B2 | C579T | S159F |
| 23 | KRP2B2 | G753A | E172K |
| 24 | KRP2B2 | C760T | T174M |
| 25 | KRP2B2 | C762T | P175S |
| 26 | KRP2B2 | C775T | S179L |
| 27 | KRP2B2 | G798A | E187K |
| 28 | KRP2B2 | C807T | Q190* |
| 29 | KRP2B2 | G816A | D193N |
| 30 | KRP2B2 | G819A | E194K |
| 31 | KRP2B2 | G838A | R200K |
| 32 | KRP2B2 | G841A | R201K |
| 33 | KRP2B2 | C850T | A204V |
| 34 | KRP2B2 | G852A | A205V |
| 35 | KRP2B2 | G870A | A211T |
| 36 | KRP2B2 | G891A | E218K |
| 37 | KRP2B2 | G915A | A226T |
| 38 | KRP2B2 | G1103A | Splice junction - intron3/exon4 |
| 39 | KRP2B2 | C1135T | L258F |
| 40 | KRP2B2 | G1158A | W265* |
| 41 | KRP2B2 | G1165A | V268M |
| 356 | KRP2B2 | C807T | Q190* |

TABLE 15A

| *Triticum turgidum* ssp. *durum* (tetraploid) KRP4B TILLING ® Mutants in breeding program | | | |
|---|---|---|---|
| WH group | Gene | Nuc_Change from start codon | Effect-from beginning Met |
| 42 | KRP4B2 | N/A^ | R105K |
| 43 | KRP4B2 | N/A | P109S |
| 46 | KRP4B2 | N/A | S129N |
| 49 | KRP4B2 | N/A | A149T |
| 54 | KRP4B2 | N/A | D177N |

TABLE 15A-continued

| *Triticum turgidum* ssp. *durum* (tetraploid) KRP4B TILLING ® Mutants in breeding program | | | |
|---|---|---|---|
| WH group | Gene | Nuc_Change from start codon | Effect-from beginning Met |
| 56 | KRP4B2 | N/A | P179L |
| 58 | KRP4B2 | N/A | L180F |
| 59 | KRP4B2 | N/A | P181S |

^Full-length genomic sequence of wild type KRP4B not available; therefore nucleotide numbering is as given in Table 8.

TABLE 15B

| *Triticum aestivum* (hexaploid) KRP4B TILLING ® Mutants in breeding program | | | |
|---|---|---|---|
| WH group | Gene | Nuc_Change from start codon | Effect-from beginning Met |
| 44 | KRP4B2 | N/A^ | P109L |
| 45 | KRP4B2 | N/A | S116L |
| 47 | KRP4B2 | N/A | G117R |
| 48 | KRP4B2 | N/A | P122L |
| 50 | KRP4B2 | N/A | A157V |
| 51 | KRP4B2 | N/A | E159K |
| 52 | KRP4B2 | N/A | Splice junction - intron2/exon3 |
| 53 | KRP4B2 | N/A | P179L |
| 55 | KRP4B2 | N/A | L180F |
| 57 | KRP4B2 | N/A | W186* |

^Full-length genomic sequence of wild type KRP4B not available; therefore nucleotide numbering is as given in Table 8.

TABLE 16

| *Triticum aestivum* (hexaploid) KRP4D TILLING ® Mutants in breeding program | | | |
|---|---|---|---|
| WH group | Gene | Nuc_Change from start codon | Effect-from beginning Met |
| 60 | KRP4D2 | N/A^ | T104I |
| 61 | KRP4D2 | N/A | P109S |
| 62 | KRP4D2 | N/A | D115N |
| 63 | KRP4D2 | N/A | P122L |
| 64 | KRP4D2 | N/A | R127K |
| 65 | KRP4D2 | N/A | P140S |
| 66 | KRP4D2 | N/A | A141T |
| 67 | KRP4D2 | N/A | P146S |
| 68 | KRP4D2 | N/A | P146L |
| 69 | KRP4D2 | N/A | S148L |
| 70 | KRP4D2 | N/A | A149T |
| 71 | KRP4D2 | N/A | Q162* |
| 72 | KRP4D2 | N/A | Q164* |
| 73 | KRP4D2 | N/A | Splice junction - intron2/exon3 |
| 74 | KRP4D2 | N/A | Splice junction - intron2/exon3 |
| 75 | KRP4D2 | N/A | D173N |
| 76 | KRP4D2 | N/A | P179L |
| 77 | KRP4D2 | N/A | P181S |
| 78 | KRP4D2 | N/A | G182D |

^Full-length genomic sequence of wild type KRP4D not available; therefore nucleotide numbering is as given in Table 9.

TABLE 17

*Triticum aestivum* (hexaploid) KRP5A TILLING ® Mutants in breeding program

| WH group | Gene | Nuc_Change from start codon | Effect-from beginning Met |
|---|---|---|---|
| 79 | KRP5A2 | G1850A | G121S |
| 80 | KRP5A2 | G1875A | S129N |
| 81 | KRP5A2 | G1892A | E135K |
| 82 | KRP5A2 | C1908T | P140L |
| 83 | KRP5A2 | C1914T | S142L |
| 84 | KRP5A2 | C1920T | T144I |
| 85 | KRP5A2 | G1923A | G145E |
| 86 | KRP5A2 | G1964A | V159I |
| 87 | KRP5A2 | G1971A | R161H |
| 88 | KRP5A2 | C2013T | A175V |
| 89 | KRP5A2 | G2045A | D186N |
| 90 | KRP5A2 | C2144T | P192S |
| 91 | KRP5A2 | C2159T | P197S |
| 92 | KRP5A2 | C2166T | P199L |
| 93 | KRP5A2 | G2186A | V206M |
| 545 | KRP5A1 | C268T | Q90* |

TABLE 18

*Triticum aestivum* (hexaploid) KRP5D TILLING ® Mutants in breeding program

| WH group | Gene | Nuc_Change from start codon | Effect-from beginning Met |
|---|---|---|---|
| 112 | KRP5D2 | G1767A | G137E |
| 113 | KRP5D2 | C1776T | T140I |
| 114 | KRP5D2 | C1799T | R148C |
| 115 | KRP5D2 | C1823T | R156C |
| 116 | KRP5D2 | G1829A | V158I |
| 117 | KRP5D2 | G1836A | S160N |
| 118 | KRP5D2 | C1839T | S161L |
| 119 | KRP5D2 | G1849A | M164I |
| 120 | KRP5D2 | G1850A | D165N |
| 121 | KRP5D2 | G1871A | E172K |
| 122 | KRP5D2 | G1898A | E181K |
| 123 | KRP5D2 | G1903A | Splice junction - exon2/intron2 |
| 124 | KRP5D2 | G2008A | Splice junction - intron2/exon3 |
| 125 | KRP5D2 | C2023T | P187L |
| 126 | KRP5D2 | C2037T | P192S |
| 127 | KRP5D2 | C2040T | L193F |
| 128 | KRP5D2 | C2044T | P194L |
| 129 | KRP5D2 | G2046A | G195R |
| 130 | KRP5D2 | G2047A | G195E |
| 131 | KRP5D2 | G2059A | W199* |

TABLE 19

*Triticum aestivum* (hexaploid) KRP1B TILLING ® Mutants in breeding program

| WH group | Gene | Nuc Change from start codon | Effect from beginning Met |
|---|---|---|---|
| 147 | KRP1B | C503T | A138V |
| 148 | KRP1B | G539A | R150K |
| 149 | KRP1B | G644A | E152K |
| 150 | KRP1B | C654T | P155L |
| 151 | KRP1B | C657T | S156F |
| 152 | KRP1B | G705A | G172D |
| 153 | KRP1B | C723T | S178L |
| 154 | KRP1B | C738T | T183M |
| 155 | KRP1B | C744T | T185I |
| 156 | KRP1B | G764A | A192T |
| 157 | KRP1B | G768A | R193K |
| 158 | KRP1B | C779T | P197S |
| 159 | KRP1B | G815A | A209T |

TABLE 19-continued

*Triticum aestivum* (hexaploid) KRP1B TILLING ® Mutants in breeding program

| WH group | Gene | Nuc Change from start codon | Effect from beginning Met |
|---|---|---|---|
| 160 | KRP1B | G821A | E211K |
| 161 | KRP1B | G827A | E213K |
| 162 | KRP1B | G1000A | A241T |
| 550 | KRP1B | C733T | Q182* |
| 551 | KRP1B | G541A | Splice junction |

TABLE 20

*Triticum aestivum* (hexaploid) KRP1D TILLING ® Mutants in breeding program

| WH group | Gene | Nuc Change from start codon | Effect from beginning Met |
|---|---|---|---|
| 163 | KRP1D | G634A | Splice Junction - intron2/exon3 |
| 164 | KRP1D | C648T | P158S |
| 165 | KRP1D | C664T | P163L |
| 166 | KRP1D | C688T | S171L |
| 167 | KRP1D | G696A | A174T |
| 168 | KRP1D | C697T | A174V |
| 169 | KRP1D | C754T | P193L |
| 170 | KRP1D | C757T | A194V |
| 171 | KRP1D | G763A | R196K |
| 172 | KRP1D | C774T | P200S |
| 173 | KRP1D | C805T | A210V |
| 174 | KRP1D | G813A | E213K |
| 175 | KRP1D | G829A | R218K |
| 176 | KRP1D | G841A | C222Y |
| 177 | KRP1D | C959T | R230C |
| 178 | KRP1D | G963A | G231D |
| 179 | KRP1D | C971T | L234F |
| 180 | KRP1D | C1002T | A244V |

TABLE 21

*Triticum aestivum* (hexaploid) KRP1A TILLING ® Mutants in breeding program

| WH group | Gene | Nuc Change from start codon | Effect from beginning Met |
|---|---|---|---|
| 181 | KRP1A | G518A | A144T |
| 182 | KRP1A | G543A | R152K |
| 183 | KRP1A | G648A | E154K |
| 184 | KRP1A | C655T | T156M |
| 185 | KRP1A | C657T | P157S |
| 186 | KRP1A | C672T | P162S |
| 187 | KRP1A | C763T | P192L |
| 188 | KRP1A | C783T | P199S |
| 189 | KRP1A | C784T | P199L |
| 190 | KRP1A | G804A | E206K |
| 191 | KRP1A | C814T | A209V |
| 192 | KRP1A | G822A | E212K |
| 193 | KRP1A | G961A | R229H |
| 194 | KRP1A | C970T | P232L |
| 195 | KRP1A | C979T | S235F |
| 196 | KRP1A | G981A | G236S |
| 197 | KRP1A | G995A | W240* |
| 198 | KRP1A | C999T | P242S |
| 199 | KRP1A | G1012A | S246N |
| 200 | KRP1A | G1015A | S247N |

TABLE 22

| *Triticum aestivum* (hexaploid) KRP2D TILLING ® Mutants in breeding program | | | |
|---|---|---|---|
| WH group | Gene | Nuc Change from start codon | Effect from beginning Met |
| 201 | KRP2D | G563A | C152Y |
| 202 | KRP2D | C571T | R155C |
| 203 | KRP2D | G572A | R155H |
| 204 | KRP2D | G584A | S159N |
| 205 | KRP2D | G593A | S162N |
| 206 | KRP2D | C613T | R169W |
| 207 | KRP2D | G614A | R169Q |
| 208 | KRP2D | G753A | R171 = (splice) |
| 209 | KRP2D | C761T | T174M |
| 210 | KRP2D | C815T | A192V |
| 211 | KRP2D | C838T | R200C |
| 212 | KRP2D | C860T | T207M |
| 213 | KRP2D | C877T | P213S |
| 214 | KRP2D | C883T | H215Y |
| 215 | KRP2D | C922T | P228S |
| 216 | KRP2D | G928A | A230T |
| 217 | KRP2D | C953T | A238V |
| 218 | KRP2D | G955A | A239T |
| 219 | KRP2D | G1112A | D254N |
| 220 | KRP2D | C1121T | R257C |

Example 4

Genotyping of Wheat Krp TILLING® Mutations

Wheat KRP TILLING® mutations were genotyped by allelic discrimination primer/probe sets in a real-time PCR assay. First, genome-specific primers were used to amplify a given wheat KRP gene from a wheat genomic sample. The amplification product was then genotyped in a Taqman® allelic discrimination assay (AD assay, Applied Biosystems). The following is a specific example of an assay to genotype KRP4B2 P109L.

Forward primer TTC CTT ATT TTT TAT GAC TAT TGA TAT GTG TTC TTC (SEQ ID NO: 28) and reverse primer GTG GTC ATT TCA GAA TGA GCT GCT AAC CGT T (SEQ ID NO: 29) were used to amplify KRP4B2 from wheat genomic DNA. The PCR reaction contained 2 μL genomic DNA, 2.6 μL 10× Ex Taq reaction buffer, 2.0 μL 2.5 mM dNTPs, 0.75 μL each of 5 mM forward and reverse primers, 0.1 μL Ex Taq polymerase (5 units/μL, TaKaRa) and 17.8 μL $H_2O$ in a total reaction volume of 26 μL. PCR amplification conditions were: initial denaturation at 94° C., 2 min; 40 cycles of 94° C., 30 sec, 58° C., 30 sec, 72° C., 1 min 30 sec; final extension at 72° C., 5 min.

The amplification product was then used in an AD assay with flanking forward primer (TGTGTATGTATGTTTT-GTGGCTAGCA, SEQ ID NO: 30), flanking reverse primer (CGTTCCCGAGTCCCTAATCAAG SEQ ID NO: 31), a labeled probe specific to the wild type allele (VIC-TGC AG G GCG TCG TC-MGB-NFQ SEQ ID NO: 32) and a labeled probe specific to the mutant allele (FAM-C TGC AGA GCG TCG TC-MGB-NFQ SEQ ID NO: 33). The PCR reaction contained 2 μL of KRP4B2 amplification product, 3 μL ABI genotyping real time PCR master mix and 1 μL 6× (5.4 μM each primer/1.2 μM each probe) SNP-specific AD assay primer/probe mix in a total reaction volume of 6 μL. The real-time PCR was conducted on an ABI real-time machine per ABI PCR conditions.

Figure 2:
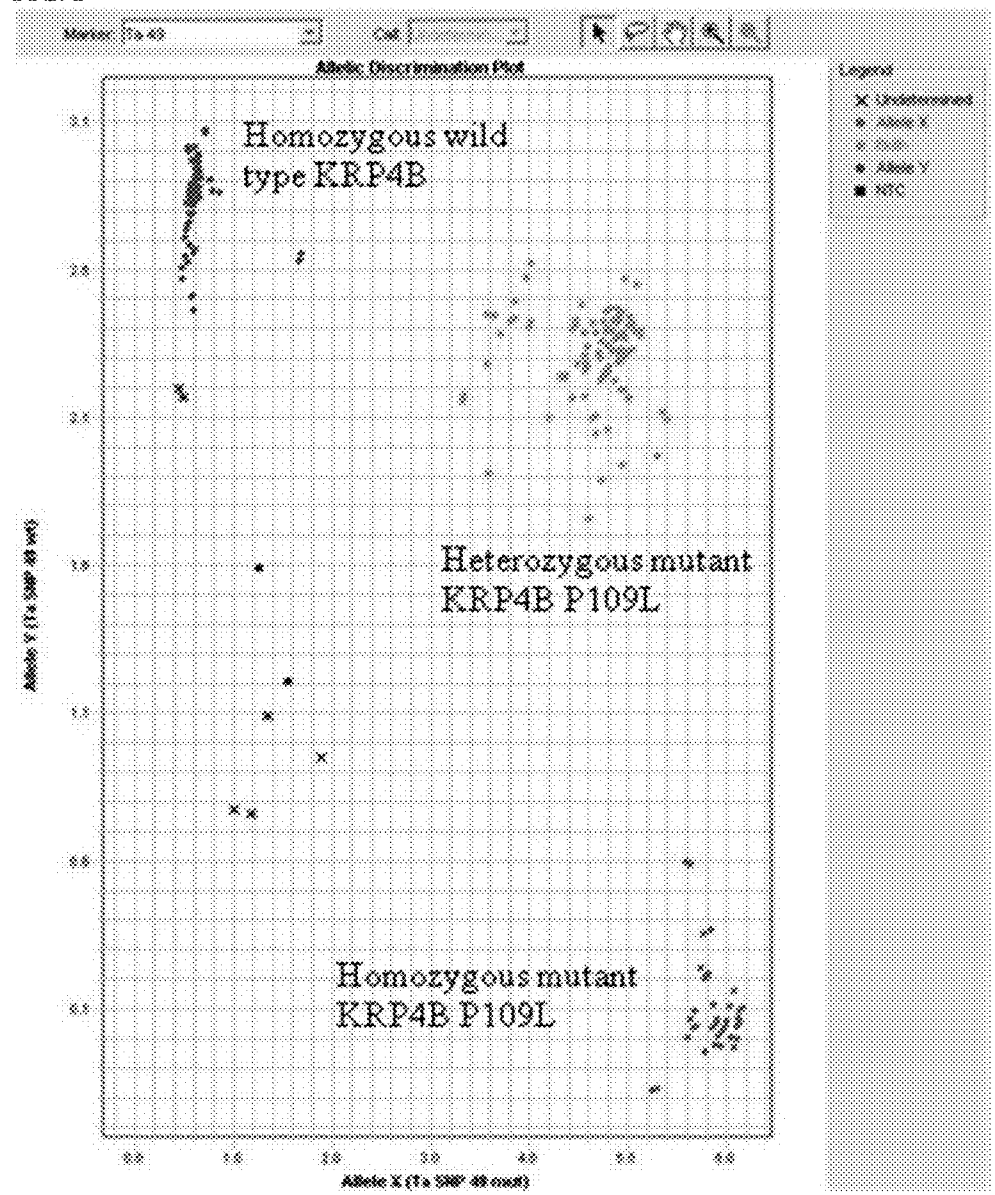
FIG. 2 depicts an allelic discrimination plot for samples in a KRP4B allelic discrimination assay. Samples homozygous for the wild type KRP4B allele are in blue, samples homozygous for the mutant KRP4B P109L allele are in red and samples heterozygous for the mutant KRP4B P109L allele are in green. Black squares represent no template controls and black x's are undetermined samples.

FIG. 1A-1C demonstrates that primer/probes can be designed to distinguish between wild type and mutant KRP4B alleles in an AD assay. A mutant heterozygous for the KRP4B P109L allele was confirmed by sequencing (FIG. 1D). FIG. 2 further shows that populations of samples homozygous for the wild type KRP4B allele, homozygous for the mutant KRP4B P109L allele, or heterozygous for the mutant KRP4B P109L allele can be easily distinguished in an AD assay.

In Vitro Assays to Test Kinase Inhibitory Activity of Mutant krp TILLING® Proteins Selected Type I severe missense and nonsense wheat KRP TILLING® mutants were tested in an in vitro assay to determine whether the mutant KRP proteins could still inhibit the kinase activity of ZmCyclinD4/ZmCDKA;1 kinase complex (FIG. 3) (assay described in Dominant Negative Mutant Kip-Related Proteins (KRP) in *Zea Mays* and Methods of their Use, PCT/US2011/060598).

Recombinant ZmCyclinD4 and ZmCDKA;1 were produced in and the complex isolated from *S. frugiperda* Sf9 insect cells. All wild-type TaKRP genes were synthesized by DNA2.0.

Mutagenesis of TaKRPs

TaKRP1A P232L (pTG1947)
TaKRP1A G236S (pTG1948)
TaKRP1A W240* (pTG1949)
TaKRP2D P228S (pTG1958)
TaKRP2D A238V (pTG1959)
TaKRP2D A239T (pTG1960)
TaKRP2D D254N (pTG1961)
TaKRP2D R257C (pTG1962)
TaKRP4A W186* (pTG1950)
TaKRP5A W199* (pTG1951)

Primers to generate the mutants listed above are found in Table 28.

General methods for recombinant protein expression in bacteria, purification and detection are described below:

I. Insect Cells and Media

The *baculovirus* expression system is a versatile eukaryotic system for heterologous gene expression. This system provides correct protein folding, disulfide bond formation and other important post-translational modifications. All methods were taken from the *Baculovirus expression vector system*: Procedures and methods manual. (BD Biosciences, Pharmingen, San Diego, Calif. 6th Ed.). Sf9 insect cells were grown at 27° C. in TNM-FH insect cell media (BD Biosciences) for the reported studies. It should be noted that alternative media are well known to the skilled artisan and are also useful. Similarly, alternative insect cell lines such as Sf21 and High Five™ cells will also work for virus production and protein production.

II. Western Blots and IPs

The recombinant protein expressed in insect cells was monitored by Western blot. Protein extracts (35 μg) were boiled in the presence of Laemmli buffer, run on 10% or 12% SDS-PAGE gels and transferred to a PVDF membrane using a submerged transfer apparatus (BioRad). Following the transfer, the membrane was blocked in TBS-T (25 mM Tris pH 7.5; 75 mM NaCl; 0.05% Tween) containing 5% non-fat dry milk powder. Primary antibody was used at 1:1000 dilution overnight in TBS-T blocking buffer. Blots were washed three times 15 minutes at room temperature. An appropriate secondary antibody conjugated to horse radish peroxidase (HRP) was used at 1:10,000 dilution in TBS-T blocking buffer. Blots were incubated in secondary antibody for 1 hour and then washed three times in TBS-T, 15 min each. Blots were then processed as described in the ECL system protocol (Amersham Biosciences). Antibodies commonly used were: anti-flag M2 monoclonal antibody (Sigma), anti-HA monoclonal or polyclonal antibody (Babco), anti-PSTAIR antibody (Sigma-Aldrich), anti-myc 9E10 monoclonal or polyclonal (A-14) (Santa Cruz Biotechnology). Secondary antibodies used were anti-mouse IgG-HRP, and anti-rabbit IgG-HRP (GE Healthcare).

III. *Baculovirus* Vector Construction

The *Baculovirus* system was Bac-to-bac (Invitrogen). Alternative *Baculovirus* genomes can also be used. All bacmids containing our genes of interest were independently transfected into 293 cells using lipid based transfection reagents such as Fugene or Lipofectamine. *S. frugiperda* Sf9 cells were seeded at $9\times10^6$ cells on 60 mm dish and transiently transfected with 1 μg bacmid using 3 μl Fugene 6 transfection reagent according to the manufacturer's protocol (Roche Diagnostics). After 4 hours of transfection the Fugene/DNA solution was removed and replaced with 3 ml of TNM-FH media. Four (4) days later, the supernatant was collected and subsequently used to infect more cells for amplification of the virus. This amplification was repeated until the virus titer was at least $10^9$ virus particles/ml. The virus was amplified by infecting Sf9 cells at a multiplicity of infection (moi) of <1. The virus titer was monitored using light and fluorescence microscopy.

IV. Recombinant Protein Expression in Bacteria and Purification

All bacterial expression plasmids carrying inserts were transformed into BL21 RosettaBlue (DE3) (Novagen). Bacterial colonies from this fresh transformation was used to inoculate 400 ml of LB containing 100 μg/ml of ampicillin and grown at 37° C. When the culture reached an $OD_{600}$ between 0.6 and 0.8 recombinant protein expression was induced with 1 mM isopropyl-D-thiogalactopyranoside (IPTG). Cells were then grown at 30° C. for three hours. Cells were collected by centrifugation in a JLA 10.500 Beckman rotor. Bacterial cell pellet was either stored at −80° C. or lysed immediately. Bacteria were lysed in 10 ml Phosphate lysis buffer (100 mM Phosphate buffer pH 7.0, 150 mM NaCl, 1% Triton X100) containing protease inhibitors and lacking EDTA. The resuspended bacterial culture was lysed via a French press or repeated sonication. Lysed cells were centrifuged at 14,000 rpm in a Beckman JA20.1 rotor for 15 minutes at 4° C. Tagged KRP molecules were mainly insoluble. Insoluble tagged KRPs were solubilized in Urea buffer (8M Urea, 100 mM Phosphate buffer pH 7.0) manually with a pipette aid. Urea-insoluble proteins were eliminated by centrifugation at 14,000 rpm in a Beckman JA20.1 rotor for 15 minutes at 4° C. Tagged KRPs were purified in batch using BD Talon $Co^{2+}$ metal affinity resin equilibrated in Urea buffer. Batch purification was incubated at 4° C. 3 hrs to overnight under slow rotation. Slurry was loaded on a column and resin was washed with 36 bed volumes of Urea buffer followed by 12 bed volumes of Urea buffer containing 5 mM Imidazole pH 7.0. Bound tagged KRP protein was eluted using Urea buffer containing 300 mM Imidazole pH 7.0. Fractions were monitored for tagged KRP by SDS-PAGE and/or by Bradford protein assay (Bio-Rad). Refolding of the denatured tagged KRP1 was carried out using step-wise dilution dialysis. Fractions containing the majority of tagged KRP protein were combined and dialyzed in a 1M Urea, 100 mM Phosphate buffer pH 7.0, and 1 mM Dithiothreitol for 20 hrs at 4° C. Dialysis buffer was then changed to 0.5 M Urea, 100 mM Phosphate buffer pH 7.0, and 1 mM Dithiothreitol and continued for an additional 12 hrs. Recombinant protein was collected, quantified by Bradford assay and stored at 4° C.

Figure 4:
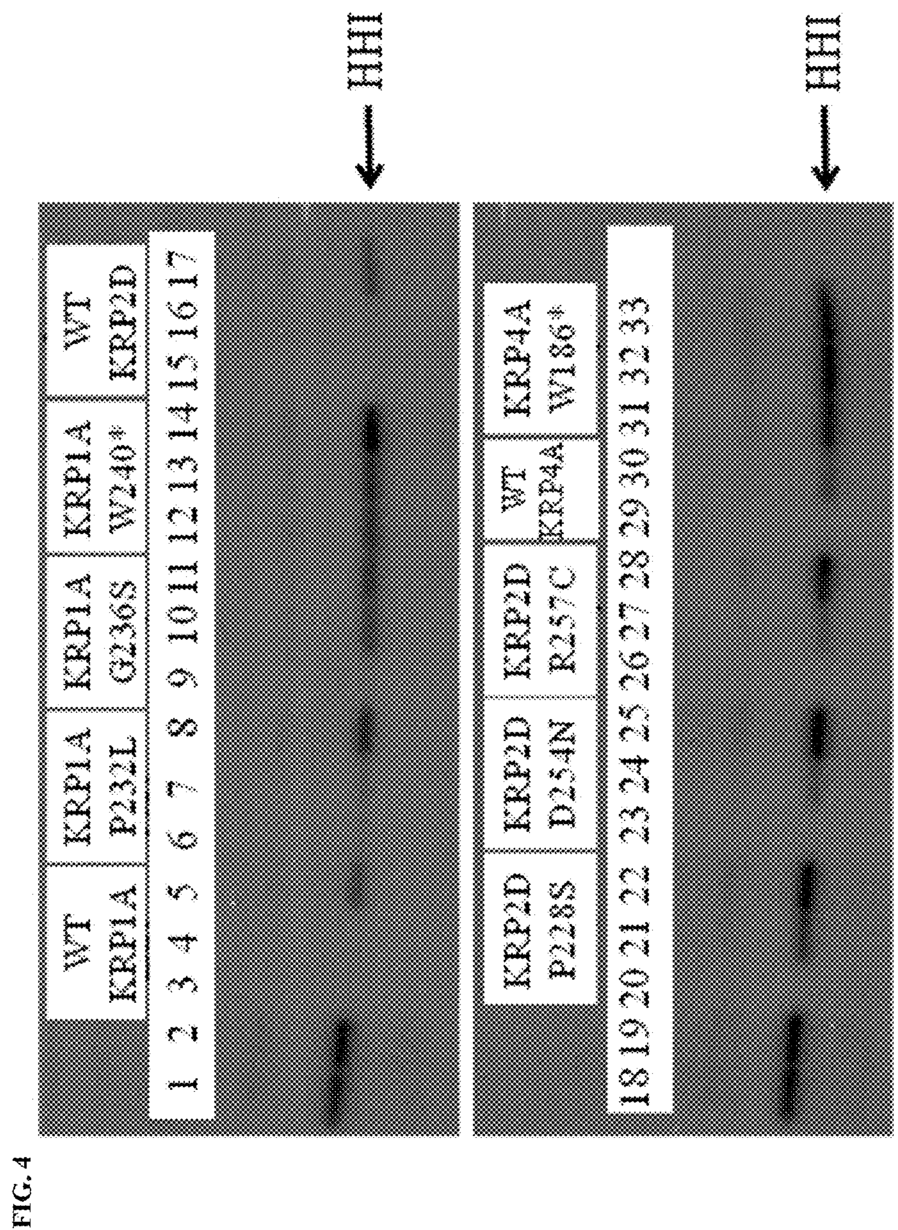
FIG. 4 depicts an autoradiograph of kinase assays using ZmCyclinD4/CDKA;1 kinase complex, indicated wild-type *Triticum aestivum* KRP and indicated *Triticum aestivum* KRP TILLING® mutant. Histone H1 (HH1) was used as the substrate for phosphorylation. Lanes 1 and 18: kinase complex without any wild-type or KRP TILLING® mutant. Lanes 2 and 19: only kinase complex in buffer. Lanes 3, 4, 5: kinase complex and wild-type TaKRP1A at 0.5, 0.25 and 0.1 μg, respectively. Lanes 6, 7, 8: kinase complex and mutant TaKRP1A P232L at 0.5, 0.25 and 0.1 μg, respectively. Lanes 9, 10, 11: kinase complex and mutant TaKRP1A G236S at 0.5, 0.25 and 0.1 μg, respectively. Lanes 12, 13, 14: kinase complex and mutant TaKRP1A W240* at 0.5, 0.25 and 0.1 μg, respectively. Lanes 15, 16, 17: kinase complex and wild-type TaKRP2D at 0.5, 0.25 and 0.1 μg, respectively. Lanes 20, 21, 22: kinase complex and mutant TaKRP2D P228S at 0.5, 0.25 and 0.1 μg, respectively. Lanes 23, 24, 25: kinase complex and mutant TaKRP2D D254N at 0.5, 0.25 and 0.1 μg, respectively. Lanes 26, 27, 28: kinase complex and mutant TaKRP2D R257C at 0.5, 0.25 and 0.1 μg, respectively. Lanes 29, 30: kinase complex and wild-type TaKRP4A at 0.25 and 0.1 μg, respectively. Lanes 31, 32, 33: kinase complex and mutant TaKRP4A W186* at 0.5, 0.25 and 0.1 μg, respectively.
Figure 5:
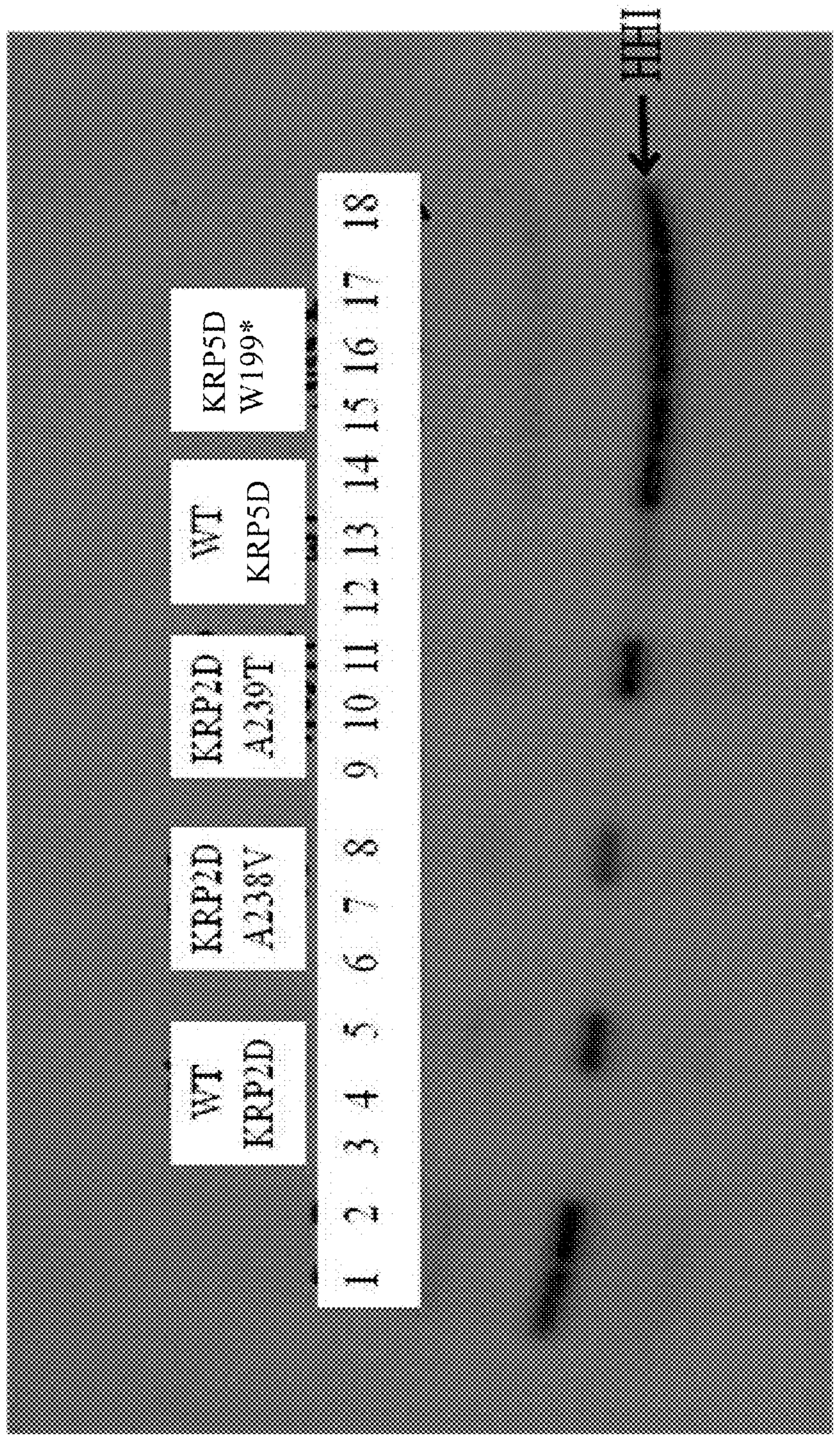
FIG. 5 depicts an autoradiograph of kinase assays using ZmCyclinD4/CDKA;1 kinase complex, indicated wild-type *Triticum aestivum* KRP and indicated *Triticum aestivum* KRP TILLING® mutant. Histone H1 (HH1) was used as the substrate for phosphorylation. Lane 1: kinase complex without any wild-type or KRP TILLING® mutant. Lanes 2 and 18: only kinase complex in buffer. Lanes 3, 4, 5: kinase complex and wild-type TaKRP2D at 0.5, 0.25 and 0.1 μg, respectively. Lanes 6, 7, 8: kinase complex and mutant TaKRP2D A238V at 0.5, 0.25 and 0.1 μg, respectively. Lanes 9, 10, 11: kinase complex and mutant TaKRP2D A239T at 0.5, 0.25 and 0.1 μg, respectively. Lanes 12, 13, 14: kinase complex and wild-type TaKRP5A at 0.5, 0.25 and 0.1 μg, respectively. Lanes 15, 16, 17: kinase complex and mutant TaKRP5A W199* at 0.5, 0.25 and 0.1 μg, respectively.
Figure 6:
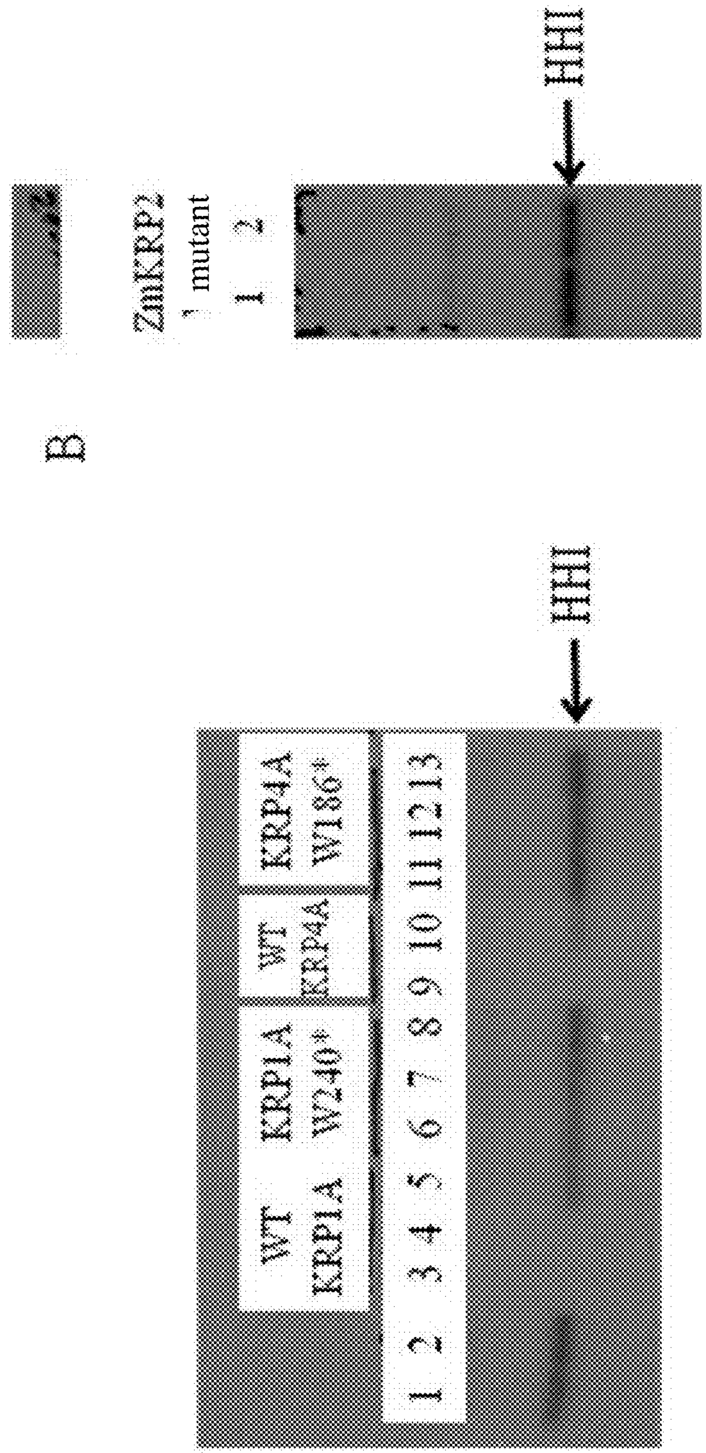
FIG. 6A depicts an autoradiograph of repeat kinase assays using ZmCyclinD4/CDKA;1 kinase complex, indicated wild-type *Triticum aestivum* KRP and indicated *Triticum aestivum* KRP TILLING® mutant. Histone H1 (HHI) was used as the substrate for phosphorylation. Lane 1: kinase complex without any wild-type or KRP TILLING® mutant. Lane 2: only kinase complex in buffer. Lanes 3, 4, 5: kinase complex and wild-type TaKRP1A at 0.5, 0.25 and 0.1 μg, respectively. Lanes 6, 7, 8: kinase complex and mutant TaKRP1A W240* at 0.5, 0.25 and 0.1 μg, respectively. Lanes 9, 10: kinase complex and wild-type TaKRP4A at 0.25 and 0.1 μg, respectively. Lanes 11, 12, 13: kinase complex and mutant TaKRP4A W186* at 0.5, 0.25 and 0.1 μg, respectively.
FIG. 6B depicts an autoradiograph of kinase assays using ZmCyclinD4/CDKA;1 kinase complex and ZmKRP2 W250*. ZmKRP2 W250* is the mutant corn krp2 protein with an equivalent premature stop codon very close to the end of the protein. Lanes 1 and 2: kinase complex and mutant ZmKRP2 W250* at 0.3 and 3 μg, respectively.

In in vitro kinase assays, a few TaKRP mutant proteins exhibited reduced inhibitory activity toward the cyclin/CDK kinase complex, while others behaved like their wild-type TaKRPs. Notably, TaKRP4A W186* (FIGS. 4 and 6A) and TaKRP5A W199* (FIG. 5) did not inhibit the kinase activity of ZmCyclinD4/ZmCDKA;1 at 0.1, 0.25 or 0.5 μg. TaKRP1A W240* also did not inhibit the kinase activity of ZmCyclinD4/ZmCDKA;1 at 0.1, 0.25 or 0.5 μg, although its inhibitory activity was not as compromised at 0.25 and 0.5 μg (FIGS. 4 and 6A). TaKRP1A G236S could only strongly inhibit ZmCyclinD4/ZmCDKA;1 at 0.5 μg and weakly at 0.25 μg (FIG. 4). Similarly, TaKRP2D P228S could only strongly inhibit ZmCyclinD4/ZmCDKA;1 at 0.5 μg and very weakly at 0.25 μg (FIG. 4). TaKRP4A W186*, TaKRP5A W199* and TaKRP1A W240* contain premature stop codons very close to the end of the KRP proteins and thus still retain the cyclin- and CDK-binding domains. However, the elimination of the last 8 amino acids for TaKRP1A W240*, the last 6 amino acids for TaKRP5A W199* and the last 5 amino acids for TaKRP4A W186* compromises the ability of the mutant KRPs to inhibit the kinase complex. A mutant corn KRP2 protein, ZmKRP2 W250*, with an equivalent premature stop codon near the end of the protein, also was not able to inhibit the ZmCyclinD4/ZmCDKA;1 complex at 0.3 or 3 μg (FIG. 6B).

Other mutants, such as TaKRP1A P232L (FIG. 4), TaKRP2D A238V (FIG. 5), TaKRP2D A239T (FIG. 5), TaKRP2D D254N (FIG. 4) and TaKRP2D R257C (FIG. 4), inhibit the ZmCyclinD4/ZmCDKA;1 complex as well as their wild-type counterparts at the indicated protein concentrations.

The inhibitory activities for various wheat KRP TILLING® mutants compared to their wild-type counterparts are summarized in Table 23.

TABLE 23

Inhibitory activity of wild-type wheat KRP or mutant wheat KRP on ZmCyclinD4/CDKA; 1 kinase complex

| Wheat Krp | Inhibitory activity |
|---|---|
| Krp1A wild type (WT) | ++++ |
| Krp1A (E212K) | Not tested |
| Krp1A (P232L) | ++++ |
| Krp1A (G236S) | ++ |
| Krp1A (W240*) | + |
| Krp2D WT | ++++ |
| Krp2D (P228S) | +++ |
| Krp2D (A238V) | ++++ |
| Krp2D (A239T) | ++++ |
| Krp2D (D254N) | ++++ |
| Krp2D (R257C) | ++++ |
| Krp4A WT | ++++ |
| Krp4A (W186*) | − |
| Krp5A WT | ++++ |
| Krp5A (G200D) | Not tested |
| Krp5A (G200R) | Not tested |
| Krp5A (W199*) | − |

Example 5

Preliminary Field Trial Results on M Generation Wheat KRP TILLING® Mutants

The M5 generation of selected wheat KRP TILLING® mutants were grown in Yuma, Ariz. in fall 2009-winter 2010 to determine yield. Sixty entries (Table 24) were in the yield trial, with each entry being replicated three times randomly throughout the trial. Each plot was 4 ft by 10 ft with 7 rows per plot and 7 inches between rows. About 75 g of seed were planted per plot, or about 2500 seeds/plot or about 360 seeds per 10-ft row. Planting took place in October.

Where available, the wild type segregant of a given homozygous or heterozygous KRP TILLING® mutant was planted for comparison. The parent variety, Express, was also included in the trial. The stand rate was taken prior to harvest, the maturity rate was taken at flowering, and the peduncle rate, head number, kernel number, spike length and awn length were taken after harvest from subsamples. Maturity rate and peduncle rate were on a comparative scoring system, relative to the Express background parent. Maturity: 1 is early, 3 is similar to Express, 5 is late/vegetative. Peduncle: 1 is very thin, 3 is similar to Express, 5 is very thick (Table 24).

Harvest was conducted in two rounds in May. Plots in replicate 1 were hand sickled and plants bundled and allowed to dry in the field for a few days prior to stationary threshing. The second round utilized a plot combine to harvest the remaining plots. Prior to the second harvest, heads from five plants per plot of replicates 2 and 3 (so 10 heads total per entry) were collected for head measurements. The cut was made approximately 5-6 inches below the base of the spike.

Seed weight and seed count were determined for each 5-head subsample, from which a weight per seed could be calculated. The plot weight was determined by hand. Seed count per plot was calculated from weight per seed and plot weight. Thousand kernel weight (TKW) is weight per seed multiplied by 1000.

A number of KRP mutants demonstrated excellent seed yield. These included WH68, WH3, WH91, WH124, WH4 and WH16 (Table 24). WH68 (KRP4D, P146L) was ranked first in yield at 3584.90 lbs/acre. Two mutants, WH3 and WH4, with changes in adjacent nucleotides that result in a splice mutation at the same intron/exon junction both showed good yield, ranking second (WH3) and sixth (WH4) out of the 60 entries. Another splice mutant in KRP5D, WH124, was ranked fifth in yield. A mutant, WH16, ranked seventh in yield interestingly has two mutations within the KRP2A gene (V258M and G169S).

TABLE 24

Yield and agronomic data for wheat KRP TILLING ® mutants, Yuma, AZ

| No | Entry | Zygosity | Group | Variant | Type | Stand rate | Maturity rate | Grain yield Lbs/acre | Peduncle rate | Head number | Kernel number | TKW g/1000 | Spike length cm | Awn length cm |
|---|---|---|---|---|---|---|---|---|---|---|---|---|---|---|
| 1 | WH11-120M5 | HOM | 11 | KRP2A2 | SPLCE | 5.00 | 2.00 | 2771.91 (18) | 3.33 | 3.21 | 77.30 | 40.53 | 14.00 | 7.00 |
| 2 | WH11-124M5 | HOM | 11 | KRP2A2 | SPLCE | 5.00 | 2.33 | 2295.06 (39) | 3.33 | 2.92 | 60.70 | 46.92 | 12.50 | 8.50 |
| 3 | WH11-125M5 | HOM | 11 | KRP2A2 | SPLCE | 5.00 | 2.33 | 2416.27 (34) | 3.33 | 2.63 | 75.50 | 42.13 | 12.50 | 8.00 |
| 4 | WH11-126M5 | HOM | 11 | KRP2A2 | SPLCE | 5.00 | 3.33 | 2137.06 (48) | 3.33 | 2.87 | 73.70 | 37.05 | 12.50 | 6.00 |
| 5 | WH11-126M5 | HOM | 11 | KRP2A2 | SPLCE | 5.00 | 3.00 | 2286.10 (40) | 3.00 | 3.51 | 66.60 | 38.56 | 11.00 | 5.50 |
| 6 | WH11-129M5 | HOM | 11 | KRP2A2 | SPLCE | 4.67 | 2.00 | 2090.37 (49) | 3.00 | 2.95 | 61.60 | 39.44 | 10.50 | 7.00 |
| 7 | WH116-1212M5 | HOM | 116 | KRP5D2 | MSSE | 5.00 | 1.33 | 2633.43 (25) | 2.67 | 3.11 | 63.20 | 46.50 | 13.00 | 7.50 |
| 8 | WH124-1275M5 | HOM | 124 | KRP5D2 | SPLCE | 5.00 | 1.67 | 2164.89 (46) | 3.00 | 2.87 | 71.40 | 40.75 | 11.50 | 8.00 |
| 9 | WH124-1276M5 | HOM | 124 | KRP5D2 | SPLCE | 5.00 | 2.00 | 3241.41 (5) | 3.00 | 3.36 | 82.90 | 41.34 | 13.50 | 8.00 |
| 10 | WH124-1277M5 | HOM | 124 | KRP5D2 | SPLCE | 5.00 | 2.00 | 2572.98 (29) | 3.33 | 2.82 | 74.20 | 42.79 | 12.00 | 8.50 |
| 11 | WH125-1288M5 | HOM | 125 | KRP5D2 | MSSE | 4.67 | 2.33 | 1862.65 (55) | 2.67 | 2.18 | 65.40 | 43.13 | 12.50 | 6.00 |
| 12 | WH125-1290M5 | WT | 125 | KRP5D2 | MSSE | 4.67 | 2.67 | 1641.34 (58) | 2.67 | 2.26 | 69.30 | 37.56 | 14.00 | 6.00 |
| 13 | WH131-1336M5 | WT | 131 | KRP5D2 | STOP | 5.00 | 2.00 | 2363.50 (36) | 3.33 | 2.77 | 74.90 | 40.26 | 11.50 | 8.00 |
| 14 | WH131-1337M5 | HET | 131 | KRP5D2 | STOP | 5.00 | 2.00 | 2447.61 (32) | 3.33 | 2.97 | 67.00 | 42.82 | 11.00 | 6.50 |
| 15 | WH131-1342M5 | HOM | 131 | KRP5D2 | STOP | 5.00 | 2.00 | 1975.23 (53) | 3.00 | 2.21 | 82.70 | 35.81 | 12.00 | 9.00 |
| 16 | WH131-1346M5 | HOM | 131 | KRP5D2 | STOP | 5.00 | 2.00 | 2330.24 (38) | 3.33 | 2.93 | 65.80 | 41.20 | 11.50 | 7.50 |
| 17 | WH14-164M5 | HOM | 14 | KRP2A2 | MSSE | 4.33 | 2.00 | 2931.82 (10) | 3.33 | 3.62 | 75.50 | 37.99 | 12.50 | 5.50 |
| 18 | WH14-172M5 | WT | 14 | KRP2A2 | MSSE | 5.00 | 2.00 | 2771.59 (19) | 3.33 | 3.34 | 76.90 | 37.25 | 12.00 | 6.50 |
| 19 | WH16-185M5 | HOM | 16 | KRP2A2 | MSSE | 5.00 | 2.00 | 3063.27 (7) | 3.33 | 3.37 | 80.70 | 41.37 | 11.50 | 6.50 |
| 20 | WH3-2009M5 | HOM | 3 | KRP2A2 | SPLCE | 5.00 | 2.00 | 3304.74 (2) | 3.67 | 2.78 | 93.30 | 45.17 | 15.00 | 7.50 |
| 21 | WH37-423M5 | HOM | 37 | KRP2B2 | MSSE | 4.67 | 1.67 | 2753.68 (21) | 3.33 | 3.17 | 73.70 | 39.52 | 11.00 | 6.00 |
| 22 | WH37-428M5 | WT | 37 | KRP2B2 | MSSE | 4.67 | 2.33 | 2551.87 (30) | 3.33 | 2.58 | 77.50 | 40.53 | 11.00 | 5.50 |
| 23 | WH38-432M5 | HOM | 38 | KRP2B2 | SPLCE | 4.33 | 1.67 | 1534.19 (59) | 3.33 | 1.87 | 55.10 | 44.07 | 11.50 | 7.50 |
| 24 | WH38-433M5 | HOM | 38 | KRP2B2 | SPLCE | 5.00 | 1.67 | 1926.94 (54) | 3.33 | 1.99 | 77.30 | 43.89 | 13.00 | 7.00 |
| 25 | WH39-437M5 | HET | 39 | KRP2B2 | MSSE | 5.00 | 1.67 | 2962.53 (8) | 3.33 | 2.55 | 82.40 | 46.44 | 14.50 | 7.50 |
| 26 | WH4-2060M5 | HOM | 4 | KRP2A2 | SPLCE | 5.00 | 2.00 | 3117.00 (6) | 3.00 | 3.63 | 74.60 | 43.67 | 14.00 | 6.00 |
| 27 | WH4-2066M5 | HOM | 4 | KRP2A2 | SPLCE | 5.00 | 2.00 | 2623.19 (26) | 3.33 | 2.82 | 76.80 | 45.48 | 13.00 | 6.00 |
| 28 | WH4-41M5 | HET | 4 | KRP2A2 | SPLCE | 4.67 | 2.00 | 2645.26 (24) | 3.33 | 2.77 | 77.40 | 45.39 | 13.50 | 8.00 |
| 29 | WH4-53M5 | HOM | 4 | KRP2A2 | SPLCE | 4.67 | 2.33 | 2782.79 (15) | 3.00 | 3.20 | 72.30 | 45.01 | 13.50 | 7.00 |
| 30 | WH40-440M5 | WT | 40 | KRP2B2 | STOP | 5.00 | 2.67 | 2360.30 (37) | 2.67 | 2.62 | 66.90 | 48.78 | 13.50 | 8.50 |
| 31 | WH40-443M5 | HOM | 40 | KRP2B2 | STOP | 4.33 | 2.67 | 2004.66 (51) | 3.00 | 2.20 | 60.60 | 46.35 | 11.50 | 8.50 |
| 32 | WH44-460M5 | HOM | 44 | KRP4B2 | MSSE | 4.33 | 2.00 | 2372.77 (35) | 3.00 | 2.38 | 76.90 | 42.89 | 10.50 | 6.50 |
| 33 | WH44-461M5 | HOM | 44 | KRP4B2 | MSSE | 4.67 | 2.00 | 2911.36 (11) | 3.00 | 2.88 | 80.70 | 45.74 | 13.00 | 9.50 |
| 34 | WH44-461M5 | HOM | 44 | KRP4B2 | MSSE | 4.67 | 2.00 | 2777.99 (16) | 3.33 | 2.85 | 76.30 | 44.97 | 13.00 | 8.00 |
| 35 | WH44-462M5 | HOM | 44 | KRP4B2 | MSSE | 4.00 | 2.00 | 2246.76 (42) | 3.33 | 2.66 | 64.20 | 40.99 | 10.00 | 8.50 |
| 36 | WH48-487M5 | WT | 48 | KRP4B2 | MSSE | 5.00 | 2.00 | 2938.54 (9) | 3.00 | 3.48 | 78.00 | 46.63 | 13.00 | 8.00 |
| 37 | WH52-513M5 | HOM | 52 | KRP4B2 | SPLCE | 4.67 | 1.67 | 2245.16 (43) | 3.33 | 2.67 | 59.40 | 31.35 | 11.00 | 6.50 |
| 38 | WH52-522M5 | WT | 52 | KRP4B2 | SPLCE | 5.00 | 2.67 | 1498.37 (60) | 3.00 | 2.26 | 65.40 | 32.97 | 11.50 | 6.50 |
| 39 | WH52-524M5 | HOM | 52 | KRP4B2 | SPLCE | 5.00 | 2.00 | 1688.03 (57) | 3.33 | 2.31 | 66.40 | 37.24 | 12.00 | 7.00 |
| 40 | WH63-634M5 | HOM | 63 | KRP4D2 | MSSE | 5.00 | 2.00 | 2773.19 (17) | 3.00 | 2.78 | 69.70 | 49.53 | 11.50 | 7.50 |
| 41 | WH63-635M5 | HOM | 63 | KRP4D2 | MSSE | 5.00 | 2.00 | 2514.45 (31) | 3.00 | 2.96 | 59.00 | 48.83 | 11.00 | 6.50 |
| 42 | WH68-676M5 | HOM | 68 | KRP4D2 | MSSE | 5.00 | 2.00 | 3584.90 (1) | 3.33 | 3.63 | 72.80 | 47.40 | 12.50 | 8.50 |
| 43 | WH71-2083M5 | HOM | 71 | KRP4D2 | STOP | 5.00 | 2.00 | 2691.00 (23) | 3.33 | 2.34 | 86.40 | 45.78 | 11.50 | 6.50 |
| 44 | WH71-708M5 | HET | 71 | KRP4D2 | STOP | 5.00 | 2.00 | 2820.21 (13) | 3.00 | 3.24 | 73.20 | 42.86 | 12.00 | 8.50 |
| 45 | WH71-712M5 | HET | 71 | KRP4D2 | STOP | 5.00 | 1.67 | 2580.66 (27) | 3.00 | 3.10 | 73.70 | 42.43 | 12.00 | 8.00 |
| 46 | WH71-713M5 | HOM | 71 | KRP4D2 | STOP | 4.67 | 2.33 | 2808.69 (14) | 3.00 | 2.90 | 66.80 | 45.58 | 13.00 | 7.00 |
| 47 | WH71-714M5 | HOM | 71 | KRP4D2 | STOP | 5.00 | 2.33 | 2902.08 (12) | 3.33 | 3.10 | 73.10 | 46.60 | 13.00 | 7.50 |
| 48 | WH72-724M5 | HOM | 72 | KRP4D2 | STOP | 5.00 | 2.00 | 2763.92 (20) | 3.33 | 2.86 | 71.50 | 47.42 | 11.50 | 6.50 |

TABLE 24-continued

Yield and agronomic data for wheat KRP TILLING ® mutants, Yuma, AZ

| No | Entry | Zygosity | Group | Variant | Type | Stand rate | Maturity rate | Grain yield Lbs/acre | Peduncle rate | Head number | Kernel number | TKW g/1000 | Spike length cm | Awn length cm |
|---|---|---|---|---|---|---|---|---|---|---|---|---|---|---|
| 49 | WH72-725M5 | WT | 72 | KRP4D2 | STOP | 4.33 | 2.00 | 2173.52 (44) | 3.33 | 2.31 | 76.00 | 49.16 | 12.50 | 7.50 |
| 50 | WH72-729M5 | HOM | 72 | KRP4D2 | STOP | 5.00 | 2.00 | 2447.61 (33) | 3.00 | 2.25 | 76.60 | 48.64 | 12.00 | 7.00 |
| 51 | WH72-734M5 | HOM | 72 | KRP4D2 | STOP | 5.00 | 2.00 | 2730.02 (22) | 3.33 | 2.90 | 73.10 | 47.05 | 10.50 | 6.00 |
| 52 | WH73-739M5 | HOM | 73 | KRP4D2 | SPLCE | 5.00 | 2.00 | 2167.13 (45) | 3.00 | 2.41 | 76.10 | 40.87 | 12.50 | 3.50 |
| 53 | WH73-740M5 | HOM | 73 | KRP4D2 | SPLCE | 5.00 | 2.00 | 2151.13 (47) | 3.33 | 2.56 | 73.30 | 42.25 | 12.00 | 6.00 |
| 54 | WH73-747M5 | HOM | 73 | KRP4D2 | SPLCE | 5.00 | 2.00 | 2068.30 (50) | 3.33 | 2.28 | 79.10 | 40.77 | 15.00 | 4.50 |
| 55 | WH91-1000M5 | HOM | 91 | KRP5A2 | MSSE | 4.67 | 2.00 | 2257.00 (41) | 2.67 | 3.53 | 72.10 | 34.98 | 13.00 | 9.00 |
| 56 | WH91-1003M5 | WT | 91 | KRP5A2 | MSSE | 5.00 | 2.00 | 2576.18 (28) | 3.00 | 2.60 | 89.50 | 39.92 | 13.50 | 7.00 |
| 57 | WH91-1004M5 | WT | 91 | KRP5A2 | MSSE | 5.00 | 2.00 | 1817.24 (56) | 2.67 | 3.02 | 72.80 | 31.98 | 14.00 | 7.00 |
| 58 | WH91-1005M5 | HET | 91 | KRP5A2 | MSSE | 5.00 | 1.33 | 3256.13 (4) | 3.00 | 2.83 | 83.90 | 46.63 | 12.50 | 9.00 |
| 59 | WH91-1008M5 | WT | 91 | KRP5A2 | MSSE | 4.67 | 2.33 | 2000.18 (52) | 3.00 | 2.44 | 74.10 | 39.26 | 13.50 | 7.50 |
| 60 | Express | RP | 1000 | Express | CTL | 5.00 | 2.00 | 3269.88 (3) | 3.33 | 2.98 | 81.30 | 46.49 | 12.00 | 8.50 |
| p < F | | | | | | ** | ** | ** | NA | * | ** | ** | * | ** |
| CV (%) | | | | | | 7 | 17 | 18 | 13 | 17 | 10 | 5 | 10 | 13 |
| LSD (0.05) | | | | | | 0.57 | 0.57 | 723.95 | 0.65 | 0.95 | 14.96 | 4.16 | 2.50 | 1.87 |
| Mean | | | | | | 4.86 | 2.07 | 2493.27 | 3.15 | 2.81 | 73.24 | 42.58 | 12.36 | 7.17 |

Example 6

Rice Krp TILLING® Mutant

A rice TILLING® library was screened for mutations in rice KRPs 1, 2, 4 and 5 (SEQ ID NOs: 100-107). A mutant containing a premature stop codon in OsKRP4 was identified (Table 25). M3 seeds from two distinct M2 sibling plants heterozygous for the R167* mutation were planted in the greenhouse and genotyped to identify plants homozygous for the R167* allele or homozygous for the wild type allele. Homozygous R167* and wild type plants were selfed to obtain homozygous mutant and wild type M4 seed. Additionally, homozygous R167* plants were backcrossed to the recurrent Cypress parent to obtain F1 seed.

Seed number and seed weight were determined for the homozygous R167* and homozygous wild type M4 seed (Table 26). There is an indication that RI527 R167* homozygotes have at least a general increase in thousand kernel weight (TKW) compared to their wild type siblings (Table 27), and the RI526 R167* homozygotes may be better than their control for seed number. These same measurements will be taken again on seed from successive backcrossed generations.

F1 and M4 seeds were planted in the greenhouse in the next cycle. F1 plants were genotyped to confirm the heterozygosity of R167*. Heterozygous R167* plants are backcrossed a second time to the recurrent parent to obtain BC1F1 seed. Simultaneously, heterozygous R167* F1 plants are selfed to obtain segregating F2 seed. Homozygous R167* F2 plants are identified by genotyping and seed expanded to F3 for field trials.

BC1F1 seed are grown in the greenhouse and the plants genotyped to identify ones heterozygous for the R167* allele or wild type allele. Heterozygous R167* plants are backcrossed to obtain BC2F1 and selfed to obtain BC1F2. Homozygous R167* BC1F2 plants are identified by genotyping and seed expanded to BC1F3 for field trials. Backcrossing may be continued to the BC3 or BC4 level. Throughout the backcrossing and selfing, wild type siblings are carried forward to serve as controls. Backcrosses are also done to Nipponbare to move the mutation into short grain rice.

TABLE 25

*Oryza sativa* KRP4 TILLING ® Mutant in breeding program

| RI group | Gene | Nuc_Change | Effect-from beginning Met |
|---|---|---|---|
| 526^ | KRP4_2-3§ | C593T | R167* |
| 527 | KRP4_2-3 | C593T | R167* |

^The two RI groups represent two distinct M2 sibling plants heterozygous for the R167* mutation.
§The designation "2-3" indicates that exons 2-3 of OsKRP4 were TILL'ed.

TABLE 26

Seed number and seed weight for OsKRP4 R167* M4 seed

| Plant ID | # of seeds | Total seed weight (g) | weight/seed (g) | TKW (g) |
|---|---|---|---|---|
| 526 HOMO #12 | 178 | 3.76 | 0.021 | 21.1 |
| 526 HOMO #13 | 164 | 3.39 | 0.021 | 20.7 |
| 526 HOMO #15 | 33 | 0.69 | 0.021 | 20.9 |
| 526 HOMO #21 | 258 | 4.91 | 0.019 | 19.0 |
| 526 HOMO #22 | 220 | 5.14 | 0.023 | 23.4 |
| 526 HOMO #27 | 261 | 5.90 | 0.023 | 22.6 |
| 526 HOMO #33 | 209 | 4.43 | 0.021 | 21.2 |
| 526 HOMO #35 | 141 | 2.81 | 0.020 | 19.9 |
| 526 HOMO #37 | 155 | 3.33 | 0.021 | 21.5 |
| 526 HOMO #4 | 169 | 3.77 | 0.022 | 22.3 |
| 526 HOMO #41 | 245 | 5.33 | 0.022 | 21.8 |
| 526 HOMO #8 | 151 | 2.94 | 0.019 | 19.5 |
| 526 WT #14 | 72 | 1.39 | 0.019 | 19.3 |
| 526 WT #19 | 161 | 3.43 | 0.021 | 21.3 |
| 526 WT #23 | 229 | 5.10 | 0.022 | 22.3 |
| 526 WT #24 | 165 | 3.74 | 0.023 | 22.7 |
| 526 WT #25 | 273 | 5.98 | 0.022 | 21.9 |
| 526 WT #3 | 181 | 3.70 | 0.020 | 20.4 |
| 526 WT #30 | 165 | 3.69 | 0.022 | 22.4 |
| 526 WT #32 | 121 | 2.51 | 0.021 | 20.7 |
| 526 WT #36 | 1 | 0.02 | 0.020 | 20.0 |
| 526 WT #6 | 137 | 2.80 | 0.020 | 20.4 |
| 526 WT #7 | 260 | 5.48 | 0.021 | 21.1 |
| 526 WT #9 | 203 | 4.40 | 0.022 | 21.7 |
| 527 HOMO #1 | 197 | 4.50 | 0.023 | 22.8 |
| 527 HOMO #14 | 220 | 4.93 | 0.022 | 22.4 |
| 527 HOMO #2 | 215 | 5.13 | 0.024 | 23.9 |
| 527 HOMO #20 | 4 | 0.11 | 0.028 | 27.5 |
| 527 HOMO #24 | 179 | 4.40 | 0.025 | 24.6 |
| 527 HOMO #35 | 142 | 3.06 | 0.022 | 21.5 |
| 527 HOMO #38 | 37 | 0.61 | 0.016 | 16.5 |
| 527 HOMO #6 | 142 | 2.96 | 0.021 | 20.8 |

TABLE 26-continued

Seed number and seed weight for OsKRP4 R167* M4 seed

| Plant ID | # of seeds | Total seed weight (g) | weight/seed (g) | TKW (g) |
|---|---|---|---|---|
| 527 WT #10 | 201 | 4.67 | 0.023 | 23.2 |
| 527 WT #11 | 6 | 0.10 | 0.017 | 16.7 |
| 527 WT #13 | 38 | 0.70 | 0.018 | 18.4 |
| 527 WT #19 | 12 | 0.20 | 0.017 | 16.7 |
| 527 WT #23 | 261 | 6.19 | 0.024 | 23.7 |
| 527 WT #30 | 248 | 5.52 | 0.022 | 22.3 |
| 527 WT #32 | 189 | 4.20 | 0.022 | 22.2 |
| 527 WT #34 | 187 | 4.32 | 0.023 | 23.1 |
| 527 WT #36 | 68 | 1.54 | 0.023 | 22.6 |
| 527 WT #7 | 189 | 3.85 | 0.020 | 20.4 |
| Nipponbare | 10 | 0.24 | 0.024 | 24.0 |
| Cypress | 10 | 0.23 | 0.023 | 23.0 |

TABLE 27

Mean seed number and seed weight for OsKRP4 genotypes

| Plant ID | Mean seed number | Mean TKW (g) |
|---|---|---|
| 526 homo | 182.00 | 21.15 |
| 526 wild type | 164.00 | 21.18 |
| 527 homo | 142.00 | 22.51 |
| 527 wild type | 139.90 | 20.93 |

Example 7

Mutations of *Glycine max* KRP Genes Identified in TILLING®

Candidate *Glycine max* (soybean) KRP genes were searched on the Phytozome and nine KRP genes (SEQ ID NOs: 111-128) were identified. A soy TILLING® library was screened for mutations in these soy KRPs.

Representative mutations in *Glycine max* KRPs are displayed in Tables 29 to 37 below (* indicates the mutation results in a stop codon). This is only a representative list and should not be construed to be limiting in any way.

TABLE 29

*Glycine max* Gm 0003 × 00821 representative TILLING ® Mutants

| Gene | Nuc Change^ | Effect from beginning Met | Mutation Score |
|---|---|---|---|
| KRP Gm0003 × 00821 | C533T | A17V | Missense |
| KRP Gm0003 × 00821 | C542T | A20V | Missense |
| KRP Gm0003 × 00821 | G610A | A43T | Missense |
| KRP Gm0003 × 00821 | G628A | G49R | Missense |
| KRP Gm0003 × 00821 | C650T | S56F | Missense |
| KRP Gm0003 × 00821 | G655A | A58T | Missense |
| KRP Gm0003 × 00821 | A674T | N64I | Missense |

TABLE 28

Primer sequences used to generate mutant Krps

| Wheat Krp | forward primer 5' → 3' | reverse primer 5' → 3' |
|---|---|---|
| Krp1A (E212K) | Cgaagagttctttgcggcggctaaagaggcggaagcacgccg (SEQ ID NO: 34) | Cggcgtgcttccgcctctttagccgccgcaaagaactcttcg (SEQ ID NO: 35) |
| Krp1A (P232L) | Cgacgttgcacgcggcgtgcttctggattccggtcgctatgag (SEQ ID NO: 36) | Ctcatagcgaccggaatccagaagcacgccgcgtgcaacgtcg (SEQ ID NO: 37) |
| Krp1A (0236S) | Cggcgtgcctctggattccagtcgctatgagtggaccccggc (SEQ ID NO: 38) | Gccggggtccactcgtagcgactggaatccagaggcacgccg (SEQ ID NO: 39) |
| Krp1A (W240*) | Ggattccggtcgctatgagtgaaccccggcagtttccagcag (SEQ ID NO: 40) | Ctgctggaaactgccggggttcactcatagcgaccggaatcc (SEQ ID NO: 41) |
| Krp2D (P228S) | Ccgtgcccgtgcgcgtatgtcaccggcagcggaaatcgacg (SEQ ID NO: 42) | Cgtcgatttccgctgccggtgacatacgcgcacgggcacgg (SEQ ID NO: 43) |
| Krp2D (A238V) | Cgacgagttttcgcggttgcggagaaagcccaggcagag (SEQ ID NO: 44) | Ctctgcctgggctttctccgcaaccgcgaaaaactcgtcg (SEQ ID NO: 45) |
| Krp2D (A239T) | Cgacgagttttcgcggctacggagaaagcccaggcagagcg (SEQ ID NO: 46) | Cgctctgcctgggctttctccgtagccgcgaaaaactcgtcg (SEQ ID NO: 47) |
| Krp2 D (D254N) | Cgccgcgaagtataactttaatgtggcccgtggcgttccgctg (SEQ ID NO: 48) | Cagcggaacgccacgggccacattaaagttatacttcgcggcg (SEQ ID NO: 49) |
| Krp2D (R257C) | Ctttgatgtggcctgtggcgttccgctgaatgctggtcgc (SEQ ID NO: 50) | Gcgaccagcattcagcggaacgccacaggccacatcaaag (SEQ ID NO: 51) |
| Krp4A (W186*) | Gccaggtcgttatgaataggtcaagctggactaactcgag (SEQ ID NO: 52) | Ctcgagttagtccagcttgacctattcataacgacctggc (SEQ ID NO: 53) |
| Krp5A (G200E) | Ctcgtggctgcccgctgccggatcgttacgagtggaccgtc (SEQ ID NO: 54) | Gacggtccactcgtaacgatccggcagcgggcagccacgag (SEQ ID NO: 55) |
| Krp5A (G200R) | Ctcgtggctgcccgctgccgaggcgttacgagtggaccgtc (SEQ ID NO: 56) | Gacggtccactcgtaacgcctcggcagcgggcagccacgag (SEQ ID NO: 57) |
| Krp5A (W199*) | Gctgccgggtcgttacgagtgaaccgtcctggactgctaactc (SEQ ID NO: 58) | Gagttagcagtccaggacggttcactcgtaacgacccggcagc (SEQ ID NO: 59) |

TABLE 29-continued

*Glycine max* Gm 0003 × 00821 representative TILLING ® Mutants

| Gene | Nuc Change^ | Effect from beginning Met | Mutation Score |
|---|---|---|---|
| KRP Gm0003 × 00821 | G721A | E80K | Severe Missense |
| KRP Gm0003 × 00821 | G873A | D92N | Missense |
| KRP Gm0003 × 00821 | A1274G | Splice Junction | Splice |
| KRP Gm0003 × 00821 | G1275A | Splice Junction | Splice |
| KRP Gm0003 × 00821 | A1277T | R102* | Nonsense |
| KRP Gm0003 × 00821 | C1320T | S116F | Severe Missense |
| KRP Gm0003 × 00821 | G1328A | E119K | Missense |
| KRP Gm0003 × 00821 | T1332A | V120E | Missense |
| KRP Gm0003 × 00821 | A1365T | K131I | Missense |
| KRP Gm0003 × 00821 | C1392T | T140M | Severe Missense |
| KRP Gm0003 × 00821 | G1400A | E143K | Severe Missense |
| KRP Gm0003 × 00821 | G1421A | A150T | Missense |
| KRP Gm0003 × 00821 | A1428G | E152G | Severe Missense |

^Nucleotide numbering is dependent upon the location of TILLING ® primers.

TABLE 30

*Glycine max* Gm0013 representative TILLING ® Mutants

| Gene | Nuc Change^ | Effect from beginning Met | Mutation score |
|---|---|---|---|
| KRP Gm0013 | C574T | S28F | Severe Missense |
| KRP Gm0013 | C622T | S44F | Missense |
| KRP Gm0013 | T648C | S53P | Severe Missense |
| KRP Gm0013 | C649T | S53F | Severe Missense |
| KRP Gm0013 | A685T | Q65L | Missense |
| KRP Gm0013 | C727T | S79F | Severe Missense |
| KRP Gm0013 | T732G | C81G | Severe Missense |
| KRP Gm0013 | T732A | C81S | Severe Missense |
| KRP Gm0013 | C736T | S82F | Severe Missense |
| KRP Gm0013 | A738T | S83C | Severe Missense |
| KRP Gm0013 | G783A | D98N | Severe Missense |
| KRP Gm0013 | G792A | Splice Junction | Splice |
| KRP Gm0013 | G1315C | E121Q | Missense |
| KRP Gm0013 | G1320A | M122I | Missense |
| KRP Gm0013 | A1334T | E127V | Missense |
| KRP Gm0013 | G1360A | E136K | Missense |
| KRP Gm0013 | C1448T | A165V | Missense |
| KRP Gm0013 | C1462T | Q170* | Nonsense |
| KRP Gm0013 | G1671A | G189R | Severe Missense |
| KRP Gm0013 | A1690T | Q195L | Missense |

^Nucleotide numbering is dependent upon the location of TILLING ® primers.

TABLE 31

*Glycine max* Gm0043 representative TILLING ® Mutants

| Gene | Nuc Change^ | Effect from beginning Met | Mutation score |
|---|---|---|---|
| KRP Gm0043_1-2§ | A582T | Q42L | Missense |
| KRP Gm0043_1-2 | T585A | F43Y | Severe Missense |
| KRP Gm0043_1-2 | T586A | F43L | Severe Missense |
| KRP Gm0043_1-2 | G599A | V48I | Missense |
| KRP Gm0043_1-2 | G638A | V61I | Missense |
| KRP Gm0043_1-2 | G645A | G63D | Missense |
| KRP Gm0043_1-2 | G647T | D64Y | Missense |
| KRP Gm0043_1-2 | A720T | Q88L | Missense |
| KRP Gm0043_1-2 | T904A | Y102N | Missense |
| KRP Gm0043_3-4€ | C1194T | S113F | Severe Missense |
| KRP Gm0043_3-4 | C1215T | A120V | Missense |
| KRP Gm0043_3-4 | C1227T | A124V | Missense |
| KRP Gm0043_3-4 | C1235T | R127W | Missense |
| KRP Gm0043_3-4 | G1259A | A135T | Missense |
| KRP Gm0043_3-4 | G1289A | E145K | Severe Missense |
| KRP Gm0043_3-4 | G1302A | R149Q | Missense |
| KRP Gm0043_3-4 | C1513T | P165L | Severe Missense |
| KRP Gm0043_3-4 | G1521A | G168S | Severe Missense |
| KRP Gm0043_3-4 | C1524T | R169C | Severe Missense |

^Nucleotide numbering is dependent upon the location of TILLING ® primers.
§The designation “1-2” indicates that exons 1-2 of soy KRP Gm0043 were TILLed.
€The designation “3-4” indicates that exons 3-4 of soy KRP Gm0043 were TILLed.

TABLE 32

*Glycine max* Gm0053 representative TILLING ® Mutants

| Gene | Nuc Change^ | Effect from beginning Met | Mutation score |
|---|---|---|---|
| KRP Gm0053 | G629A | R10Q | Missense |
| KRP Gm0053 | C728T | S43F | Severe Missense |
| KRP Gm0053 | C758T | A53V | Missense |
| KRP Gm0053 | C814A | Q72K | Missense |
| KRP Gm0053 | C866T | S89F | Severe Missense |
| KRP Gm0053 | A868T | S90C | Severe Missense |
| KRP Gm0053 | G869A | S90N | Severe Missense |
| KRP Gm0053 | C1125T | T117M | Severe Missense |
| KRP Gm0053 | G1408A | R127K | Missense |
| KRP Gm0053 | A1409T | R127S | Severe Missense |
| KRP Gm0053 | G1527A | E167K | Severe Missense |

^Nucleotide numbering is dependent upon the location of TILLING ® primers.

TABLE 33

*Glycine max* Gm0087 representative TILLING ® Mutants

| Gene | Nuc Change^ | Effect from beginning Met | Mutation score |
|---|---|---|---|
| KRP Gm0087_2-3§ | G3098A | R137K | Severe Missense |
| KRP Gm0087_2-3 | G3178A | A164T | Missense |
| KRP Gm0087_2-3 | G3191A | R168Q | Missense |
| KRP Gm0087_2-3 | G3194A | R169K | Severe Missense |
| KRP Gm0087_2-3 | C3227T | T180I | Severe Missense |
| KRP Gm0087_2-3 | G3289A | E201K | Severe Missense |
| KRP Gm0087_2-3 | C3424T | L213F | Severe Missense |
| KRP Gm0087_2-3 | G3430A | G215R | Severe Missense |
| KRP Gm0087_2-3 | G3445A | E220K | Missense |

^Nucleotide numbering is dependent upon the location of TILLING ® primers.
§The designation “2-3” indicates that exons 2-3 of soy KRP Gm0087 were TILLed.

TABLE 34

*Glycine max* Gm0102 representative TILLING ® Mutants

| Gene | Nuc Change^ | Effect from beginning Met | Mutation score |
|---|---|---|---|
| KRP Gm0102_3-4§ | C722T | S120F | Missense |
| KRP Gm0102_3-4 | G724A | G121R | Severe Missense |
| KRP Gm0102_3-4 | G733A | E124K | Missense |
| KRP Gm0102_3-4 | A734T | E124V | Missense |
| KRP Gm0102_3-4 | C743T | A127V | Missense |
| KRP Gm0102_3-4 | C770T | A136V | Missense |
| KRP Gm0102_3-4 | T776A | L138Q | Missense |
| KRP Gm0102_3-4 | C790T | P143S | Severe Missense |
| KRP Gm0102_3-4 | C794T | P144L | Missense |
| KRP Gm0102_3-4 | G799A | A146T | Missense |
| KRP Gm0102_3-4 | C800T | A146V | Missense |
| KRP Gm0102_3-4 | A809T | E149V | Severe Missense |
| KRP Gm0102_3-4 | G811A | E150K | Missense |
| KRP Gm0102_3-4 | G848A | R162Q | Severe Missense |
| KRP Gm0102_3-4 | G1154A | D174N | Severe Missense |
| KRP Gm0102_3-4 | C1160T | P176S | Severe Missense |

TABLE 34-continued

| *Glycine max* Gm0102 representative TILLING ® Mutants | | | |
|---|---|---|---|
| Gene | Nuc Change^ | Effect from beginning Met | Mutation score |
| KRP Gm0102_3-4 | G1166A | E178K | Severe Missense |
| KRP Gm0102_3-4 | A1179T | Q182L | Severe Missense |

^Nucleotide numbering is dependent upon the location of TILLING ® primers.
§The designation "3-4" indicates that exons 3-4 of soy KRP Gm0102 were TILLed.

TABLE 35

| *Glycine max* Gm0119 representative TILLING ® Mutants | | | |
|---|---|---|---|
| Gene | Nuc Change^ | Effect from beginning Met | Mutation score |
| KRP Gm0119_2-3§ | G2664A | Splice Junction | Splice |
| KRP Gm0119_2-3 | C2717T | H133Y | Missense |
| KRP Gm0119_2-3 | G2857A | Splice Junction | Splice |
| KRP Gm0119_2-3 | G3040A | R193Q | Severe Missense |
| KRP Gm0119_2-3 | A3010T | D183V | Severe Missense |

^Nucleotide numbering is dependent upon the location of TILLING ® primers.
§The designation "2-3" indicates that exons 2-3 of soy KRP Gm0119 were TILLed.

TABLE 36

| *Glycine max* Gm0151 representative TILLING ® Mutants | | | |
|---|---|---|---|
| Gene | Nuc Change^ | Effect from beginning Met | Mutation score |
| KRP Gm0151_2-3§ | A2306T | R122W | Severe Missense |
| KRP Gm0151_2-3 | C2367T | T142I | Severe Missense |
| KRP Gm0151_2-3 | G2399A | E153K | Missense |
| KRP Gm0151_2-3 | G2412A | R157K | Missense |
| KRP Gm0151_2-3 | G2485A | M181I | Missense |
| KRP Gm0151_2-3 | A2647T | E191D | Missense |

^Nucleotide numbering is dependent upon the location of TILLING ® primers.
§The designation "2-3" indicates that exons 2-3 of soy KRP Gm0151 were TILLed.

TABLE 37

| *Glycine max* Gm0067 representative TILLING ® Mutants | | | |
|---|---|---|---|
| Gene | Nuc Change^ | Effect from beginning Met | Mutation score |
| KRP Gm0067_1-2§ | G631A | V4I | Severe Missense |
| KRP Gm0067_1-2 | G652A | A11T | Severe Missense |
| KRP Gm0067_1-2 | C671T | S17F | Severe Missense |
| KRP Gm0067_1-2 | T679A | S20T | Missense |
| KRP Gm0067_1-2 | C682T | P21S | Missense |
| KRP Gm0067_1-2 | G689A | R23K | Severe Missense |
| KRP Gm0067_1-2 | C739T | P40S | Missense |
| KRP Gm0067_1-2 | G748A | E43K | Missense |
| KRP Gm0067_1-2 | C773T | P51L | Severe Missense |
| KRP Gm0067_1-2 | C776T | A52V | Severe Missense |
| KRP Gm0067_1-2 | T778A | S53T | Severe Missense |
| KRP Gm0067_1-2 | C788T | S56F | Severe Missense |
| KRP Gm0067_1-2 | G818A | R66Q | Missense |
| KRP Gm0067_1-2 | A826T | K69* | Nonsense |
| KRP Gm0067_1-2 | T832A | S71T | Missense |
| KRP Gm0067_1-2 | C833T | S71L | Missense |
| KRP Gm0067_1-2 | G841A | E74K | Severe Missense |
| KRP Gm0067_1-2 | T845A | Splice Junction | Splice |

^Nucleotide numbering is dependent upon the location of TILLING ® primers.
§The designation "1-2" indicates that exons 1-2 of soy KRP Gm0067 were TILLed.

Example 8

Preliminary Field Evaluation Results on F2:3 Generation Wheat KRP TILLING® Mutants The objective was to assess the feasibility of obtaining reliable data from field evaluations of KRP TILLING® lines in spring wheat and to determine the performance of homozygous (F2:3) mutant lines.

Materials & Methods

Five field experiments were conducted during the growing season in Fort Collins, Colo. and Bozeman, Mont. (Table 38) in which a number of mutant lines were evaluated (Table 39).

TABLE 38

| Sites of evaluation of spring wheat mutant materials | | |
|---|---|---|
| Location | Water regime | Planting date |
| Bozeman, MT | Partially irrigated | May 5 |
| Fort Collins, CO | Dryland | April 11 |

TABLE 39

| Mutant materials evaluated in and Bozeman, MT and Fort Collins, CO | | | | | | | |
|---|---|---|---|---|---|---|---|
| Experiment | Number of Entries | WH group | Gene | Genome | Type | Zygosity | F1 families |
| 1 | 39 + Check | 4 | KRP2 | A | Splice | Homo<br>WT | 39D03<br>41D05<br>42D06 |
| 2 | 54 + Check | 11 | KRP2 | A | Splice | Homo<br>WT | 9051_A10 |
| 3 | 37 + Check | 71 | KRP4 | D | Stop | Homo<br>WT | 148E94<br>148E95 |
| 4 | 12 + Check | 4/38 | KRP2 | A/B | Splice/Splice | Homo<br>WT | 9052_E03 |
| 5 | 17 + Check | 44/71 | KRP4 | B/D | Miss/Stop | Homo<br>WT | 9052_G02 |

Major Results

Figure 7:
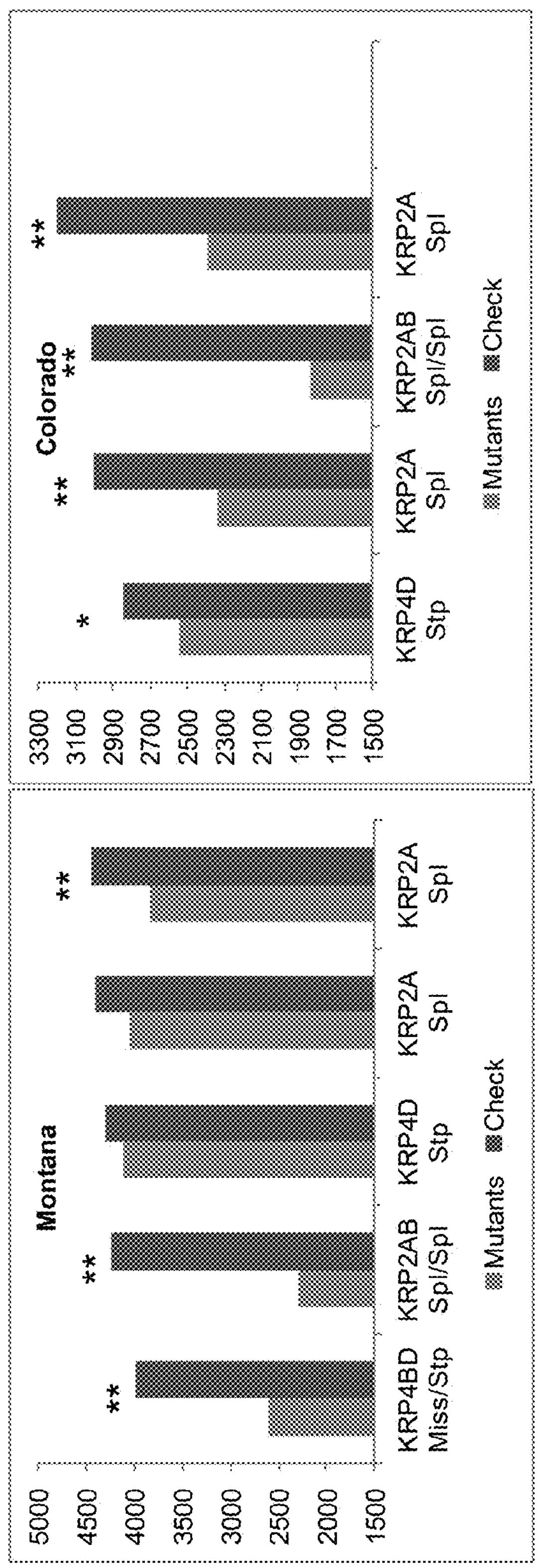
FIG. 7 depicts average grain yield (lbs/ac) of spring wheat KRP TILLING® mutants and check cultivar Express. Bozeman, Mont., Fort Collins, Colo. *, ** stands for significant difference between mutant and check cultivar at the 0.05 and 0.01 probability levels, respectively.

Mutant materials yielded significantly lower than the check cultivar (FIG. 7). This is not surprising, since the mutant lines had been crossed only once to the Express parent and may still have deleterious lesions from the EMS mutagenesis compared to the unmutagenized Express cultivar. Notably, the yield difference between mutant line and check was not significantly different for the KRP4D Stop and the KRP2A Splice WH4 under high yielding conditions (Montana). The impact of mutation appeared to be less for single mutants than for double mutants (FIG. 7). Mutant KRP2AB Splice/Splice had the highest reduction in yield (46% and 39% reductions in MT & CO), and mutant KRP4D Stop had the lowest reduction in yield (4% & 11% reductions in MT & CO).

Figure 8:
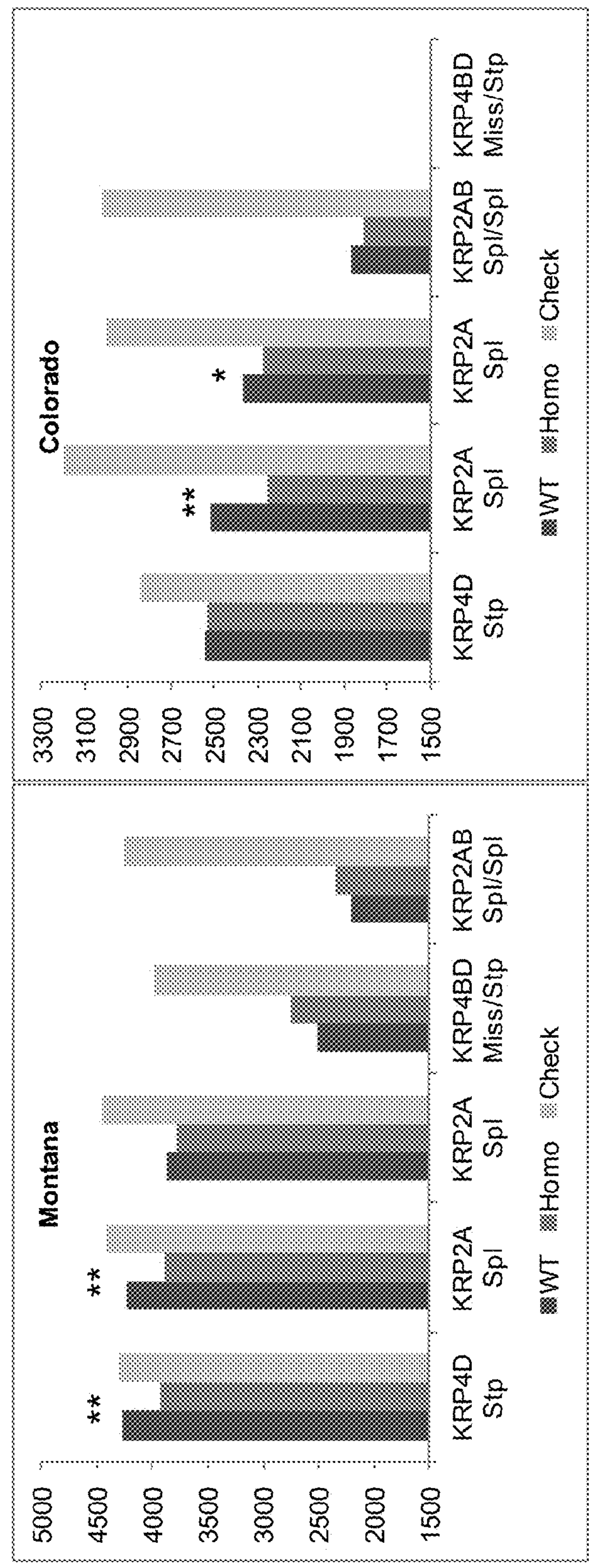
FIG. 8 depicts average grain yield (lbs/ac) of wild type (WT) and homozygous (Homo) zygotic groups for each spring wheat KRP TILLING® mutant and for check cultivar 'Express'. Bozeman, Mont., Fort Collins, Colo. *, ** stands for significant difference between wild type (WT) and homozygous (Homo) zygotic groups at the 0.05 and 0.01 probability levels, respectively.

Between zygotic groups, the wild type (WT) lines tended to yield higher than their mutant counterparts (Homo), although under high yielding conditions (Montana), the opposite appeared to be the case for the double mutants KRP4BD missense/stop and KRP2AB splice/splice (FIG. 8). Among Homo groups, mutants KRP4D Stop and KRP2A Splice WH11 showed the highest relative yield performance. Homozygous mutant KRP2A Splice WH11 performed consistently closer to the average yield of its WT counterpart under both CO and MT growing conditions.

Figure 9:
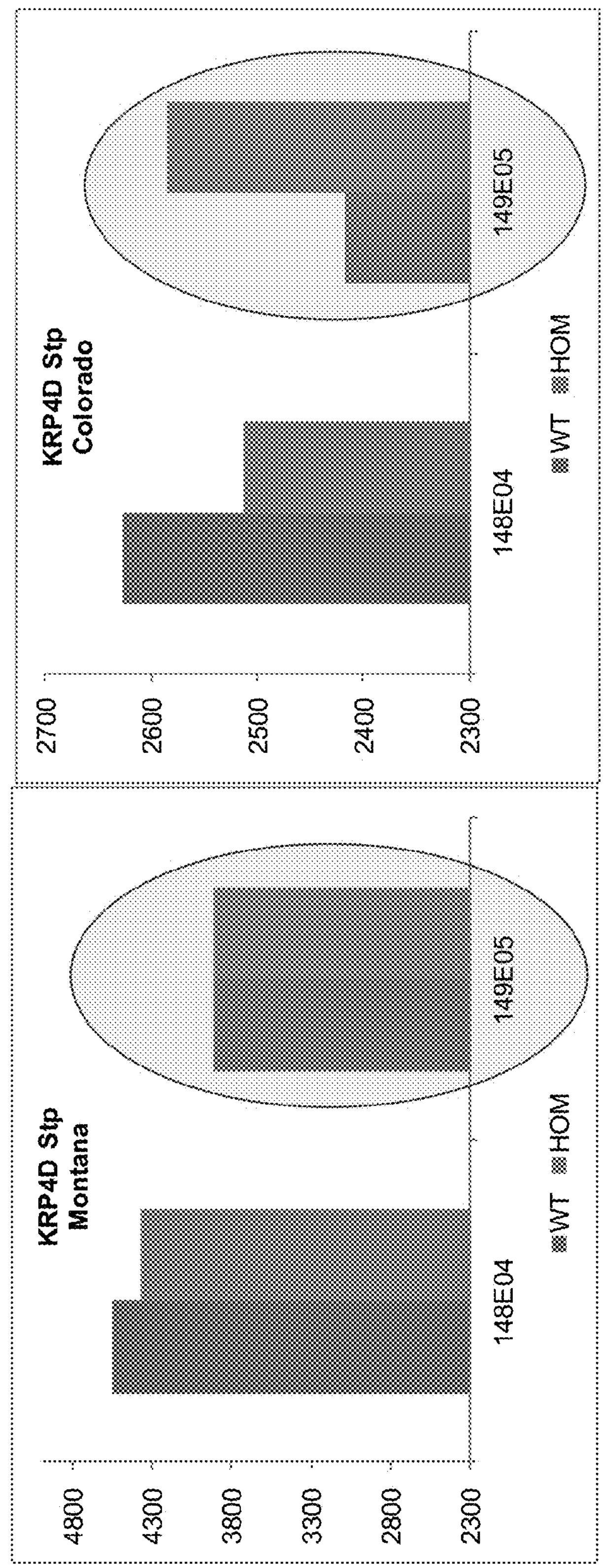
FIG. 9 depicts average grain yield (lbs/ac) of wild type (WT) and homozygous (Homo) zygotic groups within sister F1 lines '148E04' and 149E05' from spring wheat KRP TILLING® mutant KRP4D Stop. Bozeman, Mont., Fort Collins, Colo.
Figure 10:
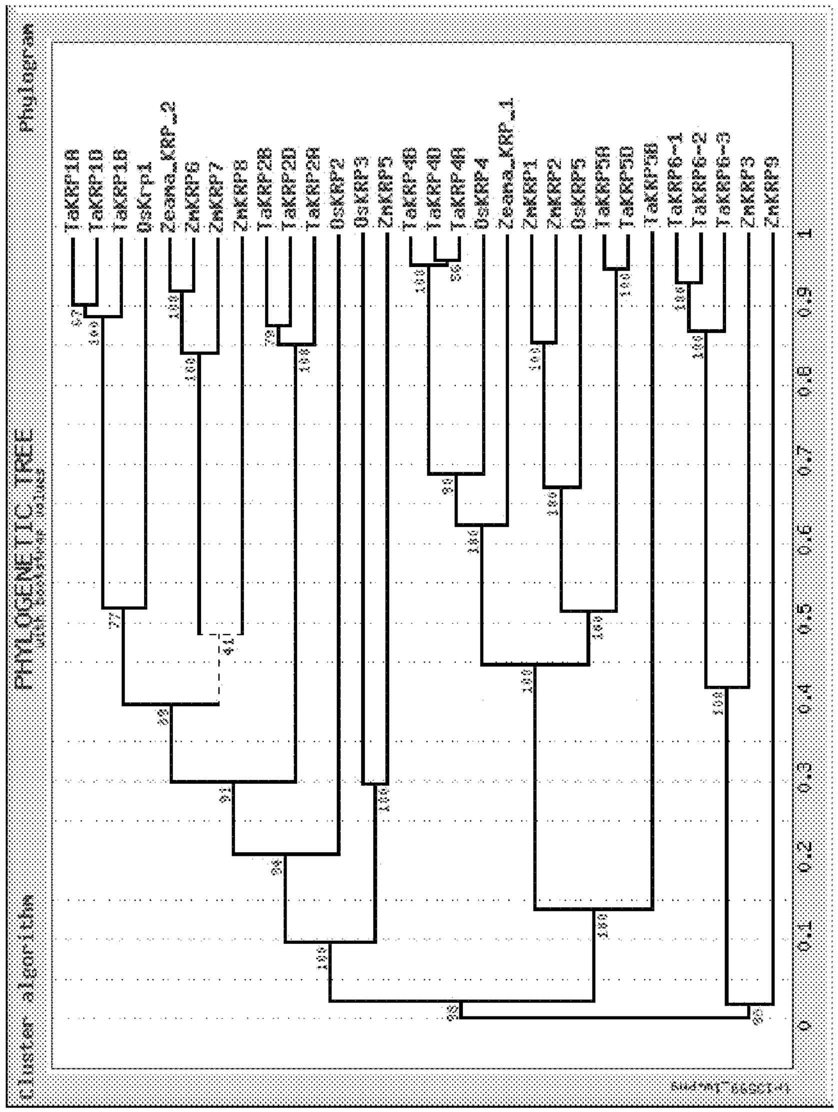
FIG. 10 depicts a phylogenetic tree of rice (Os), corn (Zm) and wheat (Ta) KRPs.

For KRP TILLING® mutants in which F1 sister lines were included, line '149E05' within the KRP4D Stop mutant showed a differential response: homozygous lines yielded above or at least the same as their wild type counterparts (FIG. 9).

The relative grain yield response between the wild type and homozygous zygotic groups can be expressed by the WT/Homo ratio for grain yield and various yield components. Putative mechanisms associated with the relative grain yield response could be discerned (Table 40). In Montana the largest positive effect on yield (WT/Homo ratio=0.92) was observed in the 'KRP4BD Missense/Stop' double mutant and was driven mainly by spike number, thousand kernel weight (TKW) and plant height, whereas the greatest negative effect on yield (WT/Homo ratio=1.09) was observed in the 'KRP2A Splice WH4' mutant, line 42D06, driven mainly by disruptions in kernel number. In Colorado the largest positive effect on yield (WT/Homo ratio=0.93) was observed in the 'KRP4D Stop' mutant, line 149E05, and was driven mainly by TKW and plant height, whereas the largest negative effect on yield (WT/Homo ratio=1.18) was observed in the variant 'KRP2A Splice WH4' mutant, line 42D06, driven mainly by disruptions in spike number and kernel number.

TABLE 40

Relative performance ratio between wild type and homozygous zygotic groups for the mutants evaluated. Bozeman, MT, Fort Collins, CO.

| Gene | F1 line | Spike number Spikes/plant | Kernel number Kernels/spike | TKW g/1000 | Plant height inches | Grain yield Lb/ac |
|---|---|---|---|---|---|---|
| | | Montana | | | | |
| KRP2A Splice | 39D03 | 1.00 | 1.03 | 1.01 | 1.02 | 1.02 |
| KRP2A Splice | 41D05 | 0.99 | 1.08 | 1.01 | 1.01 | 1.08 |
| KRP2A Splice | 42D06 | 1.00 | 1.11 | 0.98 | 0.99 | 1.09 |
| KRP2A Splice | 9051_A10 | 1.05 | 1.02 | 1.00 | 1.01 | 1.03 |
| KRP4D Stop | 148E04 | 1.12 | 1.05 | 1.01 | 0.99 | 1.04 |
| KRP4D Stop | 149E05 | 0.97 | 0.97 | 1.01 | 0.98 | 1.00 |
| KRP2AB Splice/Splice | 9052_E03 | 1.01 | 1.03 | 0.99 | 0.96 | 0.93 |
| KRP4BD Miss/Stop | 9052_G02 | 0.97 | 0.99 | 0.96 | 0.91 | 0.92 |
| | | Colorado | | | | |
| KRP2A Splice | 39D03 | 1.09 | 1.03 | 0.97 | 1.00 | 1.09 |
| KRP2A Splice | 41D05 | 1.04 | 1.03 | 1.01 | 0.99 | 1.07 |
| KRP2A Splice | 42D06 | 1.06 | 1.10 | 1.01 | 1.01 | 1.18 |
| KRP2A Splice | 9051_A10 | 1.04 | 1.01 | 0.99 | 1.02 | 1.04 |
| KRP4D Stop | 148E04 | 1.06 | 1.03 | 0.97 | 1.00 | 1.05 |
| KRP4D Stop | 149E05 | 0.99 | 0.99 | 0.96 | 0.98 | 0.93 |
| KRP2AB Splice/Splice | 9052_E03 | 1.02 | 0.98 | 1.04 | 0.98 | 1.03 |
| KRP4BD Miss/Stop | 9052_G02 | — | — | — | — | — |

Example 9

Identification and Retrieval of Other Wheat KRPs

Rice serves as a diploid model cereal species for wheat. In rice two additional KRP genes are present and expressed: KRP3 and KRP6. KRP3 is expressed at a very specific time point in seed development, while KRP6 seems to be expressed throughout seed development in rice (Mizutani et al 2010). In order to complete the portfolio of wheat KRP TILLING® mutants, other wheat KRPs are identified for future TILLING®.

The rice KRP6 DNA sequence was used to identify a wheat KRP6 EST from a BLAST search at NCBI. Then longer wheat KRP6 sequences were pulled out from a wheat genomic sequences database (WheatBP) at Univeristy of Bristol using the wheat KRP6 EST from NCBI. The wheat database had 5× coverage of the Chinese Spring variety. The wheat TILLING® library is based on the variety Express, but not many polymorphisms are expected between the two varieties.

Wheat KRP6 sequences ranged from ~300 to 800 bp. ContigExpress from Vector NTI (Invitrogen) was used to assemble the various reads into contigs. Reads were assembled into three contigs, which represented TaKRP6A, TaKRP6B and TaKRP6D. Further characterization is done to determine which contig corresponds to which genome. Exon/intron boundaries for the wheat KRP6 genes were deduced based on the rice KRP6 sequence. The deduced coding sequences were translated in Vector to generate protein sequences. Table 41 gives a comparison of KRP6 gene, cDNA and protein lengths for wheat, rice, Brachypodium, corn and sorghum.

TABLE 41

Comparison of wheat, rice, Brachypodium, corn and sorghum KRP6 sequences

| | Total length of sequence available (bp) | 5' | 3' | Length Start-Stop (3 exons, 2 introns) | cDNA | Protein |
|---|---|---|---|---|---|---|
| Ta KRP6-A (wheat) | 1678 (contig of 17 reads) | 94 | 613 | 971 | 264 | 87 aa |
| Ta KRP6-B (wheat) | 1834 (contig of 18 reads) | 164 | 729 | 941 | 264 | 87 aa |
| Ta KRP6-D (wheat) | 2141 (contig of 12 reads) | 369 | 867 | 905 | 270 | 89 aa |
| Os KRP6 (rice) | 1565 | | | 1269 | 261 | 87 aa |
| Brachypodium KRP6 | 1377 | | | 891 | 258 | 86 aa |
| Zm KRP6 (corn) | 1458 | | | 679 | 249 | 83 aa |
| Sb KRP6 (sorghum) | 1253 | | | 995 | 258 | 86 aa |

Using the sequences identified, three primer pairs were designed (Table 42). No wheat KRP6 amplification products were obtained from wheat genomic DNA using proofreading Phusion polymerase at annealing temperatures ranging from 55° C. to 65° C. Using SureBand PCR Optimization kit (Bioline) at 58° C. annealing temperature and one of the twelve buffers from the kit yielded a faint band with TaKRP6 49F and TaKRP6 258R. Repeating the amplification with the same buffer and primer pair, and testing a range of annealing temperatures from 54° C. to 66.5° C., yielded strong, unique bands at 60° C. and higher. The band was cut from the gel and the DNA purified and cloned using TA cloning and Zero Blunt cloning (Invitrogen). Colony screening showed several positive transformants. Minipreps were done on cultures from 30 colonies and all were sequenced from both ends of the insert using M13F and M13R primers.

Sequences obtained were first assembled into contigs (M13F and M13R sequences from each of the 30 clones) and then those contigs were assembled into larger contigs. After assembly and alignments, it was determined that all three versions of wheat KRP6 had been cloned: 14 clones for KRP6A, 1 clone for KRP6B and 14 clones for KRP6D.

TABLE 42

Primers to amplify wheat KRP6

| Primer | Sequence (5' to 3') | SEQ ID NO |
|---|---|---|
| TaKRP6 START | atg gcc gcc acc gcc gcg gc | 147 |
| TaKRP6 near-STOP | tcg gac cca ctc gta ccg ccc | 148 |
| TaKRP6 upstr | cct aat cct atc gtt atc tcc tcc ca | 149 |
| TaKRP6 down-str | cta cga gac aat gta cac aga taa cg | 150 |
| TaKRP6 49F | agc tgc agc aag ggc gag a | 151 |
| TaKRP6 258R | cct cac tcg gac cca ctc gta | 152 |

The rice KRP3 cDNA sequence was used in a BLAST search at NCBI. Several wheat ESTs were identified. The wheat KRP6 sequences identified above were used to search for wheat KRP contigs in the cereal database. Using thisapproach, a contig was identified in the wheat database that looked similar but was not identical to KRP6 or other known wheat KRPs.

Example 10

TILLING® of Other Wheat KRPs and Characterization of Mutants

Design and validation of genome-specific TILLING® primers and TILLING® of other wheat KRPs, such as wheat KRP6, is done as described in Materials and Methods and Example 1 above. The KRP TILLING® mutants obtained are backcrossed, introgressed into other wheat varieties and combined with other wheat KRP mutants as described in Example 3 above. Determination of yield, yield components and agronomic characteristics is as described in Examples 3, 5 and 8 above.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

1. Bentley, A., B. MacLennan, et al. (2000). "Targeted Recovery of Mutations in *Drosophila*." Genetics 156: 1169-1173.

2. Comai, L. and S. Henikoff (2006). "TILLING: practical single-nucleotide mutation discovery." Plant J 45(4): 684-94.

3. Comai, L., K. Young, et al. (2004). "Efficient discovery of DNA polymorphisms in natural populations by Ecotilling." Plant J 37(5): 778-86.

4. Cooper, J. L., E. A. Greene, et al. (2008). "Retention of induced mutations in a *Drosophila* reverse-genetic resource." Genetics 180(1): 661-7.

5. Cooper, J. L., B. J. Till, et al. (2008). "Fly-TILL: reverse genetics using a living point mutation resource." Fly (Austin) 2(6): 300-2.

6. Cooper, J. L., B. J. Till, et al. (2008). "TILLING to detect induced mutations in soybean." BMC Plant Biol 8: 9.

7. Eddy, S. R. (2004). "Where did the BLOSUM62 alignment score matrix come from?" Nat Biotechnol 22(8): 1035-6.

8. Gilchrist, E. and G. Haughn "Reverse genetics techniques: engineering loss and gain of gene function in plants." Brief Funct Genomics 9(2): 103-10. 2010?

9. Gilchrist, E. J. and G. W. Haughn (2005). "TILLING without a plough: a new method with applications for reverse genetics." Curr Opin Plant Biol 8(2): 211-5.

10. Gilchrist, E. J., G. W. Haughn, et al. (2006). "Use of Ecotilling as an efficient SNP discovery tool to survey genetic variation in wild populations of *Populus trichocarpa*." Mol Ecol 15(5): 1367-78.

11. Gilchrist, E. J., N. J. O'Neil, et al. (2006). "TILLING is an effective reverse genetics technique for *Caenorhabditis elegans*." BMC Genomics 7: 262.

12. Greene, E. A., C. A. Codomo, et al. (2003). "Spectrum of chemically induced mutations from a large-scale reverse-genetic screen in *Arabidopsis*." Genetics 164(2): 731-40.

13. Henikoff, S., B. J. Till, et al. (2004). "TILLING. Traditional mutagenesis meets functional genomics." Plant Physiol 135(2): 630-6.

14. Himelblau, E., E. J. Gilchrist, et al. (2009). "Forward and reverse genetics of rapid-cycling *Brassica oleracea*." Theor Appl Genet 118(5): 953-61.

15. McCallum, C. M., L. Comai, et al. (2000). "Targeted screening for induced mutations." Nat Biotechnol 18(4): 455-7. (referenced in Anawah patents)

16. McCallum, C. M., L. Comai, et al. (2000). "Targeting induced local lesions IN genomes (TILLING) for plant functional genomics." Plant Physiol 123(2): 439-42. (referenced in Anawah patents)

17. Ng, P. C. and S. Henikoff (2003). "SIFT: Predicting amino acid changes that affect protein function." Nucleic Acids Res 31(13): 3812-4.

18. Slade, A. J., S. I. Fuerstenberg, et al. (2005). "A reverse genetic, nontransgenic approach to wheat crop improvement by TILLING®." Nat Biotechnol 23(1): 75-81.

19. Slade, A. J. and V. C. Knauf (2005). "TILLING moves beyond functional genomics into crop improvement." Transgenic Res 14(2): 109-15.

20. Stemple, D. L. (2004). "TILLING—a high-throughput harvest for functional genomics." Nat Rev Genet 5(2): 145-50.

21. Styczynski, M. P., K. L. Jensen, et al. (2008). "BLOSUM62 miscalculations improve search performance." Nat Biotechnol 26(3): 274-5.

22. Talame, V., R. Bovina, et al. (2008). "TILLMore, a resource for the discovery of chemically induced mutants in barley." Plant Biotechnol J 6(5): 477-85.

23. Taylor, N. E. and E. A. Greene (2003). "PARSESNP: A tool for the analysis of nucleotide polymorphisms." Nucleic Acids Res 31(13): 3808-11.

24. Till, B. J., C. Burtner, et al. (2004). "Mismatch cleavage by single-strand specific nucleases." Nucleic Acids Res 32(8): 2632-41.

25. Till, B. J., T. Colbert, et al. (2006). "High-throughput TILLING® for *Arabidopsis*." Methods Mol Biol 323: 127-35.

26. Till, B. J., T. Colbert, et al. (2003). "High-throughput TILLING® for functional genomics." Methods Mol Biol 236: 205-20.

27. Till, B. J., J. Cooper, et al. (2007). "Discovery of chemically induced mutations in rice by TILLING®." BMC Plant Biol 7: 19.

28. Till, B. J., S. H. Reynolds, et al. (2003). "Large-scale discovery of induced point mutations with high-throughput TILLING®". Genome Res 13(3): 524-30.

29. Till, B. J., S. H. Reynolds, et al. (2004). "Discovery of induced point mutations in maize genes by TILLING®." BMC Plant Biol 4: 12.

30. Till, B. J., T. Zerr, et al. (2006). "A protocol for TILLING® and Ecotilling in plants and animals." Nat Protoc 1(5): 2465-77.

31. Triques, K., E. Piednoir, et al. (2008). "Mutation detection using ENDO1: application to disease diagnostics in humans and TILLING® and Eco-TILLING in plants." BMC Mol Biol 9: 42.

32. Triques, K., B. Sturbois, et al. (2007). "Characterization of *Arabidopsis thaliana* mismatch specific endonucleases: application to mutation discovery by TILLING® in pea." Plant J 51(6): 1116-25.

33. Uauy, C., F. Paraiso, et al. (2009). "A modified TILLING® approach to detect induced mutations in tetraploid and hexaploid wheat." BMC Plant Biol 9: 115.

34. Weil, C. F. and R. Monde (2007). "Getting the Point—Mutations in Maize." Crop Science 47 (S1) (No. 1): S-60-67.

35a. Zerr, T. and S. Henikoff (2005). "Automated band mapping in electrophoretic gel images using background information." Nucleic Acids Res 33(9): 2806-12.

35b. Tsai, H. et al. (2011), Discovery of Rare Mutations in Populations: TILLING by Sequencing, Plant Physiology, 156(3): 1257-1268

36. Slafer and Araus (2007), Springer, "Physiological traits for improving wheat yield under a wide range of conditions", Scale and Complexity in Plant Systems Research: Gene-Plant-Crop Relations, 147-156

37. Reynolds, "Physiological approaches to wheat breeding", *Agriculture and Consumer Protection*. Food and Agriculture Organization of the United Nations.

38. Richard et al., "Physiological Traits to Improve the Yield of Rainfed Wheat: Can Molecular Genetics Help", published by International Maize and Wheat Improvement Center.

39. Reynolds et al., "Evaluating Potential Genetic Gains in Wheat Associated with Stress-Adaptive Trait Expression in Elite Genetic Resources under Drought and Heat Stress Crop science", Crop Science 2007 47: Supplement 3: S-172-S-189

40. Setter et al., Review of wheat improvement for waterlogging tolerance in Australia and India: the importance of anaerobiosis and element toxicities associated with different soils. Annals of Botany, Volume 103(2): 221-235.

41. M. J. Foulkes, N. D. Paveley, A. Worland, S. J. Welham, J. Thomas, J. W. Snape. Major Genetic Changes in Wheat with Potential to Affect Disease Tolerance. Phytopathology, July, Volume 96, Number 7, Pages 680-688 (doi: 10.1094/PHYTO-96-0680)

42. Rosyara, U. R., K. Pant, E. Duveiller and R. C. Sharma. 2007. Variation in chlorophyll content, anatomical traits and agronomic performance of wheat genotypes differing in spot blotch resistance under natural epiphytotic conditions. Australasian Plant Pathology 36: 245-251.

43. Rosyara, U. R., R. C. Sharma, and E. Duveiller. 2006. Variation of canopy temperature depression and chlorophyll content in spring wheat genotypes and association with foliar blight resistance. J. Plant Breed. Gr. 1: 45-52.

44. Rosyara, U. R., R. C. Sharma, S. M. Shrestha, and E. Duveiller. 2005. Canopy temperature depression and its association with helminthosporium leaf blight resistance in spring wheat. Journal of Institute of Agriculture and Animal Science 26: 25-28.

45. Rosyara, U. R., R. C. Sharma, S. M. Shrestha, and E. Duveiller. 2006. Yield and yield components response to defoliation of spring wheat genotypes with different level of resistance to Helminthosporium leaf blight. Journal of Institute of Agriculture and Animal Science 27.42-48.

46. Rosyara, U. R. 2002. Physio-morphological traits associated with Helminthosporium leaf blight resistance in spring wheat. Masters' Thesis. Tribhuvan University, Institute of Agriculture and Animal Science, Rampur, Chitwan, Nepal. supported by CIMMYT International. Available at CIMMYT library 47. Hayward, M. D., N. O. Bosemark, and I. Romangosa. 1993. Plant Breeding: Principle and Prospects. Chapman and Hall, London.

48. Wood, D. R., K. M. Rawal, and M. N. Wood (eds). 1983. Crop Breeding. American Society of Agronomy, Crop Science Society of America, Madison, Wis.

49. Allard, R W. 1960. Principles of Plant Breeding. John Wily and Sons Inc. New York.

50. Simmonds, N. W. 1979. Principles of Crop Improvement. Longman Group Limited, London.

51. Singh, B. D. 2000. Plant Breeding. Sixth ED. Kalyani Publishers, New Delhi.

52. Guo et al., 2005, American Journal of Botany 92(9): 1548-1558.

53. Watson et al. 1999. Grass genera of the world: descriptions, illustrations, identification, and information retrieval; including synonyms, morphology, anatomy, physiology, phytochemistry, cytology, classification, pathogens, world and local distribution, and references. Version: 18 Aug. 1999, 54. GPWG. 2001. Phylogeny and subfamilial classification of the grasses (Poaceae). Annals of the Missouri Botanical Garden 88: 373-457.

55. Clayton et al., 1986. Genera Graminum. Kew Bulletin Additional Series XIII: 1-389.

56. Vaughan, 1994. The wild relative of rice: a genetic resources handbook. International Rice Research Institute, Manila, Philippines.

57. Donald C. M., 1968. The breeding for crop ideotypes. Euphytica. 17, 385-403.

58. Gao P. W., Wang B. L. et al., 1988. Studies on physiology and ecology for rice with high yield. Liaoning Agricultural Science. 1, 7-11.

59. International Rice research Institute, 1996. Rice research in Asia. IRRI. 1-70.

60. Shao G. J. et al., 1995. Summarization and discussion on rice breeding research and development in Liaoning Province. Liaoning Agricultural Science. 6, 28-33.

61. Wang B. L. et al., 1989. Incident light distribution over the population with high yield in rice. Liaoning Agricultural Science. 6, 27-30.

62. Wang B. L., 1992. The Trail and method of rice breeding for super high yield. The Proceedings of Rice Research. Chinese Science and Technological Press. 97-104.

63. Wang B. L. et al., 1997. Studies on genetic activities of semi-dwarfism and erect-panicle in rice. Journal of Shenyang Agricultural University. 28(2), 83-87.

64. Wang B. L., 2000. Studies on rice breeding for high yield, good quality and multiple resistance. Prospects of Rice Genetics and Breeding for the 21st Century. China Agricultural Scientech Press. 191-195.

65. Wang B. L. et al., 2002. Analysis of rice breeding in Liaoning Province in 1949-2000. Liaoning Agricultural Science. 5, 5-8.

66. Yang S. J., et al 1987. Research on rice breeding through crossing indica and japonica and its evolution in the past thirty six years. Journal of Shenyang Agricultural University. 18(3), 3-9.

67. Tan et al., The three important traits for cooking and eating quality of rice grains are controlled by a single locus in an elite rice hybrid, Shanyou 63, Thero. Appl. Genet (1999) 99:642-648

68. Yan et al., Comparative analyses of QTL for important agronomic traits between maize and rice, Yi Chuan Xue Bao, 2004, 31(12):1401-1407

69. Khush et al., Rice Genetics IV, Int. Rice Res. Inst. 2001

70. Yamamoto et al., "Towards the Understanding of Complex Traits in Rice: Substantially or Superficially?", DNA RESEARCH pp. 1-14, (2009)

71. Viraktamath et al., 1997, Hybrid rice breeding manual, ISBN 9712201031, 9789712201035

72. International Rice Research Institute, 1972, Rice Breeding

73. Rice breeding: Papers presented at the Symposium on Rice Breeding held at the International Rice Research Institute, 6-10 Sep., 1971

74. Chakraborty, 2001, Rice Breeding and Genetics, ISBN 8170228743, 9788170228745

75. International Rice Research Institute, 2003, Two-line hybrid rice breeding manual, ISBN 9712201856, 9789712201851

76. Marshall and Wadsworth, Rice science and technology, vol. 59 of Food science and technology, CRC Press, 1994, ISBN 0824788877, 9780824788872

77. Xia, Progress of chromosome engineering mediated by asymmetric somatic hybridization, J Genet Genomics. 2009 September; 36(9):547-56. Review.

78. Liu et al., Generation of high frequency of novel alleles of the high molecular weight glutenin in somatic hybridization between bread wheat and tall wheatgrass. Theor Appl Genet. 2009 April; 118(6):1193-8. Epub 2009 Feb. 8.

79. Zhou et al., Comparative study of symmetric and asymmetric somatic hybridization between common wheat and *Haynaldia villosa*. Sci China C Life Sci. 2001 June; 44(3):294-304.

80. Wang et al., Proteomic analysis on a high salt tolerance introgression strain of *Triticum aestivum/Thinopyrum ponticum*. Proteomics. 2008 April; 8(7):1470-89.

81. Cai et al., Genotyping of somatic hybrids between *Festuca arundinacea* Schreb. and *Triticum aestivum* L., Plant Cell Rep. 2007 October; 26(10):1809-19. Epub 2007 Jun. 27.

82. Deng et al., Analysis of remote asymmetric somatic hybrids between common wheat and *Arabidopsis thaliana*, Plant Cell Rep. 2007 August; 26(8):1233-41. Epub 2007 Apr. 4.

83. Zhou et al., Genetic characterization of asymmetric somatic hybrids between *Bupleurum scorzonerifolium* Willd and *Triticum aestivum* L.: potential application to the study of the wheat genome. Planta. 2006 March; 223(4):714-24. Epub 2005 Nov. 4.

84. Li et al., Regeneration of asymmetric somatic hybrid plants from the fusion of two types of wheat with Russian wildrye. Plant Cell Rep. 2004 December; 23(7):461-7. Epub 2004 Jul. 24.

85. Zhou et al., Introgression of the *Haynaldia villosa* genome into gamma-ray-induced asymmetric somatic hybrids of wheat. Plant Cell Rep. 2005 July; 24(5):289-96. Epub 2005 Jun. 3.

86. Xia et al., RAPD method for the identification of intergeneric asymmetric somatic hybrid plants of wheat. Shi Yan Sheng Wu Xue Bao. 1999 September; 32(3):265-70. Chinese.

87. Mostageer et al., Establishment of a salt tolerant somatic hybrid through protoplast fusion between rice and ditch reed Arab J. Biotech., Vol. 6, No. (1) January (2003): 1-12.

88. Nakajo et al., Somatic cell hybridization in rice (*Oryza sativa* L.) and birdsfoot trefoil (*Lotus corniculatus* L.) Japanese Journal of Breeding (March 1994)

89. Niizeki et al., Somatic hybridization in rice×soybean, Bajaj YPS (ed) Biotechnology in agriculture and forestry vol 8, Plant protoplasts and genetic engineering. Springer, Berlin Heidelberg N.Y., pp 410-434

90. Kisaka, et al., Intergeneric somatic hybridization of rice (*Oryza sativa* L.) and barley (*Hordeum vulgare* L.) by protoplast fusion, Plant Cell Reports, Volume 17, Number 5, 362-367

91. Cocking, Rice biotechnology: Somatic hybridisation for improved salinity tolerance and xylem colonisation by rhizobia for endophytic nitrogen fixation Cahiers Options, vol 40

92. Ishikawa et al., Rice interspecies hybrids show precocious or delayed developmental transitions in the endosperm without change to the rate of syncytial nuclear division. Plant J. 2011 March; 65(5):798-806.

93. X. Hu, X. Cheng, H. Jiang, S. Zhu, B. Cheng and Y. Xiang, (2010), Genome-wide analysis of cyclins in maize (*Zea mays*), Genet. Mol. Res. 9 (3): 1490-1503

94. Acquaah et al. Principles of plant genetics and breeding, Wiley-Blackwell, 2007, ISBN 1405136464, 9781405136464

95. Harten, Mutation Breeding, Cambridge University Press, 1998.

96. Roy Davies and Wall, "Artificial Mutagenesis in Plant Breeding", Nature 182, 955-956 (4 Oct. 1958)

97. Grotewold, Plant Functional Genomics, Volume 236 of Methods in molecular biology, Humana Press, ISBN 1588291456, 9781588291455

98. Braman, In vitro mutagenesis protocols, Volume 182 of Methods in molecular biology, Human Press, 2002, ISBN 0896039102, 9780896039100

99. Chusacultanachai et al., "Random mutagenesis strategies for construction of large and diverse clone libraries of mutated DNA fragments." Methods Mol Biol. 2004;270: 319-34.

100. Fujii et al., One-step random mutagenesis by error-prone rolling circle amplification, Nucl. Acids Res. (2004) 32 (19): e145.

101. Trower, In vitro mutagenesis protocols, Volume 57 of Methods in molecular biology, John M. Walker Methods in molecular biology (Clifton, N.J.) 57, ISBN 0896033325, 9780896033320

102. Katsumi, M., Foard, D. E. and Phinney, B. O. (1983) Evidence for the translocation of gibberellin A3 and gibberellin-like substances in grafts between normal, dwarf1 and dwarf5 seedlings of *Zea mays* L. Plant Cell Physiol. 24, 379-388.

103. Lacadena, J.-R. Hybrid wheat. VII. Tests on the transmission of cytoplasmic male sterility in wheat by embryo-endosperm grafting, Euphytica, 17(3), 439-444

104. Trione et al., 1968, IN VITRO CULTURE OF SOMATIC WHEAT CALLUS TISSUE American Journal of Botany, Vol. 55, No. 5, May-June, 19

105. Dodig, et al., tissue culture response of different wheat genotypes, environmental effect and association with plant traits, Options MEditerraneennes, Series A, No. 81, pages 129 to 132

106. O'HARA et al., Wheat Callus Culture: the Initiation, Growth and Organogenesis of Callus Derived from Various Explant Sources Ann Bot (1978) 42 (5): 1029-1978.

107. Zaidi et al., Optimizing tissue culture media for efficient transformation of different indica rice genotypes Agronomy Research 4(2):563-575, 2006

108. Wang et al., Tissue Culture Responses from Different Explants of Rice, Rice Science, 2005, 12(3): 229-232

109. Ting Y, Boyer A, McSweeney G (1978) Maize tissue culture. MNL 52:6

120. Martha C. Hawes, Diana Z. Sharpe, Maria-Ines Plata, Steven G. Pueppke, Prem S. Chourey, Auxin-independent growth of maize tissue culture cells, Plant Science, Volume 40, Issue 3, September 1985, Pages 197-202

121. SHERIDAN Tissue Culture of Maize, Physiologia Plantarum, 41(3):172-174, 1977

122. Mizutani et al. The syncytium-specific expression of the Orysa;KRP3 CDK inhibitor: implication of its involvement in the cell cycle control in the rice (*Oryza sativa* L.) syncytial endosperm J Exp Bot. 2010 March; 61(3): 791-798. Published online 2009 Nov. 20. doi: 10.1093/jxb/erp343

The invention claimed is:

1. A plant cell, plant part, plant tissue culture or whole plant comprising one or more non-naturally occurring mutated Kinase Inhibitor Protein (KIP) Related Protein (KRP) genes, wherein the plant is a species in the *Triticum* genus, and wherein the one or more non-naturally occurring mutations of the KRP gene comprises a mutation selected from the group consisting of a G to A substitution at nucleotide 990 from the start codon of a nucleotide sequence as set forth in SEQ ID NO: 66, a C to T substitution at nucleotide 807 from the start codon of a nucleotide sequence as set forth in SEQ ID NO: 68, and a C to T substitution at nucleotide 572 as set forth in SEQ ID NO: 79.

2. The plant cell, plant part, plant tissue culture or whole plant of claim 1, wherein the plant in the *Triticum* genus is wheat.

3. A method of increasing seed weight, seed size, seed number or seed yield of a plant in the *Triticum* genus comprising introducing one or more mutations into one or more KRPs in the plant, wherein the one or more non-naturally occurring mutations comprises a mutation selected from the group consisting of a G to A substitution at nucleotide 990 from the start codon of a nucleotide sequence as set forth in SEQ ID NO: 66, a C to T substitution at nucleotide 807 from the start codon of a nucleotide sequence as set forth in SEQ ID NO: 68, and a C to T substitution at nucleotide 572 as set forth in SEQ ID NO: 79.

4. A method of producing a plant with increased seed size, seed weight, seed number or seed yield compared to a wild type plant, comprising i) making a cross between a first plant to a second plant to produce a F1 plant, wherein the first plant is in the *Triticum* genus and comprises one or more non-naturally occurring mutations in one or more KRP genes, wherein the one or more non-naturally occurring mutations comprises a mutation selected from the group consisting of a G to A substitution at nucleotide 990 from the start codon of a nucleotide sequence as set forth in SEQ ID NO: 66, a C to T substitution at nucleotide 807 from the start codon of a nucleotide sequence as set forth in SEQ ID NO: 68, and a C to T substitution at nucleotide 572 as set forth in SEQ ID NO: 79.

5. The method of claim 4, wherein the method further comprises ii) backcrossing the F1 plant to the first or the second plant; and iii) repeating the backcrossing step to generate a near isogenic line, wherein the one or more KRP genes with one or more non-naturally occurring mutations in the first plant are integrated into the genome of the near isogenic line.

* * * * *

SEQUENCE LISTING

```
<160> NUMBER OF SEQ ID NOS: 184

<210> SEQ ID NO 1
<211> LENGTH: 1276
<212> TYPE: DNA
<213> ORGANISM: Arabidopsis sp.

<400> SEQUENCE: 1

aaattcatca tctttctttc ttcttcttcc tcatcctctc aatcatatct ctctctctca      60
```

```
cagagattgt gacttcacgc acacgtaacc taaatcgaag atggtgagaa aatatagaaa    120

agctaaagga attgtagaag ctggagtttc gtcaacgtat atgcagctac ggagccggag    180

aattgtttat gttagatcgg aaaaatcaag ctctgtctcc gtcgtcggtg ataatggagt    240

ttcgtcgtct tgtagtggaa gcaatgaata taagaagaaa gaattaatac atctggaggt    300

tatttaatgt tgttgattct agattcttgt aactgtatat gtatcattta atgttaatgt    360

attttttttt gaaattttga aatttttgta ggaggaagat aaagatggtg acactgaaac    420

gtcgacgtat cgacggtgag tgttaaaaaa aaaactgaaa atgatttgaa ttttgaaggt    480

tttattattt tcccggttat ttatttgact ctctcttcaa taaatttaga atcttgcttg    540

tgagttattt taggggtacg aagaggaagc tttttgaaaa tctgagagag gaggagaaag    600

aagaattaag taaatccatg gagaattatt catcggaatt tgaatcggcg gttaaagaat    660

cgttagattg ttgttgtagc gggaggaaaa cgatggagga gacggtgacg gcggaggagg    720

aggagaaggc gaaattgatg acggagatgc caacggaatc ggaaattgaa gatttttttg    780

tggaagctga gaaacaactc aaagaaaaat tcaagaagaa gtaagttttt attttatttt    840

gtgagtttga tttttataga taatatattt tttattcata atttaaaatt gattttgagg    900

taaaattaag agtgagttta ttttttttta attaggtaca atttcgattt cgagaaggag    960

aagccattag aaggacgtta cgaatgggta aagttagagt gaagaagaag aagaagttta   1020

tggttttttt tttaactttt tagattttaa tatttcaggg aataagttaa ttttattttg   1080

ttgatttgga aatataagat ttgtaggagg aatgttttta gaagtacgaa attgcacaga   1140

aaaagaagaa agctttttaa cagattttag agcccagaaa agtcgtgtct tttagctcta   1200

cttttacctc ttcttcgaat cttgtgtatc ttttagcata ttctttagta catttttatg   1260

tttttggtga ctgata                                                   1276
```

<210> SEQ ID NO 2
<211> LENGTH: 576
<212> TYPE: DNA
<213> ORGANISM: Arabidopsis sp.

<400> SEQUENCE: 2

```
atggtgagaa aatatagaaa agctaaagga attgtagaag ctggagtttc gtcaacgtat     60

atgcagctac ggagccggag aattgtttat gttagatcgg aaaaatcaag ctctgtctcc    120

gtcgtcggtg ataatggagt ttcgtcgtct tgtagtggaa gcaatgaata taagaagaaa    180

gaattaatac atctggagga ggaagataaa gatggtgaca ctgaaacgtc gacgtatcga    240

cggggtacga agaggaagct ttttgaaaat ctgagagagg aggagaaaga agaattaagt    300

aaatccatgg agaattattc atcggaattt gaatcggcgg ttaaagaatc gttagattgt    360

tgttgtagcg ggaggaaaac gatggaggag acggtgacgg cggaggagga ggagaaggcg    420

aaattgatga cggagatgcc aacggaatcg gaaattgaag atttttttgt ggaagctgag    480

aaacaactca aagaaaaatt caagaagaag tacaatttcg atttcgagaa ggagaagcca    540

ttagaaggac gttacgaatg ggtaaagtta gagtga                              576
```

<210> SEQ ID NO 3
<211> LENGTH: 191
<212> TYPE: PRT
<213> ORGANISM: Arabidopsis sp.

<400> SEQUENCE: 3

```
Met Val Arg Lys Tyr Arg Lys Ala Lys Gly Ile Val Glu Ala Gly Val
1               5                   10                  15

Ser Ser Thr Tyr Met Gln Leu Arg Ser Arg Arg Ile Val Tyr Val Arg
            20                  25                  30

Ser Glu Lys Ser Ser Ser Val Ser Val Val Gly Asp Asn Gly Val Ser
        35                  40                  45

Ser Ser Cys Ser Gly Ser Asn Glu Tyr Lys Lys Lys Glu Leu Ile His
    50                  55                  60

Leu Glu Glu Glu Asp Lys Asp Gly Asp Thr Glu Thr Ser Thr Tyr Arg
65                  70                  75                  80

Arg Gly Thr Lys Arg Lys Leu Phe Glu Asn Leu Arg Glu Glu Glu Lys
                85                  90                  95

Glu Glu Leu Ser Lys Ser Met Glu Asn Tyr Ser Ser Glu Phe Glu Ser
            100                 105                 110

Ala Val Lys Glu Ser Leu Asp Cys Cys Cys Ser Gly Arg Lys Thr Met
        115                 120                 125

Glu Glu Thr Val Thr Ala Glu Glu Glu Glu Lys Ala Lys Leu Met Thr
    130                 135                 140

Glu Met Pro Thr Glu Ser Glu Ile Glu Asp Phe Phe Val Glu Ala Glu
145                 150                 155                 160

Lys Gln Leu Lys Glu Lys Phe Lys Lys Lys Tyr Asn Phe Asp Phe Glu
                165                 170                 175

Lys Glu Lys Pro Leu Glu Gly Arg Tyr Glu Trp Val Lys Leu Glu
            180                 185                 190
```

<210> SEQ ID NO 4
<211> LENGTH: 513
<212> TYPE: DNA
<213> ORGANISM: Brassica napus

<400> SEQUENCE: 4

```
atggtgagaa aatgcagaaa aactaaaggg acggtgggag cttcgtctac gtatatgcag      60

cttcgcagcc ggagaatcgt ttacagatcg gaaaaagcta gctcgtcgtc gtcgtcttgt     120

tgcgcgagta acaacaatgg agttatagat cttgaggagg aaagagatgg tgagactgaa     180

acgtcgtcgt gtcgacggag tagtaagagg aagctatttg aaaaccttag agaaaaagaa     240

tctatggaga attcacagca aatcgtagct ggttttgatt ccgccgtgaa agaatcatcg     300

gattgttgtt gcagccggag aacatctttg tcaacgacgg aggagaaggg gaaatcagcg     360

acggagcaac caccaacggc agtggagatt gaagattttt tcgtggaagc tgagaaacag     420

ctccatgata atttcaagaa gaagtataac tttgatttcg aaaaggagaa gccattagaa     480

ggacgctacg agtgggttaa attatcagag taa                                  513
```

<210> SEQ ID NO 5
<211> LENGTH: 170
<212> TYPE: PRT
<213> ORGANISM: Brassica napus

<400> SEQUENCE: 5

```
Met Val Arg Lys Cys Arg Lys Thr Lys Gly Thr Val Gly Ala Ser Ser
1               5                   10                  15

Thr Tyr Met Gln Leu Arg Ser Arg Arg Ile Val Tyr Arg Ser Glu Lys
            20                  25                  30

Ala Ser Ser Ser Ser Ser Ser Cys Cys Ala Ser Asn Asn Asn Gly Val
        35                  40                  45
```

```
Ile Asp Leu Glu Glu Glu Arg Asp Gly Glu Thr Glu Thr Ser Ser Cys
    50                  55                  60

Arg Arg Ser Ser Lys Arg Lys Leu Phe Glu Asn Leu Arg Glu Lys Glu
65                  70                  75                  80

Ser Met Glu Asn Ser Gln Gln Ile Val Ala Gly Phe Asp Ser Ala Val
                85                  90                  95

Lys Glu Ser Ser Asp Cys Cys Cys Ser Arg Arg Thr Ser Leu Ser Thr
            100                 105                 110

Thr Glu Glu Lys Gly Lys Ser Ala Thr Glu Gln Pro Pro Thr Ala Val
        115                 120                 125

Glu Ile Glu Asp Phe Phe Val Glu Ala Glu Lys Gln Leu His Asp Asn
    130                 135                 140

Phe Lys Lys Lys Tyr Asn Phe Asp Phe Glu Lys Glu Lys Pro Leu Glu
145                 150                 155                 160

Gly Arg Tyr Glu Trp Val Lys Leu Ser Glu
                165                 170
```

<210> SEQ ID NO 6
<211> LENGTH: 28
<212> TYPE: DNA
<213> ORGANISM: Artificial Sequence
<220> FEATURE:
<223> OTHER INFORMATION: Primer TAKRP1A_L

<400> SEQUENCE: 6
ggatacgatt cgagatctcc tttttgac 28

<210> SEQ ID NO 7
<211> LENGTH: 29
<212> TYPE: DNA
<213> ORGANISM: Artificial Sequence
<220> FEATURE:
<223> OTHER INFORMATION: Primer TAKRP1A_R

<400> SEQUENCE: 7
tgataatggt gggaatatgt gagcgagtg 29

<210> SEQ ID NO 8
<211> LENGTH: 27
<212> TYPE: DNA
<213> ORGANISM: Artificial Sequence
<220> FEATURE:
<223> OTHER INFORMATION: Primer TAKRP1B_L

<400> SEQUENCE: 8
aaacagcaag gtgagggaat tggggtc 27

<210> SEQ ID NO 9
<211> LENGTH: 29
<212> TYPE: DNA
<213> ORGANISM: Artificial Sequence
<220> FEATURE:
<223> OTHER INFORMATION: Primer TAKRP1B_R

<400> SEQUENCE: 9
taatgcttct ttccggagca tctttttcc 29

<210> SEQ ID NO 10
<211> LENGTH: 29
<212> TYPE: DNA
<213> ORGANISM: Artificial Sequence
<220> FEATURE:
<223> OTHER INFORMATION: Primer TAKRP1D_L

<400> SEQUENCE: 10
ggatacaatt cgagatctcc tttttgctg 29

<210> SEQ ID NO 11
<211> LENGTH: 29
<212> TYPE: DNA
<213> ORGANISM: Artificial Sequence
<220> FEATURE:
<223> OTHER INFORMATION: Primer TAKRP1D_R

<400> SEQUENCE: 11
taatgcttct ttccggagca tctttttcc 29

<210> SEQ ID NO 12
<211> LENGTH: 28
<212> TYPE: DNA
<213> ORGANISM: Artificial Sequence
<220> FEATURE:
<223> OTHER INFORMATION: Primer TAKRP2A2L1

<400> SEQUENCE: 12
gccactcact gccctagaat tctccgta 28

<210> SEQ ID NO 13
<211> LENGTH: 33
<212> TYPE: DNA
<213> ORGANISM: Artificial Sequence
<220> FEATURE:
<223> OTHER INFORMATION: Primer TAKRP2A2R1

<400> SEQUENCE: 13
caatttggat ggggagagag agagagctag tgt 33

<210> SEQ ID NO 14
<211> LENGTH: 29
<212> TYPE: DNA
<213> ORGANISM: Artificial Sequence
<220> FEATURE:
<223> OTHER INFORMATION: Primer TAKRP2B2L2

<400> SEQUENCE: 14
gtccactgcc ctagaattct ccgctactt 29

<210> SEQ ID NO 15
<211> LENGTH: 29
<212> TYPE: DNA
<213> ORGANISM: Artificial Sequence
<220> FEATURE:
<223> OTHER INFORMATION: Primer TAKRP2B2_ALTR

<400> SEQUENCE: 15
gccgtggcct agtgaaaggt aaaaagaaa 29

<210> SEQ ID NO 16
<211> LENGTH: 27
<212> TYPE: DNA
<213> ORGANISM: Artificial Sequence
<220> FEATURE:
<223> OTHER INFORMATION: Primer KRP2D2_ENDEX1_L

<400> SEQUENCE: 16
tccactgccc tagaattctc cgctaat 27

<210> SEQ ID NO 17

```
<211> LENGTH: 27
<212> TYPE: DNA
<213> ORGANISM: Artificial Sequence
<220> FEATURE:
<223> OTHER INFORMATION: Primer KRP2D2_ENDEX4_R

<400> SEQUENCE: 17

gtcatttgca tcatgctctg ctcacac                                          27


<210> SEQ ID NO 18
<211> LENGTH: 36
<212> TYPE: DNA
<213> ORGANISM: Artificial Sequence
<220> FEATURE:
<223> OTHER INFORMATION: Primer KRP4B_L_2_3_NEW

<400> SEQUENCE: 18

ttccttattt tttatgacta ttgatatgtg ttcttc                                36


<210> SEQ ID NO 19
<211> LENGTH: 31
<212> TYPE: DNA
<213> ORGANISM: Artificial Sequence
<220> FEATURE:
<223> OTHER INFORMATION: WKP4_BR2

<400> SEQUENCE: 19

gtggtcatta cagaatgagc tgctaaccgt t                                     31


<210> SEQ ID NO 20
<211> LENGTH: 28
<212> TYPE: DNA
<213> ORGANISM: Artificial Sequence
<220> FEATURE:
<223> OTHER INFORMATION: Primer KRP4D_L_2_3_NEW

<400> SEQUENCE: 20

ttacgaccac ggatgatatc gatatgtg                                         28


<210> SEQ ID NO 21
<211> LENGTH: 27
<212> TYPE: DNA
<213> ORGANISM: Artificial Sequence
<220> FEATURE:
<223> OTHER INFORMATION: Primer KRP4D_R_2_3_NEW

<400> SEQUENCE: 21

cattggagtt ttgagggatt agggtgt                                          27


<210> SEQ ID NO 22
<211> LENGTH: 25
<212> TYPE: DNA
<213> ORGANISM: Artificial Sequence
<220> FEATURE:
<223> OTHER INFORMATION: Primer TAKRP5A1_L

<400> SEQUENCE: 22

ggcaagtaca tgcgcaagag caagg                                            25


<210> SEQ ID NO 23
<211> LENGTH: 29
<212> TYPE: DNA
<213> ORGANISM: Artificial Sequence
<220> FEATURE:
<223> OTHER INFORMATION: Primer TAKRP5A1_R

<400> SEQUENCE: 23
```

gattttcttc tccatcagga ttgaagcgc 29

<210> SEQ ID NO 24
<211> LENGTH: 28
<212> TYPE: DNA
<213> ORGANISM: Artificial Sequence
<220> FEATURE:
<223> OTHER INFORMATION: Primer TAKRP5A2_L

<400> SEQUENCE: 24
cacattgtgt gatgtggggc acttgtta 28

<210> SEQ ID NO 25
<211> LENGTH: 29
<212> TYPE: DNA
<213> ORGANISM: Artificial Sequence
<220> FEATURE:
<223> OTHER INFORMATION: Primer TAKRP5_ALL_EST_R

<400> SEQUENCE: 25
gagctactgc tgactgcggg ctaactcta 29

<210> SEQ ID NO 26
<211> LENGTH: 26
<212> TYPE: DNA
<213> ORGANISM: Artificial Sequence
<220> FEATURE:
<223> OTHER INFORMATION: Primer TAKRP5D_L_Z_2

<400> SEQUENCE: 26
tgtctagcgt ggggcacttg caaata 26

<210> SEQ ID NO 27
<211> LENGTH: 29
<212> TYPE: DNA
<213> ORGANISM: Artificial Sequence
<220> FEATURE:
<223> OTHER INFORMATION: Primer TAKRP5_ALL_EST_R

<400> SEQUENCE: 27
gagctactgc tgactgcggg ctaactcta 29

<210> SEQ ID NO 28
<211> LENGTH: 36
<212> TYPE: DNA
<213> ORGANISM: Artificial Sequence
<220> FEATURE:
<223> OTHER INFORMATION: Primer KRP4B2 P109L-FORWARD GENOTYPING

<400> SEQUENCE: 28
ttccttattt tttatgacta ttgatatgtg ttcttc 36

<210> SEQ ID NO 29
<211> LENGTH: 31
<212> TYPE: DNA
<213> ORGANISM: Artificial Sequence
<220> FEATURE:
<223> OTHER INFORMATION: Primer KRP4B2 P109L-REVERSE GENOTYPING

<400> SEQUENCE: 29
gtggtcattt cagaatgagc tgctaaccgt t 31

<210> SEQ ID NO 30
<211> LENGTH: 26
<212> TYPE: DNA

<213> ORGANISM: Artificial Sequence
<220> FEATURE:
<223> OTHER INFORMATION: AD ASSAY WITH FLANKING FORWARD PRIMER

<400> SEQUENCE: 30
tgtgtatgta tgttttgtgg ctagca 26

<210> SEQ ID NO 31
<211> LENGTH: 22
<212> TYPE: DNA
<213> ORGANISM: Artificial Sequence
<220> FEATURE:
<223> OTHER INFORMATION: AD ASSAY WITH FLANKING REVERSE PRIMER

<400> SEQUENCE: 31
cgttcccgag tccctaatca ag 22

<210> SEQ ID NO 32
<211> LENGTH: 14
<212> TYPE: DNA
<213> ORGANISM: Artificial Sequence
<220> FEATURE:
<223> OTHER INFORMATION: LABELED PROBE SPECIFIC TO THE WILD TYPE ALLELE
<220> FEATURE:
<221> NAME/KEY: misc_feature
<222> LOCATION: (1)..(1)
<223> OTHER INFORMATION: May be VIC labeled
<220> FEATURE:
<221> NAME/KEY: misc_feature
<222> LOCATION: (14)..(14)
<223> OTHER INFORMATION: May be MGB-NFQ labeled

<400> SEQUENCE: 32
tgcagggcgt cgtc 14

<210> SEQ ID NO 33
<211> LENGTH: 15
<212> TYPE: DNA
<213> ORGANISM: Artificial Sequence
<220> FEATURE:
<223> OTHER INFORMATION: LABELED PROBE SPECIFIC TO THE MUTANT ALLELE
<220> FEATURE:
<221> NAME/KEY: misc_feature
<222> LOCATION: (1)..(1)
<223> OTHER INFORMATION: May be FAM labeled
<220> FEATURE:
<221> NAME/KEY: misc_feature
<222> LOCATION: (15)..(15)
<223> OTHER INFORMATION: May be MGB-NFQ labeled

<400> SEQUENCE: 33
ctgcagagcg tcgtc 15

<210> SEQ ID NO 34
<211> LENGTH: 42
<212> TYPE: DNA
<213> ORGANISM: Artificial Sequence
<220> FEATURE:
<223> OTHER INFORMATION: Primer KRP1A (E212K)-F

<400> SEQUENCE: 34
cgaagagttc tttgcggcgg ctaaagaggc ggaagcacgc cg 42

<210> SEQ ID NO 35
<211> LENGTH: 42
<212> TYPE: DNA
<213> ORGANISM: Artificial Sequence
<220> FEATURE:
<223> OTHER INFORMATION: Primer KRP1A (E212K)-R

<400> SEQUENCE: 35
cggcgtgctt ccgcctcttt agccgccgca aagaactctt cg 42

<210> SEQ ID NO 36
<211> LENGTH: 43
<212> TYPE: DNA
<213> ORGANISM: Artificial Sequence
<220> FEATURE:
<223> OTHER INFORMATION: Primer KRP1A (P232L)-F

<400> SEQUENCE: 36
cgacgttgca cgcggcgtgc ttctggattc cggtcgctat gag 43

<210> SEQ ID NO 37
<211> LENGTH: 43
<212> TYPE: DNA
<213> ORGANISM: Artificial Sequence
<220> FEATURE:
<223> OTHER INFORMATION: Primer KRP1A (P232L)-R

<400> SEQUENCE: 37
ctcatagcga ccggaatcca gaagcacgcc gcgtgcaacg tcg 43

<210> SEQ ID NO 38
<211> LENGTH: 42
<212> TYPE: DNA
<213> ORGANISM: Artificial Sequence
<220> FEATURE:
<223> OTHER INFORMATION: Primer KRP1A (G236S)-F

<400> SEQUENCE: 38
cggcgtgcct ctggattcca gtcgctatga gtggaccccg gc 42

<210> SEQ ID NO 39
<211> LENGTH: 42
<212> TYPE: DNA
<213> ORGANISM: Artificial Sequence
<220> FEATURE:
<223> OTHER INFORMATION: Primer KRP1A (G236S)-R

<400> SEQUENCE: 39
gccggggtcc actcgtagcg actggaatcc agaggcacgc cg 42

<210> SEQ ID NO 40
<211> LENGTH: 42
<212> TYPE: DNA
<213> ORGANISM: Artificial Sequence
<220> FEATURE:
<223> OTHER INFORMATION: Primer KRP1A (W240*)-F

<400> SEQUENCE: 40
ggattccggt cgctatgagt gaaccccggc agtttccagc ag 42

<210> SEQ ID NO 41
<211> LENGTH: 42
<212> TYPE: DNA
<213> ORGANISM: Artificial Sequence
<220> FEATURE:
<223> OTHER INFORMATION: Primer KRP1A (W240*)-R

<400> SEQUENCE: 41
ctgctggaaa ctgccggggt tcactcatag cgaccggaat cc 42

<210> SEQ ID NO 42

<211> LENGTH: 41
<212> TYPE: DNA
<213> ORGANISM: Artificial Sequence
<220> FEATURE:
<223> OTHER INFORMATION: Primer KRP2D (P228S)-F

<400> SEQUENCE: 42
ccgtgcccgt gcgcgtatgt caccggcagc ggaaatcgac g 41

<210> SEQ ID NO 43
<211> LENGTH: 41
<212> TYPE: DNA
<213> ORGANISM: Artificial Sequence
<220> FEATURE:
<223> OTHER INFORMATION: Primer KRP2D (P228S)-R

<400> SEQUENCE: 43
cgtcgatttc cgctgccggt gacatacgcg cacgggcacg g 41

<210> SEQ ID NO 44
<211> LENGTH: 40
<212> TYPE: DNA
<213> ORGANISM: Artificial Sequence
<220> FEATURE:
<223> OTHER INFORMATION: Primer KRP2D (A238V)-F

<400> SEQUENCE: 44
cgacgagttt ttcgcggttg cggagaaagc ccaggcagag 40

<210> SEQ ID NO 45
<211> LENGTH: 40
<212> TYPE: DNA
<213> ORGANISM: Artificial Sequence
<220> FEATURE:
<223> OTHER INFORMATION: Primer KRP2D (A238V)-R

<400> SEQUENCE: 45
ctctgcctgg gctttctccg caaccgcgaa aaactcgtcg 40

<210> SEQ ID NO 46
<211> LENGTH: 42
<212> TYPE: DNA
<213> ORGANISM: Artificial Sequence
<220> FEATURE:
<223> OTHER INFORMATION: Primer KRP2D (A239T)-F

<400> SEQUENCE: 46
cgacgagttt ttcgcggcta cggagaaagc ccaggcagag cg 42

<210> SEQ ID NO 47
<211> LENGTH: 42
<212> TYPE: DNA
<213> ORGANISM: Artificial Sequence
<220> FEATURE:
<223> OTHER INFORMATION: Primer KRP2D (A239T)-R

<400> SEQUENCE: 47
cgctctgcct gggctttctc cgtagccgcg aaaaactcgt cg 42

<210> SEQ ID NO 48
<211> LENGTH: 43
<212> TYPE: DNA
<213> ORGANISM: Artificial Sequence
<220> FEATURE:
<223> OTHER INFORMATION: Primer KRP2D (D254N)-F

<400> SEQUENCE: 48
cgccgcgaag tataacttta atgtggcccg tggcgttccg ctg 43

<210> SEQ ID NO 49
<211> LENGTH: 43
<212> TYPE: DNA
<213> ORGANISM: Artificial Sequence
<220> FEATURE:
<223> OTHER INFORMATION: Primer KRP2D (D254N)-R

<400> SEQUENCE: 49
cagcggaacg ccacgggcca cattaaagtt atacttcgcg gcg 43

<210> SEQ ID NO 50
<211> LENGTH: 40
<212> TYPE: DNA
<213> ORGANISM: Artificial Sequence
<220> FEATURE:
<223> OTHER INFORMATION: Primer KRP2D (R257C)-F

<400> SEQUENCE: 50
ctttgatgtg gcctgtggcg ttccgctgaa tgctggtcgc 40

<210> SEQ ID NO 51
<211> LENGTH: 40
<212> TYPE: DNA
<213> ORGANISM: Artificial Sequence
<220> FEATURE:
<223> OTHER INFORMATION: Primer KRP2D (R257C)-R

<400> SEQUENCE: 51
gcgaccagca ttcagcggaa cgccacaggc cacatcaaag 40

<210> SEQ ID NO 52
<211> LENGTH: 40
<212> TYPE: DNA
<213> ORGANISM: Artificial Sequence
<220> FEATURE:
<223> OTHER INFORMATION: Primer KRP4A (W186*)-F

<400> SEQUENCE: 52
gccaggtcgt tatgaatagg tcaagctgga ctaactcgag 40

<210> SEQ ID NO 53
<211> LENGTH: 40
<212> TYPE: DNA
<213> ORGANISM: Artificial Sequence
<220> FEATURE:
<223> OTHER INFORMATION: Primer KRP4A (W186*)-R

<400> SEQUENCE: 53
ctcgagttag tccagcttga cctattcata acgacctggc 40

<210> SEQ ID NO 54
<211> LENGTH: 41
<212> TYPE: DNA
<213> ORGANISM: Artificial Sequence
<220> FEATURE:
<223> OTHER INFORMATION: Primer KRP5A (G200E)-F

<400> SEQUENCE: 54
ctcgtggctg cccgctgccg gatcgttacg agtggaccgt c 41

<210> SEQ ID NO 55
<211> LENGTH: 41
<212> TYPE: DNA

<213> ORGANISM: Artificial Sequence
<220> FEATURE:
<223> OTHER INFORMATION: Primer KRP5A (G200E)-R

<400> SEQUENCE: 55
gacggtccac tcgtaacgat ccggcagcgg gcagccacga g 41

<210> SEQ ID NO 56
<211> LENGTH: 41
<212> TYPE: DNA
<213> ORGANISM: Artificial Sequence
<220> FEATURE:
<223> OTHER INFORMATION: Primer KRP5A (G200R)-F

<400> SEQUENCE: 56
ctcgtggctg cccgctgccg aggcgttacg agtggaccgt c 41

<210> SEQ ID NO 57
<211> LENGTH: 41
<212> TYPE: DNA
<213> ORGANISM: Artificial Sequence
<220> FEATURE:
<223> OTHER INFORMATION: Primer KRP5A (G200R)-R

<400> SEQUENCE: 57
gacggtccac tcgtaacgcc tcggcagcgg gcagccacga g 41

<210> SEQ ID NO 58
<211> LENGTH: 43
<212> TYPE: DNA
<213> ORGANISM: Artificial Sequence
<220> FEATURE:
<223> OTHER INFORMATION: Primer KRP5A (W199*)-F

<400> SEQUENCE: 58
gctgccgggt cgttacgagt gaaccgtcct ggactgctaa ctc 43

<210> SEQ ID NO 59
<211> LENGTH: 43
<212> TYPE: DNA
<213> ORGANISM: Artificial Sequence
<220> FEATURE:
<223> OTHER INFORMATION: Primer KRP5A (W199*)-R

<400> SEQUENCE: 59
gagttagcag tccaggacgg ttcactcgta acgacccggc agc 43

<210> SEQ ID NO 60
<211> LENGTH: 1518
<212> TYPE: DNA
<213> ORGANISM: Triticum sp.

<400> SEQUENCE: 60
cctgggcgtc ggatcgggac ccgatccccc ggctcccccc ttggcgtgtt atatgcgtac 60
gcacccacgc gcacggggcg cactccggac gggggagaga atccaaagag cagcccagcg 120
gcatcatacc cctccctccc acccaccggc gccgcgctgc agacgcaaac ggccaaaggc 180
gagcggcgtg gggcggagcg cggggcgatg gggaagtaca tgcgcaagtg cagggcggag 240
gacggcgcgg tgggcggcgt ggaggtcacg caggccgtcg gcgtccgcac ccggtcccgc 300
gcggccgcgg ccaacgtcgt cgtctccaag aggaggcgcc cgctgccgcc cggctcgccg 360
tcggcctcgt cgtccctcgc tcgcgcccag ggcgggagct gctacctgaa gctgcggagc 420
cgcatgctgt tcatggcccc gccggcgccc gcatcggggg ctgccgccgg gcacgggccg 480

```
gcgccgccgc tcccggccgg cctgtcgcgc tgctccagca cggcgtcgtc cgtggacgcg    540

tcggccgcgg cgcaggacag gagcctgctc tcgtgcggct ccgacgccgc tgccaacaac    600

aaggtgaggg aattgggtcc aaaccctaga attcggatac gattcgagat ctccttttttg   660

accgaaaccc gtgtctttct ccgctctgca ggcaggcgcc ccggagggct cggcgagcaa    720

caacgcggag agcggcggca accgcgagag gtgcgagatc gaattccgtc ttctttccag    780

cgaattcttg tgaattatgc ctcctgccgt gctcctgacc ccgtcccgct cgccgttttt    840

gaaaattcag gcgagagacg acgccgtcca gccatttccc cggcgacctg agcgacctgg    900

agtcggatct ggcggggcag aacagcggcc ggtcgtcgct gccgcaaacg ccgaccgccc    960

aggcccagcc cgccgcgagg tcgagggtcc cgccggcggc cgagatcgag gagttcttcg   1020

cggccgccga ggaggccgag gccaggcggt tcgcttgcaa gtaagtgctt ttagcagcag   1080

cggaaactct aattctccac ttcgtcgccg gagttctaac gtgagagctt tctctcgccg   1140

tggccaggta caacttcgac gtggcccgcg gcgtgccgct cggctccggc cggtacgagt   1200

ggaccccggc ggtgagcagc agctaggcag gcgacgaaag cgggcgtgca aaggggggag   1260

agaagccgta gctagaaagt tactcactgt agagctgggg cgccggccgg ccggccggcc   1320

gtgtagaaag gccaagggaa aaagatgctc cggaaagaag aaaagaagca ttatagccta   1380

accaaccaac caaccaccga tcatcaacaa ctttttcttt cactcactcg ctcacatatt   1440

cccaccatta tcacttcaca ccccccttaat cctgattttt cccagcagca gcagcagtag  1500

ttttacttcc ctactggg                                                 1518
```

<210> SEQ ID NO 61
<211> LENGTH: 744
<212> TYPE: DNA
<213> ORGANISM: Triticum sp.

<400> SEQUENCE: 61

```
atggggaagt acatgcgcaa gtgcagggcg gaggacggcg cggtgggcgg cgtggaggtc     60

acgcaggccg tcggcgtccg cacccggtcc cgcgcggccg cggccaacgt cgtcgtctcc    120

aagaggaggc gcccgctgcc gcccggctcg ccgtcggcct cgtcgtccct cgctcgcgcc    180

cagggcggga gctgctacct gaagctgcgg agccgcatgc tgttcatggc cccgccggcg    240

cccgcatcgg gggctgccgc cgggcacggg ccggcgccgc cgctcccggc cggcctgtcg    300

cgctgctcca gcacggcgtc gtccgtggac gcgtcggccg cggcgcagga caggagcctg    360

ctctcgtgcg gctccgacgc cgctgccaac aacaaggcag gcgcccccgga gggctcggcg   420

agcaacaacg cggagagcgg cggcaaccgc gagaggcgag agacgacgcc gtccagccat    480

ttccccggcg acctgagcga cctggagtcg gatctggcgg ggcagaacag cggccggtcg    540

tcgctgccgc aaacgccgac cgcccaggcc cagcccgccg cgaggtcgag ggtcccgccg    600

gcggccgaga tcgaggagtt cttcgcggcc gccgaggagg ccgaggccag gcggttcgct    660

tgcaagtaca acttcgacgt ggcccgcggc gtgccgctcg actccggccg gtacgagtgg    720

accccggcgg tgagcagcag ctag                                           744
```

<210> SEQ ID NO 62
<211> LENGTH: 1251
<212> TYPE: DNA
<213> ORGANISM: Triticum sp.

<400> SEQUENCE: 62

```
cgcgctgcgc actgcagacg gaaacggcca aaggagggca ggcaggagcg cgcggcgtgg      60

ggcgatgggg aagtacatgc gcaagtgcag ggcggaggac ggcgtgggcg gcgtggaggt     120

cacgcaggcc gtcggcgtcc ggacccggtc gcgggcggcc gcggccaacg tcgtcgtttc     180

caagaggagg cggccgctgc cgccaagctc gcccctcggc ggcgccgccg ctcgcgccca     240

gagcgggagc tgctacctga agctgcggag ccgcatgctg ttcatggccc cgccggcgcc     300

tgcatcggct gctggcccag ggcacaggcc ggcgccgccg ctcccggcgg gcctctcgcg     360

ctgctccagc acggcgtcgt ccgtggacgc gtcggccgcg ggacaggata ggagcctgcc     420

gtcgtgcggc tccgacgccg ctgcaaacag caaggtgagg gaattggggt ccaaacccta     480

gagttcggat acgattcgag atctcctttt tttgctgaaa atcgtggctt tctccgctct     540

acaggcaggc gctccggagg gctcagcaag caacaacgcg gagagcggcg gcaaccgcga     600

gaggtgcgag atcgaattcc ctcctgtctc cggccaattc ttgtgaatta tgcctcctga     660

cgtgctcctg accccgtccc gctcgtcgct tttgaaaatt caggcgagag acgacgccgt     720

ccagccattt ccccggcgac ctgagcgacc tggagtcgga tctggcgggc cagaacagcg     780

gccggtcgtc gctgccgcaa acgccgaccg cccaggtcca gccggccgcg aggtcgagga     840

tcccgccggc ggccgagatc gaggagttct tcgcggccgc cgaggaggcc gaggccaggc     900

gcttcgcttg caagtaagta ctttagcagc agcggaaatt tccttatctt gcggccgccg     960

tcgccgtcgc cggaattcta acgtgcgagc tctctgtgcc aggtacaact tcgacgtggc    1020

ccgcggcgtg cctctcgact ccggccggta cgagtggacc ccggcggtga gcagcaacta    1080

gccagccgag aaagcgggcg tgcaaagggg ggagagaagc cgtagctaga aagttactca    1140

ctgtagagct ggggcgccgg ccggccggcc ggccgtgtag aaaggcgaag ggaaaaagat    1200

gctccggaaa gaagcattat agcctaacca accaacctac caccgatcat c             1251
```

```
<210> SEQ ID NO 63
<211> LENGTH: 738
<212> TYPE: DNA
<213> ORGANISM: Triticum sp.

<400> SEQUENCE: 63

atggggaagt acatgcgcaa gtgcagggcg gaggacggcg tgggcggcgt ggaggtcacg      60

caggccgtcg gcgtccggac ccggtcgcgg gcggccgcgg ccaacgtcgt cgtttccaag     120

aggaggcggc cgctgccgcc aagctcgccc ctcggcggcg ccgccgctcg cgcccagagc     180

gggagctgct acctgaagct gcggagccgc atgctgttca tggccccgcc ggcgcctgca     240

tcggctgctg gcccagggca caggccggcg ccgccgctcc cggcgggcct ctcgcgctgc     300

tccagcacgg cgtcgtccgt ggacgcgtcg gccgcgggac aggataggag cctgccgtcg     360

tgcggctccg acgccgctgc aaacagcaag gcaggcgctc cggagggctc agcaagcaac     420

aacgcggaga gcggcggcaa ccgcgagagg cgagagacga cgccgtccag ccatttcccc     480

ggcgacctga gcgacctgga gtcggatctg gcgggccaga acagcggccg gtcgtcgctg     540

ccgcaaacgc cgaccgccca ggtccagccg gccgcgaggt cgaggatccc gccggcggcc     600

gagatcgagg agttcttcgc ggccgccgag gaggccgagg ccaggcgctt cgcttgcaag     660

tacaacttcg acgtggcccg cggcgtgcct ctcgactccg gccggtacga gtggaccccg     720

gcggtgagca gcaactag                                                  738

<210> SEQ ID NO 64
<211> LENGTH: 1304
```

<212> TYPE: DNA
<213> ORGANISM: Triticum sp.

<400> SEQUENCE: 64

```
atccaaaggg cgagccgaac aacccagcgg catcatatcc ctcccaccgg cgccgcgctg     60
cgcactgcag acggaaacgg ccaaaggaga gcggcgtggg gcggagcggg gggcgatggg    120
gaagtacatg cgcaagtgca gggcggagga cgtcgcggtg ggcggcgtgg aggtcacgca    180
ggccgtcggc gtccggacgc ggtcccgggc ggccgcggcc aacgtcgtcg tctccaagag    240
gaggcgcccg ctgccgcccg cctcgccgtc ggcctcgtcg gccctcgctc gcgcccaggg    300
cgggagctgc tacctgaagc tgcggagccg catgctgttc atggccccgc cggcgcctgc    360
gtcggcgtcg gccgctgccg ccgggcacgg ggcgccgccg ccgctcccgg ccggcctctc    420
gcgctgctcc agcacggcct cgtccgtgga cgcgtcggcc gcggcgcagg acaggagcct    480
gccgtcgtgc ggctccgacg ccgctgccaa caaggtgagg gaattgggtc caaaccctag    540
aattcggata caattcgaga tctccttttt gctgaaaacc gtggctttct ccgccctaca    600
ggcaggcgct ccggagggct cggcgagcaa caacgcggag agcggcggca accgcgagag    660
gtgcgagatc gaattccctc ctgtctccgg ccaattcttc cgaattatgc atcctaaccc    720
cgtcccgctc gctgcttttc aaaattcagg cgagagacga cgccgtccag ccatttcccc    780
ggcgacctga gcgacctgga gtcggatctg gcgggcaaga acagcggccg gtcgtcgctg    840
ccgcaaacgc tggccgccca ggctcagccc gccgcgaggt cgagggtccc gccggcggcc    900
gagatcgagg agttcttcgc ggccgccgag gaggccgagg ccaggcgctt cgcttgcaag    960
taagtactcc tactttagca gcagcggaaa tttccttatc ttgcggccgc cgtcgccgtc   1020
gccggaattc taacgtggga gctctctacg ccaggtacaa cttcgacgtg gcccgcggcg   1080
tgcccctcga ctccggccgg tacgagtgga ccccggcggt gagcagcagc taggcaggcg   1140
acgaaagcgg gcgtgcaaag gggggagaga agccgtagct agaaagttac tcactgtaga   1200
gctggggcgc cggccggccg gccggccgtg tagaaaggcg aagggaaaaa gatgctccgg   1260
aaagaagcat tatagcctaa ccaaccaacc taccaccgat catc                    1304
```

<210> SEQ ID NO 65
<211> LENGTH: 747
<212> TYPE: DNA
<213> ORGANISM: Triticum sp.

<400> SEQUENCE: 65

```
atggggaagt acatgcgcaa gtgcagggcg gaggacgtcg cggtgggcgg cgtggaggtc     60
acgcaggccg tcggcgtccg gacgcggtcc cgggcggccg cggccaacgt cgtcgtctcc    120
aagaggaggc gcccgctgcc gcccgcctcg ccgtcggcct cgtcggccct cgctcgcgcc    180
cagggcggga gctgctacct gaagctgcgg agccgcatgc tgttcatggc cccgccggcg    240
cctgcgtcgg cgtcggccgc tgccgccggg cacggggcgc cgccgccgct cccggccggc    300
ctctcgcgct gctccagcac ggcctcgtcc gtggacgcgt cggccgcggc gcaggacagg    360
agcctgccgt cgtgcggctc cgacgccgct gccaacaagg caggcgctcc ggagggctcg    420
gcgagcaaca acgcggagag cggcggcaac cgcgagaggc gagagacgac gccgtccagc    480
catttccccg gcgacctgag cgacctggag tcggatctgg cgggcaagaa cagcggccgg    540
tcgtcgctgc cgcaaacgct ggccgcccag gctcagcccg ccgcgaggtc gagggtcccg    600
ccggcggccg agatcgagga gttcttcgcg gccgccgagg aggccgaggc caggcgcttc    660
```

```
gcttgcaagt acaacttcga cgtggcccgc ggcgtgcccc tcgactccgg ccggtacgag    720

tggaccccgg cggtgagcag cagctag                                        747


<210> SEQ ID NO 66
<211> LENGTH: 1371
<212> TYPE: DNA
<213> ORGANISM: Triticum sp.
<220> FEATURE:
<221> NAME/KEY: misc_feature
<222> LOCATION: (1092)..(1092)
<223> OTHER INFORMATION: n is a, c, g, or t

<400> SEQUENCE: 66

ttcgtccgtt cgcggatggg gaagtacatg cggaagtgcc gggccgcgcc gcgccgcggg     60

cggcggcaag gcggcgccgc cgtcgtggag caccgcgcgc cggtggccct cggcgtccgc    120

acgcggtccc gcgcggccgc cctcaacgcg aagatgagga agcagcagca ggcgacgacg    180

tccacggcgg cgcgcgcggt ggaggatgcg ttgctgggcc gtgacggcgg cgacgcggcc    240

gccgggtgct acctgcatct ccggagcagg aggctgttca tgcctgcttc cgcggcggtg    300

gatcagctcc ggggacttgg ggcggacgag gaggcttcga cggcggggct gccggattct    360

cggccctcgg tggaggcggc ggtcgtggcc ggggtctcgc gctgctccag caccgcgtcg    420

acggcggtgg acgtggcggc tagagagagg agcggcgacg aagcggaggt gagtgggcca    480

ctcactgccc tagaattctc cgtaaattcg gccggtcgat cggcagtttc tgctgctgaa    540

ttacgagatt tggttctgac tgtcttggtc gatcagcagg cgtgcgagag tggcgacgtg    600

gagagctccg tcagcgactc tgagtgcggc ggccgggaca ggtgagtcct cctctctcga    660

taccgacagg aattctgctg aattatccat tgttttctat tctccagggt gatcttgagt    720

tcttgacccg gttttgcttc tgaatttgac ctgtttgaat tgtggtaatc caggagggag    780

accacgccgt cgagccattc cccggcagat ttgagcgacc tggagtcgag ccagtcggcg    840

gacgagcaga agcacaaacg caggaggtat ccggcaacaa cgacgacgac cgcagcgcca    900

ttccgcttag acttggaggc gagagcaagg atgccaccgg cggcagagat cgacgagttc    960

ttcgccgccg cggagaaggc ccaggccgag cgcttcgccg ccaagtaagt ggaaattaca   1020

attgagcaca caagtacaca tacgtcttgg cacttggcag tcgctctatc gccgtcacag   1080

acgccgccac gnctaagcct tgtgctctcg ctgcctcact gcaggtacaa cttcgacgtc   1140

gcgcgcggcg tgcctctcaa cgccggccgg ttcgagtgga ccccggtggc caccgtctga   1200

ggctctgagc atgatgcaaa atgacgggaa gctagcggcg gcgcgcgtag aaagggaagg   1260

cctgctggga gtgaaaagag acgctgatcc aacccgcaaa ggaaaacagt aaagagaaag   1320

aggagtgaaa aaagaacaga ataatcccat gcacagcagc ctagagctag a            1371


<210> SEQ ID NO 67
<211> LENGTH: 822
<212> TYPE: DNA
<213> ORGANISM: Triticum sp.

<400> SEQUENCE: 67

atggggaagt acatgcggaa gtgccgggcc gcgccgcgcc gcgggcggcg gcaaggcggc     60

gccgccgtcg tggagcaccg cgcgccggtg gccctcggcg tccgcacgcg gtcccgcgcg    120

gccgccctca acgcgaagat gaggaagcag cagcaggcga cgacgtccac ggcggcgcgc    180

gcggtggagg atgcgttgct gggccgtgac ggcggcgacg cggccgccgg gtgctacctg    240

catctccgga gcaggaggct gttcatgcct gcttccgcgg cggtggatca gctccgggga    300
```

```
cttggggcgg acgaggaggc ttcgacggcg gggctgccgg attctcggcc ctcggtggag    360

gcggcggtcg tggccggggt ctcgcgctgc tccagcaccg cgtcgacggc ggtggacgtg    420

gcggctagag agaggagcgg cgacgaagcg gaggcgtgcg agagtggcga cgtggagagc    480

tccgtcagcg actctgagtg cggcggccgg gacaggaggg agaccacgcc gtcgagccat    540

tccccggcag atttgagcga cctggagtcg agccagtcgg cggacgagca gaagcacaaa    600

cgcaggaggt atccggcaac aacgacgacg accgcagcgc cattccgctt agacttggag    660

gcgagagcaa ggatgccacc ggcggcagag atcgacgagt tcttcgccgc cgcggagaag    720

gcccaggccg agcgcttcgc cgccaagtac aacttcgacg tcgcgcgcgg cgtgcctctc    780

aacgccggcc ggttcgagtg gaccccggtg gccaccgtct ga                        822
```

<210> SEQ ID NO 68
<211> LENGTH: 1364
<212> TYPE: DNA
<213> ORGANISM: Triticum sp.

<400> SEQUENCE: 68

```
tttcgtccgt tcgcggatgg ggaagtacat gcggaagtgc aggggcgcgg ccgcgggcgg      60

cggcagggcg gcgccggccg tcgtggagca ccgcgcgccg gtggccctcg gcgtccgcac    120

gcggtcccgc gcggccgcct tcgacgctaa gaggaggaag cagcaggcga cgacgtccac    180

ggcagcgcgc gcggtggacg atgcgttgct gggccgtgac ggcggcgacg cggccggcgg    240

gtgctacctg catctccgga gcaggaggct gttcatgcct gcttccgcgg tggtggatcg    300

gctccgggga cagggggcgg acgaggaggc ttcgacggcg aggctggcgg attccgggcc    360

ttccgtggag gcgggggtcg tcgccggggt ctcgcgctgc tcgagcaccg cgtccacggc    420

agcagacgtg gcggctagag agaggagcgg cgacgaagca gaggtgagtg gtccactgcc    480

ctagaattct ccgctacttc gagctgtcga tcgggccatt tctgctgctg aattaggagg    540

tttggttcct atgtcttgtc ctgcaggcgt gcgagagtcg cgacgtggag agctccgtca    600

gcgactctga gtgcggcggc cgggacaggt gagtcctcct ctctcgatat ataccgacgg    660

gaattctgct gaattatcca ttgttttcta ctccacaagg tgatcttgag ttgaggggcc    720

tggctttgct tctgaatttg acctgttgga ttgtactaat ccaggaggga ggcgacgccg    780

tcgagccgtt cgccggtaga tttgagcgac ctggagtcga gccaggcggc ggacgagcag    840

aagcacaaac gcaggaggtg tccggcagca acgacggcgg cagcagcgcc attccactta    900

gactcggagg cgagagcaag gatgccaccc gcggcagaga tcgacgagtt cttcgccgcc    960

gccgagaagg cccaggccga gcacttcgcg gccaagtaag tggaaattta caatcgagcg   1020

catccgcacg cacgtacata ctcccgtctt ggcagtcgct ccatcgtcgt cacagacgtc   1080

cccgtgccta gctaagcatt gtgctgccgc tgcctcattg caggtacaac ttcgacgtcg   1140

cgcgcggcgt gcctctcaac gccggccggt tcgagtggac cccggtggcc accgtctgag   1200

gctctgatgc aattggcggg gagcgtagcg gcggctcgcg tagaaaggga aggcctgctg   1260

ggagtgaaaa gagacgctga tccaaccccc aaaggaaaac agtaaagaga aagaggagtg   1320

aaaaagaaca gaataatccc atgcacagca ggcctagagc taga                    1364
```

<210> SEQ ID NO 69
<211> LENGTH: 816
<212> TYPE: DNA
<213> ORGANISM: Triticum sp.

<400> SEQUENCE: 69

```
atggggaagt acatgcggaa gtgcaggggc gcggccgcgg gcggcggcag ggcggcgccg     60
gccgtcgtgg agcaccgcgc gccggtggcc ctcggcgtcc gcacgcggtc ccgcgcggcc    120
gccttcgacg ctaagaggag gaagcagcag gcgacgacgt ccacggcagc gcgcgcggtg    180
gacgatgcgt tgctgggccg tgacggcggc gacgcggccg gcgggtgcta cctgcatctc    240
cggagcagga ggctgttcat gcctgcttcc gcggtggtgg atcggctccg gggacagggg    300
gcggacgagg aggcttcgac ggcgaggctg gcggattccg ggccttccgt ggaggcgggg    360
gtcgtcgccg gggtctcgcg ctgctcgagc accgcgtcca cggcagcaga cgtggcggct    420
agagagagga gcggcgacga agcagaggcg tgcgagagtc gcgacgtgga gagctccgtc    480
agcgactctg agtgcggcgg ccgggacagg agggaggcga cgccgtcgag ccgttcgccg    540
gtagatttga gcgacctgga gtcgagccag gcggcggacg agcagaagca caaacgcagg    600
aggtgtccgg cagcaacgac ggcggcagca gcgccattcc acttagactc ggaggcgaga    660
gcaaggatgc cacccgcggc agagatcgac gagttcttcg ccgccgccga gaaggcccag    720
gccgagcact tcgcggccaa gtacaacttc gacgtcgcgc gcggcgtgcc tctcaacgcc    780
ggccggttcg agtggacccc ggtggccacc gtctga                              816
```

<210> SEQ ID NO 70
<211> LENGTH: 1388
<212> TYPE: DNA
<213> ORGANISM: Triticum sp.

<400> SEQUENCE: 70

```
gttctttctt ttcgtccgtt cgcggatggg gaagtacatg cggaagtgca gggccgcggc     60
cgcgggcggc ggcagggcgg cgccggccgt cgtggagcac cgcgcgccgg tggccctcgg    120
cgtccgcacg cggtcccgcg cggccgccct cgacgcgaag atgaggaagc agcagcaggc    180
gacgacgtcc acggcggcgc gcgcggtgga ggatgcgttg ctgggccgtg acggcggcga    240
cgcggccgcc gggtgctacc tgcatctccg gagcaggagg ctgttcatgc ctgctgccgc    300
ggtggtggat cagctgcggg gacagggggt gtgtgaggag gcttccacag cggggctgcc    360
ggactctggg ccctcggtgg aggcggcggt cggggccggg gtctcgcgct gctccagcac    420
cgcgtccacg gcggtcgacg tggcggctag agagaggagc ggggatgaag cggaggtgag    480
tggtccactg ccctagaatt ctccgctaat tcgagctatc gatcgggccg tttctgctgc    540
tgaattacga gatttggttc tgactgtctt ggtcgatcag caggcgtgcg agagtcgcga    600
cgtggagagc tccgtcagcg actctgagtg cggcggccgg gacaggtgag tcctcctctc    660
tcgataccga cgggaattct gctgaattac ccattgtttt ctactctcca gggtgatctt    720
gagttgaggg acctggtttt gcttctgaat ttgacctgtt ggattgtggc aatccaggag    780
ggagacgacg ccgtcgagcc gttcgccggt agatttgagc gacctggagt cgagccaggc    840
ggcggacgag cagaagcaca aacgcaggag gtgtccggca acaacgacga cgaccgcagc    900
gccattgcac tatgacttgg aggcgagagc aagagcaagg atgccaccag cggcagagat    960
cgacgagttc ttcgccgccg cggagaaggc ccaggccgag cgcttcgccg ccaagtaagt   1020
ggaaatttac aattgagcaa atccgcacgc acgtcttggc agtcgctcga tcgtcctcac   1080
agacgccgcc gcgcctaagc attgtgctac cgctgcctca ttgcaggtac aacttcgacg   1140
tcgcgcgcgg cgtgcctctc aacgccggcc ggttcgagtg gaccccggtg gccaccgtgt   1200
gagcagagca tgatgcaaat gacggggagc tagcggcggc gcgcgtagaa agggaaggcc   1260
```

```
tgctgggagt gaaaagagac gctgatccaa ccccccaaag gaaaacagta aagagaaaga   1320

ggagtaaaaa agaacagaat aatcccatgc acagctgcct agagctaggc atgcagtagc   1380

cctctccc                                                            1388
```

<210> SEQ ID NO 71
<211> LENGTH: 825
<212> TYPE: DNA
<213> ORGANISM: Triticum sp.

<400> SEQUENCE: 71

```
atggggaagt acatgcggaa gtgcagggcc gcggccgcgg gcggcggcag ggcggcgccg     60

gccgtcgtgg agcaccgcgc gccggtggcc ctcggcgtcc gcacgcggtc ccgcgcggcc    120

gccctcgacg cgaagatgag gaagcagcag caggcgacga cgtccacggc ggcgcgcgcg    180

gtggaggatg cgttgctggg ccgtgacggc ggcgacgcgg ccgccgggtg ctacctgcat    240

ctccggagca ggaggctgtt catgcctgct gccgcggtgg tggatcagct gcggggacag    300

ggggtgtgtg aggaggcttc cacagcgggg ctgccggact ctgggccctc ggtggaggcg    360

gcggtcgggg ccggggtctc gcgctgctcc agcaccgcgt ccacggcggt cgacgtggcg    420

gctagagaga ggagcgggga tgaagcggag gcgtgcgaga gtcgcgacgt ggagagctcc    480

gtcagcgact ctgagtgcgg cggccgggac aggagggaga cgacgccgtc gagccgttcg    540

ccggtagatt tgagcgacct ggagtcgagc caggcggcgg acgagcagaa gcacaaacgc    600

aggaggtgtc cggcaacaac gacgacgacc gcagcgccat tgcactatga cttggaggcg    660

agagcaagag caaggatgcc accagcggca gagatcgacg agttcttcgc cgccgcggag    720

aaggcccagg ccgagcgctt cgccgccaag tacaacttcg acgtcgcgcg cggcgtgcct    780

ctcaacgccg gccggttcga gtggaccccg gtggccaccg tgtga                    825
```

<210> SEQ ID NO 72
<211> LENGTH: 652
<212> TYPE: DNA
<213> ORGANISM: Triticum sp.

<400> SEQUENCE: 72

```
ctcgcttaaa tccgccaaag cgcacccagc ggggccccaa accctagccc gggccgcgcc     60

gcgcatgggc aagtacatgc gcaagcccaa ggtctccggc gaggtggccg tcatggaggt    120

cgccgccgcg ccgctggggg tccgcacccg cgcgcgggcg ctcgcgatgc agaggcagcc    180

gcagggggcg ccgggggcca aggaccaggg ggagtacctg gagctcagga gccggaagct    240

cgagaagctg cccccgccgc cgccgccggc gaggaggagg gcggccgcgg cggagcgtgt    300

cgaggccgag gccgaggccg acaaggtgtc cttcggggag aacgtgctcg agccggaggc    360

catggggagg tgagccttct cctgcgcccg cgattttctt cggttcatgg ggttttattt    420

ctcggcgggg ggattataac cgtgccaggg tttagggttt tgtgtcgtac cgagaagctt    480

tggattgctt cttctgtttc gcgcttcggc tcgttccatt tttccttgtc aatttggctt    540

gttctatccg tgctgcgtgc ggggctcgaa tttggtgtcg atgctatttt ccccaatatc    600

tttcttatta agctttgctg tttattgggg attttttctg tcccaactct tc            652
```

<210> SEQ ID NO 73
<211> LENGTH: 905
<212> TYPE: DNA
<213> ORGANISM: Triticum sp.

<400> SEQUENCE: 73
aggcaaattc ggtagaaatg tgtagccaat tgtggcattg ctaggcctag ttagaaccaa 60
acaaccccgg atactcataa ggggggggatt ccttattttt ttatgaccac ggatgatatc 120
gatatgtttt cttcttttttg catacccctgt taagttacag gtgatttttt ccccttttgct 180 acgcgtcctc gctatggttg tttctaaaaa ttgagtgtgt atgtatgttt tgtggctagc 240
aggggtacca gggagacgac gccctgcagc ttgattaggg actcgggaat gataagcact 300
cctggatcca caacaagacc gagccactcg aattcccatc gcagggtgca agctccagcg 360
cgccatatta ttccaagttc agcagagatg aatgagttct tctctgctgc agagcaaccg 420
caacagcaag ccttcatcga caagtacgac attgtttggt tctctcagtc agttaacctt 480
gtctaattaa aaaaaatctt tcaatatctt tgcagtgaag aatgccaact cagcgtgcaa 540
tgtggttttg acacgtgata tgttcatgcc tttgctcttg ataaaaagtg tgattataac 600
actaacaaca tggtttcatg gcttaataat cttcaggtac aactttgatc ctgtgaacga 660
ctgtcctctc ccaggccgat acgagtgggt gaagctagac tgataattct ccaggaagga 720
gagcaccatg tatctctctg ctccctccac cttagcgtcg tggtagaggc gcgcaccgtc 780
gtgttagctt tgtttccgtt gtaaaaagaa ttagggttag cctgtagtag cctcaatggt 840
tgtgtaacat acagaagtaa tgctgagtta caccctatcc ctcaaactcc ccaaatgtcg 900
gtagc 905

<210> SEQ ID NO 74
<211> LENGTH: 573
<212> TYPE: DNA
<213> ORGANISM: Triticum sp.

<400> SEQUENCE: 74
atgggcaagt acatgcgcaa gcccaaggtc tccggcgagg tggccgtcat ggaggtcgcc 60
gccgcgccgc tgggggtccg cacccgcgcg cgggcgctcg cgatgcagag gcagccgcag 120
ggggcgccgg gggccaagga ccagggggag tacctggagc tcaggagccg gaagctcgag 180
aagctgcccc cgccgccgcc gccggcgagg aggagggcgg ccgcggcgga gcgtgtcgag 240
gccgaggccg aggccgacaa ggtgtccttc ggggagaacg tgctcgagcc ggaggccatg 300
gggaggggta ccagggagac gacgccctgc agcttgatta gggactcggg aatgataagc 360
actcctggat ccacaacaag accgagccac tcgaattccc atcgcagggt gcaagctcca 420
gcgcgccata ttattccaag ttcagcagag atgaatgagt tcttctctgc tgcagagcaa 480
ccgcaacagc aagccttcat cgacaagtac aactttgatc ctgtgaacga ctgtcctctc 540
ccaggccgat acgagtgggt gaagctagac tga 573

<210> SEQ ID NO 75
<211> LENGTH: 651
<212> TYPE: DNA
<213> ORGANISM: Triticum sp.

<400> SEQUENCE: 75
ctcgcttaaa tccgcaaggc gcacccaggg gggcccaaac cctagcccgg gccgcgccgc 60
gcatgggcaa gtacatgcgc aagcccaagg tctccggcga ggtggccgtc atggaggtcg 120
ccgccgcgcc gctaggggtc cgcacccgcg cacgagcgct cgcgatgcag aggcagccgc 180
agggggcggc ggtggccaag gaccaggggg agtacctgga gctcaggagt cggaagctcg 240
agaagctgcc cccgccgccg ccgccggcga ggaggagggc ggccgcggcg gagcgtgtcg 300

```
aggccgaggc cgaggccgac gaggtgtcct tcggtgagaa cgtgctcgag tcggaggcca    360

tggggaggtg agccttctcc tgcgccggcg attttcttcg gttattgggg ttttatttct    420

cggcgggggg attattaccg tgctagggtt tagggttttg tgtcgtaccg agaagctttg    480

gattgcttct tctatttcgc gcttcggctc gtttcatttc tccttgtcaa tttggcttgt    540

tctatccgtg ctgcgtgcgg ggctcgaatt tggtgtggat gctattttcc ccaatatctt    600

tgttactatt aaactttgct gtttattggg gatttttccg tctaactctt c             651
```

<210> SEQ ID NO 76
<211> LENGTH: 1071
<212> TYPE: DNA
<213> ORGANISM: Triticum sp.

<400> SEQUENCE: 76

```
ttgggggggg ttactagccc caccattctt ttgtttccca tgggccttgt gtttcggttg     60

tgtgctagcc tttatatggc atatgagata gattgaaggg ctgtttagtt aggcaacttg    120

tggccccaat ctgtttgaac taaccttagg caagtttggt aagaaatgtg tggcaaattg    180

tggcattgct aggcctagtt agaaccaaac aaccccggat actcataagg gggggattcc    240

ttattttta tgactattga tatgtgttct tctttttcca taccctgtta agttacaggt    300

gattttttcc cttttgctat gcttcctctc tatggttgtt tctaaaaatt gagtgtgtat    360

gtatgttttg tggctagcag gggtaccagg gagacgacgc cctgcagctt gattagggac    420

tcgggaacga taagcactcc tggatccaca acaagaccga gccactcgaa ttcccatcgc    480

agggtgcaag ctccagcgcg ccatattatt ccatgttcag cagagatgaa tgagttcttc    540

tctgctgcgg agcaaccgca acagcaagcc ttcatcgaca agtacggcat tgtttggttc    600

tctcagtcag ttaaccttgt ctaatttaaa aaaagggaaa tctttcaata tcttcgcagt    660

gaagaatgcc aactcagcgt gcaatgtggt tttgacacgt gatatgttta cgcctttgct    720

cttgataaaa agtgtgatta taacactaac aacatggttt catggcttaa taatcttcag    780

gtacaacttt gatcctgtga acgactgtcc tctcccaggc cgatacgagt gggtgaagct    840

agactgataa ttctccagga aggagagcat catgtacttc tccgctccct ccaccttagc    900

gtcgtggtaa aggcgcgccc cgtcgtgtta gctttgtttc cgttgtaaaa agaattaggt    960

tagcctgtag tagcctcaat ggtcgtgtaa catacagaag taatgctgag ttacacccta   1020

atccctcaaa ctccaatgta acggttagca gctcattctg aaatgaccac a            1071
```

<210> SEQ ID NO 77
<211> LENGTH: 573
<212> TYPE: DNA
<213> ORGANISM: Triticum sp.

<400> SEQUENCE: 77

```
atgggcaagt acatgcgcaa gcccaaggtc tccggcgagg tggccgtcat ggaggtcgcc     60

gccgcgccgc taggggtccg cacccgcgca cgagcgctcg cgatgcagag gcagccgcag    120

ggggcggcgg tggccaagga ccagggggag tacctggagc tcaggagtcg gaagctcgag    180

aagctgcccc cgccgccgcc gccggcgagg aggagggcgg ccgcggcgga gcgtgtcgag    240

gccgaggccg aggccgacga ggtgtccttc ggtgagaacg tgctcgagtc ggaggccatg    300

gggaggggta ccagggagac gacgccctgc agcttgatta gggactcggg aacgataagc    360

actcctggat ccacaacaag accgagccac tcgaattccc atcgcagggt gcaagctcca    420
```

```
gcgcgccata ttattccatg ttcagcagag atgaatgagt tcttctctgc tgcggagcaa    480

ccgcaacagc aagccttcat cgacaagtac aactttgatc ctgtgaacga ctgtcctctc    540

ccaggccgat acgagtgggt gaagctagac tga                                 573


<210> SEQ ID NO 78
<211> LENGTH: 651
<212> TYPE: DNA
<213> ORGANISM: Triticum sp.

<400> SEQUENCE: 78

ctcgcttaaa tccgcaaggc gcacccaggg gggcccaaac cctagcccgg gccgccccgc     60

gcatgggcaa gtacatgcgc aagcccaagg tctccggcga ggtggccgtc atggaggtcg    120

ccgccgcgcc gctgggtgtc cgcacccgcg cgcgagcgct cgcgatgcag aggcagccgc    180

agggggcgcc gggggccaag gaccaggggg agtacctgga gctcaggagc cggaagctcg    240

agaagctgcc cctgccgccg ccgccggcga ggaggagggc ggccgcggcg gagcgtgtcg    300

aggccgaggc cgaggccgac gaggtgtcct tcggggagaa cgtgctcgag tcggaggcca    360

tggggaggtg agccgccttc tcctgcgccg gcgattttct tcggttctgg ggttttattt    420

ctcggcgggg ggattattac cgtgctaggg tttagggttt tgtgtcgtac cgagaagctt    480

tggattgctt gttccatttc acgcttcggc tcgtttcttt tttccttgtc agtttggctt    540

gttctgtccg tgctgcgtgc ggggctcgaa tttggtgtgg atgctatttt ccccaatatc    600

tttgttaagc ttggctgttt tattggggat ttttttcctg gctaactctt c             651


<210> SEQ ID NO 79
<211> LENGTH: 1073
<212> TYPE: DNA
<213> ORGANISM: Triticum sp.

<400> SEQUENCE: 79

ggggggggtt aactagccca ccattttttt gtttcccatg ggccttgtgt tttggttgtg     60

tgctagcctt tatatggcat atgagataga ttgaagggct gtttggttag gcaacttgtg    120

gctccaattt gtttgaacta accttaggca agtttggtga gaaatgtgtg gcaaattgtg    180

gcattgctag gcctagttag aaccaaacaa ccccggatac tcataagggg gggattcctt    240

atttcttacg accacggatg atatcgatat gtgttcttct ttttgcatac cctgttaagt    300

tacaggtgat ttttcccctt ttgctatact tcctctctat ggttgtttct aaaaattgag    360

tgtgtatgta tgttttgtgg ctagcagggg taccagggag acgacgccct gcagcttgat    420

tagggactcg ggaacgataa gcactcctgg atccacaaca agaccaagcc actcgaattc    480

ccatcgcagg gtgcaagctc cagcgcgcca tattattcca tgttcagcag agatgaatga    540

gttcttctct gctgcggagc aaccgcaaca gcaagccttc atcgacaagt acggcattgt    600

ttggttctct cagtcagtta accttgtcta attaaaaaaa tctttcaata tcttcgcagt    660

gaagaatgcc aactcagagt gcaatgtggt tttgacacgt gatatgttca cgcctttgct    720

cttgataaaa agtgtgatta taacactaac aacatggttt catggcttaa taatcttcag    780

gtacaacttt gatcctgtga acgactgtcc tctcccaggc cgatacgagt gggtgaagct    840

agactgataa ttctccagga aggagagcac catgtacctc tccgctccct ccaccttagc    900

gtcgtggtag aggcgcgcac cgccgtgtta gctttgtttc cgttgtaaaa agaattaggg    960

ttagcctgta gtagcctcaa tggtcttgta acatacagaa gtaatgctga gttacaccct   1020

aatccctcaa aactccaatg taacggttag cagctcattc tgtaatgacc aca          1073
```

<210> SEQ ID NO 80
<211> LENGTH: 573
<212> TYPE: DNA
<213> ORGANISM: Triticum sp.

<400> SEQUENCE: 80
atgggcaagt acatgcgcaa gcccaaggtc tccggcgagg tggccgtcat ggaggtcgcc 60
gccgcgccgc tgggtgtccg cacccgcgcg cgagcgctcg cgatgcagag gcagccgcag 120
ggggcgccgg gggccaagga ccagggggag tacctggagc tcaggagccg gaagctcgag 180
aagctgcccc tgccgccgcc gccggcgagg aggagggcgg ccgcggcgga gcgtgtcgag 240
gccgaggccg aggccgacga ggtgtccttc ggggagaacg tgctcgagtc ggaggccatg 300
gggaggggta ccagggagac gacgccctgc agcttgatta gggactcggg aacgataagc 360
actcctggat ccacaacaag accaagccac tcgaattccc atcgcagggt gcaagctcca 420
gcgcgccata ttattccatg ttcagcagag atgaatgagt tcttctctgc tgcggagcaa 480
ccgcaacagc aagccttcat cgacaagtac aactttgatc ctgtgaacga ctgtcctctc 540
ccaggccgat acgagtgggt gaagctagac tga 573

<210> SEQ ID NO 81
<211> LENGTH: 2259
<212> TYPE: DNA
<213> ORGANISM: Triticum sp.
<220> FEATURE:
<221> NAME/KEY: misc_feature
<222> LOCATION: (2103)..(2103)
<223> OTHER INFORMATION: n is a, c, g, or t

<400> SEQUENCE: 81
aagccggcgc catgggcaag tacatgcgca agagcaaggc ctcgggggag gtggccgtca 60
tggaggtcgc cggcgcgctg ctcggcgtcc gcacccgctc ccgcaccctc gccgcgcagc 120
agcagcgcgc tccgtcccct tcgccgcagc gcaagggcca cgaggacggc gactacctcg 180
agctcaggag caggaggctc gagaagcagc cgccgccggg gcccaaggac aaggaggacg 240
cgccgcagcc gccggccgcc ggtgggagga ggatggagca ggcgccgtcg tcgttcgccg 300
ccgagggctt cgaggccgac ctcgaggtct ccttcggcga caacgtcctg gactgggacg 360
ccaccgacag gtaacaacag agcaccagac ttttctctcc tccccttcct cttccgccaa 420 tccccccct ccgcctcagt cagcaatccc ctctcgcgcc ccgccccggc cgatacgaat 480
acgactgagg tttagggttt atccgccgcc gtgtcgccgt cctgctccat tagcgccgcc 540
gcgtgctctc aaatctcaac tctcaggcgc cggcaacctc aagaaccccc tccctatcag 600
ttttctcaga cgagcgccgc cgctggtccg gcgattttct tctccatcag gattgaagcg 660
cccaaatagc cacaccttcc gctgattgtg cccggatgcc tgcaagaatc aaggcctccg 720
ctggccttga tttcctcaag ccttagccgt tggctggctg gagcttgaaa gaatcgaaga 780
aacgcctgtc cgctgtgttg acccggggaa aaaggccccc ctatttcccc ccctccagaa 840
aagccgccat tttccccctc caaacaaaga tgcatccagg cgcactcaat caaccccaa 900 tcaaagtggg cgctgcactt gattagtgga gcctcctcct cctcctcctc cagtggccgt 960
ggccgtggcc tccgcctttt ccccgtagtg gcaggggaaa gtagcccct ttccccttcc 1020 ccaccacagc cgccctccat tggcctggcc ccaatctttc ccaacagcaa ccagagggag 1080
agaggcccct ctcccgccct ttcgccagca atttcaatcc cacaaagccg agcgccaccg 1140

```
ccgtcgcgct cagggcccca ttcgccaccg ccgtgggtga aaatggcaag ctgctcatca   1200

ttggcccttg taccggagcg ccaccgccgc cattgaatgc ctgcccttgt ctggagggat   1260

atggctggac ctttccgctt gaatggacac tctgaccgga ccacgttttt gttctagcca   1320

gtgcctccat tcatatttac cccttggccc ttgttgtgag catttgcacc agccacttga   1380

agagaaaaga ttttacttct agtaattcag gccttggaag acctcggtaa atgtttcccc   1440

agcttcttta attccacacc ttgttcgtag gattgatctc gcgcgtggtc ccttgtcccc   1500

cggcgtatgc atgttgaacg tgctcccccc atttagcagc ttgcttggcc gtattaggcc   1560

aagttgttgc ttgcttgtca gcattcagtc attcagcgtg cttgtgctgc tgctgcgcca   1620

ataatcaggc acacctcaca ttgtgtgatg tggggcactt gttagcaatg aaatggacaa   1680

gatcatgcgg catgctagaa aatgaatgag ctgtcgtgtt cagcttcctg tagcttggtc   1740

tcatctgagc tcaccaacca ggcttgattc tgcagcagta ctacgtaatt tgcaaggccc   1800

tcttgtgcat ttctagcttc tgaacctcat gttgtgctgt tcgtcggtgc tgcgtgcagg   1860

ggcgccaggg agacgacgcc gtgcagcctc atctacagct cggagacgat gagcaccccc   1920

gggtcggcga ccggaggagc ccgcaaccac tcccgccgca gggcgcagac gccggtctgc   1980

cgctacgtgc cgagctcgct ggagatggac gagttcttcg ccgccgccga gcagcagcaa   2040

caccagacct tcagggacaa gtaagagcat gcttccttct gctcttcttc acatactgta   2100

aanagaaact tgctaacact cgactgtgat gttgaaatca ggtacaactt ctgtcctgcg   2160

aggggctgcc cgctccccgg gcggtacgag tggacggtgc tagactgcta gggcttcata   2220

cctcacacca ccaccaggag ctcctccatt gatctctgt                          2259
```

<210> SEQ ID NO 82
<211> LENGTH: 630
<212> TYPE: DNA
<213> ORGANISM: Triticum sp.

<400> SEQUENCE: 82

```
atgggcaagt acatgcgcaa gagcaaggcc tcgggggagg tggccgtcat ggaggtcgcc     60

ggcgcgctgc tcggcgtccg cacccgctcc cgcaccctcg ccgcgcagca gcagcgcgct    120

ccgtcccctt cgccgcagcg caagggccac gaggacggcg actacctcga gctcaggagc    180

aggaggctcg agaagcagcc gccgccgggg cccaaggaca aggaggacgc gccgcagccg    240

ccggccgccg gtgggaggag gatggagcag gcgccgtcgt cgttcgccgc cgagggcttc    300

gaggccgacc tcgaggtctc cttcggcgac aacgtcctgg actgggacgc caccgacagg    360

ggcgccaggg agacgacgcc gtgcagcctc atctacagct cggagacgat gagcaccccc    420

gggtcggcga ccggaggagc ccgcaaccac tcccgccgca gggcgcagac gccggtctgc    480

cgctacgtgc cgagctcgct ggagatggac gagttcttcg ccgccgccga gcagcagcaa    540

caccagacct tcagggacaa gtacaacttc tgtcctgcga ggggctgccc gctccccggg    600

cggtacgagt ggacggtgct agactgctag                                     630
```

<210> SEQ ID NO 83
<211> LENGTH: 2282
<212> TYPE: DNA
<213> ORGANISM: Triticum sp.

<400> SEQUENCE: 83

```
ctccccatta ttccgcgatt cccctcccct cccctccctc ccagccagct gcccaccgga     60

agcagaggga agcagaggag aggccggggc cggcgccatg ggaagtaca tgcgcaagag    120
```

```
caaggcctcg gggggaggtgg ccgtcatgga ggtcgccggc gcgctgctcg gcgtccgcac    180
ccgctcccgc accctcgccg cgcagcagca gcgcgccccc tccccgtccc cctcgccgca    240
gcgcaagggg caggaggacg gcgaccccgg ggctggcgac tacctcgagc tcaggagcag    300
gcggctcgag aagcagccgc cgccgggggc cagggagaag gaggacgcgc cgcagccggc    360
cgcgaggagg gccgccgccg ctggcgggag gaggatggag caggcgccgt cgttcgccgc    420
cgaggggttc gaggccgacc tcgaggtctc cttcggcgac aacgtgctgg actgggacgc    480
caccgacagg taacaacaga gcaccagttc tttctttctt tctttcttcc cccaatcccc    540
cctctccggt tcagccagca atcccttgtc gcgcccgggt gataccaata cgattgggat    600
ttatgcttta tcgcgctcca ttagcgccgc cgcgtggtct caaatctcaa ctctgaagcg    660
ccggcaacct caagaatccc ctccctatga gtttcctcag acgagcgccg acgctggttt    720
tctttctccc caggattgaa gcgcccaaac atccacagct tccgctgatt gtgccgggat    780
tcttgcaaga atcatcggtt ctccgttttc agcctgaatg aatttcctca accattagcc    840
gttggcgtcc gctcgaaaga atccaagaaa gaaacgcctg cccgccgtgt tgacccggcg    900
aaaaaggccc ccatttcccc ccctccaaag aagccaccat tttcccgtc caaacaatca    960
aaggcgcact caatcaaccc aacccccaat caaagtgggc gctgcacttg attagtggag   1020
cctcctccag aaatcagtgg agcctcctcc ccctccagtg gccgcggccg tggctccgcc   1080
ttttcccgat agtggcagag gaaagtagcc ccctttccat tccccttccc caccacagcc   1140
gccctccatt ggctcggccc caatctttcc tctcccgctc tttcccgggc aatttcaacc   1200
ccccaaaggc gccaccgccg tcgcactcag ggcccagttt ctcgcccgcc cgcccgccag   1260
ccgccaccgc cgtgggcgaa aatggcatgc agctcatcat cagcacttgt accagagcgc   1320
caccgccgcc attgaatgct cgctggcctc ctgttagctt cctgaccggg ccttgagtgg   1380
acgccggacc acgtttttgt tcggaacaga ttttactttg gtcaggccgt ggaagacctc   1440
agtaaatata tctttctccg gcttatttag ttctacgtat gttcgcatga ttgatcccgt   1500
ggtccctttg cccggcgtat gcatgttgga cgcacgcgcc catttagctc gcttgcttgg   1560
ccgtgttagg ccaagttgtt gcttgtttgt cagcgtccag tcattcagcg tgcttgtgct   1620
tgcgctgcac caataatcag gtgcgcctca cattgtctag cgtggggcac ttgcaagcaa   1680
tgaaatggac aagatcatgc atgctagaaa atgaatgagc tgtcgtgttc gacttcctgt   1740
agcttgctgt cacccgagct caccaaccaa gcttgcatct gcagtagtaa tttgcaagac   1800
ctcgtgtgca tttcagcttc tgaacctcat gtgctgttgg ttgcttgcag gggcaccagg   1860
gagacgacgc cgtgcagcct gatctacagc tcggagacga tgagcacccc ggggtcggcg   1920
acgggagccc gcaaccattc ccggcgcagg gcgcagacgc cggtgtgccg ctacgtcccg   1980
agctcgctcg agatggacga gttcttcgcc gccgcggagc agcagcagca ccagagcttc   2040
agggacaagt aagaagaact ctgcctcctc ctcctcctcc tcttcacctg aactatgcat   2100
acggcaaagc gaaacttgct gacactggac tgctctgatc taaaaataac caggtacaac   2160
ttctgcccgg cgagcgagcg cccgctcccg gggcggtacg agtggacggt gctagactgc   2220
tagggcttcc tcatacctca caccaccacc accaccacca ggagctcctc cattgatctc   2280
gt                                                                   2282
```

<210> SEQ ID NO 84
<211> LENGTH: 660
<212> TYPE: DNA

<213> ORGANISM: Triticum sp.

<400> SEQUENCE: 84

```
atggggaagt acatgcgcaa gagcaaggcc tcgggggagg tggccgtcat ggaggtcgcc      60
ggcgcgctgc tcggcgtccg cacccgctcc cgcaccctcg ccgcgcagca gcagcgcgcc     120
ccctccccgt cccccctcgcc gcagcgcaag gggcaggagg acggcgaccc cggggctggc     180
gactacctcg agctcaggag caggcggctc gagaagcagc cgccgccggg ggccagggag     240
aaggaggacg cgccgcagcc ggccgcgagg agggccgccg ccgctggcgg gaggaggatg     300
gagcaggcgc cgtcgttcgc cgccgagggg ttcgaggccg acctcgaggt ctccttcggc     360
gacaacgtgc tggactggga cgccaccgac aggggcacca gggagacgac gccgtgcagc     420
ctgatctaca gctcggagac gatgagcacc ccggggtcgg cgacgggagc ccgcaaccat     480
tcccggcgca gggcgcagac gccggtgtgc cgctacgtcc cgagctcgct cgagatggac     540
gagttcttcg ccgccgcgga gcagcagcag caccagagct tcagggacaa gtacaacttc     600
tgcccggcga gcgagcgccc gctcccgggg cggtacgagt ggacggtgct agactgctag     660
```

<210> SEQ ID NO 85
<211> LENGTH: 2430
<212> TYPE: DNA
<213> ORGANISM: Triticum sp.
<220> FEATURE:
<221> NAME/KEY: misc_feature
<222> LOCATION: (2415)..(2415)
<223> OTHER INFORMATION: n is a, c, g, or t

<400> SEQUENCE: 85

```
aatggggaag tacatgcgta agagcaaggc ctcgggggag gtggccgtca tggaggtcgc      60
cggcgcgctg ctcggcgtcc gcacccgctc ccgcaccctc gccgcgcagc agcagcgcgc     120
tccgtcccct tcgccgcagc gcaagggcca cgaggacggc gactacctcg agctcaggag     180
caggaggctc gagaagcagc cgccgccggg gcccaaggac aaggaggacg cgccgcagcc     240
gccggccgcc ggtgggaggg ggatggagtc gttcgcggcc gaggggttcg aggccgacct     300
cgaggtctcc ttcggcgaca acgtgctgga ctgggacgcc accgacaggt aagaacagag     360
caccagcgcc ttctttcctc ccccttcct ctcccctcaa tccttcccct ccggttcagt     420
cggcaatccc ctccgccccg gccgatacca atacgattga ggtttagggt tcatatccgc     480
cgctgtttcg ttctgctcca ttagcgccgc cgctgcgcgg cctcgaatct caacacgaat     540
cccctcccct ctcaaacgag cgccgccgct ggcccgctgg ttttctccac aggattgagc     600
caaaccttgt gctgatttcg cccggatgct tgcgggaata atcccttgca gtttcctgat     660
tttcctcaag ctggagccgt tggccgtagc tttgaaagaa tccaagaaac gcctgcccgc     720
cgtgttgacc cggcgaaaaa gggcccccat tttcccccct ccaaaaaagc cgccattttt     780
cccggccaaa caaagatgca tccatcaagg cgcactcaat caacccccaa tcaaagtggg     840
cgctgcactc gattagtgga gcctcctcct ccagtggccg tggccttttc cccgtagtgg     900
caggggaaag tagccttccc caccatagcc gccctccatt ggcttggcct caatctttcc     960
caacagcaac cagagggaga ggcccctctc ccgctctttc gccagcaatt tcaatccccc    1020
aaaggcgcca ccgccgtcgc ggtcagggcc ccatttctcg cccgcccgcc agtcgccacc    1080
gccgtgggtg aaaatggctt gctgctcatc attggccctt gtaccagagc gccaccgccg    1140
ccattgaatg cttgctggcc tcttgttagc ttcctgaccg gacgttgaat ggacaccgga    1200
ccacgttatt gttcagacgc ttggggtgaa agggagctgc ctccgttaaa ttacctggtg    1260
```

```
ttgtgagtgc accagccact tgaacagcac aaattttact tactggtagt tcaggccttg   1320

gaagacctca gtaaatatat ctttctccgg cttatttaat tctacttacg ttcgtatgat   1380

tgatctcgtg gtcccgttgt ccggcgtatg catgttgaac gcgcccattt agcttgcttg   1440

gccgtgttag gccaagttgt tgtttgtttg tcagcatcca gtcattcagt gtgcttgtgc   1500

tgcaccaatt atcaggtaca cctgacattg tctagcgtgg ggcacttgca aataatgaaa   1560

tggacaaaat catgctagaa catgagctgt cgtgttcaac ttcctgtagc ttggtctcat   1620

ctgagctcac caacccagct tgcatctgca gtaatttgca agacctcgtg tgcatttcag   1680

cttctgaacc tcatgttgct tgcaggggcg ccagggagac gacgccgtgc agcctgatct   1740

acagctcgga gacgatgagc acccccgggt cggcgaccgg ggcccgcaac cattcccgcc   1800

gcagggcgca gacgccggtc tgccgctacg tcccgagctc gctcgagatg gacgagttct   1860

tcgccgccgc ggagcagcag caacaccaga ccttcaggga gaagtaagaa ctctgcctcc   1920

tcctaccacc atcatttaaa catgctcact gaagatcaag cttcttgttc atacaattgt   1980

tctaacactc gctgcttcat tctaatcagg tacaacttct gtcccgcgag cgagcgcccg   2040

ctccccggac ggtacgagtg gacggtgctg gactgctagg gcttcttcat acctcacatc   2100

accaccacca ccaggagctc ctccattgat ctctgtaaca ccagaatgac caccaccatc   2160

agcagcagca gcagcatgtc atatgccgtg ggcgcgatgc aaatgcagta gcgttaggtt   2220

tctgattcac ctgttgtaaa aacttagagt tagcccgcag tcagcagtag ctcagccagc   2280

cagccatctc tcagcctgat ccccaacctc actgtaaccg tcgttagtta acaacatctc   2340

atttccgtag gctctagctt gattagcagc tcggttatct tctgtatccc ggtcctccat   2400

caatgaatga atcanagcta gatttatttt                                     2430
```

```
<210> SEQ ID NO 86
<211> LENGTH: 615
<212> TYPE: DNA
<213> ORGANISM: Triticum sp.

<400> SEQUENCE: 86

atggggaagt acatgcgtaa gagcaaggcc tcgggggagg tggccgtcat ggaggtcgcc     60

ggcgcgctgc tcggcgtccg cacccgctcc cgcaccctcg ccgcgcagca gcagcgcgct    120

ccgtcccctt cgccgcagcg caagggccac gaggacggcg actacctcga gctcaggagc    180

aggaggctcg agaagcagcc gccgccgggg cccaaggaca aggaggacgc gccgcagccg    240

ccggccgccg gtgggagggg gatggagtcg ttcgcggccg aggggttcga ggccgacctc    300

gaggtctcct tcggcgacaa cgtgctggac tgggacgcca ccgacagggg cgccagggag    360

acgacgccgt gcagcctgat ctacagctcg gagacgatga gcacccccgg gtcggcgacc    420

ggggcccgca accattcccg ccgcagggcg cagacgccgg tctgccgcta cgtcccgagc    480

tcgctcgaga tggacgagtt cttcgccgcc gcggagcagc agcaacacca gaccttcagg    540

gagaagtaca acttctgtcc cgcgagcgag cgcccgctcc ccggacggta cgagtggacg    600

gtgctggact gctag                                                     615
```

```
<210> SEQ ID NO 87
<211> LENGTH: 247
<212> TYPE: PRT
<213> ORGANISM: Triticum sp.

<400> SEQUENCE: 87
```

```
Met Gly Lys Tyr Met Arg Lys Cys Arg Ala Glu Asp Gly Ala Val Gly
1               5                   10                  15

Gly Val Glu Val Thr Gln Ala Val Gly Val Arg Thr Arg Ser Arg Ala
            20                  25                  30

Ala Ala Ala Asn Val Val Val Ser Lys Arg Arg Arg Pro Leu Pro Pro
        35                  40                  45

Gly Ser Pro Ser Ala Ser Ser Ser Leu Ala Arg Ala Gln Gly Gly Ser
    50                  55                  60

Cys Tyr Leu Lys Leu Arg Ser Arg Met Leu Phe Met Ala Pro Pro Ala
65                  70                  75                  80

Pro Ala Ser Gly Ala Ala Ala Gly His Gly Pro Ala Pro Pro Leu Pro
                85                  90                  95

Ala Gly Leu Ser Arg Cys Ser Ser Thr Ala Ser Ser Val Asp Ala Ser
            100                 105                 110

Ala Ala Ala Gln Asp Arg Ser Leu Leu Ser Cys Gly Ser Asp Ala Ala
        115                 120                 125

Ala Asn Asn Lys Ala Gly Ala Pro Glu Gly Ser Ala Ser Asn Asn Ala
    130                 135                 140

Glu Ser Gly Gly Asn Arg Glu Arg Arg Glu Thr Thr Pro Ser Ser His
145                 150                 155                 160

Phe Pro Gly Asp Leu Ser Asp Leu Glu Ser Asp Leu Ala Gly Gln Asn
                165                 170                 175

Ser Gly Arg Ser Ser Leu Pro Gln Thr Pro Thr Ala Gln Ala Gln Pro
            180                 185                 190

Ala Ala Arg Ser Arg Val Pro Pro Ala Ala Glu Ile Glu Glu Phe Phe
        195                 200                 205

Ala Ala Ala Glu Glu Ala Glu Ala Arg Arg Phe Ala Cys Lys Tyr Asn
    210                 215                 220

Phe Asp Val Ala Arg Gly Val Pro Leu Gly Ser Gly Arg Tyr Glu Trp
225                 230                 235                 240

Thr Pro Ala Val Ser Ser Ser
                245
```

<210> SEQ ID NO 88
<211> LENGTH: 245
<212> TYPE: PRT
<213> ORGANISM: Triticum sp.

<400> SEQUENCE: 88

```
Met Gly Lys Tyr Met Arg Lys Cys Arg Ala Glu Asp Gly Val Gly Gly
1               5                   10                  15

Val Glu Val Thr Gln Ala Val Gly Val Arg Thr Arg Ser Arg Ala Ala
            20                  25                  30

Ala Ala Asn Val Val Val Ser Lys Arg Arg Arg Pro Leu Pro Pro Ser
        35                  40                  45

Ser Pro Leu Gly Gly Ala Ala Ala Arg Ala Gln Ser Gly Ser Cys Tyr
    50                  55                  60

Leu Lys Leu Arg Ser Arg Met Leu Phe Met Ala Pro Pro Ala Pro Ala
65                  70                  75                  80

Ser Ala Ala Gly Pro Gly His Arg Pro Ala Pro Pro Leu Pro Ala Gly
                85                  90                  95

Leu Ser Arg Cys Ser Ser Thr Ala Ser Ser Val Asp Ala Ser Ala Ala
            100                 105                 110

Gly Gln Asp Arg Ser Leu Pro Ser Cys Gly Ser Asp Ala Ala Ala Asn
        115                 120                 125
```

```
Ser Lys Ala Gly Ala Pro Glu Gly Ser Ala Ser Asn Asn Ala Glu Ser
    130                 135                 140

Gly Gly Asn Arg Glu Arg Arg Glu Thr Thr Pro Ser Ser His Phe Pro
145                 150                 155                 160

Gly Asp Leu Ser Asp Leu Glu Ser Asp Leu Ala Gly Gln Asn Ser Gly
                165                 170                 175

Arg Ser Ser Leu Pro Gln Thr Pro Thr Ala Gln Val Gln Pro Ala Ala
            180                 185                 190

Arg Ser Arg Ile Pro Pro Ala Ala Glu Ile Glu Glu Phe Phe Ala Ala
        195                 200                 205

Ala Glu Glu Ala Glu Ala Arg Arg Phe Ala Cys Lys Tyr Asn Phe Asp
    210                 215                 220

Val Ala Arg Gly Val Pro Leu Asp Ser Gly Arg Tyr Glu Trp Thr Pro
225                 230                 235                 240

Ala Val Ser Ser Asn
                245


<210> SEQ ID NO 89
<211> LENGTH: 248
<212> TYPE: PRT
<213> ORGANISM: Triticum sp.

<400> SEQUENCE: 89

Met Gly Lys Tyr Met Arg Lys Cys Arg Ala Glu Asp Val Ala Val Gly
1               5                   10                  15

Gly Val Glu Val Thr Gln Ala Val Gly Val Arg Thr Arg Ser Arg Ala
            20                  25                  30

Ala Ala Ala Asn Val Val Val Ser Lys Arg Arg Arg Pro Leu Pro Pro
        35                  40                  45

Ala Ser Pro Ser Ala Ser Ser Ala Leu Ala Arg Ala Gln Gly Gly Ser
    50                  55                  60

Cys Tyr Leu Lys Leu Arg Ser Arg Met Leu Phe Met Ala Pro Pro Ala
65                  70                  75                  80

Pro Ala Ser Ala Ser Ala Ala Ala Ala Gly His Gly Ala Pro Pro Pro
                85                  90                  95

Leu Pro Ala Gly Leu Ser Arg Cys Ser Ser Thr Ala Ser Ser Val Asp
            100                 105                 110

Ala Ser Ala Ala Ala Gln Asp Arg Ser Leu Pro Ser Cys Gly Ser Asp
        115                 120                 125

Ala Ala Ala Asn Lys Ala Gly Ala Pro Glu Gly Ser Ala Ser Asn Asn
    130                 135                 140

Ala Glu Ser Gly Gly Asn Arg Glu Arg Arg Glu Thr Thr Pro Ser Ser
145                 150                 155                 160

His Phe Pro Gly Asp Leu Ser Asp Leu Glu Ser Asp Leu Ala Gly Lys
                165                 170                 175

Asn Ser Gly Arg Ser Ser Leu Pro Gln Thr Leu Ala Ala Gln Ala Gln
            180                 185                 190

Pro Ala Ala Arg Ser Arg Val Pro Pro Ala Ala Glu Ile Glu Glu Phe
        195                 200                 205

Phe Ala Ala Ala Glu Glu Ala Glu Ala Arg Arg Phe Ala Cys Lys Tyr
    210                 215                 220

Asn Phe Asp Val Ala Arg Gly Val Pro Leu Asp Ser Gly Arg Tyr Glu
225                 230                 235                 240

Trp Thr Pro Ala Val Ser Ser Ser
```

245

<210> SEQ ID NO 90
<211> LENGTH: 273
<212> TYPE: PRT
<213> ORGANISM: Triticum sp.

<400> SEQUENCE: 90

```
Met Gly Lys Tyr Met Arg Lys Cys Arg Ala Ala Pro Arg Arg Gly Arg
1               5                   10                  15

Arg Gln Gly Gly Ala Ala Val Val Glu His Arg Ala Pro Val Ala Leu
            20                  25                  30

Gly Val Arg Thr Arg Ser Arg Ala Ala Ala Leu Asn Ala Lys Met Arg
        35                  40                  45

Lys Gln Gln Gln Ala Thr Thr Ser Thr Ala Ala Arg Ala Val Glu Asp
    50                  55                  60

Ala Leu Leu Gly Arg Asp Gly Gly Asp Ala Ala Ala Gly Cys Tyr Leu
65                  70                  75                  80

His Leu Arg Ser Arg Arg Leu Phe Met Pro Ala Ser Ala Ala Val Asp
                85                  90                  95

Gln Leu Arg Gly Leu Gly Ala Asp Glu Glu Ala Ser Thr Ala Gly Leu
            100                 105                 110

Pro Asp Ser Arg Pro Ser Val Glu Ala Ala Val Val Ala Gly Val Ser
        115                 120                 125

Arg Cys Ser Ser Thr Ala Ser Thr Ala Val Asp Val Ala Ala Arg Glu
    130                 135                 140

Arg Ser Gly Asp Glu Ala Glu Ala Cys Glu Ser Gly Asp Val Glu Ser
145                 150                 155                 160

Ser Val Ser Asp Ser Glu Cys Gly Gly Arg Asp Arg Arg Glu Thr Thr
                165                 170                 175

Pro Ser Ser His Ser Pro Ala Asp Leu Ser Asp Leu Glu Ser Ser Gln
            180                 185                 190

Ser Ala Asp Glu Gln Lys His Lys Arg Arg Arg Tyr Pro Ala Thr Thr
        195                 200                 205

Thr Thr Thr Ala Ala Pro Phe Arg Leu Asp Leu Glu Ala Arg Ala Arg
    210                 215                 220

Met Pro Pro Ala Ala Glu Ile Asp Glu Phe Phe Ala Ala Ala Glu Lys
225                 230                 235                 240

Ala Gln Ala Glu Arg Phe Ala Ala Lys Tyr Asn Phe Asp Val Ala Arg
                245                 250                 255

Gly Val Pro Leu Asn Ala Gly Arg Phe Glu Trp Thr Pro Val Ala Thr
            260                 265                 270

Val
```

<210> SEQ ID NO 91
<211> LENGTH: 271
<212> TYPE: PRT
<213> ORGANISM: Triticum sp.

<400> SEQUENCE: 91

```
Met Gly Lys Tyr Met Arg Lys Cys Arg Gly Ala Ala Ala Gly Gly Gly
1               5                   10                  15

Arg Ala Ala Pro Ala Val Val Glu His Arg Ala Pro Val Ala Leu Gly
            20                  25                  30

Val Arg Thr Arg Ser Arg Ala Ala Ala Phe Asp Ala Lys Arg Arg Lys
        35                  40                  45
```

```
Gln Gln Ala Thr Thr Ser Thr Ala Ala Arg Ala Val Asp Asp Ala Leu
    50                  55                  60

Leu Gly Arg Asp Gly Gly Asp Ala Ala Gly Gly Cys Tyr Leu His Leu
65                  70                  75                  80

Arg Ser Arg Arg Leu Phe Met Pro Ala Ser Ala Val Val Asp Arg Leu
                85                  90                  95

Arg Gly Gln Gly Ala Asp Glu Glu Ala Ser Thr Ala Arg Leu Ala Asp
            100                 105                 110

Ser Gly Pro Ser Val Glu Ala Gly Val Val Ala Gly Val Ser Arg Cys
        115                 120                 125

Ser Ser Thr Ala Ser Thr Ala Ala Asp Val Ala Ala Arg Glu Arg Ser
    130                 135                 140

Gly Asp Glu Ala Glu Ala Cys Glu Ser Arg Asp Val Glu Ser Ser Val
145                 150                 155                 160

Ser Asp Ser Glu Cys Gly Gly Arg Asp Arg Arg Glu Ala Thr Pro Ser
                165                 170                 175

Ser Arg Ser Pro Val Asp Leu Ser Asp Leu Glu Ser Ser Gln Ala Ala
            180                 185                 190

Asp Glu Gln Lys His Lys Arg Arg Arg Cys Pro Ala Ala Thr Thr Ala
        195                 200                 205

Ala Ala Ala Pro Phe His Leu Asp Ser Glu Ala Arg Ala Arg Met Pro
    210                 215                 220

Pro Ala Ala Glu Ile Asp Glu Phe Phe Ala Ala Ala Glu Lys Ala Gln
225                 230                 235                 240

Ala Glu His Phe Ala Ala Lys Tyr Asn Phe Asp Val Ala Arg Gly Val
                245                 250                 255

Pro Leu Asn Ala Gly Arg Phe Glu Trp Thr Pro Val Ala Thr Val
            260                 265                 270


<210> SEQ ID NO 92
<211> LENGTH: 274
<212> TYPE: PRT
<213> ORGANISM: Triticum sp.

<400> SEQUENCE: 92

Met Gly Lys Tyr Met Arg Lys Cys Arg Ala Ala Ala Ala Gly Gly Gly
1               5                   10                  15

Arg Ala Ala Pro Ala Val Val Glu His Arg Ala Pro Val Ala Leu Gly
            20                  25                  30

Val Arg Thr Arg Ser Arg Ala Ala Ala Leu Asp Ala Lys Met Arg Lys
        35                  40                  45

Gln Gln Gln Ala Thr Thr Ser Thr Ala Ala Arg Ala Val Glu Asp Ala
    50                  55                  60

Leu Leu Gly Arg Asp Gly Gly Asp Ala Ala Ala Gly Cys Tyr Leu His
65                  70                  75                  80

Leu Arg Ser Arg Arg Leu Phe Met Pro Ala Ala Ala Val Val Asp Gln
                85                  90                  95

Leu Arg Gly Gln Gly Val Cys Glu Glu Ala Ser Thr Ala Gly Leu Pro
            100                 105                 110

Asp Ser Gly Pro Ser Val Glu Ala Ala Val Gly Ala Gly Val Ser Arg
        115                 120                 125

Cys Ser Ser Thr Ala Ser Thr Ala Val Asp Val Ala Ala Arg Glu Arg
    130                 135                 140

Ser Gly Asp Glu Ala Glu Ala Cys Glu Ser Arg Asp Val Glu Ser Ser
```

```
145                 150                 155                 160

Val Ser Asp Ser Glu Cys Gly Gly Arg Asp Arg Arg Glu Thr Thr Pro
                165                 170                 175

Ser Ser Arg Ser Pro Val Asp Leu Ser Asp Leu Glu Ser Ser Gln Ala
            180                 185                 190

Ala Asp Glu Gln Lys His Lys Arg Arg Arg Cys Pro Ala Thr Thr Thr
        195                 200                 205

Thr Thr Ala Ala Pro Leu His Tyr Asp Leu Glu Ala Arg Ala Arg Ala
    210                 215                 220

Arg Met Pro Pro Ala Ala Glu Ile Asp Glu Phe Phe Ala Ala Ala Glu
225                 230                 235                 240

Lys Ala Gln Ala Glu Arg Phe Ala Ala Lys Tyr Asn Phe Asp Val Ala
                245                 250                 255

Arg Gly Val Pro Leu Asn Ala Gly Arg Phe Glu Trp Thr Pro Val Ala
            260                 265                 270

Thr Val


<210> SEQ ID NO 93
<211> LENGTH: 190
<212> TYPE: PRT
<213> ORGANISM: Triticum sp.

<400> SEQUENCE: 93

Met Gly Lys Tyr Met Arg Lys Pro Lys Val Ser Gly Glu Val Ala Val
1               5                   10                  15

Met Glu Val Ala Ala Ala Pro Leu Gly Val Arg Thr Arg Ala Arg Ala
            20                  25                  30

Leu Ala Met Gln Arg Gln Pro Gln Gly Ala Pro Gly Ala Lys Asp Gln
        35                  40                  45

Gly Glu Tyr Leu Glu Leu Arg Ser Arg Lys Leu Glu Lys Leu Pro Pro
    50                  55                  60

Pro Pro Pro Pro Ala Arg Arg Arg Ala Ala Ala Ala Glu Arg Val Glu
65                  70                  75                  80

Ala Glu Ala Glu Ala Asp Lys Val Ser Phe Gly Glu Asn Val Leu Glu
                85                  90                  95

Pro Glu Ala Met Gly Arg Gly Thr Arg Glu Thr Thr Pro Cys Ser Leu
            100                 105                 110

Ile Arg Asp Ser Gly Met Ile Ser Thr Pro Gly Ser Thr Thr Arg Pro
        115                 120                 125

Ser His Ser Asn Ser His Arg Arg Val Gln Ala Pro Ala Arg His Ile
    130                 135                 140

Ile Pro Ser Ser Ala Glu Met Asn Glu Phe Phe Ser Ala Ala Glu Gln
145                 150                 155                 160

Pro Gln Gln Gln Ala Phe Ile Asp Lys Tyr Asn Phe Asp Pro Val Asn
                165                 170                 175

Asp Cys Pro Leu Pro Gly Arg Tyr Glu Trp Val Lys Leu Asp
            180                 185                 190


<210> SEQ ID NO 94
<211> LENGTH: 190
<212> TYPE: PRT
<213> ORGANISM: Triticum sp.

<400> SEQUENCE: 94

Met Gly Lys Tyr Met Arg Lys Pro Lys Val Ser Gly Glu Val Ala Val
1               5                   10                  15
```

```
Met Glu Val Ala Ala Ala Pro Leu Gly Val Arg Thr Arg Ala Arg Ala
            20                  25                  30

Leu Ala Met Gln Arg Gln Pro Gln Gly Ala Ala Val Ala Lys Asp Gln
        35                  40                  45

Gly Glu Tyr Leu Glu Leu Arg Ser Arg Lys Leu Glu Lys Leu Pro Pro
    50                  55                  60

Pro Pro Pro Ala Ala Arg Arg Arg Ala Ala Ala Ala Glu Arg Val Glu
65                  70                  75                  80

Ala Glu Ala Glu Ala Asp Glu Val Ser Phe Gly Glu Asn Val Leu Glu
                85                  90                  95

Ser Glu Ala Met Gly Arg Gly Thr Arg Glu Thr Thr Pro Cys Ser Leu
            100                 105                 110

Ile Arg Asp Ser Gly Thr Ile Ser Thr Pro Gly Ser Thr Thr Arg Pro
        115                 120                 125

Ser His Ser Asn Ser His Arg Arg Val Gln Ala Pro Ala Arg His Ile
    130                 135                 140

Ile Pro Cys Ser Ala Glu Met Asn Glu Phe Phe Ser Ala Ala Glu Gln
145                 150                 155                 160

Pro Gln Gln Gln Ala Phe Ile Asp Lys Tyr Asn Phe Asp Pro Val Asn
                165                 170                 175

Asp Cys Pro Leu Pro Gly Arg Tyr Glu Trp Val Lys Leu Asp
            180                 185                 190


<210> SEQ ID NO 95
<211> LENGTH: 190
<212> TYPE: PRT
<213> ORGANISM: Triticum sp.

<400> SEQUENCE: 95

Met Gly Lys Tyr Met Arg Lys Pro Lys Val Ser Gly Glu Val Ala Val
1               5                   10                  15

Met Glu Val Ala Ala Ala Pro Leu Gly Val Arg Thr Arg Ala Arg Ala
            20                  25                  30

Leu Ala Met Gln Arg Gln Pro Gln Gly Ala Pro Gly Ala Lys Asp Gln
        35                  40                  45

Gly Glu Tyr Leu Glu Leu Arg Ser Arg Lys Leu Glu Lys Leu Pro Leu
    50                  55                  60

Pro Pro Pro Pro Ala Arg Arg Arg Ala Ala Ala Ala Glu Arg Val Glu
65                  70                  75                  80

Ala Glu Ala Glu Ala Asp Glu Val Ser Phe Gly Glu Asn Val Leu Glu
                85                  90                  95

Ser Glu Ala Met Gly Arg Gly Thr Arg Glu Thr Thr Pro Cys Ser Leu
            100                 105                 110

Ile Arg Asp Ser Gly Thr Ile Ser Thr Pro Gly Ser Thr Thr Arg Pro
        115                 120                 125

Ser His Ser Asn Ser His Arg Arg Val Gln Ala Pro Ala Arg His Ile
    130                 135                 140

Ile Pro Cys Ser Ala Glu Met Asn Glu Phe Phe Ser Ala Ala Glu Gln
145                 150                 155                 160

Pro Gln Gln Gln Ala Phe Ile Asp Lys Tyr Asn Phe Asp Pro Val Asn
                165                 170                 175

Asp Cys Pro Leu Pro Gly Arg Tyr Glu Trp Val Lys Leu Asp
            180                 185                 190
```

```
<210> SEQ ID NO 96
<211> LENGTH: 209
<212> TYPE: PRT
<213> ORGANISM: Triticum sp.

<400> SEQUENCE: 96

Met Gly Lys Tyr Met Arg Lys Ser Lys Ala Ser Gly Glu Val Ala Val
1               5                   10                  15

Met Glu Val Ala Gly Ala Leu Leu Gly Val Arg Thr Arg Ser Arg Thr
            20                  25                  30

Leu Ala Ala Gln Gln Gln Arg Ala Pro Ser Pro Ser Pro Gln Arg Lys
        35                  40                  45

Gly His Glu Asp Gly Asp Tyr Leu Glu Leu Arg Ser Arg Arg Leu Glu
    50                  55                  60

Lys Gln Pro Pro Pro Gly Pro Lys Asp Lys Glu Asp Ala Pro Gln Pro
65                  70                  75                  80

Pro Ala Ala Gly Gly Arg Arg Met Glu Gln Ala Pro Ser Ser Phe Ala
                85                  90                  95

Ala Glu Gly Phe Glu Ala Asp Leu Glu Val Ser Phe Gly Asp Asn Val
            100                 105                 110

Leu Asp Trp Asp Ala Thr Asp Arg Gly Ala Arg Glu Thr Thr Pro Cys
        115                 120                 125

Ser Leu Ile Tyr Ser Ser Glu Thr Met Ser Thr Pro Gly Ser Ala Thr
    130                 135                 140

Gly Gly Ala Arg Asn His Ser Arg Arg Arg Ala Gln Thr Pro Val Cys
145                 150                 155                 160

Arg Tyr Val Pro Ser Ser Leu Glu Met Asp Glu Phe Phe Ala Ala Ala
                165                 170                 175

Glu Gln Gln Gln His Gln Thr Phe Arg Asp Lys Tyr Asn Phe Cys Pro
            180                 185                 190

Ala Arg Gly Cys Pro Leu Pro Gly Arg Tyr Glu Trp Thr Val Leu Asp
        195                 200                 205

Cys


<210> SEQ ID NO 97
<211> LENGTH: 140
<212> TYPE: PRT
<213> ORGANISM: Triticum sp.

<400> SEQUENCE: 97

Met Gly Lys Tyr Met Arg Lys Ser Lys Ala Ser Gly Glu Val Ala Val
1               5                   10                  15

Met Glu Val Ala Gly Ala Leu Leu Gly Val Arg Thr Arg Ser Arg Thr
            20                  25                  30

Leu Ala Ala Gln Gln Gln Arg Ala Pro Ser Pro Ser Pro Ser Pro Gln
        35                  40                  45

Arg Lys Gly Gln Glu Asp Gly Asp Pro Gly Ala Gly Asp Tyr Leu Glu
    50                  55                  60

Leu Arg Ser Arg Arg Leu Glu Lys Gln Pro Pro Pro Gly Ala Arg Glu
65                  70                  75                  80

Lys Glu Asp Ala Pro Gln Arg Pro Arg Gly Gly Pro Pro Pro Leu Ala
                85                  90                  95

Gly Gly Gly Trp Ser Arg Arg Arg Arg Ser Pro Pro Arg Gly Ser Arg
            100                 105                 110

Pro Thr Ser Arg Ser Pro Ser Ala Thr Thr Cys Trp Thr Gly Thr Pro
        115                 120                 125
```

```
Pro Thr Gly Ala Pro Gly Arg Arg Arg Arg Ala Ala
    130                 135                 140


<210> SEQ ID NO 98
<211> LENGTH: 204
<212> TYPE: PRT
<213> ORGANISM: Triticum sp.

<400> SEQUENCE: 98

Met Gly Lys Tyr Met Arg Lys Ser Lys Ala Ser Gly Glu Val Ala Val
1               5                   10                  15

Met Glu Val Ala Gly Ala Leu Leu Gly Val Arg Thr Arg Ser Arg Thr
            20                  25                  30

Leu Ala Ala Gln Gln Gln Arg Ala Pro Ser Pro Ser Pro Gln Arg Lys
        35                  40                  45

Gly His Glu Asp Gly Asp Tyr Leu Glu Leu Arg Ser Arg Arg Leu Glu
    50                  55                  60

Lys Gln Pro Pro Pro Gly Pro Lys Asp Lys Glu Asp Ala Pro Gln Pro
65                  70                  75                  80

Pro Ala Ala Gly Gly Arg Gly Met Glu Ser Phe Ala Ala Glu Gly Phe
                85                  90                  95

Glu Ala Asp Leu Glu Val Ser Phe Gly Asp Asn Val Leu Asp Trp Asp
            100                 105                 110

Ala Thr Asp Arg Gly Ala Arg Glu Thr Thr Pro Cys Ser Leu Ile Tyr
        115                 120                 125

Ser Ser Glu Thr Met Ser Thr Pro Gly Ser Ala Thr Gly Ala Arg Asn
    130                 135                 140

His Ser Arg Arg Arg Ala Gln Thr Pro Val Cys Arg Tyr Val Pro Ser
145                 150                 155                 160

Ser Leu Glu Met Asp Glu Phe Phe Ala Ala Ala Glu Gln Gln Gln His
                165                 170                 175

Gln Thr Phe Arg Glu Lys Tyr Asn Phe Cys Pro Ala Ser Glu Arg Pro
            180                 185                 190

Leu Pro Gly Arg Tyr Glu Trp Thr Val Leu Asp Cys
        195                 200


<210> SEQ ID NO 99
<211> LENGTH: 262
<212> TYPE: PRT
<213> ORGANISM: Oryza sativa

<400> SEQUENCE: 99

Met Gly Lys Tyr Met Arg Lys Phe Arg Gly Ala Thr Gly Glu Glu Leu
1               5                   10                  15

Ala Ala Met Glu Val Thr Gln Val Val Gly Val Arg Thr Arg Ser Arg
            20                  25                  30

Ser Ala Ala Ala Ala Gly Ala Thr Thr Thr Lys Val Lys Ala Ala Ser
        35                  40                  45

Ala Ala Ser Thr Arg Arg Arg Lys Ala Leu Leu Pro Thr Ala Val Val
    50                  55                  60

Gly Thr Thr Arg Arg Asp Gly Gly Ser Cys Tyr Leu Gln Leu Arg Ser
65                  70                  75                  80

Arg Met Leu Phe Met Ala Pro Pro Arg Pro Ala Pro Ala Ala Arg Ala
                85                  90                  95

Pro Val Val Ala Glu Ala Ala Gly Ser Gly Asn Gly Ala Ala Ala His
            100                 105                 110
```

```
Ala Ala Ala Gly Leu Ser Arg Cys Ser Ser Thr Ala Ser Ser Val Asp
        115                 120                 125

Ala Ala Ala Gln Asp Arg Ser Leu Ala Cys Arg Ser Asp Val Ala Glu
    130                 135                 140

Ala Gly Ser Glu His Val Pro Glu Gly Ser Ala Ser Asp Ser Ala Ser
145                 150                 155                 160

Gly Arg Asp Arg Glu Arg Arg Glu Thr Thr Pro Ser Ser Phe Leu Pro
                165                 170                 175

Gly Glu Val Ser Asp Leu Glu Ser Asp Leu Ala Gly Gly Gln Lys Arg
            180                 185                 190

Ser Arg Pro Leu Pro Ser Ala Ala Thr Ala Ser Ala Gln Gln Ala Thr
        195                 200                 205

Arg Pro Lys Ile Pro Pro Ala Ala Glu Ile Glu Ala Phe Phe Ala Ala
    210                 215                 220

Ala Glu Glu Ala Glu Ala Lys Arg Phe Ala Ala Lys Tyr Asn Phe Asp
225                 230                 235                 240

Val Val Arg Gly Val Pro Leu Asp Ala Gly Arg Phe Glu Trp Thr Pro
                245                 250                 255

Val Val Ser Ser Arg Ser
            260
```

<210> SEQ ID NO 100
<211> LENGTH: 1265
<212> TYPE: DNA
<213> ORGANISM: Oryza sativa

<400> SEQUENCE: 100

```
agggaaacgg ccaaagaagg cgacggcggc ggcgcaggag gggcgcgcac gcggcgcaga      60

tgggcaagta catgaggaag ttcagggggg ccacggggga ggagttggcc gccatggagg     120

tcacgcaggt ggttggcgtc cggacgaggt cgaggtcggc agcggcggcg ggcgcgacga     180

cgacgaaggt gaaggcggcg tcggcggcgt ccaccaggag gaggaaggcg ctgctgccga     240

cggcggtcgt ggggactact cgccgtgacg gcgggagctg ctacctccag ctgaggagcc     300

gcatgctgtt catggccccg ccgaggccgg cgccggccgc gagggctccg gttgtagcgg     360

aggcggcggg ttccgggaac ggagcggcgg cgcatgcggc ggctggcctc tcgcgttgct     420

ccagcacggc gtcgtccgtg gacgcggcgg ctcaggacag gagcctcgcg tgccgctccg     480

acgtcgcgga ggcaggcagc gagcatgtcc cggagggctc cgcgagcgac tcggcgagcg     540

gccgtgaccg cgagaggaga gaaacaactc catcaagctt tctccccgga gaggtgagcg     600

atctggagtc ggatctggct ggaggacaga agcgcagccg tccactacct tctgcggcaa     660

cagcctcagc acagcaagcc acgcggccga agattccgcc ggccgccgag atcgaggcgt     720

tcttcgcggc ggccgaggag gctgaggcca agcgcttcgc cgccaagtac aacttcgacg     780

tcgttcgcgg cgtgcccctc gacgccggtc ggttcgagtg gactccggtg gtcagcagcc     840

gaagctgaag cgagcgtgca gattaagcgg aagctagaaa ggaaggtaca ggggggcgcc     900

gtgtagaaag ggaaggcgag ctagagagag gagaagaaga agaagaaaag atgctcatcc     960

aaagggaata aactggaaaa gtgggagact acaaaaaaag aagcattata gcctaacaac    1020

caccgattcg actctttttt ctttcacatt ttctttgcat ttttactctt actgtgtact    1080

agaaagtagt agcagtagta aactagtaat tcgtcccagt atttatcaga ggtttatctc    1140

gataggaata gatatattat ccccttactg taattgcctc catcttgtat ttggatggaa    1200
```

attaaattta ctgtacagca gcagcagctg ttctgcaagt ttaagttaac catcaccgtt 1260
ttatt 1265

<210> SEQ ID NO 101
<211> LENGTH: 789
<212> TYPE: DNA
<213> ORGANISM: Oryza sativa

<400> SEQUENCE: 101
atgggcaagt acatgaggaa gttcaggggg gccacggggg aggagttggc cgccatggag 60
gtcacgcagg tggttggcgt ccggacgagg tcgaggtcgg cagcggcggc gggcgcgacg 120
acgacgaagg tgaaggcggc gtcggcggcg tccaccagga ggaggaaggc gctgctgccg 180
acggcggtcg tggggactac tcgccgtgac ggcgggagct gctacctcca gctgaggagc 240
cgcatgctgt tcatggcccc gccgaggccg gcgccggccg cgagggctcc ggttgtagcg 300
gaggcggcgg gttccgggaa cggagcggcg gcgcatgcgg cggctggcct ctcgcgttgc 360
tccagcacgg cgtcgtccgt ggacgcggcg gctcaggaca ggagcctcgc gtgccgctcc 420
gacgtcgcgg aggcaggcag cgagcatgtc ccggagggct ccgcgagcga ctcggcgagc 480
ggccgtgacc gcgagaggag agaaacaact ccatcaagct ttctccccgg agaggtgagc 540
gatctggagt cggatctggc tggaggacag aagcgcagcc gtccactacc ttctgcggca 600
acagcctcag cacagcaagc cacgcggccg aagattccgc cggccgccga gatcgaggcg 660
ttcttcgcgg cggccgagga ggctgaggcc aagcgcttcg ccgccaagta caacttcgac 720
gtcgttcgcg gcgtgcccct cgacgccggt cggttcgagt ggactccggt ggtcagcagc 780
cgaagctga 789

<210> SEQ ID NO 102
<211> LENGTH: 750
<212> TYPE: DNA
<213> ORGANISM: Oryza sativa

<400> SEQUENCE: 102
atggggaaga agaagaagcg cgacggcgcg gcggcgagga ggcaggcgcg ggtggtggtc 60
ggcggcgtcc gtacgcgggc cgccgtcacg gcgaggaggg tggtggcgag cgcggaggag 120
ggttgtggtt tggtgggccg tggcggtggc ggtggcagtg gcggagacga tggcgagggc 180
ggatgctatc tgcgtctgcg gagcaggagg ctgcccttcg tggcggccgc ggtggtgtcg 240
tcgcggaggg aggaggcgct cggtgattcg gtggcggagg cggcttcgtc gtcgtcgtcg 300
cgggcggtgg aattgttggg ctgttctggt gaggaggagg ctatggccga gaaggtttgc 360
acgcaggcag gcgaggatca cgacgaggag agctccgtcg gcgactccgg ctgcggccgc 420
gagaggagcg cgacgacgcc gtcgagccgc cggccgccgg gagacgcgga ctcgagcgac 480
gcggagtcaa accaggaggc caagcagcaa atgtgccgcc ggagttcgac gacctcagca 540
gctgcatttc acgcgggagc gacgacgagg agcttcagga tgatggcacc gccggcggcg 600
gcggcagaga tcgaggagtt cctcgccgct gcggagaggt ccgaggccga gcgcttcgcc 660
gccaagtaca acttcgacgt ggtgcgcggc gtgccgctcg acgccggcgg cgccgggcgg 720
ttcgaatgga ccgcggtggg cagcggctga 750

<210> SEQ ID NO 103
<211> LENGTH: 750
<212> TYPE: DNA
<213> ORGANISM: Oryza sativa

<400> SEQUENCE: 103
atggggaaga agaagaagcg cgacggcgcg gcggcgagga ggcaggcgcg ggtggtggtc 60
ggcggcgtcc gtacgcgggc cgccgtcacg gcgaggaggg tggtggcgag cgcggaggag 120
ggttgtggtt tggtgggccg tggcggtggc ggtggcagtg gcggagacga tggcgagggc 180
ggatgctatc tgcgtctgcg gagcaggagg ctgcccttcg tggcggccgc ggtggtgtcg 240
tcgcggaggg aggaggcgct cggtgattcg gtggcggagg cggcttcgtc gtcgtcgtcg 300
cgggcggtgg aattgttggg ctgttctggt gaggaggagg ctatggccga gaaggtttgc 360
acgcaggcag gcgaggatca cgacgaggag agctccgtcg gcgactccgg ctgcggccgc 420
gagaggagcg cgacgacgcc gtcgagccgc cggccgccgg gagacgcgga ctcgagcgac 480
gcggagtcaa accaggaggc caagcagcaa atgtgccgcc ggagttcgac gacctcagca 540
gctgcatttc acgcgggagc gacgacgagg agcttcagga tgatggcacc gccggcggcg 600
gcggcagaga tcgaggagtt cctcgccgct gcggagaggt ccgaggccga gcgcttcgcc 660
gccaagtaca acttcgacgt ggtgcgcggc gtgccgctcg acgccggcgg cgccgggcgg 720
ttcgaatgga ccgcggtggg cagcggctga 750

<210> SEQ ID NO 104
<211> LENGTH: 1025
<212> TYPE: DNA
<213> ORGANISM: Oryza sativa

<400> SEQUENCE: 104
ccctccaaat ccacccgggg tccccctacc attttaaccc cgcggcctta gccgctaatg 60
ctccgcgttt gaaatcgcta agcgcacccg aaaccctagc cccctcccct cccgagtccc 120
gaccgccatg ggcaagtaca tgcgcaaggc caaggtggtg gtctccggcg aggtggtggc 180
cgccgccgtc atggagctcg ccgcggcgcc gctcggggtg cgcacccgcg cccgctccct 240
cgcgctgcag aagaggcagg gcggggagta cctcgagctc aggagccgca ggctcgagaa 300
gctccctcct cccccgccgc cgccgccgag gaggagggcg acggctgcgg ctgcgactgc 360
tgatgcgacg gcggcggaga gcgcggaggc ggaggtgtcg ttcggggggg agaacgtcct 420
cgagctggag gccatggaaa ggaataccag ggagacgaca ccttgcagct tgatcaggga 480
ccccgatacg attagcaccc ctggatctac cacaaggcgc agccactcga gttctcattg 540
caaggtgcaa acacccgtgc gccacaacat tattccagca tcagcagagc tggaagcgtt 600
cttcgctgcc gaagagcaac ggcaacgaca ggctttcatc gacaagtata actttgatcc 660
tgtgaatgac tgccctcttc ccggccggtt tgaatgggtc aagctagact gatagatttt 720
caggaaaaga agggcaccat ggacctctct gctccctcca cagtagtagc gtggcagagg 780
cgcttaccgt caagttagct ttgatcctgt tgtaaaaatt tagggttagc ctgtagactc 840
aatggtcaat gtgaacatac agaactgatg ctgagttaca accctaatcc ctcaactaca 900
atgtaaccct taacagctca ttctgtaagg aaccacctcc tcctctaggg cctagctagc 960
cttatcatct gttattacca gttgctggat taatgaagtt agatctagat attgtgtcac 1020
agttt 1025

<210> SEQ ID NO 105
<211> LENGTH: 585
<212> TYPE: DNA
<213> ORGANISM: Oryza sativa

<400> SEQUENCE: 105
atgggcaagt acatgcgcaa ggccaaggtg gtggtctccg gcgaggtggt ggccgccgcc 60
gtcatggagc tcgccgcggc gccgctcggg gtgcgcaccc gcgcccgctc cctcgcgctg 120
cagaagaggc agggcgggga gtacctcgag ctcaggagcc gcaggctcga gaagctccct 180
cctcccccgc cgccgccgcc gaggaggagg gcgacggctg cggctgcgac tgctgatgcg 240
acggcggcgg agagcgcgga ggcggaggtg tcgttcgggg gggagaacgt cctcgagctg 300
gaggccatgg aaaggaatac cagggagacg acaccttgca gcttgatcag ggaccccgat 360
acgattagca cccctggatc taccacaagg cgcagccact cgagttctca ttgcaaggtg 420
caaacacccg tgcgccacaa cattattcca gcatcagcag agctggaagc gttcttcgct 480
gccgaagagc aacggcaacg acaggctttc atcgacaagt ataactttga tcctgtgaat 540
gactgccctc ttcccggccg gtttgaatgg gtcaagctag actga 585

<210> SEQ ID NO 106
<211> LENGTH: 1045
<212> TYPE: DNA
<213> ORGANISM: Oryza sativa

<400> SEQUENCE: 106
aaacgcgcgc cgtttcccgc ttccactccc ctccccccat tattcccgcg attctcctcc 60
cttcctcccg ccgcgcgcgc cttggccatg gggaagtaca tgcggaaggg gaaggtgtcg 120
ggggaggtgg cggtgatgga ggtgggcggg gcgctgctcg gcgtccgcac ccgctcccgc 180
acgctcgcgc tgcagcggac gacctcgtcg cagaagccgc cggagaaggg ggagggggac 240
cccggtgcgg gcgcgggcgc gggggcggag tacctcgagc tcaggagccg gaggctcgag 300
aagccgcctc cgcacacgcc gccggccaag gagaaggaga ccgccaggag ggcttccgcc 360
gccgccgccg ccgccgtgag gatgccggcg gcgccgcaag cggccgagga gttcgaggcg 420
gaggtcgagg tgtccttcgg cgacaacgtt cttgacctcg acggcgacgc catggagagg 480
agtaccaggg agacaacgcc ttgcagttta attaggagct cagaaatgat aagcacccct 540
ggctccacaa ctaaaaccaa cacctcgatc agttcccggc gcagaatgga gacctctgtt 600
tgtcgttacg ttccgagttc tcttgagatg gaagagttct ttgcagctgc tgaacaacag 660
caacatcagg ctttcagaga gaggtataac ttctgtcctg tgaacgactg cccacttcct 720
ggacggtacg aatggacaag gctagactgc tagattttca tcttgagagc tccattgatc 780
tctccacaca gttgactagc accaccatgg cagaggcaaa atgcaattcg attaggtttc 840
ttctctgttg taaaaaaaaa atagagttag tcagtagctc aatgatcttg tgtaacaaac 900
ataagtgatg ttgagttaca catcctgatc cccccaccaa catgtaaccg ttaactgctc 960
attctgtaac gaaccacctc ttttaggcct agctttatta tctgtcccca gtcgatttaa 1020
tgaatttagt tagaatttct ctagc 1045

<210> SEQ ID NO 107
<211> LENGTH: 666
<212> TYPE: DNA
<213> ORGANISM: Oryza sativa

<400> SEQUENCE: 107
atggggaagt acatgcggaa ggggaaggtg tcgggggagg tggcggtgat ggaggtgggc 60
ggggcgctgc tcggcgtccg cacccgctcc cgcacgctcg cgctgcagcg gacgacctcg 120
tcgcagaagc cgccggagaa gggggagggg gaccccggtg cgggcgcggg cgcgggggcg 180

```
gagtacctcg agctcaggag ccggaggctc gagaagccgc ctccgcacac gccgccggcc    240

aaggagaagg agaccgccag gagggcttcc gccgccgccg ccgccgccgt gaggatgccg    300

gcggcgccgc aagcggccga ggagttcgag gcggaggtcg aggtgtcctt cggcgacaac    360

gttcttgacc tcgacggcga cgccatggag aggagtacca gggagacaac gccttgcagt    420

ttaattagga gctcagaaat gataagcacc cctggctcca caactaaaac caacacctcg    480

atcagttccc ggcgcagaat ggagacctct gtttgtcgtt acgttccgag ttctcttgag    540

atggaagagt tctttgcagc tgctgaacaa cagcaacatc aggctttcag agagaggtat    600

aacttctgtc ctgtgaacga ctgcccactt cctggacggt acgaatggac aaggctagac    660

tgctag                                                                666
```

```
<210> SEQ ID NO 108
<211> LENGTH: 249
<212> TYPE: PRT
<213> ORGANISM: Oryza sativa

<400> SEQUENCE: 108

Met Gly Lys Lys Lys Lys Arg Asp Gly Ala Ala Ala Arg Arg Gln Ala
1               5                   10                  15

Arg Val Val Val Gly Gly Val Arg Thr Arg Ala Ala Val Thr Ala Arg
            20                  25                  30

Arg Val Val Ala Ser Ala Glu Glu Gly Cys Gly Leu Val Gly Arg Gly
        35                  40                  45

Gly Gly Gly Gly Ser Gly Gly Asp Asp Gly Glu Gly Gly Cys Tyr Leu
    50                  55                  60

Arg Leu Arg Ser Arg Arg Leu Pro Phe Val Ala Ala Ala Val Val Ser
65                  70                  75                  80

Ser Arg Arg Glu Glu Ala Leu Gly Asp Ser Val Ala Glu Ala Ala Ser
                85                  90                  95

Ser Ser Ser Ser Arg Ala Val Glu Leu Leu Gly Cys Ser Gly Glu Glu
            100                 105                 110

Glu Ala Met Ala Glu Lys Val Cys Thr Gln Ala Gly Glu Asp His Asp
        115                 120                 125

Glu Glu Ser Ser Val Gly Asp Ser Gly Cys Gly Arg Glu Arg Ser Ala
    130                 135                 140

Thr Thr Pro Ser Ser Arg Arg Pro Pro Gly Asp Ala Asp Ser Ser Asp
145                 150                 155                 160

Ala Glu Ser Asn Gln Glu Ala Lys Gln Gln Met Cys Arg Arg Ser Ser
                165                 170                 175

Thr Thr Ser Ala Ala Ala Phe His Ala Gly Ala Thr Thr Arg Ser Phe
            180                 185                 190

Arg Met Met Ala Pro Pro Ala Ala Ala Ala Glu Ile Glu Glu Phe Leu
        195                 200                 205

Ala Ala Ala Glu Arg Ser Glu Ala Glu Arg Phe Ala Ala Lys Tyr Asn
    210                 215                 220

Phe Asp Val Val Arg Gly Val Pro Leu Asp Ala Gly Gly Ala Gly Arg
225                 230                 235                 240

Phe Glu Trp Thr Ala Val Gly Ser Gly
                245
```

```
<210> SEQ ID NO 109
<211> LENGTH: 194
<212> TYPE: PRT
```

<213> ORGANISM: Oryza sativa

<400> SEQUENCE: 109

```
Met Gly Lys Tyr Met Arg Lys Ala Lys Val Val Val Ser Gly Glu Val
1               5                   10                  15

Val Ala Ala Ala Val Met Glu Leu Ala Ala Ala Pro Leu Gly Val Arg
            20                  25                  30

Thr Arg Ala Arg Ser Leu Ala Leu Gln Lys Arg Gln Gly Gly Glu Tyr
        35                  40                  45

Leu Glu Leu Arg Ser Arg Arg Leu Glu Lys Leu Pro Pro Pro Pro Pro
    50                  55                  60

Pro Pro Pro Arg Arg Arg Ala Thr Ala Ala Ala Ala Thr Ala Asp Ala
65                  70                  75                  80

Thr Ala Ala Glu Ser Ala Glu Ala Glu Val Ser Phe Gly Gly Glu Asn
                85                  90                  95

Val Leu Glu Leu Glu Ala Met Glu Arg Asn Thr Arg Glu Thr Thr Pro
            100                 105                 110

Cys Ser Leu Ile Arg Asp Pro Asp Thr Ile Ser Thr Pro Gly Ser Thr
        115                 120                 125

Thr Arg Arg Ser His Ser Ser Ser His Cys Lys Val Gln Thr Pro Val
    130                 135                 140

Arg His Asn Ile Ile Pro Ala Ser Ala Glu Leu Glu Ala Phe Phe Ala
145                 150                 155                 160

Ala Glu Glu Gln Arg Gln Arg Gln Ala Phe Ile Asp Lys Tyr Asn Phe
                165                 170                 175

Asp Pro Val Asn Asp Cys Pro Leu Pro Gly Arg Phe Glu Trp Val Lys
            180                 185                 190

Leu Asp
```

<210> SEQ ID NO 110
<211> LENGTH: 221
<212> TYPE: PRT
<213> ORGANISM: Oryza sativa

<400> SEQUENCE: 110

```
Met Gly Lys Tyr Met Arg Lys Gly Lys Val Ser Gly Glu Val Ala Val
1               5                   10                  15

Met Glu Val Gly Gly Ala Leu Leu Gly Val Arg Thr Arg Ser Arg Thr
            20                  25                  30

Leu Ala Leu Gln Arg Thr Thr Ser Ser Gln Lys Pro Pro Glu Lys Gly
        35                  40                  45

Glu Gly Asp Pro Gly Ala Gly Ala Gly Ala Gly Ala Glu Tyr Leu Glu
    50                  55                  60

Leu Arg Ser Arg Arg Leu Glu Lys Pro Pro Pro His Thr Pro Pro Ala
65                  70                  75                  80

Lys Glu Lys Glu Thr Ala Arg Arg Ala Ser Ala Ala Ala Ala Ala Ala
                85                  90                  95

Val Arg Met Pro Ala Ala Pro Gln Ala Ala Glu Glu Phe Glu Ala Glu
            100                 105                 110

Val Glu Val Ser Phe Gly Asp Asn Val Leu Asp Leu Asp Gly Asp Ala
        115                 120                 125

Met Glu Arg Ser Thr Arg Glu Thr Thr Pro Cys Ser Leu Ile Arg Ser
    130                 135                 140

Ser Glu Met Ile Ser Thr Pro Gly Ser Thr Thr Lys Thr Asn Thr Ser
145                 150                 155                 160
```

```
Ile Ser Ser Arg Arg Arg Met Glu Thr Ser Val Cys Arg Tyr Val Pro
                165                 170                 175

Ser Ser Leu Glu Met Glu Glu Phe Phe Ala Ala Ala Glu Gln Gln Gln
            180                 185                 190

His Gln Ala Phe Arg Glu Arg Tyr Asn Phe Cys Pro Val Asn Asp Cys
        195                 200                 205

Pro Leu Pro Gly Arg Tyr Glu Trp Thr Arg Leu Asp Cys
    210                 215                 220


<210> SEQ ID NO 111
<211> LENGTH: 3220
<212> TYPE: DNA
<213> ORGANISM: Glycine sp.

<400> SEQUENCE: 111

aatgcctcct ttaaatactt actgaagtct cgaaatgcaa aaaaatatta ttacagtaaa     60

attaaaaata aacacacgag gcaaagacag aaaaagaaag agaaagagtg acacaatagt    120

actgcagctg tactgtactg gctaaaaccc caatccaaga accctaataa aactccttcc    180

ctttcctttc ctttccattc cccacgccta aattctcact ccctctaaaa acccctcttt    240

cctttccctc tctttttcta atttctttct tttcgattcc tgcaaaaccc ttacatgggc    300

aagtacatga agaagtccaa aatcgccggc gacgtcgccg ccgtgatcat ggaggctccg    360

ccgccgcact cccacctcgg cgtccgcacc cgcgccaaga ccctcgctct ccagaacaac    420

accacctccc cggacccctc cgcctacctc cagctccgca gccgccgcct cctcaagctc    480

ccccctaccc cgccggaaaa tccccgccgc tcctccgccg aaaccgccgc caatttccgc    540

ctcgccaacg cccaaaagct tgcatctttc gaagacgaca acaacaccga atgctctttc    600

ggcgagaatt tcttagacgc cgagcccaga gaagaaaggt atataatata ttatatacat    660

aattcccttt cttcaatttc tctgctctta gttatttttt atttgtattt tttcatgtgt    720

ttttattcct ttcacccttc gtctgtgttt ctcttatttt tattattttt ttgtttaaat    780

taaccatttt atggggttat ttgccgatta tttagggctt tacggtaagc cctgtttgtt    840

ctcgcttcat gcatatgtat ggactgattt ttttttttgg gtttaatata tttttaattt    900

ctgtaaacag ggcaattttt atttagtccc tatcaactaa attctctttc ttttctcttt    960

ttatgaaatg gttcataata aaaatcacat aatgacatat tttcaaggag gaggggctaa   1020

aggttaatat tgaatagaat tttagtcaac tttttgttgt tgcattccag tgttgcaatg   1080

attttgagaa tttccataag tttgttttat ttttttatgt tattttcttt tcatttgaat   1140

tgtttatttt agtttctgaa tttcttctgt ttatgcgttt ttactttctt gtgattgttt   1200

gtgttttgct aaaattgtta catttttcag tggagtgaga gtcatgtgag gttgtggaag   1260

ggaaagggtt ttattatcat gactctctct tgaaagtcac cgctcttttg attctcatgc   1320

tttttctatt gttggtgtca ttactaaccg ttgttgttaa acctcgtgag gtcttagtcc   1380

cttaactttt tggttattat gtgttttaac tttcatgtga tttgttttga tttcccactc   1440

tgtcaaatct gtgtactgtg ataaagctct gttggtacaa agggttgctc agatttgtga   1500

cttgtgtgtg acttgtgata ggttccgcac cttgcatgcc ctcaggatag ttatttactg   1560

caacttgtat ttttctgtgg tattaatctt tgcatgtcag acataattta taaatttcta   1620

ttagaaaatc ctattttctg tagttatcat tttatataaa tgggttataa ccaataacgt   1680

agagagttga tgatttttca agtaaataga accaactaaa tgttaaacaa gttttgtaac   1740
```

-continued

```
ttggttcaaa aaaaggaaga acatctccaa gtccaaattg agtgaattga tgtgcattaa   1800
ttgtccttct gcagatccag ttgttgacaa attttgtgat tggacaattt tcgtacagat   1860
ataattcgag gccctttgtt atttttagtc catttctctc aattttttta tgaacttaaa   1920
atttttgtaa ttagaaatgt ttctgtcttg aatccaaaat gcatttaccc ttgattgtcc   1980
ttgtttactt ttgatctgca agaagcctgc atgaccttga agcttagcac tcctccgtaa   2040
atggtcaagt tgaaaaaaat ggattttagt aataggagca gccataagtc ttatgactca   2100
tgttagcaat gaggtgtcat gtacatgggg cctagttttc agattgatgt tttttggat    2160
tcctatttgg gtttgcggtg aagtgagaaa gatttggccg tctctttatt tgtatttttt   2220
tagtgcatga gcccactgag tcagaacttg tcccattaaa tggcagttac tttttatag    2280
tagcaaaatt tgtctctagt tctactacac tgagttgtag ttggagattg tgggaggaaa   2340
aaatgatctg tttcttctct cacttatttt gctgtcagcg gttagcatgc aacttctgat   2400
gtagaaactt ttcataacaa gtcagcatta tttgtattta tatataactg ctatttttat   2460
tttttataat ttttataagc ttatatatat gttcattaaa attttattgt gttttaataa   2520
caggagcacc agggaaggca ccccttgtag tttaataagg gactcaaatg ccattcatac   2580
ccctggttca accacaaggc caaggactcg ccaaataatc catgaacacg tacaaagaaa   2640
tattccaacg gcttatgaga tggaggagtt ctttgcttat gctgagaagc agcaacagac   2700
aatatttatg gacaagtatg tactctttta tagtcttata ttccacaagt ccctttctt    2760
ttgttttaaa cattaggggt atttttattt ggatttcttc ctaattaata atgtaattat   2820
gtaatgtgct tatgtataaa ttgtctgtgt tttgcaggta caatttcgac attgtcaatg   2880
acgtacctct gcctggacgg tacgagtggg tcccagtact ccactaggag tgtcatatgg   2940
tggtgattat atatatggat tgcaagaacc attcgacgtg tattttaatt ttaacaacta   3000
gaagaagctt tcactaacca tttagattgc ttgaggctgt tgtttaacaa gctacaaggg   3060
aaaggatctg tttagaaatt tccaatatct gattagtagt ttagtagtgt ctttctgatt   3120
tgtagggtgt aggggggta tatggtatat ctagttttta ggtcatcttt attgtaattt    3180
cattaccttc tgtttatata attcagtggg gattagacat                         3220
```

<210> SEQ ID NO 112
<211> LENGTH: 606
<212> TYPE: DNA
<213> ORGANISM: Glycine sp.

<400> SEQUENCE: 112

```
atgggcaagt acatgaagaa gtccaaaatc gccggcgacg tcgccgccgt gatcatggag     60
gctccgccgc cgcactccca cctcggcgtc cgcacccgcg ccaagaccct cgctctccag    120
aacaacacca cctccccgga cccctccgcc tacctccagc tccgcagccg ccgcctcctc    180
aagctccccc ctaccccgcc ggaaaatccc cgccgctcct ccgccgaaac cgccgccaat    240
ttccgcctcg ccaacgccca aaagcttgca tctttcgaag acgacaacaa caccgaatgc    300
tctttcggcg agaatttctt agacgccgag cccagagaag aaaggagcac cagggaaggc    360
accccttgta gtttaataag ggactcaaat gccattcata cccctggttc aaccacaagg    420
ccaaggactc gccaaataat ccatgaacac gtacaaagaa atattccaac ggcttatgag    480
atggaggagt tctttgctta tgctgagaag cagcaacaga caatatttat ggacaagtac    540
aatttcgaca ttgtcaatga cgtacctctg cctggacggt acgagtgggt cccagtactc    600
cactag                                                               606
```

<210> SEQ ID NO 113
<211> LENGTH: 3290
<212> TYPE: DNA
<213> ORGANISM: Glycine sp.

<400> SEQUENCE: 113

```
ttaaaggaaa aattgcctcc tttaaataaa aaaaatatta ttacattaaa aaataataaa      60
tacatgaggc aacaaagaga tagtgagagt gacacagtag tagtactgca cctgtcctcg     120
ctaaaacccc aaagtaagcc ccaatccaac cctaataaaa ctccttccct ttgcccattc     180
tatcaaattt tccctctctc tctcaaattt tctctccctc aaaaaaccct tcactccttt     240
ccctctcttt tctaattttt tttttagatt cacccaaaac ccgacaaccc acacatgggg     300
aagtacatga agaagtccaa aatcgccggt gacgtcgccg ccgtgatcat ggaggctccg     360
ccgccgcact cccacctcgg cgtccgcacc cgcgccaaga ctctcgccct ccagaatacc     420
tccccggact cctccgccta cctccagctc cgcagccgcc gcctcctcaa gctccccccct    480
accccgccgg aaaatccccg ccgctccgcc gccgaaaccg ccgccaattc ccgcctcgcc     540
aaaacgacgt cgtcccgtaa cgccgaaaag ttcgcatctt tcgatgacga caacaatacc     600
gaatgctctt tcggcgaaaa tttcttagac gccgaaccca gggaggaaag gtatatataa     660
ttataaataa ttattccctt tcttcaattt ctctgttttt caatcatttt tcttgtgttt     720
ttattccttt ctccctttgt gtctctgttt ctcttgttta tttatttatt tatttatttt     780
gtttaaatta gccattttat ggggttattt gccggttatt tagggctcta ctgtaagttc     840
ttgctgtttt tccttgcttc atgcatgtgt gtattttttg ttggatttga tgtattttta     900
attccttcta attgtgcaat ttttattttt agtccctatc aaataaattc tcattctttt     960
ctcttgttta tgaaatgggt catatgtggt tttttgtctt tctcaaaaaa ttgtttcgtt    1020
ttggtctctt ttatgaaaat aaaaatcaca tgatgacata ttttcgtgaa agacgggggc    1080
aaaagacctt ttatttgtga ggggctaaaa gtgaatattg aataaaattt tagtcaactt    1140
tttgttgttg ttacaggtaa gtgtttaccg tgattttgag aattctcaca agttttttat    1200
gttcttttat tttgtattat ttaattttta gtttcagaat tttcttctgt ttatgcgttt    1260
tcattttctt gtgattgttt gtgttttgct aaaattgttg catttttcag tggagtgaca    1320
gccatgtaag tttgtggaag gaaagggttt tgatattctc tcttgaaagt caccgctcat    1380
ttgattctca tgccttttttc tattgttggt gtcattacta accgttgttg ttgaacctcg   1440
tgaggtttta gtcccttgac tttttggtta ttatgtgttt taactttcat gtgatttgtg    1500
ttgatttttc actctgtcaa atccgtgtac tgtgataaaa gctctgttag tacaaagggt    1560
tgctcagatt tgtgacttgt gtgtgacttg tgataggttc tgcaccttgc atgccctcag    1620
gatagttatt tactgcaatt tgtatttttc tgtggtatta atgtttgcat gtcagacaca    1680
tactctataa atttgttctt agaaatccta tttgctgtaa ttatcatttt acataaatgg    1740
gttataacca atactgtaga gagttgatgt tttttcaagt aaatagaacc aactaaatgt    1800
taaacaagtt ttgtaacttg gttcaaaaaa aggaagaaca tctccaagtc caaattgaat    1860
gaattgatgt gcattaattg tctctctgga gatccagtag ttgacaaatt gtgtgatttg    1920
acaattttca ttcagttata attcgcggcc ctttgtcatt tcaagttcat ttctctcaaa    1980
ttttgatgaa cttaaaatct tagtatttag aaatgttttt gtcatgaatc caaaatgcat    2040
ttacccttga ttgtccttgt ttacttttga tctgcaagac acctgcatga ccctgaagct    2100
```

```
tagcactccg taaatggtca agttgaaaaa aaaatggatt ttagtaatag gagcagccat   2160

aactcttatg actcgtgtta gcaacgaggt gtcacgtaca tggggcctag tttgcagatt   2220

gatgtttttt ttggattcct atttgggttt gcggtgaagt gagaaagatt tggccgtctc   2280

tttctttgta tttttttagt gcatgagccc actgagtcag aacttgtccc attaaatgcc   2340

agttactttt ttatagtagc aaaatttgtc tttagttcca cactgagctg tagtaggaga   2400

ttgtgggagg aaaaaaatga gctgtttctt ctcacttatt ttgctgtcag cggttagcat   2460

gcaacttctg gtgtagaaac ttttcatacc aagtcagcat tttttgtatt tatatatgac   2520

tgctattttt ttctttttat aatttctata agcttctatc ttcattaaaa ttttgttgtg   2580

ttttaataac aggagcacca gggaaagcac cccttgtagt tttataaggg actcaaatgc   2640

cattcatacc cctggttcaa ccacaaggcc aaggactcgc caaataatcc atgagcacat   2700

ccaaagaaac attccaacgg cttatgagat ggaggagttc tttgcttatg ccgagaagca   2760

gcaacaaaca atatttatgg acaagtgtgt atactcttat attccacaag tccttttttt   2820

tgtttctaac atatgggtat ttgtatttag atttcttcct catttattaa tgtaattatg   2880

taacgtgctt atgtctaaac tgtctgtatt atgcaggtac aatttcgaca ttgtcaatga   2940

agtacctctg cctggacggt acgagtgggt cccagtactc cactaggagt gtcatatggt   3000

gataatatgg gatttcaaga gccattagac ttgtatttta attttaacaa ctagaagaag   3060

ctttgactaa ccatttagat tgcttgaggc tcttgtttaa caagctacaa gggaaaggat   3120

ctgtttagaa atttccaata tccgattagt agtttagtag tgtctttctg atctgtaggg   3180

tgtagggggg gtatatggta tatctagttt ctaagtcatc tttaatgtaa tttcattacc   3240

ttctgtttat ataattcagc ggggattaga catgatgttc ttgtagagag              3290
```

```
<210> SEQ ID NO 114
<211> LENGTH: 618
<212> TYPE: DNA
<213> ORGANISM: Glycine sp.

<400> SEQUENCE: 114

atggggaagt acatgaagaa gtccaaaatc gccggtgacg tcgccgccgt gatcatggag     60

gctccgccgc cgcactccca cctcggcgtc cgcacccgcg ccaagactct cgccctccag    120

aatacctccc cggactcctc cgcctacctc cagctccgca gccgccgcct cctcaagctc    180

ccccctaccc cgccggaaaa tccccgccgc tccgccgccg aaaccgccgc caattcccgc    240

ctcgccaaaa cgacgtcgtc ccgtaacgcc gaaaagttcg catctttcga tgacgacaac    300

aataccgaat gctctttcgg cgaaaatttc ttagacgccg aacccaggga ggaaaggagc    360

accagggaaa gcaccccttg tagttttata agggactcaa atgccattca tacccctggt    420

tcaaccacaa ggccaaggac tcgccaaata atccatgagc acatccaaag aaacattcca    480

acggcttatg agatggagga gttctttgct tatgccgaga agcagcaaca aacaatattt    540

atggacaagt acaatttcga cattgtcaat gaagtacctc tgcctggacg gtacgagtgg    600

gtcccagtac tccactag                                                  618
```

```
<210> SEQ ID NO 115
<211> LENGTH: 1728
<212> TYPE: DNA
<213> ORGANISM: Glycine sp.

<400> SEQUENCE: 115

aacctcatga ttctcgtttt ctcattcttc ccctcccccc aaccaaccgt gacagcatca     60
```

```
atttccgttt ccgacacccc ctcaaccgtc acttcccgcc acgtgtcact ccctcattcg    120
ccctcctttc ggcgcctgtg atcaccgcta tcaaaaccct caacacctca accttttcga    180
gtttgtaacc tctttgtcac gttttcctcg tcgcacaaac accacactac acttttgaac    240
actgaaaatt gagatcgcag aagaagaata ttaatggaga tggctcaggt taaggcacga    300
gctcgaactg cattggccat ggccgcttcc gcaagttcac ggaagagaag aaaaatctcg    360
atcaacaaca acttcgttca aatcaagagt ttgagcaacg caaccgtgcc ggcgacgggg    420
gaacgaatct ccggggaatc tccggcgtct tgctgctcca gcaacggatc cgtcgacgat    480
gaaaaccgaa tcatcaaatt ctcagatcta gaggtgaatg ttaataataa ataataacaa    540
ttactaatta ttaattgaac tggcgttttg tctctcctta aattgcttct cattaatgtg    600
tagttgtgat gtaacgcatt ttttttcagg ttgagagcac gcgagttgta acgtcgacgt    660
gcgactgcgg tgaacaacaa caacaaataa ggtctcgaat tttaaattaa attttaatta    720
atttgaagtt caaaaaaagg gaaaaggaaa aggccaaaaa aaagaaaaga aaagaaaaga    780
aagtgcttac aatcgtttca aatctttaat ggttcggttt tgtttgaatt caaaacaatt    840
aaaaaggtgt gattgagtga gtttatcgta tggtatgtgt aagtcatcat catgattatt    900
gttccttctg ttaaaaaaaa aaactaattc tgtaactctc tgacatgcat gtatatcaat    960
tatgcgcata tatatatcat atgcatcatc ataaatatct ctgcattatt attacacatt   1020
ctgaaaatta accagaaaaa aacattgtgt tgttgtgttc tttcaggaga gagatgagtc   1080
tcacgagcga gcttcgaatc acgaattctt cttcgcaaga ggtggattca gcggaggagc   1140
agatcaccca aaccaaatct ttgccgccgc agaaaatgcc gacggagttg gagctcgatg   1200
aattcttcgc cgctgctgag aaagatattc ggaaacgctt ctcagacaag taatataata   1260
gtagtagtaa taacaaattt ccatttcaaa aaatgggaaa ttaaaactga aaaatggagt   1320
atatgatatt gttgattaat aaatctgcag gtataattat gatattgtga aggacgtgtc   1380
attggaagga cgatacgagt gggttaaatt gaagccataa aagtgagagt accaaccttg   1440
aaggaaggaa ggaacaatag aagaacacgg ttaataaaaa aatgccactt gctgacatta   1500
ttcttacgtt aatttacttt aggtacttga tttttcactt caattttccg tctttcacag   1560
tagtactacg ctttgtttgg tgtacagtta aatattattt ttcttctatg gttatttgtg   1620
tacggtttat gatatagtta tacggagaag ctagttctgt gaattccgtt gagggaggtg   1680
actagcgaaa acggttccta caaggctgta acaaaattgt agtctcat                1728
```

<210> SEQ ID NO 116
<211> LENGTH: 489
<212> TYPE: DNA
<213> ORGANISM: Glycine sp.

<400> SEQUENCE: 116

```
atggagatgg ctcaggttaa ggcacgagct cgaactgcat tggccatggc cgcttccgca     60
agttcacgga agagaagaaa aatctcgatc aacaacaact tcgttcaaat caagagtttg    120
agcaacgcaa ccgtgccggc gacgggggaa cgaatctccg gggaatctcc ggcgtcttgc    180
tgctccagca acggatccgt cgacgatgaa aaccgaatca tcaaattctc agatctagag    240
gttgagagca cgcgagttgt aacgtcgacg tgcgactgcg gtgaacaaca acaacaaata    300
aggagagaga tgagtctcac gagcgagctt cgaatcacga attcttcttc gcaagaggtg    360
gattcagcgg aggagcagat cacccaaacc aaatctttgc cgccgcagaa aatgccgacg    420
```

gagttggagc tcgatgaatt cttcgccgct gctgagaaag atattcggaa acgcttctca 480
gacaagtaa 489

<210> SEQ ID NO 117
<211> LENGTH: 1466
<212> TYPE: DNA
<213> ORGANISM: Glycine sp.

<400> SEQUENCE: 117
gattcttcct tcctaacctc atgattctcg tttactcatt cccctcccaa ctaaccgtga 60
cagcatcctt ttgcgttttc aacaccctct caaccgtcac ctcccgccac gtgtcactcc 120
ctcattcgcc ctcctccggc gcctgtgatc accgcttccc accgctatca aaaccccccaa 180 cacctcaacc tttcttcttt ttttttttc cttcttctct tcgtcacgat ttctatcctc 240
gtcgcacttt cgaacactga aaattgagat tgcagaagaa tatcaatgga gatggctcag 300
gttaaggcac gagctcgaac tgcattggcc atggcagctt ccgcaacttc accgaagaga 360
agaaaaatct ccttcgttca aatcaagagt ttgagcaacg ctacctctcc gacgacggag 420
gaacgaatct ccggcgaatc tccggcttcg tgctgctcca gcaacggatc cttcgacaac 480
gaaaaccgaa tcatcaaatc ctcagatcta gaggtgaata ttatcaataa attataaatt 540
ataatgataa ttactaatta ttatatatca atgaattagt ttgattgaac ttgcgttttg 600
tctctcctta aattgcttct cattaatgtg ttgtaataat gtaacttaat tttttcaggt 660
tgagagtgcg caagttgaaa catggacgtg caactgcggt gaacaacaac aacaaaaaat 720
aaggtctcga attttagatt caaaaaagga aaacaacaaa ataaaatagt gattgcaata 780
gtttcaaatc ttgaatgatt cggtttcgtt tgaattcaaa acgattaaaa aggtgtgagt 840
gagtgagtgt atcgtatcgt atgtgcaagt catcatcatg attattgttc cttcctttca 900
aaaaaactaa ttctgtaact ctctgacatg catgtatcaa ttatgctcat gtatatgtat 960
atatatgcat catcatacat atgtgcatta ttattacaca ttctgaaaat taaccgaaaa 1020
aaattgtgtc gttgcaggag agagatgagt ctcacgcgcg aggtggattc aacggaggag 1080
catatcacca aaaccaaatc tcgctgcgtt ccaacggagt cggagctcga agatttcttc 1140
gctgctgcgg agaaagacat tcagaaacgc ttcacagaca agtaagataa caattcattg 1200
ccatttttaa aatgtgaaat taaaactgaa ttaaaaatat ggtatatata tatatatata 1260
tatatatatt tattgatgtg tttggaattt tgcatattat atttattttt gttcattaat 1320
ctgcaggtat aattatgatt ttgtgaagga catgcctttg gagggacaat acgagtgggt 1380
taaattgaag tcataaaagt gaaagtacca accttgaaag aagaagaaga agaagaccgt 1440
taattaaaaa atcatgccac ttgctg 1466

<210> SEQ ID NO 118
<211> LENGTH: 366
<212> TYPE: DNA
<213> ORGANISM: Glycine sp.

<400> SEQUENCE: 118
atggctcagg ttaaggcacg agctcgaact gcattggcca tggcagcttc cgcaacttca 60
ccgaagagaa gaaaaatctc cttcgttcaa atcaagagtt tgagcaacgc tacctctccg 120
acgacggagg aacgaatctc cggcgaatct ccggcttcgt gctgctccag caacggatcc 180
ttcgacaacg aaaaccgaat catcaaatcc tcagatctag aggagagaga tgagtctcac 240
gcgcgaggtg gattcaacgg aggagcatat caccaaaacc aaatctcgct gcgttccaac 300

```
ggagtcggag ctcgaagatt tcttcgctgc tgcggagaaa gacattcaga aacgcttcac    360

agacaa                                                               366
```

<210> SEQ ID NO 119
<211> LENGTH: 1648
<212> TYPE: DNA
<213> ORGANISM: Glycine sp.

<400> SEQUENCE: 119

```
actttcatca gcaaaaacca aaacctgaaa aaggaagagt gtgtggaaat tggcatcgct     60

cgcaagagca acaactagta gtacctaaag agacagagag tgtgcacatc tatgtcatct    120

caggtcggtg tcaggacacg agcccgagcc gcattagcca tggaagctgc tactgccagt    180

tcagctcaac cctcttcgaa gagaaagaag atctacgaca ctaaccatgt ggcaaaactc    240

tccaaaactc cgagaacaag ttcttcctcc ttcttcatac ctgcgacggt gacggagatt    300

gttcaggaac gctgcctcag ccctacctcc agtgaaattc cggcttcttg ctgctccagc    360

aacggatcca ttggcctcga tgaggatagg atcaagctct tagatctgga ggtaatcgat    420

actattaaac actcgctttg ttgctacgat ttattgctgt gttgtagatt ttgtaattga    480

acactcgttt ttaatttgtt gctgtccttg attaatttac cgctttagtt tgtagagcct    540

ttcgctcatt catttttcc ttcacctaaa ttaatgcacc ggattcgacg ttccttttat    600

ttacaggtgg agagcgcgca agttgaaacg tcgacgtgca atggtggtca agaaattgag    660

aggttttgaa tgaaactgat ttatttaatt taaatttgaa attgcttcaa gtcactttta    720

atttcctggt agaattctat tttcaaaatt ttgaataatt caggtccatt gagttcgaaa    780

cgcacgagat actcaacagt cataatttct tccgttcaaa actccaactc agtttttctc    840

gcgcgtgtgt gtgtatatat tcattcgtgc cactgcacat tctgtctaca attctgaacc    900

ataataattt tttggtgtcg gccgttgcag gagagagatg aaaagttcca gcgagcttcg    960

agagaattca caggagccgg agccaatgga gatcaattct caccgtgcct tatcaaaggc   1020

aaaagccatg cctaccgagt tggagctcga ggaattcttc gttgctgcgg agaaggacat   1080

tcagaaacga tttcaagaca agtaagttaa aatcagtgga attaattaat tttcttctct   1140

ctctctctct ctctccactg tttcttcttt ttcttttaaa atttttgaca tcataattag   1200

tatatcatat agctccatcc atcattcctt tcaattaaaa aattattttg caggtacaat   1260

tatgatattg ttaaggacgt accactggaa ggacgctacg agtgggttca gttgaagcca   1320

tgaacgtgtg cgtctcgcca ccgaagaaga aaaactccga tcaatttgaa catgtcattt   1380

tggtctattt atatattgtt aattaagtct agtctaggtc tttgatttca atcttaatta   1440

tctttttaat tttacaccag ccaagactct tttatattct ggttgcagct ttttttatat   1500

ttcggtgtga ttataggtta agggtaaaca ggaattcagc ttcgtttgtt ctctgtacgg   1560

agaagcagct taaagctagc ttgtgcagaa aaatactgta aatttccctt ggtgaagaag   1620

aacaaacgct tccattttac agacttca                                      1648
```

<210> SEQ ID NO 120
<211> LENGTH: 597
<212> TYPE: DNA
<213> ORGANISM: Glycine sp.

<400> SEQUENCE: 120

```
atgtcatctc aggtcggtgt caggacacga gcccgagccg cattagccat ggaagctgct     60
```

```
actgccagtt cagctcaacc ctcttcgaag agaaagaaga tctacgacac taaccatgtg    120

gcaaaactct ccaaaactcc gagaacaagt tcttcctcct tcttcatacc tgcgacggtg    180

acggagattg ttcaggaacg ctgcctcagc cctacctcca gtgaaattcc ggcttcttgc    240

tgctccagca acggatccat tggcctcgat gaggatagga tcaagctctt agatctggag    300

gtggagagcg cgcaagttga aacgtcgacg tgcaatggtg gtcaagaaat tgagaggaga    360

gagatgaaaa gttccagcga gcttcgagag aattcacagg agccggagcc aatggagatc    420

aattctcacc gtgccttatc aaaggcaaaa gccatgccta ccgagttgga gctcgaggaa    480

ttcttcgttg ctgcggagaa ggacattcag aaacgatttc aagacaagta caattatgat    540

attgttaagg acgtaccact ggaaggacgc tacgagtggg ttcagttgaa gccatga       597


<210> SEQ ID NO 121
<211> LENGTH: 1724
<212> TYPE: DNA
<213> ORGANISM: Glycine sp.

<400> SEQUENCE: 121

tgaacccctt tcgtcattat cacaattttc gtcttctccg tactacacgc gcgcaccaac     60

ttacgctcac gccactcctc ccttctttcc tttcttcacc cctagtttct ctctcttaca    120

ttagcaaaaa ccaaaacccg aaaaaacgca cagcacagca tcgagcacag caacacctga    180

aaaaggaagg gttagtgagt gtgtgtgtgg aaattgtcat cgctcgcaag agcaacaaca    240

actagtactt aaagagacag agagtgtgca catcaatgtc tgctcaggtc ggtgtcagga    300

cacgagccca agccgcatta gccatggaag ctgttagttc tgctgaacca tcatccaaga    360

gaaagaagat cagcaacagt actaaccaag agccaaaact ctccaagact ccgagaacga    420

gttcttcctc cgctgtcaaa ccagcgacgg tgacggagat ggttcagccg gtgtcgccgg    480

agatggttca gcaacgctgc ctgagcccta cctccagtga aattccggcg tcttgctgct    540

ccagcaacgg atccattggc ctcgatcagg acaggatcaa gctcttagat ctggaggtaa    600

tggatattga gcactcgctt tgttactagg ctttactgct cttgtagatt ttctaattga    660

acactcgttt taattaattt accgctttag tgaagagcct ttcgctcatt catttttttcc   720

ttcacctaaa ttaatgcacc gcattcattc aacgttcctt ttatttaaca ggtggagagc    780

gcgcaagttg aaacgtcgac gtgcaatggt ggtcatgaaa ttgagaggtg tttgaatgaa    840

actgatttat ttatttattt atttaatttt gaaattactc caggtcagtt ttaatttcat    900

ggtggaattc tcatttcaaa attttcgaaa cgcacgaaat aaattaaatt atagtatgtc    960

tcaacagtca taatttcttc cgttcaaaac tccaactcgt atgtgtatat atattcgtgc   1020

actgcacaca ttctacctac agttctgaat cataataatt ttttgtatct gccattgcag   1080

gagagagatg aaacgttcca gcgagcttcg cgagaattct caggagccgg agccaatgga   1140

gatcaattct caccgtgtct tatcaaaggc aaaagccatg cctaccgaat tggagctcga   1200

ggaattcttc gctgcctcgg agaaagacat tcagaaacga tttcaagaca ggtaagttaa   1260

aatcagtgga attaatttc ttctttctct ctctttactg tttcttctta atttttcttt    1320

ttttttttat aatttttttgg catcataatt agtgtatcat tcctttcaat taaaaaattc   1380

ttttgcagat acaattatga tattgttaag gacgtaccgc tggaaggacg ctacgagtgg   1440

gttcagttga agccttgaac gtgtgcgtcc cagttcgtat cgccatcgaa gaagaaaagc   1500

tccgatcaaa ttgaacatgt cattttggcc tatttatata ttgttaatta agtctagtct   1560

aggtctttga tttcaatcta aattatcttt ttaatttaca ccagccaaga ctcttttatg   1620
```

atctggtgta cagctttttt atatttattt cggtgtggtt agttattggt taagggtaaa 1680
caggaatgaa ttcagcttcg tttgttctct gtacggagag cagc 1724

<210> SEQ ID NO 122
<211> LENGTH: 618
<212> TYPE: DNA
<213> ORGANISM: Glycine sp.

<400> SEQUENCE: 122
atgtctgctc aggtcggtgt caggacacga gcccaagccg cattagccat ggaagctgtt 60
agttctgctg aaccatcatc caagagaaag aagatcagca acagtactaa ccaagagcca 120
aaactctcca agactccgag aacgagttct tcctccgctg tcaaaccagc gacggtgacg 180
gagatggttc agccggtgtc gccggagatg gttcagcaac gctgcctgag ccctacctcc 240
agtgaaattc cggcgtcttg ctgctccagc aacggatcca ttggcctcga tcaggacagg 300
atcaagctct tagatctgga ggtggagagc gcgcaagttg aaacgtcgac gtgcaatggt 360
ggtcatgaaa ttgagaggag agagatgaaa cgttccagcg agcttcgcga gaattctcag 420
gagccggagc caatggagat caattctcac cgtgtcttat caaaggcaaa agccatgcct 480
accgaattgg agctcgagga attcttcgct gcctcggaga aagacattca gaaacgattt 540
caagacagat acaattatga tattgttaag gacgtaccgc tggaaggacg ctacgagtgg 600
gttcagttga agccttga 618

<210> SEQ ID NO 123
<211> LENGTH: 2714
<212> TYPE: DNA
<213> ORGANISM: Glycine sp.

<400> SEQUENCE: 123
tttcctttct ctctcactcg aaacaaaaca aaacaacaca accggaaaac caaaccacct 60
ctccctgctc ccgccgctgt tttccgccgc tgtcgccgtc gttcccgcct caccgtggcg 120
gcgcgcgcgt ctccgatggg aaagtacatg aagaaagcga agccgaaagg agaactcgcg 180
ctcgtcgaat ccaccaccag caacaccacc acctcctaca tgggggtccg aacccgcgcc 240
aaaaccctag cgcttcagaa atcgcacgcg cagcagcacg agctcgccgc cacctccgac 300
tcctacctcc agctccggag ccgtcgcctc cagaagcctc cgattttggt ccactctccg 360
aagcgcccta agcacccgaa ccctaaatcc ccaatccccg aacctcccag gctcggactc 420
gcttcggagc gcgacgctac cctcaaccac aacaaggaca atactttgca tgagaatgcc 480
gagcctcagg aagcgtcgtt cggggaaaat gttttggatt ttgaaggtag agagaggtga 540 gtttcgttt tcccctttc aaatttaatc ccaattcgtt ttgatttttg cactcataaa 600
gctgcttacg gattttctca tttaaattat tattattatt atttttgtga tgaaaaaaaa 660
aattaaatta gtgaatgccc tattttttgg ggggtattat gatttcgtct tgggtggaag 720
acgactgtgg ggcaaagtac taaaacgtgg atttgaaatt gattttttc tttttctctc 780 tggttttatg gtgttttgtt cggttgagtt aaccgtgttt tgaagatcaa agtgtttttg 840
aagcaattgt aaaacttcat ggccttattt gctgcaatgt aattcggttt ctttcctgaa 900
tatcagtcag aactcagaaa gatgattgag tgtggggatt tttgttttct tctttaacgg 960
ttcagtgttg tgttcctatt cttgtggtaa gaggttgatt tgctgcacag cttttcttct 1020
cttcggacat tttgtgctct tttttttttt ttttggatga tcttttcagt tatgcatgca 1080

```
attcttgtga aatttttgag ctagattttt tctgtgaaag tattttcttc attgtcttct   1140
atcatatttt ccccccaatt caaggattca ctgaagaaag atgttttgtt ttctcttcct   1200
accaaaactt ttagtatatg tttccaatat cgaaagtcgt gtgaccattt tctttggaca   1260
tgttcacctg atatcctaaa aatgcttcct attgatctga agatgttaat tagaaaataa   1320
tctacgaaat ctattcaagg ggaatacttc attttttta tatcctgccg ttggagtact   1380
ttgttggcag aaaatgttga tatttgataa ttcgtcagaa agttcgcctc tttttcctca   1440
atttgacgtt tttatttatt gttttagcga ttgaaatatt tcactaattt ctctggtcgt   1500
gtgctattag atttgtatat aataatgata ataatagtaa taattaatat taaccataat   1560
aatgtagtgt agagcggaaa aaataatcaa ttttttttt caactgagag aatgatgtga   1620
tctgtataaa ccatcaaaag aagagatatc ccttattaag caatctccca tttcctgcaa   1680
acttcttttt tctggcggaa acgaggttag aacttgaatc gttaaatatt ctcatatctg   1740
aatcgacata tgcacagtga ttttgaaacc ttgttctttg gctttaaatg tggtgctggt   1800
cagccttgat tttacgagca ttatcatttt tgccgttttg agactagctc ttacctctta   1860
cctaaaatat tgttttgcct tttgccacta atatgctttc attttttgtg tgtgtttcta   1920
ttctactact ttacggttaa attgttaaat tgatatattt attattcgct gcagaagcac   1980
tagggaatcc acaccttgca gtttgataag ggactcggat actgtcagga ctccgggttc   2040
aactaccagg cctacttgtt cagctgaagc ttatcgaaga acagagcatg cagctagaag   2100
gcaaatccca acctcccgtg aaatggatga attctttgct gaaattgaag aggctcagca   2160
aaaaaaattc attgagaagt atgctttatt gctttgaatt tatttagttc tttcttgcta   2220
aactgcaacg tctgttgcat ccccacaaac tagttaatca cttgagttca attgcaggta   2280
caactttgat cctgtgaatg agaagccgct ctcagggcgc tatgaatggg aaaagttgaa   2340
accctagaag ggtaatgtag tgttccatca agacatcttt gaagtagcag gcaggcagca   2400
gggttagaat ttgttgaagc ggtggtggcg ttatttcact tttccatcac cttctattta   2460
cttgtaaaga aagtaggact cttaaaactg tgtagactaa tggtctgtaa ctttacagag   2520
gttgttgatt acacaacaat acaaatcaaa ggcctttgtc taacagatca ttttaaggaa   2580
gggggcaagg gaagaagggg ctgtagcgcg taggattagg gatcagtcaa attaggtcag   2640
tatgaggtac aggaatttac ctaggttttc tcttgttctt gtattttact catcttttgt   2700
ctatacttgt actg                                                     2714
```

```
<210> SEQ ID NO 124
<211> LENGTH: 675
<212> TYPE: DNA
<213> ORGANISM: Glycine sp.

<400> SEQUENCE: 124
```

```
atgggaaagt acatgaagaa agcgaagccg aaaggagaac tcgcgctcgt cgaatccacc     60
accagcaaca ccaccacctc ctacatgggg gtccgaaccc gcgccaaaac cctagcgctt    120
cagaaatcgc acgcgcagca gcacgagctc gccgccacct ccgactccta cctccagctc    180
cggagccgtc gcctccagaa gcctccgatt ttggtccact ctccgaagcg ccctaagcac    240
ccgaacccta aatccccaat ccccgaacct cccaggctcg gactcgcttc ggagcgcgac    300
gctaccctca accacaacaa ggacaatact ttgcatgaga atgccgagcc tcaggaagcg    360
tcgttcgggg aaaatgtttt ggattttgaa ggtagagaga gaagcactag ggaatccaca    420
ccttgcagtt tgataaggga ctcggatact gtcaggactc cgggttcaac taccaggcct    480
```

```
acttgttcag ctgaagctta tcgaagaaca gagcatgcag ctagaaggca aatcccaacc    540
tcccgtgaaa tggatgaatt ctttgctgaa attgaagagg ctcagcaaaa aaaattcatt    600
gagaagtaca actttgatcc tgtgaatgag aagccgctct cagggcgcta tgaatgggaa    660
aagttgaaac cctag                                                     675
```

<210> SEQ ID NO 125
<211> LENGTH: 1775
<212> TYPE: DNA
<213> ORGANISM: Glycine sp.

<400> SEQUENCE: 125

```
agaagagaag agaagaggct aaaagggtag caatgatcgt aacgatgtcg tttagtggcc     60
actgtagctg gagaaggacg aaggggaggg agacaagagg gacccacctt ctgattaata    120
aattaaatct gaaccgtcca aggatcgatt cactgcgctc agtaaatatt ctctgcgatc    180
accctctttt taagctccct ctacctctct ccctaagcct accccatctc aaaatagaaa    240
aaagaaactc tcccacaata caaacacaga cacagagaaa gaaaagaata atgggtgagt    300
gtaaacgctg ctgctctctc acagttctgg ccatggaaga accttcttca agccaacatt    360
ccattttcaa aaaaagaaaa accaccgcta ctgctgctca ttccacttcc ttccagttat    420
gctcttccga tatgcagttt ccccacacta tcgtctcgcc ggaagtttca tttagttccg    480
cctgcacggt tgtttccggc gagttttgct ccgatcgctc ctgctgcagc tccagccacg    540
ttaaggacct ccactccgtg ccgtcagatc tgcaggttcg gtcctcgaaa ttctgaatta    600
ttattattat ttttattttt attgcgaact gtttttactt tcttaatttt ccgagttacc    660
tttccaaatt ttcctgtgtt taattaacct atttaatttc tatatttatt gatattcttc    720
gccgattaat gcagaccaag ggtttcgaaa cggtagaaga ctcaaccagc ctcaatttca    780
aatcgttcag gtttttgttc tacttttttt tttttttgt tctacttgtt tctcatgtac    840
gcacgatcaa attttcaaac gaaacgttgt cgcaactgaa acgctacatt tatttattta    900
tttatttgtt tcggttttgg ttgttcagtt tgttgagtga gttttccgga gactcggagg    960
aatcggcgat gattccggcg aagtcttccg cggcggtgct gaaagtgaag acgccgccga   1020
aggcggagat cgaagagttt ttcgcgatgg ctgaaaagta cgagcaaaaa cggttcacag   1080
agaagtaagt agtagtatat atagttgatt gctacaaata aaagttttaa tattgcaaat   1140
tactggtgca gtctcaatta cagtcacaag ccttgatgat acgacctaaa ccagggtcgc   1200
gaaccctttt ttaaaacctt ctatggtcta agagtatttt attttatttt ttcatttcgc   1260
gcgacacagg ataaggaatg tgagccacct cgcactctag cggtaccaga aatcgaaccc   1320
taactaacta actaacaact ttcccttggg tgcaggtaca actttgatat tgttagagat   1380
ttgccgttgg agggtcgcta ccagtgggtt cgtttacatt gaatgccttc aatgagagag   1440
agagagatag agtttgcatt tttagtttta gaaagagaaa tggaggttga tgagagggtg   1500
agtttgtagt gtatgtttag ccattggagt acactggtga ggaagctaac ctgacacgag   1560
gtaaaacgaa aacgagcatg caacttttgt tggttgctct gaaaagacgg tgctagtggt   1620
agtggtgatg ggttggttta tgtatagcta actgttttct ctttcttttt atgtgggata   1680
caacaaggtg gcttttctgc aaactctgca ctcagaatag aactagtaga accttctttg   1740
tgaggtgatg aagaaaaaga aagaaaagga aaaag                              1775
```

<210> SEQ ID NO 126

<211> LENGTH: 564
<212> TYPE: DNA
<213> ORGANISM: Glycine sp.

<400> SEQUENCE: 126

```
atgggtgagt gtaaacgctg ctgctctctc acagttctgg ccatggaaga accttcttca     60

agccaacatt ccattttcaa aaaaagaaaa accaccgcta ctgctgctca ttccacttcc    120

ttccagttat gctcttccga tatgcagttt ccccacacta tcgtctcgcc ggaagtttca    180

tttagttccg cctgcacggt tgtttccggc gagttttgct ccgatcgctc ctgctgcagc    240

tccagccacg ttaaggacct ccactccgtg ccgtcagatc tgcagaccaa gggtttcgaa    300

acggtagaag actcaaccag cctcaatttc aaatcgttca gtttgttgag tgagttttcc    360

ggagactcgg aggaatcggc gatgattccg gcgaagtctt ccgcggcggt gctgaaagtg    420

aagacgccgc cgaaggcgga gatcgaagag tttttcgcga tggctgaaaa gtacgagcaa    480

aaacggttca cagagaagta caactttgat attgttagag atttgccgtt ggagggtcgc    540

taccagtggg ttcgtttaca ttga                                           564
```

<210> SEQ ID NO 127
<211> LENGTH: 2149
<212> TYPE: DNA
<213> ORGANISM: Glycine sp.

<400> SEQUENCE: 127

```
tttcatcgtg tcgatatttg ccctagcttg gccccaccgg tgacggaaaa aaaaaccttt     60

aattctataa tttcaatatg tgagtgattg atttatttgt aaaaaataat tcaacgagca    120

aacttatttg taaaaaaaag aaaagaaggt atttttattt actgatttca aattattctg    180

taattttggt cataaaaatc taaaactgaa cataagttta ttattattta gaagagagaa    240

gaagaggcta aaagggagag tagcagtagc aatgatcgta acgatgtcgt ttagcgggta    300

ctgtagctgg agaaagacaa gagggaccat ccacgaatcg attcactgcg ctcagtaaat    360

attcctctgc gatcactctc tttttaagct ccctccacct ctctccctaa gcctagccca    420

tctcaaaata gaaacacaac acaacacaac acagagaatg ggtgagtgta aacgctgctc    480

tctcacaatt gccgccatag aacaaccttc ttcaagccaa cattccattt ccaagaaaag    540

aaaaaccacc gcttccttcc agttacgctc ttccgatacg cagtttcccg acactatcgt    600

ctcgccggaa gcttccgtca gttctaccgg cacggttgtt tccggcgatt tttgctccga    660

tcgctcttgc tgcagctcca gccactttaa ggacctccac tccgtgccgt cagatctgca    720

ggttcgctcc tcgaaattct gaattattat tatgaattgt taatttactt tcgtaatttt    780

ccgagttata acctgtccaa attttcctgt gtttaatttc tttatatcta tttatttatt    840

gatattcctc gccgattaat gcagaccaag ggtttccaaa cggtagagga ctcaaccaac    900

cgctacttca agccgttcag gtttttattc tacttatttt ttgttcgagt tctttctcat    960

gtacgcgcac acgatcaatc ttctaacgaa acgttgccac cgaaacactg cgtatacata   1020

catttatttt attttatttt atttatttat ttgcttcggt tttggttgtt cagtttgttg   1080

agtgagtttt ctggagactc ggaggaatcg gcgaagtctt ccgcggcagt gcggaaattg   1140

aagacgccac cacaagcaga gatcgaagag tttttcgcga tggcggaaaa gtacgagcga   1200

aaacggttca cagagaagta agtagtgtag tgtatatagt tgatggcaac attaagctaa   1260

gagtgtttta ttttaatttt ttatttcgcg cgacacagaa taaggaatgt gagccagctc   1320

acactcaagc ggtgccagaa atcgaaccct aactgactaa caactttccc ttgcgtgcag   1380
```

```
gtacaacttt gatattgtta gagatttgcc gttggagggt cgctaccagt gggttcgttt   1440

acattgaatg ccttcaatga aagagagaga gagagagaga gagtttgcat tttttagttt   1500

tagagagaga aatggaggtt gatgagtttg tagtgtttag tcatttgagt acactggtaa   1560

ggaagctaac ctgacacgag gtaaaacgaa aacgagcgtg caactttttc tggttgcttt   1620

gaaaaagacg gtggtggtgg tgggttggtt tacgtatagc taactgtttt ctctttctct   1680

ttatgttgga tacaacaagc tagctttttc tgcaatctct gcactctgat agaagtagta   1740

gaaccttctt tgtgaggtga tgaagaaaaa caaaaaacaa aattgggttt tgtgggaaat   1800

atacaaagaa cacaagaatt tccgctatga atattggtga tctaaaatat gttaatgtaa   1860

ttgagagttt gagaccgtct ccttcagtgt ttccagaaca ataagggggt tcagctaatt   1920

catgcggctg ttttttttta aaaaataatt attcattatc agaagaattc atggatagaa   1980

gaatattaat tgttatttgg ttactaattt tctatgaaaa gtgtcttttc ttcgaccttc   2040

ccctcttgcc tgcatgtttc cttttcagct ttccgtagct tcattcaatt acctttttttt   2100

atgtctggca ttcttttttc ctttaggcca tttggaatat cctctccat              2149
```

```
<210> SEQ ID NO 128
<211> LENGTH: 531
<212> TYPE: DNA
<213> ORGANISM: Glycine sp.

<400> SEQUENCE: 128

atgggtgagt gtaaacgctg ctctctcaca attgccgcca tagaacaacc ttcttcaagc     60

caacattcca tttccaagaa aagaaaaacc accgcttcct tccagttacg ctcttccgat    120

acgcagtttc ccgacactat cgtctcgccg gaagcttccg tcagttctac cggcacggtt    180

gtttccggcg atttttgctc cgatcgctct tgctgcagct ccagccactt taaggacctc    240

cactccgtgc cgtcagatct gcagaccaag ggtttccaaa cggtagagga ctcaaccaac    300

cgctacttca agccgttcag tttgttgagt gagttttctg gagactcgga ggaatcggcg    360

aagtcttccg cggcagtgcg gaaattgaag acgccaccac aagcagagat cgaagagttt    420

ttcgcgatgg cggaaaagta cgagcgaaaa cggttcacag agaagtacaa ctttgatatt    480

gttagagatt tgccgttgga gggtcgctac cagtgggttc gtttacattg a             531
```

```
<210> SEQ ID NO 129
<211> LENGTH: 201
<212> TYPE: PRT
<213> ORGANISM: Glycine sp.

<400> SEQUENCE: 129

Met Gly Lys Tyr Met Lys Lys Ser Lys Ile Ala Gly Asp Val Ala Ala
1               5                   10                  15

Val Ile Met Glu Ala Pro Pro Pro His Ser His Leu Gly Val Arg Thr
            20                  25                  30

Arg Ala Lys Thr Leu Ala Leu Gln Asn Asn Thr Thr Ser Pro Asp Pro
        35                  40                  45

Ser Ala Tyr Leu Gln Leu Arg Ser Arg Arg Leu Leu Lys Leu Pro Pro
    50                  55                  60

Thr Pro Pro Glu Asn Pro Arg Arg Ser Ser Ala Glu Thr Ala Ala Asn
65                  70                  75                  80

Phe Arg Leu Ala Asn Ala Gln Lys Leu Ala Ser Phe Glu Asp Asp Asn
                85                  90                  95
```

```
Asn Thr Glu Cys Ser Phe Gly Glu Asn Phe Leu Asp Ala Glu Pro Arg
            100                 105                 110

Glu Glu Arg Ser Thr Arg Glu Gly Thr Pro Cys Ser Leu Ile Arg Asp
        115                 120                 125

Ser Asn Ala Ile His Thr Pro Gly Ser Thr Thr Arg Pro Arg Thr Arg
    130                 135                 140

Gln Ile Ile His Glu His Val Gln Arg Asn Ile Pro Thr Ala Tyr Glu
145                 150                 155                 160

Met Glu Glu Phe Phe Ala Tyr Ala Glu Lys Gln Gln Gln Thr Ile Phe
                165                 170                 175

Met Asp Lys Tyr Asn Phe Asp Ile Val Asn Asp Val Pro Leu Pro Gly
            180                 185                 190

Arg Tyr Glu Trp Val Pro Val Leu His
        195                 200


<210> SEQ ID NO 130
<211> LENGTH: 205
<212> TYPE: PRT
<213> ORGANISM: Glycine sp.

<400> SEQUENCE: 130

Met Gly Lys Tyr Met Lys Lys Ser Lys Ile Ala Gly Asp Val Ala Ala
1               5                   10                  15

Val Ile Met Glu Ala Pro Pro Pro His Ser His Leu Gly Val Arg Thr
            20                  25                  30

Arg Ala Lys Thr Leu Ala Leu Gln Asn Thr Ser Pro Asp Ser Ser Ala
        35                  40                  45

Tyr Leu Gln Leu Arg Ser Arg Arg Leu Leu Lys Leu Pro Pro Thr Pro
    50                  55                  60

Pro Glu Asn Pro Arg Arg Ser Ala Ala Glu Thr Ala Ala Asn Ser Arg
65                  70                  75                  80

Leu Ala Lys Thr Thr Ser Ser Arg Asn Ala Glu Lys Phe Ala Ser Phe
                85                  90                  95

Asp Asp Asp Asn Asn Thr Glu Cys Ser Phe Gly Glu Asn Phe Leu Asp
            100                 105                 110

Ala Glu Pro Arg Glu Glu Arg Ser Thr Arg Glu Ser Thr Pro Cys Ser
        115                 120                 125

Phe Ile Arg Asp Ser Asn Ala Ile His Thr Pro Gly Ser Thr Thr Arg
    130                 135                 140

Pro Arg Thr Arg Gln Ile Ile His Glu His Ile Gln Arg Asn Ile Pro
145                 150                 155                 160

Thr Ala Tyr Glu Met Glu Glu Phe Phe Ala Tyr Ala Glu Lys Gln Gln
                165                 170                 175

Gln Thr Ile Phe Met Asp Lys Tyr Asn Phe Asp Ile Val Asn Glu Val
            180                 185                 190

Pro Leu Pro Gly Arg Tyr Glu Trp Val Pro Val Leu His
        195                 200                 205


<210> SEQ ID NO 131
<211> LENGTH: 162
<212> TYPE: PRT
<213> ORGANISM: Glycine sp.

<400> SEQUENCE: 131

Met Glu Met Ala Gln Val Lys Ala Arg Ala Arg Thr Ala Leu Ala Met
1               5                   10                  15
```

```
Ala Ala Ser Ala Ser Ser Arg Lys Arg Arg Lys Ile Ser Ile Asn Asn
            20                  25                  30

Asn Phe Val Gln Ile Lys Ser Leu Ser Asn Ala Thr Val Pro Ala Thr
        35                  40                  45

Gly Glu Arg Ile Ser Gly Glu Ser Pro Ala Ser Cys Cys Ser Ser Asn
    50                  55                  60

Gly Ser Val Asp Asp Glu Asn Arg Ile Ile Lys Phe Ser Asp Leu Glu
65                  70                  75                  80

Val Glu Ser Thr Arg Val Val Thr Ser Thr Cys Asp Cys Gly Glu Gln
                85                  90                  95

Gln Gln Gln Ile Arg Arg Glu Met Ser Leu Thr Ser Glu Leu Arg Ile
            100                 105                 110

Thr Asn Ser Ser Ser Gln Glu Val Asp Ser Ala Glu Glu Gln Ile Thr
        115                 120                 125

Gln Thr Lys Ser Leu Pro Pro Gln Lys Met Pro Thr Glu Leu Glu Leu
    130                 135                 140

Asp Glu Phe Phe Ala Ala Ala Glu Lys Asp Ile Arg Lys Arg Phe Ser
145                 150                 155                 160

Asp Lys


<210> SEQ ID NO 132
<211> LENGTH: 144
<212> TYPE: PRT
<213> ORGANISM: Glycine sp.

<400> SEQUENCE: 132

Met Ala Gln Val Lys Ala Arg Ala Arg Thr Ala Leu Ala Met Ala Ala
1               5                   10                  15

Ser Ala Thr Ser Pro Lys Arg Arg Lys Ile Ser Phe Val Gln Ile Lys
            20                  25                  30

Ser Leu Ser Asn Ala Thr Ser Pro Thr Thr Glu Glu Arg Ile Ser Gly
        35                  40                  45

Glu Ser Pro Ala Ser Cys Cys Ser Ser Asn Gly Ser Phe Asp Asn Glu
    50                  55                  60

Asn Arg Ile Ile Lys Ser Ser Asp Leu Glu Val Glu Ser Ala Gln Val
65                  70                  75                  80

Glu Thr Trp Thr Cys Asn Cys Gly Glu Gln Gln Gln Gln Lys Ile Arg
                85                  90                  95

Arg Glu Met Ser Leu Thr Arg Glu Val Asp Ser Thr Glu Glu His Ile
            100                 105                 110

Thr Lys Thr Lys Ser Arg Cys Val Pro Thr Glu Ser Glu Leu Glu Asp
        115                 120                 125

Phe Phe Ala Ala Ala Glu Lys Asp Ile Gln Lys Arg Phe Thr Asp Lys
    130                 135                 140


<210> SEQ ID NO 133
<211> LENGTH: 198
<212> TYPE: PRT
<213> ORGANISM: Glycine sp.

<400> SEQUENCE: 133

Met Ser Ser Gln Val Gly Val Arg Thr Arg Ala Arg Ala Ala Leu Ala
1               5                   10                  15

Met Glu Ala Ala Thr Ala Ser Ser Ala Gln Pro Ser Ser Lys Arg Lys
            20                  25                  30

Lys Ile Tyr Asp Thr Asn His Val Ala Lys Leu Ser Lys Thr Pro Arg
```

```
        35                  40                  45

Thr Ser Ser Ser Ser Phe Phe Ile Pro Ala Thr Val Thr Glu Ile Val
    50                  55                  60

Gln Glu Arg Cys Leu Ser Pro Thr Ser Ser Glu Ile Pro Ala Ser Cys
65                  70                  75                  80

Cys Ser Ser Asn Gly Ser Ile Gly Leu Asp Glu Asp Arg Ile Lys Leu
                85                  90                  95

Leu Asp Leu Glu Val Glu Ser Ala Gln Val Glu Thr Ser Thr Cys Asn
            100                 105                 110

Gly Gly Gln Glu Ile Glu Arg Arg Glu Met Lys Ser Ser Ser Glu Leu
        115                 120                 125

Arg Glu Asn Ser Gln Glu Pro Glu Pro Met Glu Ile Asn Ser His Arg
    130                 135                 140

Ala Leu Ser Lys Ala Lys Ala Met Pro Thr Glu Leu Glu Leu Glu Glu
145                 150                 155                 160

Phe Phe Val Ala Ala Glu Lys Asp Ile Gln Lys Arg Phe Gln Asp Lys
                165                 170                 175

Tyr Asn Tyr Asp Ile Val Lys Asp Val Pro Leu Glu Gly Arg Tyr Glu
            180                 185                 190

Trp Val Gln Leu Lys Pro
        195


<210> SEQ ID NO 134
<211> LENGTH: 205
<212> TYPE: PRT
<213> ORGANISM: Glycine sp.

<400> SEQUENCE: 134

Met Ser Ala Gln Val Gly Val Arg Thr Arg Ala Gln Ala Ala Leu Ala
1               5                   10                  15

Met Glu Ala Val Ser Ser Ala Glu Pro Ser Ser Lys Arg Lys Lys Ile
            20                  25                  30

Ser Asn Ser Thr Asn Gln Glu Pro Lys Leu Ser Lys Thr Pro Arg Thr
        35                  40                  45

Ser Ser Ser Ser Ala Val Lys Pro Ala Thr Val Thr Glu Met Val Gln
    50                  55                  60

Pro Val Ser Pro Glu Met Val Gln Gln Arg Cys Leu Ser Pro Thr Ser
65                  70                  75                  80

Ser Glu Ile Pro Ala Ser Cys Cys Ser Ser Asn Gly Ser Ile Gly Leu
                85                  90                  95

Asp Gln Asp Arg Ile Lys Leu Leu Asp Leu Glu Val Glu Ser Ala Gln
            100                 105                 110

Val Glu Thr Ser Thr Cys Asn Gly Gly His Glu Ile Glu Arg Arg Glu
        115                 120                 125

Met Lys Arg Ser Ser Glu Leu Arg Glu Asn Ser Gln Glu Pro Glu Pro
    130                 135                 140

Met Glu Ile Asn Ser His Arg Val Leu Ser Lys Ala Lys Ala Met Pro
145                 150                 155                 160

Thr Glu Leu Glu Leu Glu Glu Phe Phe Ala Ala Ser Glu Lys Asp Ile
                165                 170                 175

Gln Lys Arg Phe Gln Asp Arg Tyr Asn Tyr Asp Ile Val Lys Asp Val
            180                 185                 190

Pro Leu Glu Gly Arg Tyr Glu Trp Val Gln Leu Lys Pro
        195                 200                 205
```

<210> SEQ ID NO 135
<211> LENGTH: 224
<212> TYPE: PRT
<213> ORGANISM: Glycine sp.

<400> SEQUENCE: 135

```
Met Gly Lys Tyr Met Lys Lys Ala Lys Pro Lys Gly Glu Leu Ala Leu
1               5                   10                  15

Val Glu Ser Thr Thr Ser Asn Thr Thr Thr Ser Tyr Met Gly Val Arg
            20                  25                  30

Thr Arg Ala Lys Thr Leu Ala Leu Gln Lys Ser His Ala Gln Gln His
        35                  40                  45

Glu Leu Ala Ala Thr Ser Asp Ser Tyr Leu Gln Leu Arg Ser Arg Arg
    50                  55                  60

Leu Gln Lys Pro Pro Ile Leu Val His Ser Pro Lys Arg Pro Lys His
65                  70                  75                  80

Pro Asn Pro Lys Ser Pro Ile Pro Glu Pro Pro Arg Leu Gly Leu Ala
                85                  90                  95

Ser Glu Arg Asp Ala Thr Leu Asn His Asn Lys Asp Asn Thr Leu His
            100                 105                 110

Glu Asn Ala Glu Pro Gln Glu Ala Ser Phe Gly Glu Asn Val Leu Asp
        115                 120                 125

Phe Glu Gly Arg Glu Arg Ser Thr Arg Glu Ser Thr Pro Cys Ser Leu
    130                 135                 140

Ile Arg Asp Ser Asp Thr Val Arg Thr Pro Gly Ser Thr Thr Arg Pro
145                 150                 155                 160

Thr Cys Ser Ala Glu Ala Tyr Arg Arg Thr Glu His Ala Ala Arg Arg
                165                 170                 175

Gln Ile Pro Thr Ser Arg Glu Met Asp Glu Phe Phe Ala Glu Ile Glu
            180                 185                 190

Glu Ala Gln Gln Lys Lys Phe Ile Glu Lys Tyr Asn Phe Asp Pro Val
        195                 200                 205

Asn Glu Lys Pro Leu Ser Gly Arg Tyr Glu Trp Glu Lys Leu Lys Pro
    210                 215                 220
```

<210> SEQ ID NO 136
<211> LENGTH: 187
<212> TYPE: PRT
<213> ORGANISM: Glycine sp.

<400> SEQUENCE: 136

```
Met Gly Glu Cys Lys Arg Cys Cys Ser Leu Thr Val Leu Ala Met Glu
1               5                   10                  15

Glu Pro Ser Ser Ser Gln His Ser Ile Phe Lys Lys Arg Lys Thr Thr
            20                  25                  30

Ala Thr Ala Ala His Ser Thr Ser Phe Gln Leu Cys Ser Ser Asp Met
        35                  40                  45

Gln Phe Pro His Thr Ile Val Ser Pro Glu Val Ser Phe Ser Ser Ala
    50                  55                  60

Cys Thr Val Val Ser Gly Glu Phe Cys Ser Asp Arg Ser Cys Cys Ser
65                  70                  75                  80

Ser Ser His Val Lys Asp Leu His Ser Val Pro Ser Asp Leu Gln Thr
                85                  90                  95

Lys Gly Phe Glu Thr Val Glu Asp Ser Thr Ser Leu Asn Phe Lys Ser
            100                 105                 110
```

```
Phe Ser Leu Leu Ser Glu Phe Ser Gly Asp Ser Glu Glu Ser Ala Met
        115                 120                 125

Ile Pro Ala Lys Ser Ser Ala Ala Val Leu Lys Val Lys Thr Pro Pro
    130                 135                 140

Lys Ala Glu Ile Glu Glu Phe Phe Ala Met Ala Glu Lys Tyr Glu Gln
145                 150                 155                 160

Lys Arg Phe Thr Glu Lys Tyr Asn Phe Asp Ile Val Arg Asp Leu Pro
                165                 170                 175

Leu Glu Gly Arg Tyr Gln Trp Val Arg Leu His
            180                 185


<210> SEQ ID NO 137
<211> LENGTH: 176
<212> TYPE: PRT
<213> ORGANISM: Glycine sp.

<400> SEQUENCE: 137

Met Gly Glu Cys Lys Arg Cys Ser Leu Thr Ile Ala Ala Ile Glu Gln
1               5                   10                  15

Pro Ser Ser Ser Gln His Ser Ile Ser Lys Lys Arg Lys Thr Thr Ala
            20                  25                  30

Ser Phe Gln Leu Arg Ser Ser Asp Thr Gln Phe Pro Asp Thr Ile Val
        35                  40                  45

Ser Pro Glu Ala Ser Val Ser Ser Thr Gly Thr Val Val Ser Gly Asp
    50                  55                  60

Phe Cys Ser Asp Arg Ser Cys Cys Ser Ser Ser His Phe Lys Asp Leu
65                  70                  75                  80

His Ser Val Pro Ser Asp Leu Gln Thr Lys Gly Phe Gln Thr Val Glu
                85                  90                  95

Asp Ser Thr Asn Arg Tyr Phe Lys Pro Phe Ser Leu Leu Ser Glu Phe
            100                 105                 110

Ser Gly Asp Ser Glu Glu Ser Ala Lys Ser Ser Ala Ala Val Arg Lys
        115                 120                 125

Leu Lys Thr Pro Pro Gln Ala Glu Ile Glu Glu Phe Phe Ala Met Ala
    130                 135                 140

Glu Lys Tyr Glu Arg Lys Arg Phe Thr Glu Lys Tyr Asn Phe Asp Ile
145                 150                 155                 160

Val Arg Asp Leu Pro Leu Glu Gly Arg Tyr Gln Trp Val Arg Leu His
                165                 170                 175


<210> SEQ ID NO 138
<211> LENGTH: 1678
<212> TYPE: DNA
<213> ORGANISM: Triticum sp.

<400> SEQUENCE: 138

gcagagcata gcaccaccac cggcacagcg cggcgcgtag ggtggaaaaa gtagagagag      60

agaacaggaa gagaaggaag aaagaaaaaa gccgatggcc gccaccgccg cggccaccgt     120

gacggcgacg gcggcggcgt cgagctgcag caagggcgag agcgtcggca ttgcggcgcc     180

cgccgacttg tcagtctcca gctctccctc tccctgcctt ccttccttcc ttctctcctc     240

acgacaaacc attcgaagcc gtgctgctgc gtatggagtt cttctgctca cgccttggct     300

gctgtttgtc gtcgtgcgca ggacgaagaa ggcgaagaag ggcaggtcgc cgccggcgga     360

ggagatggag gccttcttcg ctgcggcgga gggcgacgtc gcgcggcgct tcgctgccaa     420

gtgagtaccg cgcacatgca tgagtcaggc aacagcttcc tcctatcctc ttggggaaaa     480
```

```
gccgccgtgg atttatatgg gagtagctag ctagcaatgc atgcgtagca gtgggcctgt    540

aaattctgct caagtaacat gaggcctctg ctgccgaaga tctcggttgt cagtcagttt    600

ggtgttgcac agaacacacg cacactcaca gtaaaaaaaa cacccgccaa gcatgtgctt    660

tgccctccaa ttctctgtcg ccggttttct ttttctcttg attgaagagg ccagctgctg    720

gtgctagtgt atgaaggaat ttgaacaaaa tcactacacg tatagactgt tttgagcacc    780

ccaaaaaagt agttttgggg atcttggtct ttaaaaaaaa actggaacgg accggaagat    840

ttctcaacag caaaggaaaa aatggttcca acttaatttt tgtatctgtc aaattagctc    900

aagcaattat atttccagaa ataaaaagtg aagttggcag tgcagtacta ctcctgttct    960

tttctaacgt ttggatcttg cgctttggat tgaaggtaca actatgacgt cgtcacagac   1020

gctcccatgg atgggcggta cgagtgggtc cgagtgaggc cgtaggaagg aaggatatgc   1080

cgccgcagcc agtcaagtgt cagaggcccg cacagacaga ccacgttgtg tcctttttaa   1140

tcattctttt gtagttacct tgtcatgctt tattagctgt aattattgct caccagatgc   1200

ctaatcatgc actgtattag ctcaccatgt aagtcgccag tgtattgttc cacctgtagc   1260

tagcttgcct tttaacttgt cgtgatatgt tttgttccat caagaaaaag gaagtgtcgt   1320

tatctgtgta cattgtctcg tagtagtagt agtaggtact ccctccgtcc caaaattctt   1380

gtcttagatt tatctagata cagatgtatc taacactaaa acgtgaatag atacgtccgt   1440

atgtagacaa atctaagaca agaattttga gacggaggga gtagtacttt tgttctggca   1500

ctgcatatct caacacctca tagcatggta agagcaaatc tacggcctac tttcaaagaa   1560

aagtcattca gagccggact agacaaatac gaccctaggc gtctgtagac gcacaggaca   1620

tgtccgggac agtgtgccct caaatgttct actgcacatc acacccttcg tatcaaaa     1678
```

<210> SEQ ID NO 139
<211> LENGTH: 264
<212> TYPE: DNA
<213> ORGANISM: Triticum sp.

<400> SEQUENCE: 139

```
atggccgcca ccgccgcggc caccgtgacg gcgacggcgg cggcgtcgag ctgcagcaag     60

ggcgagagcg tcggcattgc ggcgcccgcc gacttgacga agaaggcgaa gaagggcagg    120

tcgccgccgg cggaggagat ggaggccttc ttcgctgcgg cggagggcga cgtcgcgcgg    180

cgcttcgctg ccaagtacaa ctatgacgtc gtcacagacg ctcccatgga tgggcggtac    240

gagtgggtcc gagtgaggcc gtag                                           264
```

<210> SEQ ID NO 140
<211> LENGTH: 87
<212> TYPE: PRT
<213> ORGANISM: Triticum sp.

<400> SEQUENCE: 140

```
Met Ala Ala Thr Ala Ala Ala Thr Val Thr Ala Thr Ala Ala Ala Ser
1               5                   10                  15

Ser Cys Ser Lys Gly Glu Ser Val Gly Ile Ala Ala Pro Ala Asp Leu
            20                  25                  30

Thr Lys Lys Ala Lys Lys Gly Arg Ser Pro Pro Ala Glu Glu Met Glu
        35                  40                  45

Ala Phe Phe Ala Ala Ala Glu Gly Asp Val Ala Arg Arg Phe Ala Ala
    50                  55                  60
```

```
Lys Tyr Asn Tyr Asp Val Val Thr Asp Ala Pro Met Asp Gly Arg Tyr
65                  70                  75                  80

Glu Trp Val Arg Val Arg Pro
                85


<210> SEQ ID NO 141
<211> LENGTH: 1834
<212> TYPE: DNA
<213> ORGANISM: Triticum sp.

<400> SEQUENCE: 141

acctaatcct atcgttatct cctcccaccc agccccagcc cccactccgg ccccgtaata     60

cccagcgagc agagcacagc acccaccacc ggcacaggcg cgcgcgtggg tggaaaaaag    120

tagagagaga acaggagaga aggaagaaaa gaaagaaaaa aggcatggcc gccaccgccg    180

cggccatcgt gacggcgacg gcggcggcgt cgagctgcag caagcgcgag agcgtcggca    240

ttgcggcgcc cgccgacttg tcagtctcca gctcccttcc ttccttctcc tcacggcacg    300

gcgctggccg ttccaagccg tgctgctgcg tgtggagttc tcttctcacg ctttggctgc    360

tgcctgttgt cgtgcgcagg acgaagaagg cgaagaaggg gaggtcgcca ccggcggagg    420

agatggaggc cttcttcgcc gcggcggagg gcgacgtcgc gcggcgcttc gctgccaagt    480

gagtaccgca catgcatgag tcaggcaaca gcttcctcct atacgcttgg ggaaaagcca    540

ccgtggattt atatgggagt agctagctag caatgcatgc gtagcagtgg gcctgtaaat    600

tctgctcaag taacatgagg cctctgctga agatctcggt tgtcagtcag tttggtgttg    660

cacacactca cacagtaaaa aaaacgctag catgtgtttt tctgttgctg ttttcttttt    720

ctcttgaaaa ggccagctgc tggtgctagt gtatgaagga atttgaagaa aatcactaca    780

cagataggga gtttttgagc aaacaaaaaa agaaaaatgg ggatcttggt cttttgtaaa    840

aacccacaca cgcaacgggg acggactggg agaattcaga gcagcaaagg aaaaaatgat    900

ttcaactcaa ttatggattt tggcaaatca gctcaagcaa ttatacacta ctatttccaa    960

gaaaaagtga ggttggcagt gcagtgcttc tcccggttct tttctaacgt ttggatcttg   1020

cgctttggat tgaaggtaca actataacgt cgtcacagac gctcccatgg atgggcggta   1080

cgagtgggtc cgagtgaggc cgtagcaagg aaggatatgc cgccgcagcc agtcaagtgt   1140

cagaagcccg cacagacaga ccacgttgtg tcctttttaa tcattctttt gtagttaccc   1200

tgtcatgctt tattagctgt aattattgct cacgagatgc ctaatcatgt gaaagctcac   1260

catgtaaaag tcgccagtgg atgccctgtt tctcctgtag ctagcttgct tttattaact   1320

tgtcgtgata tgttttgttt catcaagaaa aacaaagcgt cgttatctgt gtacattgtc   1380

tcgtagtact agtacttttg ttctgacact gcatatctct aacacatcat agcatggtaa   1440

gtccagccta ctttcaaagc aaaaacatac agaactggga cagatccgac ccgtgaacgt   1500

ctgtagacgc acccggacac gtccaagaca gtgtccacgg cctcttaaat gccctactgt   1560

acatcacact gctcgtatcg aaatctcaaa tccatgcaca tggatcatac acatgaatcg   1620

cataaataac atttgttcat agcgaaaaaa atacataatt taaatataaa atttgtttca   1680

agtgtacagt tcaaacatta aactcccttt ttctgttgtg ggtctccata tgctccacaa   1740

gcgtgcacat ttcgatctcg aagattccga tgcatcttca gaaagttcac aaatatgctt   1800

cgcgtcatgt ttcgggaggt ggacttgtac tctt                               1834


<210> SEQ ID NO 142
<211> LENGTH: 264
```

<212> TYPE: DNA
<213> ORGANISM: Triticum sp.

<400> SEQUENCE: 142

```
atggccgcca ccgccgcggc catcgtgacg gcgacggcgg cggcgtcgag ctgcagcaag      60

cgcgagagcg tcggcattgc ggcgcccgcc gacttgacga agaaggcgaa gaaggggagg     120

tcgccaccgg cggaggagat ggaggccttc ttcgccgcgg cggagggcga cgtcgcgcgg     180

cgcttcgctg ccaagtacaa ctataacgtc gtcacagacg ctcccatgga tgggcggtac     240

gagtgggtcc gagtgaggcc gtag                                            264
```

<210> SEQ ID NO 143
<211> LENGTH: 87
<212> TYPE: PRT
<213> ORGANISM: Triticum sp.

<400> SEQUENCE: 143

```
Met Ala Ala Thr Ala Ala Ala Ile Val Thr Ala Thr Ala Ala Ala Ser
1               5                   10                  15

Ser Cys Ser Lys Arg Glu Ser Val Gly Ile Ala Ala Pro Ala Asp Leu
            20                  25                  30

Thr Lys Lys Ala Lys Lys Gly Arg Ser Pro Pro Ala Glu Glu Met Glu
        35                  40                  45

Ala Phe Phe Ala Ala Ala Glu Gly Asp Val Ala Arg Arg Phe Ala Ala
    50                  55                  60

Lys Tyr Asn Tyr Asn Val Val Thr Asp Ala Pro Met Asp Gly Arg Tyr
65                  70                  75                  80

Glu Trp Val Arg Val Arg Pro
                85
```

<210> SEQ ID NO 144
<211> LENGTH: 2141
<212> TYPE: DNA
<213> ORGANISM: Triticum sp.

<400> SEQUENCE: 144

```
tgcacgggta aaaaccaagc cgccttccgg tttgggcact gcggcgctcc tgtgcaccag      60

gtccttccta gctagctaca gtgagtagct gctgttaatt atactagtag tagctggtag     120

tactcctgct cggaatctct cggctcggac gtcgtacgac cacctataag ctcgctcgct     180

cgcggcctcc accgtttcat ttcccaccta atcctatcgt tatctcctcc cacccagccc     240

ccagccccac tccggccccg taacacccag cgagcagagc acagcaccca ccaccggcac     300

agccgcgcgc gtgggagggt ggaaaaaagt agagaaagaa caggagagaa ggaagaaaag     360

gaaaaaggca tggccgccac cgccgcggcc accgtgacgg cgacggcgac ggcggcggcg     420

tcgagctgca gcaagcgcga gagcgccggc attgcggcgc ccgccgactt gtcagtctcc     480

cgctcccttc cttccttcca cccacggcac agcgctgacc gttcgaggct gtgctgccgc     540

gtatggaata gttcttctgc tcactcttcg gcctcttttt gttgtggtgt gcagggcgaa     600

gaaggcgaag aaggcgaggt cgccgccggc ggaggagatg gagggcttct tcgcggcggc     660

ggagggcgac gtcgcgcggc gcttcgctgc caagtgagtt ctaccgcaca tgcatgcgtc     720

aggcaacagc ttcctcctat actcttgggg aaaagccgcc gtggatttat atgggagcag     780

ctagctagca atgcatgcgc agcagtgggc ctgtaaattc tgctctcgag taacatgagg     840

cctctgctgc tcaagatctg ggtgtcagt cagtttggtg ttgcacacaa cacacgcaca      900
```

```
ctcacactgt aaaaaaacgc aagcatgtgc tttgccctcc aattctctgt cgccgttttt    960
cttttctct tgattgaaaa ggccagctgc tggtgctagt gtatgaagga atttgaacaa    1020
aatcactaca catatagact gttctgagca tacacacaaa aaaaggtaat tcgggggatc   1080
ttggtttttt gcatttgtca aattagctca agcaattata tttccagaaa caaaaagtga   1140
ggttggcagt gcagtactac tcccgttctt ttctaacgtt tggatcttgc gctttggatt   1200
gaaggtacaa ctatgacgtc gtcgcagacg ctcccatgga cgggcggtac gagtgggtcc   1260
gactgaggcc gtaggaagga gggatatgcc gccgcagcca gtcaagcgtc agaactcaga   1320
agcccgcaca gacagacaga ccacgttgtg tcctttttaa tcaattcttt tgcagttacc   1380
ctgtcatgct ttgttagctg taattattgc tcacgagatg cctaatcatg taaaagctca   1440
ccatgtataa gtcgccagtg gatgccctgt ttcacctgta gctagcttcg cttttattaa   1500
cttgtcgtca tatgttttgt ttcatcaaga aaaacaaggc gtcgttatct gtgtacattg   1560
tctcgtagca ggagtacttt tgttctgaca ctgcatatct caacacatca tagcatggta   1620
agtccagcct actttcaaag caaaaacaat cagagctagg acaaatccga cccgtgaaca   1680
tttctagacg tacccggaca tgatccgaga cagcgcccac ggccccttaa atgccctact   1740
gcacatcaca ctgctcgtat taaaacctta aatccatgca catcgatcat acacatgaat   1800
cgcataaata gcatttgttc atagcgaaaa aaatcatagt tcaaacataa aatttatttt   1860
gaatgcacaa ttcaaacatt aaactccttg tttctattat gtgtctgcat atgctccaca   1920
agcgcaaaca tttagatccc gaagattccg atacatcttc agaaagttca caaatatgct   1980
tcacatcatg ttttcgggag gcggactttg tactcttggc ttctcaaaat catgtgttcg   2040
ggctgcccct tcaccttcat caccctcgac aatcatactg tgcaaaatga caaaacatgt   2100
cgccagctgc cactaaagtc tctgatttcc ccatatcatt g                       2141
```

<210> SEQ ID NO 145
<211> LENGTH: 270
<212> TYPE: DNA
<213> ORGANISM: Triticum sp.

<400> SEQUENCE: 145

```
atggccgcca ccgccgcggc caccgtgacg gcgacggcga cggcggcggc gtcgagctgc     60
agcaagcgcg agagcgccgg cattgcggcg cccgccgact tggcgaagaa ggcgaagaag    120
gcgaggtcgc cgccggcgga ggagatggag ggcttcttcg cggcggcgga gggcgacgtc    180
gcgcggcgct tcgctgccaa gtacaactat gacgtcgtcg cagacgctcc catggacggg    240
cggtacgagt gggtccgact gaggccgtag                                     270
```

<210> SEQ ID NO 146
<211> LENGTH: 89
<212> TYPE: PRT
<213> ORGANISM: Triticum sp.

<400> SEQUENCE: 146

```
Met Ala Ala Thr Ala Ala Ala Thr Val Thr Ala Thr Ala Thr Ala Ala
1               5                   10                  15

Ala Ser Ser Cys Ser Lys Arg Glu Ser Ala Gly Ile Ala Ala Pro Ala
            20                  25                  30

Asp Leu Ala Lys Lys Ala Lys Lys Ala Arg Ser Pro Pro Ala Glu Glu
        35                  40                  45

Met Glu Gly Phe Phe Ala Ala Ala Glu Gly Asp Val Ala Arg Arg Phe
    50                  55                  60
```

```
Ala Ala Lys Tyr Asn Tyr Asp Val Val Ala Asp Ala Pro Met Asp Gly
65                  70                  75                  80

Arg Tyr Glu Trp Val Arg Leu Arg Pro
                85
```

<210> SEQ ID NO 147
<211> LENGTH: 20
<212> TYPE: DNA
<213> ORGANISM: Artificial Sequence
<220> FEATURE:
<223> OTHER INFORMATION: Primer TaKRP6 START

<400> SEQUENCE: 147
atggccgcca ccgccgcggc 20

<210> SEQ ID NO 148
<211> LENGTH: 21
<212> TYPE: DNA
<213> ORGANISM: Artificial Sequence
<220> FEATURE:
<223> OTHER INFORMATION: Primer TaKRP6 nearSTOP

<400> SEQUENCE: 148
tcggacccac tcgtaccgcc c 21

<210> SEQ ID NO 149
<211> LENGTH: 26
<212> TYPE: DNA
<213> ORGANISM: Artificial Sequence
<220> FEATURE:
<223> OTHER INFORMATION: Primer TaKRP6 upstr

<400> SEQUENCE: 149
cctaatccta tcgttatctc ctccca 26

<210> SEQ ID NO 150
<211> LENGTH: 26
<212> TYPE: DNA
<213> ORGANISM: Artificial Sequence
<220> FEATURE:
<223> OTHER INFORMATION: Primer TaKRP6 downstr

<400> SEQUENCE: 150
ctacgagaca atgtacacag ataacg 26

<210> SEQ ID NO 151
<211> LENGTH: 19
<212> TYPE: DNA
<213> ORGANISM: Artificial Sequence
<220> FEATURE:
<223> OTHER INFORMATION: Primer TaKRP6 49F

<400> SEQUENCE: 151
agctgcagca agggcgaga 19

<210> SEQ ID NO 152
<211> LENGTH: 21
<212> TYPE: DNA
<213> ORGANISM: Artificial Sequence
<220> FEATURE:
<223> OTHER INFORMATION: Primer TaKRP6 258R

<400> SEQUENCE: 152
cctcactcgg acccactcgt a 21

<210> SEQ ID NO 153
<211> LENGTH: 61
<212> TYPE: PRT
<213> ORGANISM: Zea mays

<400> SEQUENCE: 153

Thr Ala Gln Ala Gln Pro Ala Ala Arg Ser Arg Val Pro Pro Ala Ala
1               5                   10                  15

Glu Ile Glu Glu Phe Phe Ala Ala Ala Glu Glu Ala Glu Ala Arg Arg
            20                  25                  30

Phe Ala Cys Lys Tyr Asn Phe Asp Val Ala Arg Gly Val Pro Leu Asp
        35                  40                  45

Ser Gly Arg Tyr Glu Trp Thr Pro Ala Val Ser Ser Ser
    50                  55                  60

<210> SEQ ID NO 154
<211> LENGTH: 60
<212> TYPE: PRT
<213> ORGANISM: Zea mays

<400> SEQUENCE: 154

His Tyr Asp Leu Glu Ala Arg Ala Arg Ala Arg Met Pro Pro Ala Ala
1               5                   10                  15

Glu Ile Asp Glu Phe Phe Ala Ala Ala Glu Lys Ala Gln Ala Glu Arg
            20                  25                  30

Phe Ala Ala Lys Tyr Asn Phe Asp Val Ala Arg Gly Val Pro Leu Asn
        35                  40                  45

Ala Gly Arg Phe Glu Trp Thr Pro Val Ala Thr Val
    50                  55                  60

<210> SEQ ID NO 155
<211> LENGTH: 55
<212> TYPE: PRT
<213> ORGANISM: Zea mays

<400> SEQUENCE: 155

Arg Val Gln Ala Pro Ala Arg His Ile Ile Pro Ser Ser Ala Glu Met
1               5                   10                  15

Asn Glu Phe Phe Ser Ala Ala Glu Gln Pro Gln Gln Gln Ala Phe Ile
            20                  25                  30

Asp Lys Tyr Asn Phe Asp Pro Val Asn Asp Cys Pro Leu Pro Gly Arg
        35                  40                  45

Tyr Glu Trp Val Lys Leu Asp
    50                  55

<210> SEQ ID NO 156
<211> LENGTH: 56
<212> TYPE: PRT
<213> ORGANISM: Zea mays

<400> SEQUENCE: 156

Arg Ala Gln Thr Pro Val Cys Arg Tyr Val Pro Ser Ser Leu Glu Met
1               5                   10                  15

Asp Glu Phe Phe Ala Ala Ala Glu Gln Gln Gln His Gln Thr Phe Arg
            20                  25                  30

Asp Lys Tyr Asn Phe Cys Pro Ala Arg Gly Cys Pro Leu Pro Gly Arg
        35                  40                  45

Tyr Glu Trp Thr Val Leu Asp Cys
    50                  55

```
<210> SEQ ID NO 157
<211> LENGTH: 55
<212> TYPE: PRT
<213> ORGANISM: Zea mays

<400> SEQUENCE: 157

Ala Ala Glu Leu Ile Val Pro Pro Ala His Glu Ile Gln Glu Phe Phe
1               5                   10                  15

Ala Ala Ala Glu Ala Ala Gln Ala Lys Arg Phe Ala Ser Lys Tyr Asn
            20                  25                  30

Phe Asp Phe Val Arg Gly Val Pro Leu Asp Ala Gly Gly Arg Phe Glu
        35                  40                  45

Trp Ala Pro Val Val Ser Ile
    50                  55


<210> SEQ ID NO 158
<211> LENGTH: 55
<212> TYPE: PRT
<213> ORGANISM: Zea mays

<400> SEQUENCE: 158

Ala Ala Glu Leu Ile Val Pro Pro Ala His Glu Ile Gln Glu Phe Phe
1               5                   10                  15

Ala Ala Ala Glu Ala Ala Gln Ala Lys Arg Phe Ala Ser Lys Tyr Asn
            20                  25                  30

Phe Asp Phe Val Arg Gly Val Pro Leu Asp Ala Gly Gly Arg Phe Glu
        35                  40                  45

Trp Ala Pro Val Val Ser Ile
    50                  55


<210> SEQ ID NO 159
<211> LENGTH: 55
<212> TYPE: PRT
<213> ORGANISM: Zea mays

<400> SEQUENCE: 159

Ala Ala Glu Leu Ile Val Pro Pro Ala His Glu Ile Gln Glu Phe Phe
1               5                   10                  15

Ala Ala Ala Glu Ala Ala Gln Ala Lys Arg Phe Ala Ser Lys Tyr Asn
            20                  25                  30

Phe Asp Phe Val Arg Gly Val Pro Leu Asp Ala Gly Gly Arg Phe Glu
        35                  40                  45

Trp Ala Pro Val Val Ser Ile
    50                  55


<210> SEQ ID NO 160
<211> LENGTH: 19
<212> TYPE: PRT
<213> ORGANISM: Zea mays

<400> SEQUENCE: 160

Ser Ala Ala Glu Leu Ile Val Pro Pro Ala Gln Glu Ile Gln Glu Phe
1               5                   10                  15

Phe Ala Ala


<210> SEQ ID NO 161
<211> LENGTH: 49
<212> TYPE: PRT
<213> ORGANISM: Zea mays
```

<400> SEQUENCE: 161

```
Ser Pro Pro Ala Glu Glu Val Glu Ala Phe Leu Ala Ala Ala Glu Arg
1               5                   10                  15

Gly Met Ala Arg Arg Phe Ala Val Lys Tyr Asn Tyr Asp Val Val Lys
            20                  25                  30

Asp Ala Pro Met Asp Gly Gly Arg Tyr Glu Trp Val Arg Val Arg Pro
        35                  40                  45

Gly
```

<210> SEQ ID NO 162
<211> LENGTH: 58
<212> TYPE: PRT
<213> ORGANISM: Oryza sativa

<400> SEQUENCE: 162

```
Ala Ala Ala Ala Ala Gly Arg Arg Pro Pro Leu Ser Pro Pro Glu Ala
1               5                   10                  15

Glu Ile Glu Ala Phe Phe Ala Ala Ala Glu Leu Ala Glu Arg Arg Arg
            20                  25                  30

Phe Ala Glu Lys Tyr Asn Tyr Asp Ile Ala Leu Asp Arg Pro Leu Gln
        35                  40                  45

Gly Arg Tyr Glu Trp Glu Pro Val Ser Thr
    50                  55
```

<210> SEQ ID NO 163
<211> LENGTH: 65
<212> TYPE: PRT
<213> ORGANISM: Zea mays

<400> SEQUENCE: 163

```
Ser Gln Thr Pro Ser Pro Ser Pro Ser Pro Pro Pro Pro Pro Thr Glu
1               5                   10                  15

Thr Glu Ile Glu Ala Phe Phe Ala Asp Ala Glu Leu Ala Glu Arg Arg
            20                  25                  30

Arg Phe Ala Glu Ala Tyr Asn Tyr Asp Val Ala Leu Asp Arg Pro Leu
        35                  40                  45

Glu Gly Arg Phe Glu Trp Val Pro Leu Pro Leu Thr Gly Gly Arg Arg
    50                  55                  60

Trp
65
```

<210> SEQ ID NO 164
<211> LENGTH: 47
<212> TYPE: PRT
<213> ORGANISM: Zea mays

<400> SEQUENCE: 164

```
Ala Val Pro Ser Ser Arg Glu Met Asn Glu Tyr Phe Ala Ala Glu Gln
1               5                   10                  15

Arg Arg Gln Gln Gln Asp Phe Ile Asp Lys Tyr Asn Phe Asp Pro Ala
            20                  25                  30

Asn Asp Cys Pro Leu Pro Gly Arg Phe Glu Trp Val Lys Leu Asp
        35                  40                  45
```

<210> SEQ ID NO 165
<211> LENGTH: 47
<212> TYPE: PRT
<213> ORGANISM: Zea mays

<400> SEQUENCE: 165

```
Ala Leu Pro Ser Ser Thr Glu Met Asn Glu Tyr Phe Ala Ala Glu Gln
1               5                   10                  15

Arg Arg Gln Gln Gln Ala Phe Ile Asp Lys Tyr Asn Phe Asp Pro Val
            20                  25                  30

Asn Asp Cys Pro Leu Pro Gly Arg Phe Glu Trp Val Lys Leu Asp
        35                  40                  45
```

<210> SEQ ID NO 166
<211> LENGTH: 48
<212> TYPE: PRT
<213> ORGANISM: Zea mays

<400> SEQUENCE: 166

```
Phe Ile Pro Ser Ser Leu Glu Met Glu Glu Phe Phe Ser Ala Ala Glu
1               5                   10                  15

Gln Gln Glu Gln His Ser Phe Arg Glu Lys Tyr Asn Phe Cys Pro Val
            20                  25                  30

Asn Asp Cys Pro Leu Pro Gly Arg Tyr Glu Trp Ala Arg Leu Asp Cys
        35                  40                  45
```

<210> SEQ ID NO 167
<211> LENGTH: 48
<212> TYPE: PRT
<213> ORGANISM: Zea mays

<400> SEQUENCE: 167

```
Phe Ile Pro Ser Ser Leu Glu Met Glu Glu Phe Phe Ser Ala Ala Glu
1               5                   10                  15

Gln Gln Glu Gln His Asn Phe Arg Glu Lys Tyr Asn Phe Cys Pro Val
            20                  25                  30

Asn Asp Cys Pro Leu Pro Gly Arg Tyr Glu Trp Ala Arg Leu Asp Cys
        35                  40                  45
```

<210> SEQ ID NO 168
<211> LENGTH: 58
<212> TYPE: PRT
<213> ORGANISM: Brassica napus

<400> SEQUENCE: 168

```
Ala Asp Asp Arg Lys Ser Ser Pro Glu Val Ser Lys Ser Pro Thr Pro
1               5                   10                  15

Gly Glu Ile Asp Glu Phe Leu Ser Glu Leu Glu Ser Lys Asp Gln Lys
            20                  25                  30

Arg Phe Met Asp Lys Tyr Asn Phe Asp Ile Val Asn Asp Lys Pro Leu
        35                  40                  45

Gln Gly Arg Tyr Lys Trp Asp Arg Val Lys
    50                  55
```

<210> SEQ ID NO 169
<211> LENGTH: 61
<212> TYPE: PRT
<213> ORGANISM: Brassica napus

<400> SEQUENCE: 169

```
Ala Asp Asp Arg Lys Ser Ser Pro Glu Val Ser Lys Ser Pro Thr Pro
1               5                   10                  15

Ala Glu Ile Glu Glu Phe Leu Ser Glu Leu Glu Asn Lys Asp Gln Lys
            20                  25                  30
```

```
Arg Phe Met Asp Lys Tyr Asn Phe Asp Ile Val Asn Asp Lys Pro Leu
        35                  40                  45

Gln Gly Arg Tyr Lys Trp Asp Arg Val Lys Pro Leu Lys
    50                  55                  60


<210> SEQ ID NO 170
<211> LENGTH: 58
<212> TYPE: PRT
<213> ORGANISM: Arabidopsis thaliana

<400> SEQUENCE: 170

Ala Thr Lys Arg Lys Gln Pro Gly Val Arg Lys Thr Pro Thr Ala Ala
1               5                   10                  15

Glu Ile Glu Asp Leu Phe Ser Glu Leu Glu Ser Pro Asp Asp Lys Lys
            20                  25                  30

Lys Gln Phe Ile Glu Lys Tyr Asn Phe Asp Ile Val Asn Asp Glu Pro
        35                  40                  45

Leu Glu Gly Arg Tyr Lys Trp Asp Arg Leu
    50                  55


<210> SEQ ID NO 171
<211> LENGTH: 64
<212> TYPE: PRT
<213> ORGANISM: Arabidopsis thaliana

<400> SEQUENCE: 171

Thr Glu Met Arg Asp Gln Arg Lys Thr Glu Lys Lys Lys Lys Met Glu
1               5                   10                  15

Lys Ser Pro Thr Gln Ala Glu Leu Asp Asp Phe Phe Ser Ala Ala Glu
            20                  25                  30

Arg Tyr Glu Gln Lys Arg Phe Thr Glu Lys Tyr Asn Tyr Asp Ile Val
        35                  40                  45

Asn Asp Thr Pro Leu Glu Gly Arg Tyr Gln Trp Val Ser Leu Lys Pro
    50                  55                  60


<210> SEQ ID NO 172
<211> LENGTH: 57
<212> TYPE: PRT
<213> ORGANISM: Brassica napus

<400> SEQUENCE: 172

Glu Glu Lys Gly Lys Ser Ala Thr Glu Gln Pro Pro Thr Ala Val Glu
1               5                   10                  15

Ile Glu Asp Phe Phe Val Glu Ala Glu Lys Gln Leu His Asp Asn Phe
            20                  25                  30

Lys Lys Lys Tyr Asn Phe Asp Phe Glu Lys Glu Lys Pro Leu Glu Gly
        35                  40                  45

Arg Tyr Glu Trp Val Lys Leu Ser Glu
    50                  55


<210> SEQ ID NO 173
<211> LENGTH: 57
<212> TYPE: PRT
<213> ORGANISM: Brassica napus

<400> SEQUENCE: 173

Glu Asp Lys Gly Lys Pro Thr Ala Glu Gln Pro Pro Thr Ala Val Glu
1               5                   10                  15

Ile Glu Glu Phe Phe Val Glu Ala Glu Lys Gln Leu His Asp Lys Phe
```

```
            20                  25                  30

Lys Lys Lys Tyr Asn Phe Asp Phe Glu Lys Glu Lys Pro Leu Glu Gly
        35                  40                  45

Arg Tyr Glu Trp Val Lys Leu Ser Glu
    50                  55


<210> SEQ ID NO 174
<211> LENGTH: 57
<212> TYPE: PRT
<213> ORGANISM: Arabidopsis thaliana

<400> SEQUENCE: 174

Glu Glu Glu Glu Lys Ala Lys Leu Met Thr Glu Met Pro Thr Glu Ser
1               5                   10                  15

Glu Ile Glu Asp Phe Phe Val Glu Ala Glu Lys Gln Leu Lys Glu Lys
            20                  25                  30

Phe Lys Lys Lys Tyr Asn Phe Asp Phe Glu Lys Glu Lys Pro Leu Glu
        35                  40                  45

Gly Arg Tyr Glu Trp Val Lys Leu Glu
    50                  55


<210> SEQ ID NO 175
<211> LENGTH: 64
<212> TYPE: PRT
<213> ORGANISM: Brassica napus

<400> SEQUENCE: 175

Ser Asp Asn Ser Asn Gln Arg Glu Asp Ser Phe Ser Gly Ser His Arg
1               5                   10                  15

His Leu Pro Thr Thr Pro Glu Met Asp Glu Phe Phe Ser Ala Ala Glu
            20                  25                  30

Glu Glu Gln Gln Lys Gln Phe Ile Glu Lys Tyr Asn Phe Asp Pro Val
        35                  40                  45

Asn Glu Gln Pro Leu Pro Gly Arg Phe Glu Trp Lys Lys Val Asp Asp
    50                  55                  60


<210> SEQ ID NO 176
<211> LENGTH: 42
<212> TYPE: PRT
<213> ORGANISM: Brassica napus

<400> SEQUENCE: 176

Ser Gly Asn Ser Asn Gln Arg Glu Asp Ser Phe Ser Gly Ser His Arg
1               5                   10                  15

His Leu Pro Thr Thr Pro Glu Met Asp Glu Phe Phe Ser Ala Ala Glu
            20                  25                  30

Glu Glu Gln Gln Lys Gln Phe Ile Glu Lys
        35                  40


<210> SEQ ID NO 177
<211> LENGTH: 63
<212> TYPE: PRT
<213> ORGANISM: Arabidopsis thaliana

<400> SEQUENCE: 177

Ser Glu Ser Asn Gln Arg Glu Asp Ser Leu Ser Arg Ser His Arg Arg
1               5                   10                  15

Arg Pro Thr Thr Pro Glu Met Asp Glu Phe Phe Ser Gly Ala Glu Glu
            20                  25                  30
```

Glu Gln Gln Lys Gln Phe Ile Glu Lys Tyr Asn Phe Asp Pro Val Asn
35 40 45

Glu Gln Pro Leu Pro Gly Arg Phe Glu Trp Thr Lys Val Asp Asp
50 55 60

<210> SEQ ID NO 178
<211> LENGTH: 51
<212> TYPE: PRT
<213> ORGANISM: Brassica napus

<400> SEQUENCE: 178

Glu Ala Thr Gln Ser Val Pro Ser His Glu Ile Glu Glu Phe Phe Ala
1 5 10 15

Phe Ala Glu Gln Gln Gln Gln Arg Phe Phe Thr Glu Lys Tyr Asn Phe
20 25 30

Asp Ile Val Ser Glu Asn Pro Leu Pro Gly Arg Tyr Glu Trp Ile Lys
35 40 45

Val Val Pro
50

<210> SEQ ID NO 179
<211> LENGTH: 51
<212> TYPE: PRT
<213> ORGANISM: Brassica napus

<400> SEQUENCE: 179

Glu Ala Ile Gln Ser Val Pro Ser His Glu Ile Glu Asp Phe Phe Ala
1 5 10 15

Phe Ala Glu Gln Gln Gln Gln Arg Phe Phe Thr Glu Lys Tyr Asn Phe
20 25 30

Asp Ile Val Ser Glu Asn Pro Leu Pro Gly Arg Tyr Glu Trp Ile Lys
35 40 45

Val Val Pro
50

<210> SEQ ID NO 180
<211> LENGTH: 47
<212> TYPE: PRT
<213> ORGANISM: Arabidopsis thaliana

<400> SEQUENCE: 180

Lys Ser Ile Gln Ser Glu Ile Glu Asp Phe Phe Ala Ser Ala Glu Gln
1 5 10 15

Gln Gln Gln Arg Phe Phe Ile Gln Lys Tyr Asn Phe Asp Ile Val Ser
20 25 30

Asp Asn Pro Leu Pro Gly Arg Tyr Glu Trp Val Lys Val Met Pro
35 40 45

<210> SEQ ID NO 181
<211> LENGTH: 54
<212> TYPE: PRT
<213> ORGANISM: Brassica napus

<400> SEQUENCE: 181

Thr Pro Ala Arg Asp Ser Thr Val Pro Thr Ile Gly Glu Leu Glu Glu
1 5 10 15

Phe Phe Ala Tyr Ala Glu Gln Gln Gln Gln Arg Leu Phe Met Glu Lys
20 25 30

Tyr Asn Phe Asp Ile Val Asn Asp Val Pro Leu Pro Gly Gly Tyr Glu
35 40 45

```
Trp Val Gln Val Ser Pro
    50


<210> SEQ ID NO 182
<211> LENGTH: 54
<212> TYPE: PRT
<213> ORGANISM: Brassica napus

<400> SEQUENCE: 182

Thr Pro Thr Lys Asp Ser Thr Val Pro Thr Ile Gly Glu Leu Glu Glu
1               5                   10                  15

Phe Phe Ala Tyr Ala Glu Gln Gln Gln Gln Arg Leu Phe Val Glu Lys
            20                  25                  30

Tyr Asn Phe Asp Ile Val Asn Asp Val Pro Leu Thr Gly Arg Tyr Glu
        35                  40                  45

Trp Val Gln Val Ser Pro
    50


<210> SEQ ID NO 183
<211> LENGTH: 59
<212> TYPE: PRT
<213> ORGANISM: Arabidopsis thaliana

<400> SEQUENCE: 183

Ala Thr Lys Glu Tyr Thr Arg Glu Gln Asp Asn Val Ile Pro Thr Thr
1               5                   10                  15

Ser Glu Met Glu Glu Phe Phe Ala Tyr Ala Glu Gln Gln Gln Gln Arg
            20                  25                  30

Leu Phe Met Glu Lys Tyr Asn Phe Asp Ile Val Asn Asp Ile Pro Leu
        35                  40                  45

Ser Gly Arg Tyr Glu Trp Val Gln Val Lys Pro
    50                  55


<210> SEQ ID NO 184
<211> LENGTH: 62
<212> TYPE: PRT
<213> ORGANISM: Arabidopsis thaliana

<400> SEQUENCE: 184

Ser Arg Arg Arg Leu Arg Lys Ser Leu His Glu Thr Val Lys Glu Ala
1               5                   10                  15

Glu Leu Glu Asp Phe Phe Gln Val Ala Glu Lys Asp Leu Arg Asn Lys
            20                  25                  30

Leu Leu Glu Cys Ser Met Lys Tyr Asn Phe Asp Phe Glu Lys Asp Glu
        35                  40                  45

Pro Leu Gly Gly Gly Arg Tyr Glu Trp Val Lys Leu Asn Pro
    50                  55                  60
```